US010377817B2

(12) United States Patent
Economides et al.

(10) Patent No.: US 10,377,817 B2
(45) Date of Patent: Aug. 13, 2019

(54) HUMAN ANTIBODIES TO GREM1

(71) Applicant: Regeneron Pharmaceuticals, Inc., Tarrytown, NY (US)

(72) Inventors: Aris N. Economides, Tarrytown, NY (US); Vincent J. Idone, Brewster, NY (US); Lori C. Morton, Chappaqua, NY (US)

(73) Assignee: Regeneron Pharmaceuticals, Inc., Tarrytown, NY (US)

( * ) Notice: Subject to any disclaimer, the term of this patent is extended or adjusted under 35 U.S.C. 154(b) by 316 days.

(21) Appl. No.: 14/775,637

(22) PCT Filed: Mar. 7, 2014

(86) PCT No.: PCT/US2014/021471
§ 371 (c)(1),
(2) Date: Sep. 11, 2015

(87) PCT Pub. No.: WO2014/159010
PCT Pub. Date: Oct. 2, 2014

(65) Prior Publication Data
US 2016/0024195 A1    Jan. 28, 2016

Related U.S. Application Data

(60) Provisional application No. 61/782,874, filed on Mar. 14, 2013, provisional application No. 61/883,218, filed on Sep. 27, 2013.

(51) Int. Cl.
| | |
|---|---|
| *C07K 16/18* | (2006.01) |
| *C07K 16/24* | (2006.01) |
| *A61K 38/17* | (2006.01) |
| *A61K 39/395* | (2006.01) |
| *A61K 45/06* | (2006.01) |
| *A61N 5/00* | (2006.01) |
| *A61K 39/00* | (2006.01) |

(52) U.S. Cl.
CPC ............ *C07K 16/18* (2013.01); *A61K 38/179* (2013.01); *A61K 39/3955* (2013.01); *A61K 45/06* (2013.01); *A61N 5/00* (2013.01); *C07K 16/24* (2013.01); *A61K 2039/505* (2013.01); *A61K 2039/507* (2013.01); *C07K 2317/21* (2013.01); *C07K 2317/76* (2013.01); *C07K 2317/92* (2013.01); *C07K 2319/30* (2013.01)

(58) Field of Classification Search
None
See application file for complete search history.

(56) References Cited

U.S. PATENT DOCUMENTS

| | | | |
|---|---|---|---|
| 6,432,410 | B1 | 8/2002 | Harland et al. |
| 7,744,873 | B2 | 6/2010 | Clark et al. |
| 2009/0041747 | A1 | 2/2009 | Petersen et al. |
| 2009/0041757 | A1 | 2/2009 | Zhen et al. |

FOREIGN PATENT DOCUMENTS

| | | |
|---|---|---|
| EP | 1440159 B1 | 12/2006 |
| EP | 1777519 A1 | 4/2007 |
| EP | 2053135 A1 | 4/2009 |
| EP | 2826790 A1 | 1/2015 |
| WO | WO 14/159010 A1 | 10/2014 |

OTHER PUBLICATIONS

George et al. (Circulation. 1998; 97: 900-906).*
Gussow et al. (Methods in Enzymology. 1991; 203: 99-121).*
Lippincott-Schwartz (Current Protocols in Cell Biology, 16.0.1-16.0.2, 2002).*
Boers et al., "Transcriptional Profiling Reveals Novel Markers of Liver Fibrogenesis," J Biol Chem, 281(24):16289-16295, (2006).
Chen et al., "Expression of gremlin 1 correlates with increased angiogenesis and progression-free survival in patients with pancreatic neuroendocrine tumors," J Gastroenterol, 48:101-108, (2013).
Chiodelli et al., "Heparan Sulfate Proteoglycans Mediate the Angiogenic Activity of the Vascular Endothelial Growth Factor Receptor-2 Agonist Gremlin," Arterioscler Thromb Vasc Biol, 31:e116-e127, 12 pages, (2011).
Costello et al., "Role of Gremlin in the Lung," Am J Respir Cell Mol Biol, 42:517-523, (2010). Originally Published in Press as DOI: 10.1165/rcmb.2009-0201TR on Jul. 2, 2009.
Farkas et al., "Transient Overexpression of Gremlin Results in Epithelial Activation and Reversible Fibrosis in Rat Lungs," Am J Respir Cell Mol Biol, 44:870-878 (2011).
Kim et al., "Gremlin-1 Induces BMP-Independent Tumor Cell Proliferation, Migration, and Invasion," PLoS ONE, 7(4):e35100. doi:10.1371/journal.pone.0035100, 8 pages, (2012).
Koli et al., "Bone Morphogenetic Protein-4 Inhibitor Gremlin is Overexpressed in Idiopathic Pulmonary Fibrosis," Am J Pathol, 169(1):61-71, (2006).
Leijten et al., "Gremlin 1, Frizzled-Related Protein, and Dkk-1 Are Key Regulators of Human Articular Cartilage Homeostasis," Arthritis & Rheumatism, 64(10):3302-3312, (2012).
Lonberg, "Fully human antibodies from transgenic mouse and phage display platforms," Curr Opin Immunol, 20:450-459, (2008).
Mitola et al., "Gremlin is a novel agonist of the major proangiogenic receptor VEGI-R2," Blood, 116(18):3677-3680, (2010).

(Continued)

*Primary Examiner* — Brad Duffy
(74) *Attorney, Agent, or Firm* — Schwabe, Williamson & Wyatt PC; Christopher Westberg

(57) ABSTRACT

The present invention provides antibodies that bind to human gremlin-1 (GREM1), and methods of use. According to certain embodiments of the invention, the antibodies are fully human antibodies that bind to GREM1. The antibodies of the invention are useful for inhibiting or neutralizing GREM1 activity, thus providing a means of treating a GREM1-related disease or disorder such as fibrosis and cancer. In some embodiments, the antibodies of the present invention are used in treating at least one symptom or complication of fibrosis of the liver, lungs or kidney.

13 Claims, 1 Drawing Sheet
Specification includes a Sequence Listing.

(56) References Cited

OTHER PUBLICATIONS

Mulvihill et al., "Gremlin is Overexpressed in Lung Adenocarcinoma and Increases Cell Growth and Proliferation in Normal Lung Cells," PLoS ONE, 7(8):1-8, (2012).

Myllarniemi et al., "Gremlin-mediated Decrease in Bone Morphogenetic Protein Signaling Promotes Pulmonary Fibrosis," Am J Respir Crit Care Med, 177:321-329, (2008). Originally Published in Press as DOI: 10.1164/rccm.200706-945OC on Nov. 1, 2007.

Namkoong et al., "The bone morphogenetic protein antagonist gremlin 1 is overexpressed in human cancers and interacts with YWHAH protein," BMC Cancer, 6:74 doi:10.1186/1471-2407-6-74, 13 pages, (2006).

Roxburgh et al., "Allelic Depletion of greml Attenuates Diabetic Kidney Disease," Diabetes 58:1641-1650, (2009).

Sneddon et al., "Bone morphogenetic protein antagonist gremlin 1 is widely expressed by cancer-associated stromal cells and can promote tumor cell proliferation," PNAS, 103(40):14842-14847, (2006).

Stabile et al., "Bone morphogenic protein antagonist Dm/gremlin is a novel proangiogenic factor," Blood, 109:1834-1840, (2007).

Sun et al., "BMP4 Activation and Secretion Are Negatively Regulated by an Intracellular Gremlin-BMP4 Interaction," J Biol Chem, 281(39):29349-29356, (2006).

Wang et al., "The bone morphogenetic protein antagonist Gremlin is overexpressed in human malignant mesothelioma," Oncol Rep, 27:58-64, (2012).

Weiskirchen et al., "BMP-7 as antagonist of organ fibrosis," Front Biosci, 14:4992-5012, (2009).

WIPO Application No. PCT/US2014/021471, PCT/US2014/021471, PCT International Preliminary Report on Patentability dated Sep. 15, 2015.

WIPO Application No. PCT/US2014/021471, PCT International Search Report and Written Opinion of the International Searching Authority dated Jun. 17, 2014.

Wordinger et al., "Focus on Molecules: Gremlin," Exp Eye Res, 87(2):78-79, (2008).

Yanagita, "BMP modulators regulate the function of BMP during body patterning and disease progression," BioFactors, 35(2):113-119, (2009).

Zhang et al., "Bone morphogenetic protein-7 and Gremlin: New emergin therapeutic targets for diabetic nephropathy," Biochem Biophys Res Commun, 383:1-3, (2009).

Zhang et al., "In Vivo Delivery of Gremlin siRNA Plasmid Reveals Therapeutic Potential against Diabetic Nephropathy by Recovering Bone Morphogenetic Protein-7," PLoS ONE, 5(7):e11709, doi:10.1371/journalpone.0011709, 13 pages, (2010).

Sha et al., "Elevated levels of gremlin-1 in eutopic endometrium and peripheral serum in patients with endometriosis," Fertility and Sterility, vol. 91 (No. 2):350-358, (Feb. 2009).

U.S. Appl. No. 61/782,874, filed Mar. 14, 2013.

U.S. Appl. No. 61/883,218, filed Sep. 27, 2013.

PCT/US2014/021471, Mar. 7, 2014, WO 2014/159010.

* cited by examiner

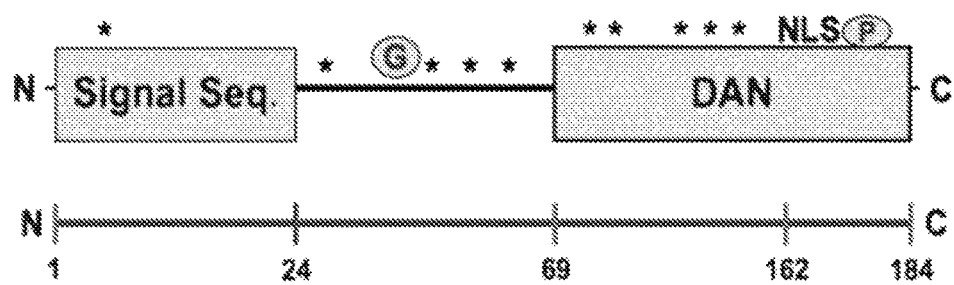
(From: Wordinger, R.J., et al 2008, Exp. Eye Res. 87: 78-79)

HUMAN ANTIBODIES TO GREM1

CROSS-REFERENCE TO RELATED APPLICATIONS

This application is a US national stage of International Application No. PCT/US2014/021471, filed Mar. 7, 2014, which claims the benefit under 35 USC § 119(e) of US Provisional Application Nos. 61/782,874, filed Mar. 14, 2013, and 61/883,218, filed Sep. 27, 2013. Each of these applications is incorporated herein by reference in its entirety for all purposes.

SEQUENCE LISTING

This application incorporates by reference the Sequence Listing submitted in Computer Readable Form as file 463287-Sequence.txt, created on Sep. 11, 2015 and containing 195,986 bytes.

FIELD OF THE INVENTION

The present invention is related to human antibodies and antigen-binding fragments of human antibodies that specifically bind to human gremlin-1 (GREM1), and therapeutic and diagnostic methods of using those antibodies.

STATEMENT OF RELATED ART

Fibrosis is a scarring process that is a common feature of chronic organ injury. It is characterized by elevated activity of transforming growth factor-beta (TGF-β) resulting in increased and altered deposition of extracellular matrix and other fibrosis-associated proteins.

Bone morphogenetic proteins (BMPs) are phylogenetically conserved signaling molecules that belong to the TGF-β superfamily and are involved in growth, development and differentiation of various cell types (Yanagita, M., 2009, Biofactors DOI: 10:1002/biof. 15). The biological responses to BMPs are negatively regulated by BMP antagonists that can directly associate with BMPs and inhibit receptor binding. Human gremlin-1 (GREM1), a member of the cysteine knot superfamily, is an antagonist for BMP signaling (Hsu, D. R., et al 1998, Mol. Cell 1: 673-683). It binds to BMP2, BMP4 and BMP7. GREM1 blocks BMP signaling, which is thought to be anti-fibrotic in many tissues by blocking the binding of BMP to its receptor.

The expression of GREM1 in normal adult kidney, liver and lung is very low. However, GREM1 expression is increased in both mouse models of fibrosis and human fibrotic diseases such as diabetic nephropathy and pulmonary fibrosis (Koli et al., 2006, Am. J. Pathol. 169: 61-71; Farkas, et al., 2011, Am. J. Respir. Cell. Mol. Biol. 44: 870-878; Lappin, et al., 2002, Nephrol. Dial. Transplant. 17: 65-67). Increased GREM1 expression leads to a reduction in anti-fibrotic BMP signaling. Increased GREM1 expression also correlates with increased serum creatinine levels and tubulointerstitial fibrosis scores in these diseases (Dolan, V., et al 2005, Am. J. Kidney Dis. 45: 1034-9). In several fibrosis models, such as lung and kidney fibrosis, the expression of GREM1 is greatly increased while BMP signaling is decreased (Myllarniemi, et al., 2008, Am. J. Respir. Crit. Care Med. 177: 321-329). Administration of BMP7 can decrease fibrosis in some models of kidney disease, but does not protect against bleomycin-induced lung or skin fibrosis (Weiskirchen, et al., 2009, 14: 4992-5012).

Mice heterozygous for GREM1 show some protection against fibrosis in an experimental model of diabetic nephropathy (Zhang, et al., 2009, BBRC 383: 1-3). These mice show no difference in the onset, severity and progression of diabetes as measured by weight loss and hyperglycemia. They do, however, have attenuated fibrotic structural changes in the kidney and reduced changes in kidney function.

GREM1 may thus serve as a potential therapeutic target for the treatment of fibrotic diseases. There is a need to develop specific GREM1 inhibitors in fibrosis treatment which do not have any side-effects.

In addition, GREM1 is an agonist of the major proangiogenic receptor vascular endothelial growth factor receptor-2 (VEGFR-2) and may play an oncogenic role especially in carcinomas of the uterine cervix, lung, ovary, kidney, breast, colon, pancreas, and sarcoma (Namkoong et al 2006, BMC Cancer 6: 74 doi:10.1186/1471-2407-6-74; Mitola et al 2010; Blood 116: 3677-3680). Heparan sulfate (HS) and heparin, glycosaminoglycans (GAGs) known for their anticoagulant effects, have been shown to bind to GREM1. GREM1 binds to heparin and activates VEGFR-2 in a BMP-independent manner (Chiodelli et al 2011; Arterioscler. Thromb. Vasc. Biol. 31: e116-e127).

Anti-GREM1 polyclonal and monoclonal antibodies are available commercially (for example, from Sigma-Aldrich, Abnova Corporation, Novus Biologicals, Genway). U.S. Pat. No. 6,432,410 discloses the nucleotide and protein sequences of human, mouse, xenopus and chick GREM1 and deletion mutants thereof. US20090203041 discloses GREM1 peptide sequences for use as BMP4 inhibitors. Kim et al disclose GREM1 antibodies which inhibit GREM1 in a manner independent of BMP or VEGFR-2 in PLoS One 7(4): e35100. doi:10.1371/journal.pone.0035100 and in WO2013137686. U.S. Pat. No. 7,744,873 discloses methods for treating glaucoma by administering a GREM1 antagonist, wherein the antagonist is an antibody that binds GREM1. Methods of treatment and formulations for glaucoma or cancer using GREM1 antagonists including antibodies have been described in EP1440159B1, EP1777519A1, EP2053135A1, and US 20090041757.

BRIEF SUMMARY OF THE INVENTION

The invention provides fully human monoclonal antibodies (mAbs) and antigen-binding fragments thereof that bind specifically to human GREM1. Such antibodies may be useful to neutralize the activity of GREM1 or to block binding of GREM1 to a bone morphogenetic protein (BMP) such as BMP2, BMP4 or BMP7. In certain other embodiments, the antibodies may be useful to neutralize the activity or block binding to heparin or heparan sulfate. The antibodies may act to halt the progression, or to lessen the severity of a fibrosis-associated condition or disease, or reduce the number, the duration, or the severity of disease recurrence, or ameliorate at least one symptom associated with fibrosis or cancer. Such antibodies may be used alone or in conjunction with a second agent useful for treating fibrosis or cancer. In certain embodiments, the antibodies specific for GREM1, may be given therapeutically in conjunction with a second agent to lessen the severity of the fibrosis-associated condition or cancer, or to reduce the number, the duration, or the severity of disease recurrence, or ameliorate at least one symptom associated with the fibrosis-associated condition or cancer. In certain embodiments, the antibodies may be used prophylactically as stand-alone therapy to protect patients who are at risk for developing a fibrosis-associated condition or disease. For example, certain patient populations may be at risk for developing a fibrosis condition or disease, including elderly patients, or patients with family history, or patients with problems of alcohol or drug abuse, or patients who have chronic and/or concomitant underlying medical conditions such as diabetes, metabolic disorders, liver injury, renal injury or lung injury that may pre-dispose them to fibrosis. Other at-risk patient populations include individuals exposed to chemicals such as asbestos or other pollutants, or smokers. Any of these patient populations may benefit from treatment with the antibodies of the invention, when given alone or in conjunction with a second agent.

The antibodies of the present invention may be used to treat fibrosis in lungs, liver, kidney, skin, heart, gut or muscle of a patient. In other embodiments, the antibodies of the invention may be used to treat cancer such as carcinoma of the uterine cervix, lung, ovary, kidney, breast, colon, or pancreas. The antibodies can be full-length (for example, an IgG1 or IgG4 antibody) or may comprise only an antigen-binding portion (for example, a Fab, F(ab')$_2$ or scFv fragment), and may be modified to affect functionality, e.g., to eliminate residual effector functions (Reddy et al., (2000), J. Immunol. 164:1925-1933).

Accordingly, in a first aspect, the invention provides an isolated fully human monoclonal antibody or antigen-binding fragment thereof that binds to human GREM1.

In one embodiment, the human monoclonal antibody binds to GREM1 of SEQ ID NO: 594 or SEQ ID NO: 595.

In one embodiment, the isolated antibody or antigen-binding fragment thereof blocks GREM1 binding to BMP2, BMP4, BMP7 or heparin.

In one embodiment, the isolated human antibody or antigen-binding fragment thereof binds to GREM1 with a $K_D$ equal to or less than $10^{-7}$ M as measured by surface plasmon resonance.

In one embodiment, the isolated antibody or antigen-binding fragment thereof exhibits one or more properties selected from the group consisting of: (a) binds GREM1 at 37° C. with a binding dissociation equilibrium constant ($K_D$) of less than about 275 nM as measured by surface plasmon resonance; (b) binds to GREM1 at 37° C. with a dissociative half-life (t %) of greater than about 3 minutes as measured by surface plasmon resonance; (c) binds GREM1 at 25° C. with a $K_D$ of less than about 280 nM as measured by surface plasmon resonance; (d) binds to GREM1 at 25° C. with a t % of greater than about 2 minutes as measured by surface plasmon resonance; (e) blocks GREM1 binding to BMP4 with an $IC_{50}$ of less than about 1.9 nM as measured in a competition ELISA assay at 25° C.; (f) blocks GREM1-mediated inhibition of BMP signaling and promotes cell differentiation; and (g) blocks GREM1 binding to heparin.

In one embodiment, the isolated human antibody or antigen-binding fragment thereof which binds to GREM1 comprises three heavy chain complementarity determining regions (CDRs) (HCDR1, HCDR2 and HCDR3) contained within any one of the heavy chain variable region (HCVR) sequences selected from the group consisting of SEQ ID NOs: 2, 18, 34, 50, 66, 82, 98, 114, 130, 146, 162, 178, 194, 210, 226, 242, 258, 274, 290, 306, 322, 338, 354, 370, 386, 402, 418, 434, 450, 466, 482, 498, 514, 530, 546, 562, and 578; and three light chain CDRs (LCDR1, LCDR2 and LCDR3) contained within any one of the light chain variable region (LCVR) sequences selected from the group consisting of SEQ ID NOs: 10, 26, 42, 58, 74, 90, 106, 122, 138, 154, 170, 186, 202, 218, 234, 250, 266, 282, 298, 314, 330, 346, 362, 378, 394, 410, 426, 442, 458, 474, 490, 506, 522, 538, 554, 570, and 586. Methods and techniques for identifying CDRs within HCVR and LCVR amino acid sequences are well known in the art and can be used to identify CDRs within the specified heavy chain variable region(s) (HCVR) and/or light chain variable region(s) (LCVR) amino acid sequences disclosed herein. Exemplary conventions that can be used to identify the boundaries of CDRs include, e.g., the Kabat definition, the Chothia definition, and the AbM definition. In general terms, the Kabat definition is based on sequence variability, the Chothia definition is based on the location of the structural loop regions, and the AbM definition is a compromise between the Kabat and Chothia approaches. See, e.g., Kabat, "Sequences of Proteins of Immunological Interest," National Institutes of Health, Bethesda, Md. (1991); Al-Lazikani et al., (1997), *J. Mol. Biol.* 273:927-948; and Martin et al., (1989), *Proc. Natl. Acad. Sci. USA* 86:9268-9272. Public databases are also available for identifying CDR sequences within an antibody.

In one embodiment, the isolated human antibody or antigen-binding fragment thereof which binds to GREM1 comprises a HCVR having an amino acid sequence selected from the group consisting of SEQ ID NOs: 2, 18, 34, 50, 66, 82, 98, 114, 130, 146, 162, 178, 194, 210, 226, 242, 258, 274, 290, 306, 322, 338, 354, 370, 386, 402, 418, 434, 450, 466, 482, 498, 514, 530, 546, 562, and 578.

In one embodiment, the isolated human antibody or antigen-binding fragment thereof which binds to GREM1 comprises a LCVR having an amino acid sequence selected from the group consisting of SEQ ID NOs: 10, 26, 42, 58, 74, 90, 106, 122, 138, 154, 170, 186, 202, 218, 234, 250, 266, 282, 298, 314, 330, 346, 362, 378, 394, 410, 426, 442, 458, 474, 490, 506, 522, 538, 554, 570 and 586.

In one embodiment, the isolated human antibody or antigen-binding fragment thereof which binds to GREM1 comprises (a) a HCVR having an amino acid sequence selected from the group consisting of SEQ ID NOs: 2, 18, 34, 50, 66, 82, 98, 114, 130, 146, 162, 178, 194, 210, 226, 242, 258, 274, 290, 306, 322, 338, 354, 370, 386, 402, 418, 434, 450, 466, 482, 498, 514, 530, 546, 562, and 578; and (b) a LCVR having an amino acid sequence selected from the group consisting of SEQ ID NO: 10, 26, 42, 58, 74, 90, 106, 122, 138, 154, 170, 186, 202, 218, 234, 250, 266, 282, 298, 314, 330, 346, 362, 378, 394, 410, 426, 442, 458, 474, 490, 506, 522, 538, 554, 570 and 586.

In one embodiment, the isolated human antibody or antigen-binding fragment thereof which binds to GREM1 comprises:
(a) a HCDR1 domain having an amino acid sequence selected from the group consisting of SEQ ID NOs: 4, 20, 36, 52, 68, 84, 100, 116, 132, 148, 164, 180, 196, 212, 228, 244, 260, 276, 292, 308, 324, 340, 356, 372, 388, 404, 420, 436, 452, 468, 484, 500, 516, 532, 548, 564, and 580;
(b) a HCDR2 domain having an amino acid sequence selected from the group consisting of SEQ ID NOs: 6, 22, 38, 54, 70, 86, 102, 118, 134, 150, 166, 182, 198, 214, 230, 246, 262, 278, 294, 310, 326, 342, 358, 374, 390, 406, 422, 438, 454, 470, 486, 502, 518, 534, 550, 566 and 582;
(c) a HCDR3 domain having an amino acid sequence selected from the group consisting of SEQ ID NOs: 8, 24, 40, 56, 72, 88, 104, 120, 136, 152, 168, 184, 200, 216, 232, 248, 264, 280, 296, 312, 328, 344, 360, 376, 392, 408, 424, 440, 456, 472, 488, 504, 520, 536, 552, 568 and 584;
(d) a LCDR1 domain having an amino acid sequence selected from the group consisting of SEQ ID NOs: 12, 28, 44, 60, 76, 92, 108, 124, 140, 156, 172, 188, 204, 220, 236, 252, 268, 284, 300, 316, 332, 348, 364, 380, 396, 412, 428, 444, 460, 476, 492, 508, 524, 540, 556, 572 and 588;

(e) a LCDR2 domain having an amino acid sequence selected from the group consisting of SEQ ID NOs: 14, 30, 46, 62, 78, 94, 110, 126, 142, 158, 174, 190, 206, 222, 238, 254, 270, 286, 302, 318, 334, 350, 366, 382, 398, 414, 430, 446, 462, 478, 494, 510, 526, 542, 558, 574, and 590; and (f) a LCDR3 domain having an amino acid sequence selected from the group consisting of SEQ ID NOs: 16, 32, 48, 64, 80, 96, 112, 128, 144, 160, 176, 192, 208, 224, 240, 256, 272, 288, 304, 320, 336, 352, 368, 384, 400, 416, 432, 448, 464, 480, 496, 512, 528, 544, 560, 576 and 592.

In one embodiment, the isolated human antibody or antigen-binding fragment thereof which binds to GREM1 comprises a HCVR/LCVR amino acid sequence pair selected from the group consisting of SEQ ID NOs: 2/10, 18/26, 34/42, 50/58, 66/74, 82/90, 98/106, 114/122, 130/138, 146/154, 162/170, 178/186, 194/202, 210/218, 226/234, 242/250, 258/266, 274/282, 290/298, 306/314, 322/330, 338/346, 354/362, 370/378, 386/394, 402/410, 418/426, 434/442, 450/458, 466/474, 482/490, 498/506, 514/52, 530/538, 546/554, 562/570, and 578/586.

In one embodiment, the invention provides a fully human monoclonal antibody or antigen-binding fragment thereof that binds to GREM1, wherein the antibody or fragment thereof exhibits one or more of the following characteristics: (i) comprises a HCVR having an amino acid sequence selected from the group consisting of SEQ ID NO: 2, 18, 34, 50, 66, 82, 98, 114, 130, 146, 162, 178, 194, 210, 226, 242, 258, 274, 290, 306, 322, 338, 354, 370, 386, 402, 418, 434, 450, 466, 482, 498, 514, 530, 546, 562, and 578, or a substantially similar sequence thereof having at least 90%, at least 95%, at least 98% or at least 99% sequence identity; (ii) comprises a LCVR having an amino acid sequence selected from the group consisting of SEQ ID NO: 10, 26, 42, 58, 74, 90, 106, 122, 138, 154, 170, 186, 202, 218, 234, 250, 266, 282, 298, 314, 330, 346, 362, 378, 394, 410, 426, 442, 458, 474, 490, 506, 522, 538, 554, 570, and 586, or a substantially similar sequence thereof having at least 90%, at least 95%, at least 98% or at least 99% sequence identity; (iii) comprises a HCDR3 domain having an amino acid sequence selected from the group consisting of SEQ ID NO: 8, 24, 40, 56, 72, 88, 104, 120, 136, 152, 168, 184, 200, 216, 232, 248, 264, 280, 296, 312, 328, 344, 360, 376, 392, 408, 424, 440, 456, 472, 488, 504, 520, 536, 552, 568, and 584, or a substantially similar sequence thereof having at least 90%, at least 95%, at least 98% or at least 99% sequence identity; and a LCDR3 domain having an amino acid sequence selected from the group consisting of SEQ ID NO: 16, 32, 48, 64, 80, 96, 112, 128, 144, 160, 176, 192, 208, 224, 240, 256, 272, 288, 304, 320, 336, 352, 368, 384, 400, 416, 432, 448, 464, 480, 496, 512, 528, 544, 560, 576, and 592, or a substantially similar sequence thereof having at least 90%, at least 95%, at least 98% or at least 99% sequence identity; (iv) comprises a HCDR1 domain having an amino acid sequence selected from the group consisting of SEQ ID NO: 4, 20, 36, 52, 68, 84, 100, 116, 132, 148, 164, 180, 196, 212, 228, 244, 260, 276, 292, 308, 324, 340, 356, 372, 388, 404, 420, 436, 452, 468, 484, 500, 516, 532, 548, 564, and 580, or a substantially similar sequence thereof having at least 90%, at least 95%, at least 98% or at least 99% sequence identity; a HCDR2 domain having an amino acid sequence selected from the group consisting of SEQ ID NO: 6, 22, 38, 54, 70, 86, 102, 118, 134, 150, 166, 182, 198, 214, 230, 246, 262, 278, 294, 310, 326, 342, 358, 374, 390, 406, 422, 438, 454, 470, 486, 502, 518, 534, 550, 566, and 582, or a substantially similar sequence thereof having at least 90%, at least 95%, at least 98% or at least 99% sequence identity; a LCDR1 domain having an amino acid sequence selected from the group consisting of SEQ ID NO: 12, 28, 44, 60, 76, 92, 108, 124, 140, 156, 172, 188, 204, 220, 236, 252, 268, 284, 300, 316, 332, 348, 364, 380, 396, 412, 428, 444, 460, 476, 492, 508, 524, 540, 556, 572, and 588, or a substantially similar sequence thereof having at least 90%, at least 95%, at least 98% or at least 99% sequence identity; and a LCDR2 domain having an amino acid sequence selected from the group consisting of SEQ ID NO: 14, 30, 46, 62, 78, 94, 110, 126, 142, 158, 174, 190, 206, 222, 238, 254, 270, 286, 302, 318, 334, 350, 366, 382, 398, 414, 430, 446, 462, 478, 494, 510, 526, 542, 558, 574, and 590, or a substantially similar sequence thereof having at least 90%, at least 95%, at least 98% or at least 99% sequence identity; (v) binds to GREM1 with a $K_D$ equal to or less than $10^{-7}$ M as measured by surface plasmon resonance.

In a second aspect, the invention provides an isolated antibody or antigen-binding fragment thereof that competes for specific binding to human GREM1 with an antibody or antigen-binding fragment comprising the complementarity determining regions (CDRs) of a heavy chain variable region (HCVR), wherein the HCVR has an amino acid sequence selected from the group consisting of SEQ ID NOs: 2, 18, 34, 50, 66, 82, 98, 114, 130, 146, 162, 178, 194, 210, 226, 242, 258, 274, 290, 306, 322, 338, 354, 370, 386, 402, 418, 434, 450, 466, 482, 498, 514, 530, 546, 562, and 578; and the CDRs of a light chain variable region (LCVR), wherein the LCVR has an amino acid sequence selected from the group consisting of SEQ ID NOs: 10, 26, 42, 58, 74, 90, 106, 122, 138, 154, 170, 186, 202, 218, 234, 250, 266, 282, 298, 314, 330, 346, 362, 378, 394, 410, 426, 442, 458, 474, 490, 506, 522, 538, 554, 570, and 586.

In one embodiment, the invention provides an isolated antibody or antigen-binding fragment thereof that binds the same epitope on human GREM1 as an antibody or antigen-binding fragment comprising the CDRs of a heavy chain variable region (HCVR), wherein the HCVR has an amino acid sequence selected from the group consisting of SEQ ID NOs: 2, 18, 34, 50, 66, 82, 98, 114, 130, 146, 162, 178, 194, 210, 226, 242, 258, 274, 290, 306, 322, 338, 354, 370, 386, 402, 418, 434, 450, 466, 482, 498, 514, 530, 546, 562, and 578; and the CDRs of a light chain variable region (LCVR), wherein the LCVR has an amino acid sequence selected from the group consisting of SEQ ID NOs: 10, 26, 42, 58, 74, 90, 106, 122, 138, 154, 170, 186, 202, 218, 234, 250, 266, 282, 298, 314, 330, 346, 362, 378, 394, 410, 426, 442, 458, 474, 490, 506, 522, 538, 554, 570, and 586.

In one embodiment, the invention provides for an isolated antibody or antigen-binding fragment thereof that blocks binding of human GREM1 to any one of BMP2, BMP4, BMP7 or heparin, the antibody comprising the complementarity determining regions (CDRs) of a heavy chain variable region (HCVR), wherein the HCVR has an amino acid sequence selected from the group consisting of SEQ ID NOs: 2, 18, 34, 50, 66, 82, 98, 114, 130, 146, 162, 178, 194, 210, 226, 242, 258, 274, 290, 306, 322, 338, 354, 370, 386, 402, 418, 434, 450, 466, 482, 498, 514, 530, 546, 562, and 578; and the CDRs of a light chain variable region (LCVR), wherein the LCVR has an amino acid sequence selected from the group consisting of SEQ ID NOs: 10, 26, 42, 58, 74, 90, 106, 122, 138, 154, 170, 186, 202, 218, 234, 250, 266, 282, 298, 314, 330, 346, 362, 378, 394, 410, 426, 442, 458, 474, 490, 506, 522, 538, 554, 570, and 586.

In one embodiment, the invention provides a fully human monoclonal antibody or antigen-binding fragment thereof that binds to GREM1, wherein the antibody or fragment thereof exhibits one or more of the following characteristics: (i) comprises a HCVR having an amino acid sequence selected from the group consisting of SEQ ID NO: 2, 18, 34, 50, 66, 82, 98, 114, 130, 146, 162, 178, 194, 210, 226, 242, 258, 274, 290, 306, 322, 338, 354, 370, 386, 402, 418, 434, 450, 466, 482, 498, 514, 530, 546, 562, and 578, or a substantially similar sequence thereof having at least 90%, at least 95%, at least 98% or at least 99% sequence identity; (ii) comprises a LCVR having an amino acid sequence selected from the group consisting of SEQ ID NO: 10, 26, 42, 58, 74, 90, 106, 122, 138, 154, 170, 186, 202, 218, 234, 250, 266, 282, 298, 314, 330, 346, 362, 378, 394, 410, 426, 442, 458, 474, 490, 506, 522, 538, 554, 570, and 586, or a substantially similar sequence thereof having at least 90%, at least 95%, at least 98% or at least 99% sequence identity; (iii) comprises a HCDR3 domain having an amino acid sequence selected from the group consisting of SEQ ID NO: 8, 24, 40, 56, 72, 88, 104, 120, 136, 152, 168, 184, 200, 216, 232, 248, 264, 280, 296, 312, 328, 344, 360, 376, 392, 408, 424, 440, 456, 472, 488, 504, 520, 536, 552, 568, and 584, or a substantially similar sequence thereof having at least 90%, at least 95%, at least 98% or at least 99% sequence identity; and a LCDR3 domain having an amino acid sequence selected from the group consisting of SEQ ID NO: 16, 32, 48, 64, 80, 96, 112, 128, 144, 160, 176, 192, 208, 224, 240, 256, 272, 288, 304, 320, 336, 352, 368, 384, 400, 416, 432, 448, 464, 480, 496, 512, 528, 544, 560, 576, and 592, or a substantially similar sequence thereof having at least 90%, at least 95%, at least 98% or at least 99% sequence identity; (iv) comprises a HCDR1 domain having an amino acid sequence selected from the group consisting of SEQ ID NO: 4, 20, 36, 52, 68, 84, 100, 116, 132, 148, 164, 180, 196, 212, 228, 244, 260, 276, 292, 308, 324, 340, 356, 372, 388, 404, 420, 436, 452, 468, 484, 500, 516, 532, 548, 564, and 580, or a substantially similar sequence thereof having at least 90%, at least 95%, at least 98% or at least 99% sequence identity; a HCDR2 domain having an amino acid sequence selected from the group consisting of SEQ ID NO: 6, 22, 38, 54, 70, 86, 102, 118, 134, 150, 166, 182, 198, 214, 230, 246, 262, 278, 294, 310, 326, 342, 358, 374, 390, 406, 422, 438, 454, 470, 486, 502, 518, 534, 550, 566, and 582, or a substantially similar sequence thereof having at least 90%, at least 95%, at least 98% or at least 99% sequence identity; a LCDR1 domain having an amino acid sequence selected from the group consisting of SEQ ID NO: 12, 28, 44, 60, 76, 92, 108, 124, 140, 156, 172, 188, 204, 220, 236, 252, 268, 284, 300, 316, 332, 348, 364, 380, 396, 412, 428, 444, 460, 476, 492, 508, 524, 540, 556, 572, and 588, or a substantially similar sequence thereof having at least 90%, at least 95%, at least 98% or at least 99% sequence identity; and a LCDR2 domain having an amino acid sequence selected from the group consisting of SEQ ID NO: 14, 30, 46, 62, 78, 94, 110, 126, 142, 158, 174, 190, 206, 222, 238, 254, 270, 286, 302, 318, 334, 350, 366, 382, 398, 414, 430, 446, 462, 478, 494, 510, 526, 542, 558, 574, and 590, or a substantially similar sequence thereof having at least 90%, at least 95%, at least 98% or at least 99% sequence identity; (v) binds to GREM1 with a $K_D$ equal to or less than $10^{-7}$M as measured by surface plasmon resonance; (vi) blocks GREM1 binding to one of BMP2, BMP4 or BMP7; (vii) blocks GREM1-inhibition of BMP signaling and promotes cell differentiation; and (viii) blocks GREM1 binding to heparin.

In a third aspect, the invention provides nucleic acid molecules encoding anti-GREM1 antibodies or fragments thereof. Recombinant expression vectors carrying the nucleic acids of the invention, and host cells into which such vectors have been introduced, are also encompassed by the invention, as are methods of producing the antibodies by culturing the host cells under conditions permitting production of the antibodies, and recovering the antibodies produced.

In one embodiment, the invention provides an antibody or fragment thereof comprising a HCVR encoded by a nucleic acid sequence selected from the group consisting of SEQ ID NO: 1, 17, 33, 49, 65, 81, 97, 113, 129, 145, 161, 177, 193, 209, 225, 241, 257, 273, 289, 305, 321, 337, 353, 369, 385, 401, 417, 433, 449, 465, 481, 497, 513, 529, 545, 561, and 577, or a substantially identical sequence having at least 90%, at least 95%, at least 98%, or at least 99% homology thereof.

In one embodiment, the antibody or fragment thereof further comprises a LCVR encoded by a nucleic acid sequence selected from the group consisting of SEQ ID NO: 9, 25, 41, 57, 73, 89, 105, 121, 137, 153, 169, 185, 201, 217, 233, 249, 265, 281, 297, 313, 329, 345, 361, 377, 393, 409, 425, 441, 457, 473, 489, 505, 521, 537, 553, 569, and 585, or a substantially identical sequence having at least 90%, at least 95%, at least 98%, or at least 99% homology thereof.

In one embodiment, the invention provides an antibody or antigen-binding fragment of an antibody comprising a HCDR3 domain encoded by a nucleotide sequence selected from the group consisting of SEQ ID NO: 7, 23, 39, 55, 71, 87, 103, 119, 135, 151, 167, 183, 199, 215, 231, 247, 263, 279, 295, 311, 327, 343, 359, 375, 391, 407, 423, 439, 455, 471, 487, 503, 519, 535, 551, 567, and 583, or a substantially similar sequence thereof having at least 90%, at least 95%, at least 98% or at least 99% sequence identity; and a LCDR3 domain encoded by a nucleotide sequence selected from the group consisting of SEQ ID NO: 15, 31, 47, 63, 79, 95, 111, 127, 143, 159, 175, 191, 207, 223, 239, 255, 271, 287, 303, 319, 335, 351, 367, 383, 399, 415, 431, 447, 463, 479, 495, 511, 527, 543, 559, 575, and 591, or a substantially similar sequence thereof having at least 90%, at least 95%, at least 98% or at least 99% sequence identity.

In one embodiment, the invention provides an antibody or fragment thereof further comprising a HCDR1 domain encoded by a nucleotide sequence selected from the group consisting of SEQ ID NO: 3, 19, 35, 51, 67, 83, 99, 115, 131, 147, 163, 179, 195, 211, 227, 243, 259, 275, 291, 307, 323, 339, 355, 371, 387, 403, 419, 435, 451, 467, 483, 499, 515, 531, 547, 563, and 579, or a substantially similar sequence thereof having at least 90%, at least 95%, at least 98% or at least 99% sequence identity; a HCDR2 domain encoded by a nucleotide sequence selected from the group consisting of SEQ ID NO: 5, 21, 37, 53, 69, 85, 101, 117, 133, 149, 165, 181, 197, 213, 229, 245, 261, 277, 293, 309, 325, 341, 357, 373, 389, 405, 421, 437, 453, 469, 485, 501, 517, 533, 549, 565, and 581, or a substantially similar sequence thereof having at least 90%, at least 95%, at least 98% or at least 99% sequence identity; a LCDR1 domain encoded by a nucleotide sequence selected from the group consisting of SEQ ID NO: 11, 27, 43, 59, 75, 91, 107, 123, 139, 155, 171, 187, 203, 219, 235, 251, 267, 283, 299, 315, 331, 347, 363, 379, 395, 411, 427, 443, 459, 475, 491, 507, 523, 539, 555, 571, and 587, or a substantially similar sequence thereof having at least 90%, at least 95%, at least 98% or at least 99% sequence identity; and a LCDR2 domain encoded by a nucleotide sequence selected from the group consisting of SEQ ID NO: 13, 29, 45, 61, 77, 93, 109, 125, 141, 157, 173, 189, 205, 221, 237, 253, 269, 285, 301, 317, 333, 349, 365, 381, 397, 413, 429, 445, 461, 477, 493, 509, 525, 541, 557, 573, and 589, or a substantially similar sequence thereof having at least 90%, at least 95%, at least 98% or at least 99% sequence identity.

In some embodiments, the antibody or antigen-binding fragment thereof to human GREM1, as described herein may be linked to a detectable label such as a radionuclide label or a MRI-detectable label.

In a fourth aspect, the invention provides a pharmaceutical composition comprising an isolated fully human monoclonal antibody or antigen-binding fragment thereof that binds to GREM1 and a pharmaceutically acceptable carrier or diluent. In one embodiment, the invention provides a pharmaceutical composition comprising an isolated fully human monoclonal antibody or antigen-binding fragment thereof that binds specifically to the secreted form of human GREM1 and a pharmaceutically acceptable carrier or diluent. In one embodiment, the invention provides a pharmaceutical composition comprising an isolated fully human monoclonal antibody or antigen-binding fragment thereof that binds specifically to the membrane-associated form of GREM1 (mature GREM1 protein) and a pharmaceutically acceptable carrier or diluent.

In one embodiment, the pharmaceutical composition comprises a fully human monoclonal antibody that binds to GREM1 having any one or more of the characteristics described herein. The antibody that binds to GREM1 binds with a $K_D$ equal to or less than $10^{-7}$ M.

In one embodiment, the composition comprises an antibody that binds to human GREM1 and has a HCVR/LCVR amino acid sequence pair selected from the group consisting of SEQ ID NOs: 2/10, 18/26, 34/42, 50/58, 66/74, 82/90, 98/106, 114/122, 130/138, 146/154, 162/170, 178/186, 194/202, 210/218, 226/234, 242/250, 258/266, 274/282, 290/298, 306/314, 322/330, 338/346, 354/362, 370/378, 386/394, 402/410, 418/426, 434/442, 450/458, 466/474, 482/490, 498/506, 514/522, 530/538, 546/554, 562/570, and 578/586.

In one embodiment, the invention features a composition, which is a combination of an antibody or antigen-binding fragment of an antibody of the invention, and a second therapeutic agent.

The second therapeutic agent may be a small molecule drug, a protein/polypeptide, an antibody, a nucleic acid molecule, such as an anti-sense oligonucleotide, or a siRNA. The second therapeutic agent may be synthetic or naturally derived.

The second therapeutic agent may be any agent that is advantageously combined with the antibody or fragment thereof of the invention, for example, an anti-fibrotic drug such as pirfenidone, an antibiotic, an anti-inflammatory drug, a non-steroidal anti-inflammatory drug (NSAID), a cytotoxic agent, a chemotherapeutic agent, a corticosteroid such as prednisone, an endothelin receptor antagonist such as Bosentan, macitentan or ambrisentan, a nutritional supplement, an anti-hypertensive agent, an antioxidant, a vascular endothelial growth factor (VEGF) antagonist [e.g., a "VEGF-Trap" such as aflibercept or other VEGF-inhibiting fusion protein as set forth in U.S. Pat. No. 7,087,411, or an anti-VEGF antibody or antigen binding fragment thereof (e.g., bevacizumab, or ranibizumab)], another antibody that binds to GREM1, or an antibody against a chemokine such as TGF-β, or against an cytokine such as IL-1, anti-LOXL2, anti-avb6integrin, a galectin-3 targeting drug, imatinib or any other PDGFR antagonist and anti-AOC3 drugs.

In certain embodiments, the second therapeutic agent may be an agent that helps to counteract or reduce any possible side effect(s) associated with the antibody or antigen-binding fragment of an antibody of the invention, if such side effect(s) should occur.

It will also be appreciated that the antibodies and pharmaceutically acceptable compositions of the present invention can be employed in combination therapies, that is, the antibodies and pharmaceutically acceptable compositions can be administered concurrently with, prior to, or subsequent to, one or more other desired therapeutics or medical procedures. The particular combination of therapies (therapeutics or procedures) to employ in a combination regimen will take into account compatibility of the desired therapeutics and/or procedures and the desired therapeutic effect to be achieved. It will also be appreciated that the therapies employed may achieve a desired effect for the same disorder (for example, an antibody may be administered concurrently with another agent used to treat the same disorder), or they may achieve different effects (e.g., control of any adverse effects). As used herein, additional therapeutic agents which are normally administered to treat or prevent a particular disease, or condition, are appropriate for the disease, or condition, being treated. When multiple therapeutics are co-administered, dosages may be adjusted accordingly, as is recognized in the pertinent art.

A fifth aspect of the invention involves a method for treating a disease or disorder associated with increased GREM1 expression, such as fibrosis or cancer. In certain embodiments, invention provides a method for treating a patient suffering from cancer, or for treating at least one symptom or complication associated with cancer, or halting the progression of cancer, the method comprising administering to the patient an effective amount of an antibody or an antigen-binding fragment thereof that binds to human GREM1; or a pharmaceutical composition comprising an effective amount of an antibody or an antigen-binding fragment thereof that binds to GREM1, such that the cancer-associated condition or disease is either prevented, or lessened in severity and/or duration, or at least one symptom or complication associated with the condition or disease is prevented, or ameliorated, or that the frequency and/or duration of, or the severity of cancer is reduced.

In certain embodiments, invention provides a method for treating a patient suffering from fibrosis, or for treating at least one symptom or complication associated with fibrosis, or halting the progression of fibrosis, or for treating a patient at risk for developing fibrosis, the method comprising administering to the patient an effective amount of an antibody or an antigen-binding fragment thereof that binds to GREM1; or a pharmaceutical composition comprising an effective amount of an antibody or an antigen-binding fragment thereof that binds to GREM1, such that the fibrosis-associated condition or disease is either prevented, or lessened in severity and/or duration, or at least one symptom or complication associated with the condition or disease is prevented, or ameliorated, or that the frequency and/or duration of, or the severity of fibrosis is reduced. In one embodiment, the antibody is administered therapeutically (administered after fibrosis has been established and given throughout the course of the condition) to a patient suffering from fibrosis-associated condition or disease, or suffering from at least one symptom or complication associated with the condition or disease. In one embodiment, the antibody is administered prophylactically (administered prior to development of the condition) to a patient at risk for developing fibrosis-associated condition or disease, or at risk for developing at least one symptom or complication associated with fibrosis. For example, such "patients at risk for developing fibrosis" include the elderly, or patients with a family history, or smokers, or patients who have some underlying medical condition that may pre-dispose them to acquiring fibrosis such as diabetes, or patients exposed to asbestos, wood, metal dust or chemicals, viral infections, certain medications, or cigarette smoke or patients with chronic liver injuries like viral hepatitis, parasitic infection, metabolic or autoimmune diseases, congenital abnormalities and drug and alcohol abuse. Other patients at risk for developing fibrosis include patients with chronic kidney disease, acute kidney injury, chronic hypertension, heart failure, kidney transplant, scleroderma, exposure to radiocontrast agent, chronic allergy, chronic asthma or lung transplant.

In another embodiment, the at least one symptom or complication associated with the fibrosis-associated condition or disease is selected from the group consisting of shortness of breath, persistent dry hacking cough, pain, weight loss, nausea, loss of appetite, fluid accumulation in abdomen, swelling in legs, fatigue, pulmonary hypertension, hyperglycemia, renal injury, urinary tract infection, liver damage, loss of liver function, loss of renal function, hypertension, decrease in quality of life, reduced life expectancy and relapse of a condition or disease associated with fibrosis. In some embodiments, the disease or condition associated with fibrosis may be present in liver, kidney, lungs, skin, gut or muscle. In another embodiment, the fibrosis-associated condition or disease is selected from the group comprising pulmonary fibrosis, pulmonary hypertension, idiopathic pulmonary fibrosis, renal fibrosis, liver fibrosis, ischemic renal injury, tubulointerstitial fibrosis, diabetic nephropathy, nephrosclerosis, and nephrotoxicity.

Embodiments of the invention relate to methods of protecting against progressive tissue damage, or inhibiting or reducing tissue degeneration in a patient suffering from fibrosis, the methods comprising administering to the patient an effective amount of an antibody or an antigen-binding fragment thereof that binds to GREM1; or a pharmaceutical composition comprising an effective amount of an antibody or an antigen-binding fragment thereof that binds to GREM1, such that the tissue in the patient is protected from progressive damage or tissue degeneration is inhibited or reduced in a patient suffering from fibrosis. In some embodiments of the invention, the tissue affected by fibrotic damage is lungs, wherein the fibrotic disease may be one of pulmonary fibrosis, pulmonary hypertension or idiopathic pulmonary fibrosis. In one embodiment, the tissue affected by fibrotic damage may be liver. In some embodiments, the tissue affected by fibrotic damage may be kidney, wherein the fibrotic disease may comprise one of renal fibrosis, ischemic renal injury, tubulointerstitial fibrosis, diabetic nephropathy, nephrosclerosis, or nephrotoxicity.

In some embodiments, the invention includes methods of treating cancer or inhibiting tumor growth, tumor cell proliferation or tumor metastasis, the methods comprising administering an isolated antibody or antigen-binding fragment thereof of the present invention that binds to GREM1. In certain embodiments, the invention includes methods for inhibiting angiogenesis, the methods comprising administering an isolated antibody or antigen-binding fragment thereof of the present invention that binds to GREM1.

In one embodiment, the pharmaceutical composition comprising the antibodies of the invention is administered to the patient in combination with a second therapeutic agent.

In another embodiment, the second therapeutic agent is selected from the group consisting of an anti-fibrotic agent such as pirfenidone, an anti-inflammatory drug, a NSAID, a corticosteroid such as prednisone, a nutritional supplement, a vascular endothelial growth factor (VEGF) antagonist [e.g., a "VEGF-Trap" such as aflibercept or other VEGF-inhibiting fusion protein as set forth in U.S. Pat. No. 7,087,411, or an anti-VEGF antibody or antigen binding fragment thereof (e.g., bevacizumab, or ranibizumab)], an antibody to a cytokine such as IL-1, IL-6, IL-13, IL-4, IL-17, IL-25, IL-33 or TGF-β, and any other palliative therapy useful for ameliorating at least one symptom associated with a fibrosis-associated condition or cancer. In some embodiments, the second therapeutic agent may be administered to manage or treat at least one complication associated with fibrosis or cancer.

In embodiments of the invention, the antibody or antigen-binding fragment thereof or the pharmaceutical composition comprising the antibody is administered subcutaneously, intravenously, intradermally, orally or intramuscularly.

In some embodiments, the antibody or antigen-binding fragment thereof is administered at doses of about 0.1 mg/kg of body weight to about 100 mg/kg of body weight, more specifically about 20 mg/kg of body weight to about 50 mg/kg of body weight.

In related embodiments, the invention includes the use of an isolated anti-GREM1 antibody or antigen binding portion of an antibody of the invention in the manufacture of a medicament for the treatment of a disease or disorder related to or caused by GREM1 activity. In one embodiment, the invention includes an isolated anti-GREM1 antibody or antigen-binding fragment thereof for use in promoting BMP signaling or cell differentiation. In one embodiment, the invention includes an isolated anti-GREM1 antibody or antigen-binding fragment thereof for use in inhibiting heparin-mediated angiogenesis. In one embodiment, the invention includes the use of an anti-GREM1 antibody of the invention in the manufacture of a medicament for treating a patient suffering from or at risk of developing fibrosis. In one embodiment, the invention includes the use of an anti-GREM1 antibody of the invention in the manufacture of a medicament for treating a patient suffering from cancer.

A sixth aspect of the invention provides for methods of predicting prognosis of fibrosis in a patient suffering from a condition or disease selected from the group comprising of pulmonary fibrosis, idiopathic pulmonary fibrosis, pulmonary hypertension, renal fibrosis, hepatic fibrosis and diabetic nephropathy, the method comprising reacting a GREM1 protein from the patient with an antibody or antigen-binding fragment of the invention, wherein binding with human GREM1 indicates poor prognosis.

In one embodiment, the invention features a method of predicting poor survival in a patient suffering from fibrosis, the method comprising reacting a GREM1 protein from the patient with an isolated antibody of the invention as described herein, wherein binding with GREM1 indicates poor survival.

In one embodiment, the tissue or cell sample containing a GREM1 protein from a patient is obtained from the patient's blood, serum, plasma, or biopsy of a tissue, such as liver, lung or kidney.

In a related embodiment, the invention features a method of diagnosing fibrosis in a tissue or monitoring fibrotic activity in a subject suspected of suffering from fibrosis, the method comprising administering an antibody or antigen-binding fragment of the invention linked to a detectable label such as a radionuclide or a MRI-detectable label and imaging the subject upon such administration, wherein GREM1 binding and detection in the image indicates fibrosis.

In one embodiment, the fibrosis is idiopathic pulmonary fibrosis. In some embodiments, the fibrosis is selected from the group comprising pulmonary hypertension, diabetic nephropathy, renal fibrosis, liver fibrosis, and tubulointerstitial fibrosis. In some embodiments, the fibrotic activity is detected in lungs or kidney or liver.

Other embodiments will become apparent from a review of the ensuing detailed description.

BRIEF DESCRIPTION OF THE DRAWINGS

FIG. 1 describes the structural features of GREM1 protein (From Wordinger, R. J., et al 2008, Exp. Eye Res. 87: 78-79). The predicted positions of structural features are shown. Signal Seq., signal sequence (positions 1-24); DAN, cysteine-rich motif (positions 69-184); , glycosylation site (position 42); *, phosphorylation sites (positions 6, 29, 44, 47, 55, 66, 76, 77, 88, 102 and 151); , PKC specific eukaryotic protein phosphorylation site (position 165); NLS, nuclear localization signal sequences (positions 145, 166, 163, 164).

DETAILED DESCRIPTION

Before the present methods are described, it is to be understood that this invention is not limited to particular methods, and experimental conditions described, as such methods and conditions may vary. It is also to be understood that the terminology used herein is for the purpose of describing particular embodiments only, and is not intended to be limiting, since the scope of the present invention will be limited only by the appended claims.

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, preferred methods and materials are now described. All publications mentioned herein are incorporated herein by reference in their entirety.

Definitions

The term "bone morphogenetic protein" or "BMP" refers to the group of growth factors which function as pivotal morphogenetic signals, orchestrating tissue architecture throughout the body. They were originally discovered by their ability to induce the formation of bone and cartilage. However, BMPs have a variety of different functions during embryonic development. They are also involved in body patterning and morphogenesis cascades. BMPS have been found to be essential in organ homeostasis. Further, BMPs play important roles in the pathophysiology of several diseases including osteoporosis, arthritis, pulmonary hypertension and kidney diseases. BMPs and their involvement in disease processes have been reviewed by Weiskirchen, R., et al in Front. Biosci. 2009, 14: 4992-5012. Twenty BMPs have been discovered so far, of which BMP2 to BMP7 belong to the transforming growth factor beta superfamily.

The term "GREM1" refers to human gremlin-1, a member of the cysteine knot superfamily. The amino acid sequence of human GREM1 is provided in GenBank as accession number NP_037504 and is also referred to herein as SEQ ID NO: 594. GREM1 is encoded by the nucleic acid provided herein as SEQ ID NO: 593, and is also found in GenBank as accession number NM_013372. GREM1 is a highly conserved 184 aa protein which has been mapped to chromosome 15q13-q15. The protein contains a signal peptide (aa 1-24) and a predicted glycosylation site (at aa 42). In addition, the protein contains a cysteine-rich region and a cysteine knot motif (aa 94-184) whose structure is shared by members of the transforming growth factor-beta (TGF-β) superfamily. GREM1 exists in both secreted and cell-associated (e.g. membrane associated) forms. GREM1 is also known as gremlin1, cysteine knot superfamily 1—BMP antagonist 1 (CKTSF1B1), DAN domain family member 2 (DAND2), Down-regulated in Mos-transformed cells protein (DRM), gremlin, GREMLIN, Gremlin-1 precursor, Increased in high glucose protein 2 (IHG-2), MGC126660, Proliferation-inducing gene 2 protein (PIG2), or Gremlin 1-like protein. GREM1 is an antagonist of bone morphogenetic proteins (BMPs). It binds to BMPs and inhibits their binding to their receptors. The interplay between GREM1 and BMPs fine-tunes the level of available BMPs and affects developmental and disease processes. GREM1 can bind to and inhibit BMP-2, BMP-4 and BMP-7. GREM1 has been found to be up regulated in fibrotic diseases, especially of the kidney, lung and liver.

The term "fibrosis", as used herein refers to the formation of excess fibrous connective tissue in an organ or tissue in a reparative or reactive process. This is as opposed to formation of fibrous tissue as a normal constituent of an organ or tissue. Scarring is confluent fibrosis that obliterates the architecture of the underlying organ or tissue. Fibrosis can affect many organs in the body. The following table shows some examples of fibrosis along with the affected organ:

| Type of fibrosis | Organ affected |
| --- | --- |
| Pulmonary fibrosis | Lungs |
| Cystic fibrosis | Lungs |
| Idiopathic pulmonary fibrosis | Lungs |
| Cirrhosis (associated with viral infection or other cause) | Liver |
| Non-alcoholic steatohepatitis | Liver |
| Endomyocardial fibrosis | Heart |
| Mediastinal fibrosis | Soft tissue of the mediastinum |
| Myelofibrosis | Bone marrow |
| Retroperitoneal fibrosis | Soft tissue of the retroperitoneum |
| Progressive massive fibrosis (a complication of coal workers' pneumoconiosis) | Lungs |
| Bronchiolitis obliterans | Lungs |
| Airway Remodeling associated with chronic asthma | Lungs |
| Kidney or Lung transplant fibrosis | Kidney, Lungs |
| Focal & Segmental Glomerulosclerosis | Kidney |
| Nephrogenic systemic fibrosis | Skin |
| Crohn's disease | Intestine |
| Keloid | Skin |
| Old myocardial infarction | Heart |
| Muscular dystrophy | Muscle |
| Scleroderma, systemic sclerosis | Skin, lungs |
| Arthrofibrosis | Knee, shoulder, other joints |
| Corneal fibrosis | Eyes |
| Retinal fibrosis associated with macular degeneration | Eyes |

The term "fibrosis" also comprises complex disorders such as pulmonary fibrosis, for example, idiopathic pulmonary fibrosis, pulmonary hypertension, diabetic nephropathy, ischemic renal injury, renal fibrosis, hepatic fibrosis, tubulointerstitial fibrosis, nephrosclerosis and nephrotoxicity.

The term "antibody", as used herein, is intended to refer to immunoglobulin molecules comprised of four polypeptide chains, two heavy (H) chains and two light (L) chains inter-connected by disulfide bonds (i.e., "full antibody molecules"), as well as multimers thereof (e.g. IgM) or antigen-binding fragments thereof. Each heavy chain is comprised of a heavy chain variable region ("HCVR" or "$V_H$") and a heavy chain constant region (comprised of domains $C_H1$, $C_H2$ and $C_H3$). Each light chain is comprised of a light chain variable region ("LCVR or "$V_L$") and a light chain constant region ($C_L$). The $V_H$ and $V_L$ regions can be further subdivided into regions of hypervariability, termed complementarity determining regions (CDR), interspersed with regions that are more conserved, termed framework regions (FR). Each $V_H$ and $V_L$ is composed of three CDRs and four FRs, arranged from amino-terminus to carboxy-terminus in the following order: FR1, CDR1, FR2, CDR2, FR3, CDR3, FR4. In certain embodiments of the invention, the FRs of the antibody (or antigen binding fragment thereof) may be identical to the human germline sequences, or may be naturally or artificially modified. An amino acid consensus sequence may be defined based on a side-by-side analysis of two or more CDRs.

Substitution of one or more CDR residues or omission of one or more CDRs is also possible. Antibodies have been described in the scientific literature in which one or two CDRs can be dispensed with for binding. Padlan et al. (FASEB J. 1995, 9:133-139) analyzed the contact regions between antibodies and their antigens, based on published crystal structures, and concluded that only about one fifth to one third of CDR residues actually contact the antigen. Padlan also found many antibodies in which one or two CDRs had no amino acids in contact with an antigen (see also, Vajdos et al. 2002 J Mol Biol 320:415-428).

CDR residues not contacting antigen can be identified based on previous studies (for example residues H60-H65 in CDRH2 are often not required), from regions of Kabat CDRs lying outside Chothia CDRs, by molecular modeling and/or empirically. If a CDR or residue(s) thereof is omitted, it is usually substituted with an amino acid occupying the corresponding position in another human antibody sequence or a consensus of such sequences. Positions for substitution within CDRs and amino acids to substitute can also be selected empirically. Empirical substitutions can be conservative or non-conservative substitutions.

The fully human anti-GREM1 monoclonal antibodies disclosed herein may comprise one or more amino acid substitutions, insertions and/or deletions in the framework and/or CDR regions of the heavy and light chain variable domains as compared to the corresponding germline sequences. Such mutations can be readily ascertained by comparing the amino acid sequences disclosed herein to germline sequences available from, for example, public antibody sequence databases. The present invention includes antibodies, and antigen-binding fragments thereof, which are derived from any of the amino acid sequences disclosed herein, wherein one or more amino acids within one or more framework and/or CDR regions are mutated to the corresponding residue(s) of the germline sequence from which the antibody was derived, or to the corresponding residue(s) of another human germline sequence, or to a conservative amino acid substitution of the corresponding germline residue(s) (such sequence changes are referred to herein collectively as "germline mutations"). A person of ordinary skill in the art, starting with the heavy and light chain variable region sequences disclosed herein, can easily produce numerous antibodies and antigen-binding fragments which comprise one or more individual germline mutations or combinations thereof. In certain embodiments, all of the framework and/or CDR residues within the $V_H$ and/or $V_L$ domains are mutated back to the residues found in the original germline sequence from which the antibody was derived. In other embodiments, only certain residues are mutated back to the original germline sequence, e.g., only the mutated residues found within the first 8 amino acids of FR1 or within the last 8 amino acids of FR4, or only the mutated residues found within CDR1, CDR2 or CDR3. In other embodiments, one or more of the framework and/or CDR residue(s) are mutated to the corresponding residue(s) of a different germline sequence (i.e., a germline sequence that is different from the germline sequence from which the antibody was originally derived). Furthermore, the antibodies of the present invention may contain any combination of two or more germline mutations within the framework and/or CDR regions, e.g., wherein certain individual residues are mutated to the corresponding residue of a particular germline sequence while certain other residues that differ from the original germline sequence are maintained or are mutated to the corresponding residue of a different germline sequence. Once obtained, antibodies and antigen-binding fragments that contain one or more germline mutations can be easily tested for one or more desired property such as, improved binding specificity, increased binding affinity, improved or enhanced antagonistic or agonistic biological properties (as the case may be), reduced immunogenicity, etc. Antibodies and antigen-binding fragments obtained in this general manner are encompassed within the present invention.

The present invention also includes fully human anti-GREM1 monoclonal antibodies comprising variants of any of the HCVR, LCVR, and/or CDR amino acid sequences disclosed herein having one or more conservative substitutions. For example, the present invention includes anti-GREM1 antibodies having HCVR, LCVR, and/or CDR amino acid sequences with, e.g., 10 or fewer, 8 or fewer, 6 or fewer, 4 or fewer, etc. conservative amino acid substitutions relative to any of the HCVR, LCVR, and/or CDR amino acid sequences disclosed herein.

The term "human antibody", as used herein, is intended to include antibodies having variable and constant regions derived from human germline immunoglobulin sequences. The human mAbs of the invention may include amino acid residues not encoded by human germline immunoglobulin sequences (e.g., mutations introduced by random or site-specific mutagenesis in vitro or by somatic mutation in vivo), for example in the CDRs and in particular CDR3. However, the term "human antibody", as used herein, is not intended to include mAbs in which CDR sequences derived from the germline of another mammalian species (e.g., mouse), have been grafted onto human FR sequences.

The term "specifically binds," or "binds specifically to", or the like, means that an antibody or antigen-binding fragment thereof forms a complex with an antigen that is relatively stable under physiologic conditions. Specific binding can be characterized by an equilibrium dissociation constant of at least about $1\times10^{-6}$ M or less (e.g., a smaller $K_D$ denotes a tighter binding). Methods for determining whether two molecules specifically bind are well known in the art and include, for example, equilibrium dialysis, surface plasmon resonance, and the like. As described herein, antibodies which bind specifically to human GREM1 have been identified by surface plasmon resonance, e.g., BIA-CORE™. Moreover, multi-specific antibodies that bind to one domain in GREM1 and one or more additional antigens or a bi-specific that binds to two different regions of GREM1 are nonetheless considered antibodies that "specifically bind", as used herein.

The term "high affinity" antibody refers to those mAbs having a binding affinity to GREM1, expressed as $K_D$, of at least $10^{-7}$ M; preferably $10^{-8}$ M; more preferably $10^{-9}$M, even more preferably $10^{-10}$ M, even more preferably $10^{-11}$ M, as measured by surface plasmon resonance, e.g., BIA-CORE™ or solution-affinity ELISA.

By the term "slow off rate", "Koff" or "kd" is meant an antibody that dissociates from GREM1, with a rate constant of $1\times10^{-3}$ $s^{-1}$ or less, preferably $1\times10^{-4}$ $s^{-1}$ or less, as determined by surface plasmon resonance, e.g., BIA-CORE™.

The terms "antigen-binding portion" of an antibody, "antigen-binding fragment" of an antibody, and the like, as used herein, include any naturally occurring, enzymatically obtainable, synthetic, or genetically engineered polypeptide or glycoprotein that specifically binds an antigen to form a complex. The terms "antigen-binding fragment" of an antibody, or "antibody fragment", as used herein, refers to one or more fragments of an antibody that retain the ability to bind to GREM1.

In specific embodiments, antibody or antibody fragments of the invention may be conjugated to a therapeutic moiety ("immunoconjugate"), such as an antibiotic, a second anti-GREM1 antibody, or an antibody to a cytokine such as IL-1, IL-6, or TGF-β, or any other therapeutic moiety useful for treating a disease or condition including pulmonary fibrosis, renal fibrosis, liver fibrosis, ischemic renal injury, tubulointerstitial fibrosis, diabetic nephropathy, nephrosclerosis, or nephrotoxicity.

An "isolated antibody", as used herein, is intended to refer to an antibody that is substantially free of other antibodies (Abs) having different antigenic specificities (e.g., an isolated antibody that specifically binds human GREM1, or a fragment thereof, is substantially free of Abs that specifically bind antigens other than GREM1.

A "blocking antibody" or a "neutralizing antibody", as used herein (or an "antibody that neutralizes GREM1 activity"), is intended to refer to an antibody whose binding to GREM1 results in inhibition of at least one biological activity of GREM1. For example, an antibody of the invention may aid in inhibiting or preventing the spread of fibrosis. Alternatively, an antibody of the invention may demonstrate the ability to treat fibrosis or at least one symptom caused by fibrosis, including dry cough or breathlessness. This inhibition of the biological activity of GREM1 can be assessed by measuring one or more indicators of GREM1 biological activity by one or more of several standard in vitro assays (such as a neutralization assay, as described herein) or in vivo assays known in the art (for example, animal models to look at protection from GREM1 activity following administration of one or more of the antibodies described herein).

The term "surface plasmon resonance", as used herein, refers to an optical phenomenon that allows for the analysis of real-time biomolecular interactions by detection of alterations in protein concentrations within a biosensor matrix, for example using the BIACORE™ system (Pharmacia Biosensor AB, Uppsala, Sweden and Piscataway, N.J.).

The term "$K_D$", as used herein, is intended to refer to the equilibrium dissociation constant of a particular antibody-antigen interaction.

The term "epitope" refers to an antigenic determinant that interacts with a specific antigen binding site in the variable region of an antibody molecule known as a paratope. A single antigen may have more than one epitope. Thus, different antibodies may bind to different areas on an antigen and may have different biological effects. The term "epitope" also refers to a site on an antigen to which B and/or T cells respond. It also refers to a region of an antigen that is bound by an antibody. Epitopes may be defined as structural or functional. Functional epitopes are generally a subset of the structural epitopes and have those residues that directly contribute to the affinity of the interaction. Epitopes may also be conformational, that is, composed of non-linear amino acids. In certain embodiments, epitopes may include determinants that are chemically active surface groupings of molecules such as amino acids, sugar side chains, phosphoryl groups, or sulfonyl groups, and, in certain embodiments, may have specific three-dimensional structural characteristics, and/or specific charge characteristics.

The term "substantial identity" or "substantially identical," when referring to a nucleic acid or fragment thereof, indicates that, when optimally aligned with appropriate nucleotide insertions or deletions with another nucleic acid (or its complementary strand), there is nucleotide sequence identity in at least about 90%, and more preferably at least about 95%, 96%, 97%, 98% or 99% of the nucleotide bases, as measured by any well-known algorithm of sequence identity, such as FASTA, BLAST or GAP, as discussed below. A nucleic acid molecule having substantial identity to a reference nucleic acid molecule may, in certain instances, encode a polypeptide having the same or substantially similar amino acid sequence as the polypeptide encoded by the reference nucleic acid molecule.

As applied to polypeptides, the term "substantial similarity" or "substantially similar" means that two peptide sequences, when optimally aligned, such as by the programs GAP or BESTFIT using default gap weights, share at least 90% sequence identity, even more preferably at least 95%, 98% or 99% sequence identity. Preferably, residue positions, which are not identical, differ by conservative amino acid substitutions. A "conservative amino acid substitution" is one in which an amino acid residue is substituted by another amino acid residue having a side chain (R group) with similar chemical properties (e.g., charge or hydrophobicity). In general, a conservative amino acid substitution will not substantially change the functional properties of a protein. In cases where two or more amino acid sequences differ from each other by conservative substitutions, the percent or degree of similarity may be adjusted upwards to correct for the conservative nature of the substitution. Means for making this adjustment are well known to those of skill in the art. See, e.g., Pearson (1994) Methods Mol. Biol. 24: 307-331, which is herein incorporated by reference. Examples of groups of amino acids that have side chains with similar chemical properties include 1) aliphatic side chains: glycine, alanine, valine, leucine and isoleucine; 2) aliphatic-hydroxyl side chains: serine and threonine; 3) amide-containing side chains: asparagine and glutamine; 4) aromatic side chains: phenylalanine, tyrosine, and tryptophan; 5) basic side chains: lysine, arginine, and histidine; 6) acidic side chains: aspartate and glutamate, and 7) sulfur-containing side chains: cysteine and methionine. Preferred conservative amino acids substitution groups are: valine-leucine-isoleucine, phenylalanine-tyrosine, lysine-arginine, alanine-valine, glutamate-aspartate, and asparagine-glutamine. Alternatively, a conservative replacement is any change having a positive value in the PAM250 log-likelihood matrix disclosed in Gonnet et al. (1992) Science 256: 1443 45, herein incorporated by reference. A "moderately conservative"

replacement is any change having a nonnegative value in the PAM250 log-likelihood matrix.

Sequence similarity for polypeptides is typically measured using sequence analysis software. Protein analysis software matches similar sequences using measures of similarity assigned to various substitutions, deletions and other modifications, including conservative amino acid substitutions. For instance, GCG software contains programs such as GAP and BESTFIT which can be used with default parameters to determine sequence homology or sequence identity between closely related polypeptides, such as homologous polypeptides from different species of organisms or between a wild type protein and a mutein thereof. See, e.g., GCG Version 6.1. Polypeptide sequences also can be compared using FASTA with default or recommended parameters; a program in GCG Version 6.1. FASTA (e.g., FASTA2 and FASTA3) provides alignments and percent sequence identity of the regions of the best overlap between the query and search sequences (Pearson (2000) supra). Another preferred algorithm when comparing a sequence of the invention to a database containing a large number of sequences from different organisms is the computer program BLAST, especially BLASTP or TBLASTN, using default parameters. See, e.g., Altschul et al. (1990) J. Mol. Biol. 215: 403-410 and (1997) Nucleic Acids Res. 25: 3389-3402, each of which is herein incorporated by reference.

In specific embodiments, the antibody or antibody fragment for use in the method of the invention may be monospecific, bi-specific, or multi-specific. Multi-specific antibodies may be specific for different epitopes of one target polypeptide or may contain antigen-binding domains specific for epitopes of more than one target polypeptide. An exemplary bi-specific antibody format that can be used in the context of the present invention involves the use of a first immunoglobulin (Ig) $C_H3$ domain and a second Ig $C_H3$ domain, wherein the first and second Ig $C_H3$ domains differ from one another by at least one amino acid, and wherein at least one amino acid difference reduces binding of the bi-specific antibody to Protein A as compared to a bi-specific antibody lacking the amino acid difference. In one embodiment, the first Ig $C_H3$ domain binds Protein A and the second Ig $C_H3$ domain contains a mutation that reduces or abolishes Protein A binding such as an H95R modification (by IMGT exon numbering; H435R by EU numbering). The second $C_H3$ may further comprise an Y96F modification (by IMGT; Y436F by EU). Further modifications that may be found within the second $C_H3$ include: D16E, L18M, N44S, K52N, V57M, and V82I (by IMGT; D356E, L358M, N384S, K392N, V397M, and V422I by EU) in the case of IgG1 mAbs; N44S, K52N, and V82I (IMGT; N384S, K392N, and V422I by EU) in the case of IgG2 mAbs; and Q15R, N44S, K52N, V57M, R69K, E79Q, and V82I (by IMGT; Q355R, N384S, K392N, V397M, R409K, E419Q, and V422I by EU) in the case of IgG4 mAbs. Variations on the bi-specific antibody format described above are contemplated within the scope of the present invention.

By the phrase "therapeutically effective amount" is meant an amount that produces the desired effect for which it is administered. The exact amount will depend on the purpose of the treatment, and will be ascertainable by one skilled in the art using known techniques (see, for example, Lloyd (1999) The Art, Science and Technology of Pharmaceutical Compounding).

General Description

As an antagonist of bone morphogenetic proteins (BMPs), GREM1 gene plays a role in regulating organogenesis, body patterning, and tissue differentiation. GREM1 has been found to play an important role in lung development. However, expression of GREM1 in a healthy adult lung is low. Upregulated levels of GREM1 have been correlated with pulmonary hypertension and pulmonary fibrosis (Costello, et al., 2010, Am. J. Respir. Cell. Mol. Biol. 42: 517-523). Pulmonary fibrosis, especially of the idiopathic type is a progressive, scar-forming and disabling disease of the lung parenchyma with a poor prognosis and no efficacious therapy. Elevated GREM1 expression correlates negatively with lung function tests in idiopathic pulmonary fibrosis, suggesting that GREM1 may be an important marker of advanced stage fibrosis (Costello, et al., 2010, Am. J. Respir. Cell. Mol. Biol. 42: 517-523).

GREM1 expression is also essential in kidney organogenesis. However, GREM1 expression in a healthy adult kidney is almost undetectable. Elevated GREM1 levels are found in patients with hyperglycemia and diabetic nephropathy (Lappin, et al., 2002, Nephrol. Dial. Transplant. 17: 65-67). GREM1 is found to be upregulated in areas of tubulointerstitial fibrosis in patients with diabetic nephropathy. Diabetic nephropathy is a complex disorder characterized by sclerosis and development of tubulointerstitial fibrosis. It is the leading cause of end-stage renal diseases and 20-40% of patients with diabetes ultimately develop diabetic nephropathy. Specific therapies to reverse or inhibit the progression of diabetic nephropathy to advanced stages are not available and current treatment strategies are limited to management of blood glucose levels and control of hypertension (Zhang et al., 2009, BBRC 383: 1-3).

GREM1 has also been found to be upregulated in liver fibrosis (Boers et al., 2006, J. Biol. Chem. 281: 16289-16295). Hepatic fibrosis is a common response to most chronic liver injuries like viral hepatitis, parasitic infection, metabolic or autoimmune diseases, congenital abnormalities and drug and alcohol abuse. Fibrosis may also contribute to progressive cirrhosis of liver. Detection of liver disease is often delayed and effective medical treatment is not readily available.

The antibodies described herein demonstrate specific binding to human GREM1 and in some embodiments, may be useful for treating patients suffering from fibrosis. The use of such antibodies may be an effective means of treating patients suffering from fibrosis, or may be used to lessen the severity of the dry cough or difficulty in breathing associated with fibrosis. They may be used alone or as adjunct therapy with other therapeutic moieties or modalities known in the art for treating fibrosis, such as, but not limited to, a non-steroidal anti-inflammatory drug (NSIAD), a corticosteroid such as prednisone, or any other palliative therapy. They may be used in conjunction with a second or third different antibody specific for GREM1, or against a cytokine such as IL-1, IL-6 or TGF-β.

In some embodiments, the antibodies described herein may be useful in treating or managing a disease or condition of fibrosis including (idiopathic) pulmonary fibrosis, renal fibrosis, liver fibrosis, ischemic renal injury, tubulointerstitial fibrosis, diabetic nephropathy, nephrosclerosis, or nephrotoxicity.

In certain embodiments, the antibodies described herein may be useful for treating or managing cancer such as sarcoma, and carcinomas of the lung, uterine cervix, colon, breast, and pancreas.

In certain embodiments, the antibodies of the invention are obtained from mice immunized with a primary immunogen, such as a native, full length human GREM1 (See GenBank accession number NP_037504 (SEQ ID NO: 594)) or with a recombinant form of GREM1 (SEQ ID NO: 595)

or GREM1 fragments, followed by immunization with a secondary immunogen, or with an immunogenically active fragment of GREM1.

The immunogen may be an immunogenic fragment of human GREM1 or DNA encoding the fragment thereof. The immunogen may GREM1 coupled to a histidine tag and/or to a fragment of Fc region of an antibody.

The amino acid sequence of full length human GREM1 (also known by Gen bank accession number NP-037504) is shown as SEQ ID NO: 594. The full length amino acid sequence of recombinant GREM1 (aa 25-184 GREM1 coupled to Fc region and a histidine tag) is shown as SEQ ID NO: 595.

The full-length DNA sequence of GREM1 is shown as SEQ ID NO: 593.

In certain embodiments, antibodies that bind specifically to human GREM1 may be prepared using fragments of the above-noted regions, or peptides that extend beyond the designated regions by about 5 to about 20 amino acid residues from either, or both, the N or C terminal ends of the regions described herein. In certain embodiments, any combination of the above-noted regions or fragments thereof may be used in the preparation of human GREM1 specific antibodies. In certain embodiments, any one or more of the above-noted regions of human GREM1, or fragments thereof may be used for preparing monospecific, bispecific, or multispecific antibodies.

Antigen-Binding Fragments of Antibodies

Unless specifically indicated otherwise, the term "antibody," as used herein, shall be understood to encompass antibody molecules comprising two immunoglobulin heavy chains and two immunoglobulin light chains (i.e., "full antibody molecules") as well as antigen-binding fragments thereof. The terms "antigen-binding portion" of an antibody, "antigen-binding fragment" of an antibody, and the like, as used herein, include any naturally occurring, enzymatically obtainable, synthetic, or genetically engineered polypeptide or glycoprotein that specifically binds an antigen to form a complex. The terms "antigen-binding fragment" of an antibody, or "antibody fragment", as used herein, refers to one or more fragments of an antibody that retain the ability to specifically bind to human GREM1. An antibody fragment may include a Fab fragment, a F(ab')$_2$ fragment, a Fv fragment, a dAb fragment, a fragment containing a CDR, or an isolated CDR. Antigen-binding fragments of an antibody may be derived, e.g., from full antibody molecules using any suitable standard techniques such as proteolytic digestion or recombinant genetic engineering techniques involving the manipulation and expression of DNA encoding antibody variable and (optionally) constant domains. Such DNA is known and/or is readily available from, e.g., commercial sources, DNA libraries (including, e.g., phage-antibody libraries), or can be synthesized. The DNA may be sequenced and manipulated chemically or by using molecular biology techniques, for example, to arrange one or more variable and/or constant domains into a suitable configuration, or to introduce codons, create cysteine residues, modify, add or delete amino acids, etc.

Non-limiting examples of antigen-binding fragments include: (i) Fab fragments; (ii) F(ab')2 fragments; (iii) Fd fragments; (iv) Fv fragments; (v) single-chain Fv (scFv) molecules; (vi) dAb fragments; and (vii) minimal recognition units consisting of the amino acid residues that mimic the hypervariable region of an antibody (e.g., an isolated complementarity determining region (CDR) such as a CDR3 peptide), or a constrained FR3-CDR3-FR4 peptide. Other engineered molecules, such as domain-specific antibodies, single domain antibodies, domain-deleted antibodies, chimeric antibodies, CDR-grafted antibodies, diabodies, triabodies, tetrabodies, minibodies, nanobodies (e.g. monovalent nanobodies, bivalent nanobodies, etc.), small modular immunopharmaceuticals (SMIPs), and shark variable IgNAR domains, are also encompassed within the expression "antigen-binding fragment," as used herein.

An antigen-binding fragment of an antibody will typically comprise at least one variable domain. The variable domain may be of any size or amino acid composition and will generally comprise at least one CDR, which is adjacent to or in frame with one or more framework sequences. In antigen-binding fragments having a $V_H$ domain associated with a $V_L$ domain, the $V_H$ and $V_L$ domains may be situated relative to one another in any suitable arrangement. For example, the variable region may be dimeric and contain $V_H$-$V_H$, $V_H$-$V_L$ or $V_L$-$V_L$ dimers. Alternatively, the antigen-binding fragment of an antibody may contain a monomeric $V_H$ or $V_L$ domain.

In certain embodiments, an antigen-binding fragment of an antibody may contain at least one variable domain covalently linked to at least one constant domain. Non-limiting, exemplary configurations of variable and constant domains that may be found within an antigen-binding fragment of an antibody of the present invention include: (i) $V_H$-$C_H$1; (ii) $V_H$-$C_H$2; (iii) $V_H$-$C_H$3; (iv) $V_H$-$C_H$1-$C_H$2; (V) $V_H$-$C_H$1-$C_H$2-$C_H$3; (vi) $V_H$-$C_H$2-$C_H$3; (vii) $V_H$-$C_L$; (viii) $V_L$-$C_H$1; (ix) $V_L$-$C_H$2; (x) $V_L$-$C_H$3; (xi) $V_L$-$C_H$1-$C_H$2; (xii) $V_L$-$C_H$1-$C_H$2-$C_H$3; (xiii) $V_L$-$C_H$2-$C_H$3; and (xiv) $V_L$-$C_L$. In any configuration of variable and constant domains, including any of the exemplary configurations listed above, the variable and constant domains may be either directly linked to one another or may be linked by a full or partial hinge or linker region. A hinge region may consist of at least 2 (e.g., 5, 10, 15, 20, 40, 60 or more) amino acids, which result in a flexible or semi-flexible linkage between adjacent variable and/or constant domains in a single polypeptide molecule. Moreover, an antigen-binding fragment of an antibody of the present invention may comprise a homo-dimer or hetero-dimer (or other multimer) of any of the variable and constant domain configurations listed above in non-covalent association with one another and/or with one or more monomeric $V_H$ or $V_L$ domain (e.g., by disulfide bond(s)).

As with full antibody molecules, antigen-binding fragments may be mono-specific or multi-specific (e.g., bi-specific). A multi-specific antigen-binding fragment of an antibody will typically comprise at least two different variable domains, wherein each variable domain is capable of specifically binding to a separate antigen or to a different epitope on the same antigen. Any multi-specific antibody format, including the exemplary bi-specific antibody formats disclosed herein, may be adapted for use in the context of an antigen-binding fragment of an antibody of the present invention using routine techniques available in the art.

Preparation of Human Antibodies

Methods for generating human antibodies in transgenic mice are known in the art. Any such known methods can be used in the context of the present invention to make human antibodies that specifically bind to human GREM1.

Using VELOCIMMUNE™ technology (see, for example, U.S. Pat. No. 6,596,541, Regeneron Pharmaceuticals, VELOCIMMUNE®) or any other known method for generating monoclonal antibodies, high affinity chimeric antibodies to human GREM1 are initially isolated having a human variable region and a mouse constant region. The VELOCIMMUNE® technology involves generation of a transgenic mouse having a genome comprising human heavy and light chain variable regions operably linked to endogenous mouse constant region loci such that the mouse produces an antibody comprising a human variable region and a mouse constant region in response to antigenic stimulation. The DNA encoding the variable regions of the heavy and light chains of the antibody are isolated and operably linked to DNA encoding the human heavy and light chain constant regions. The DNA is then expressed in a cell capable of expressing the fully human antibody.

Generally, a VELOCIMMUNE® mouse is challenged with the antigen of interest, and lymphatic cells (such as B-cells) are recovered from the mice that express antibodies. The lymphatic cells may be fused with a myeloma cell line to prepare immortal hybridoma cell lines, and such hybridoma cell lines are screened and selected to identify hybridoma cell lines that produce antibodies specific to the antigen of interest. DNA encoding the variable regions of the heavy chain and light chain may be isolated and linked to desirable isotypic constant regions of the heavy chain and light chain. Such an antibody protein may be produced in a cell, such as a CHO cell. Alternatively, DNA encoding the antigen-specific chimeric antibodies or the variable domains of the light and heavy chains may be isolated directly from antigen-specific lymphocytes.

Initially, high affinity chimeric antibodies are isolated having a human variable region and a mouse constant region. As in the experimental section below, the antibodies are characterized and selected for desirable characteristics, including affinity, selectivity, epitope, etc. The mouse constant regions are replaced with a desired human constant region to generate the fully human antibody of the invention, for example wild-type or modified IgG1 or IgG4. While the constant region selected may vary according to specific use, high affinity antigen-binding and target specificity characteristics reside in the variable region.

In general, the antibodies of the instant invention possess very high affinities, typically possessing $K_D$ of from about $10^{-12}$ through about $10^{-7}$ M, when measured by binding to antigen either immobilized on solid phase or in solution phase. The mouse constant regions are replaced with desired human constant regions to generate the fully human antibodies of the invention. While the constant region selected may vary according to specific use, high affinity antigen-binding and target specificity characteristics reside in the variable region.

Bioequivalents

The anti-human GREM1 antibodies and antibody fragments of the present invention encompass proteins having amino acid sequences that vary from those of the described antibodies, but that retain the ability to bind human GREM1. Such variant antibodies and antibody fragments comprise one or more additions, deletions, or substitutions of amino acids when compared to parent sequence, but exhibit biological activity that is essentially equivalent to that of the described antibodies. Likewise, the antibody-encoding DNA sequences of the present invention encompass sequences that comprise one or more additions, deletions, or substitutions of nucleotides when compared to the disclosed sequence, but that encode an antibody or antibody fragment that is essentially bioequivalent to an antibody or antibody fragment of the invention.

Two antigen-binding proteins, or antibodies, are considered bioequivalent if, for example, they are pharmaceutical equivalents or pharmaceutical alternatives whose rate and extent of absorption do not show a significant difference when administered at the same molar dose under similar experimental conditions, either single dose or multiple doses. Some antibodies will be considered equivalents or pharmaceutical alternatives if they are equivalent in the extent of their absorption but not in their rate of absorption and yet may be considered bioequivalent because such differences in the rate of absorption are intentional and are reflected in the labeling, are not essential to the attainment of effective body drug concentrations on, e.g., chronic use, and are considered medically insignificant for the particular drug product studied.

In one embodiment, two antigen-binding proteins are bioequivalent if there are no clinically meaningful differences in their safety, purity, and potency.

In one embodiment, two antigen-binding proteins are bioequivalent if a patient can be switched one or more times between the reference product and the biological product without an expected increase in the risk of adverse effects, including a clinically significant change in immunogenicity, or diminished effectiveness, as compared to continued therapy without such switching.

In one embodiment, two antigen-binding proteins are bioequivalent if they both act by a common mechanism or mechanisms of action for the condition or conditions of use, to the extent that such mechanisms are known.

Bioequivalence may be demonstrated by in vivo and/or in vitro methods. Bioequivalence measures include, e.g., (a) an in vivo test in humans or other mammals, in which the concentration of the antibody or its metabolites is measured in blood, plasma, serum, or other biological fluid as a function of time; (b) an in vitro test that has been correlated with and is reasonably predictive of human in vivo bioavailability data; (c) an in vivo test in humans or other mammals in which the appropriate acute pharmacological effect of the antibody (or its target) is measured as a function of time; and (d) in a well-controlled clinical trial that establishes safety, efficacy, or bioavailability or bioequivalence of an antibody.

Bioequivalent variants of the antibodies of the invention may be constructed by, for example, making various substitutions of residues or sequences or deleting terminal or internal residues or sequences not needed for biological activity. For example, cysteine residues not essential for biological activity can be deleted or replaced with other amino acids to prevent formation of unnecessary or incorrect intramolecular disulfide bridges upon renaturation. In other contexts, bioequivalent antibodies may include antibody variants comprising amino acid changes, which modify the glycosylation characteristics of the antibodies, e.g., mutations that eliminate or remove glycosylation.

Anti-GREM1 Antibodies Comprising Fc Variants

According to certain embodiments of the present invention, anti-GREM1 antibodies are provided comprising an Fc domain comprising one or more mutations which enhance or diminish antibody binding to the FcRn receptor, e.g., at acidic pH as compared to neutral pH. For example, the present invention includes anti-GREM1 antibodies comprising a mutation in the $C_H2$ or a $C_H3$ region of the Fc domain, wherein the mutation(s) increases the affinity of the Fc domain to FcRn in an acidic environment (e.g., in an endosome where pH ranges from about 5.5 to about 6.0). Such mutations may result in an increase in serum half-life of the antibody when administered to an animal. Non-limiting examples of such Fc modifications include, e.g., a modification at position 250 (e.g., E or Q); 250 and 428 (e.g., L or F); 252 (e.g., L/Y/F/W or T), 254 (e.g., S or T), and 256 (e.g., S/R/Q/E/D or T); or a modification at position 428 and/or 433 (e.g., H/L/R/S/P/Q or K) and/or 434 (e.g., A, W, H, F or Y [N434A, N434W, N434H, N434F or N434Y]); or a modification at position 250 and/or 428; or a modification at position 307 or 308 (e.g., 308F, V308F), and 434. In one embodiment, the modification comprises a 428L (e.g., M428L) and 434S (e.g., N434S) modification; a 428L, 259I (e.g., V259I), and 308F (e.g., V308F) modification; a 433K (e.g., H433K) and a 434 (e.g., 434Y) modification; a 252, 254, and 256 (e.g., 252Y, 254T, and 256E) modification; a 250Q and 428L modification (e.g., T250Q and M428L); and a 307 and/or 308 modification (e.g., 308F or 308P). In yet another embodiment, the modification comprises a 265A (e.g., D265A) and/or a 297A (e.g., N297A) modification.

For example, the present invention includes anti-GREM1 antibodies comprising an Fc domain comprising one or more pairs or groups of mutations selected from the group consisting of: 250Q and 248L (e.g., T250Q and M248L); 252Y, 254T and 256E (e.g., M252Y, S254T and T256E); 428L and 434S (e.g., M428L and N434S); 257I and 311I (e.g., P257I and Q311I); 257I and 434H (e.g., P257I and N434H); 376V and 434H (e.g., D376V and N434H); 307A, 380A and 434A (e.g., T307A, E380A and N434A); and 433K and 434F (e.g., H433K and N434F). All possible combinations of the foregoing Fc domain mutations, and other mutations within the antibody variable domains disclosed herein, are contemplated within the scope of the present invention.

The present invention also includes anti-GREM1 antibodies comprising a chimeric heavy chain constant ($C_H$) region, wherein the chimeric $C_H$ region comprises segments derived from the $C_H$ regions of more than one immunoglobulin isotype. For example, the antibodies of the invention may comprise a chimeric $C_H$ region comprising part or all of a $C_H 2$ domain derived from a human IgG1, human IgG2 or human IgG4 molecule, combined with part or all of a $C_H 3$ domain derived from a human IgG1, human IgG2 or human IgG4 molecule. According to certain embodiments, the antibodies of the invention comprise a chimeric $C_H$ region having a chimeric hinge region. For example, a chimeric hinge may comprise an "upper hinge" amino acid sequence (amino acid residues from positions 216 to 227 according to EU numbering) derived from a human IgG1, a human IgG2 or a human IgG4 hinge region, combined with a "lower hinge" sequence (amino acid residues from positions 228 to 236 according to EU numbering) derived from a human IgG1, a human IgG2 or a human IgG4 hinge region. According to certain embodiments, the chimeric hinge region comprises amino acid residues derived from a human IgG1 or a human IgG4 upper hinge and amino acid residues derived from a human IgG2 lower hinge. An antibody comprising a chimeric $C_H$ region as described herein may, in certain embodiments, exhibit modified Fc effector functions without adversely affecting the therapeutic or pharmacokinetic properties of the antibody. (See, e.g., U.S. Provisional Appl. No. 61/759,578, filed Feb. 1, 2013, the disclosure of which is hereby incorporated by reference in its entirety).

Biological Characteristics of the Antibodies

In general, the antibodies of the present invention may function by binding to human GREM1. In some embodiments, the antibodies of the present invention may bind to the catalytic domain of human GREM1, or to a fragment thereof. In some embodiments, the antibodies of the invention may bind to the secreted form of human GREM1 or to the membrane-associated form of human GREM1. In some embodiments, the antibodies of the present invention may bind to more than one domain (cross-reactive antibodies).

In certain embodiments of the invention, the antibodies may bind to an epitope located in the region between amino acid residues 25-184 of SEQ ID NO: 594 or SEQ ID NO: 595.

In certain embodiments, the antibodies of the present invention may function by blocking or inhibiting BMP signaling by binding to any other region or fragment of the full length native protein, the amino acid sequence of which is shown in SEQ ID NO: 594, which is encoded by the nucleic acid sequence shown in SEQ ID NO: 593. In one embodiment, the antibodies of the present invention may function by reversing the inhibition of BMP2, BMP4 or BMP7 by binding to full-length GREM1 or a fragment thereof. In some embodiments, the antibodies of the present invention may function by promoting BMP signaling or may block the binding between GREM1 and BMPs including BMP2, BMP4 or BMP7.

In certain embodiments, the antibodies of the present invention may function by blocking GREM1 binding to heparin and/or by inhibiting heparin-mediated VEGFR-2 activation.

In certain embodiments, the antibodies of the present invention may be bi-specific antibodies. The bi-specific antibodies of the invention may bind one epitope in one domain and may also bind one epitope in a second domain of human GREM1. In certain embodiments, the bi-specific antibodies of the invention may bind two different epitopes in the same domain.

In one embodiment, the invention provides a fully human monoclonal antibody or antigen-binding fragment thereof that binds to human GREM1, wherein the antibody or fragment thereof exhibits one or more of the following characteristics: (i) comprises a HCVR having an amino acid sequence selected from the group consisting of SEQ ID NO: 2, 18, 34, 50, 66, 82, 98, 114, 130, 146, 162, 178, 194, 210, 226, 242, 258, 274, 290, 306, 322, 338, 354, 370, 386, 402, 418, 434, 450, 466, 482, 498, 514, 530, 546, 562, and 578, or a substantially similar sequence thereof having at least 90%, at least 95%, at least 98% or at least 99% sequence identity; (ii) comprises a LCVR having an amino acid sequence selected from the group consisting of SEQ ID NO: 10, 26, 42, 58, 74, 90, 106, 122, 138, 154, 170, 186, 202, 218, 234, 250, 266, 282, 298, 314, 330, 346, 362, 378, 394, 410, 426, 442, 458, 474, 490, 506, 522, 538, 554, 570, and 586, or a substantially similar sequence thereof having at least 90%, at least 95%, at least 98% or at least 99% sequence identity; (iii) comprises a HCDR3 domain having an amino acid sequence selected from the group consisting of SEQ ID NO: 8, 24, 40, 56, 72, 88, 104, 120, 136, 152, 168, 184, 200, 216, 232, 248, 264, 280, 296, 312, 328, 344, 360, 376, 392, 408, 424, 440, 456, 472, 488, 504, 520, 536, 552, 568, and 584, or a substantially similar sequence thereof having at least 90%, at least 95%, at least 98% or at least 99% sequence identity; and a LCDR3 domain having an amino acid sequence selected from the group consisting of SEQ ID NO: 16, 32, 48, 64, 80, 96, 112, 128, 144, 160, 176, 192, 208, 224, 240, 256, 272, 288, 304, 320, 336, 352, 368, 384, 400, 416, 432, 448, 464, 480, 496, 512, 528, 544, 560, 576, and 592, or a substantially similar sequence thereof having at least 90%, at least 95%, at least 98% or at least 99% sequence identity; (iv) comprises a HCDR1 domain having an amino acid sequence selected from the group consisting of SEQ ID NO: 4, 20, 36, 52, 68, 84, 100, 116, 132, 148, 164, 180, 196, 212, 228, 244, 260, 276, 292, 308, 324, 340, 356, 372, 388, 404, 420, 436, 452, 468, 484, 500, 516, 532, 548, 564, and 580, or a substantially similar sequence thereof having at least 90%, at least 95%, at least 98% or at least 99% sequence identity; a HCDR2 domain having an amino acid sequence selected from the group consisting of SEQ ID NO: 6, 22, 38, 54, 70, 86, 102, 118, 134, 150, 166, 182, 198, 214, 230, 246, 262, 278, 294, 310, 326, 342, 358, 374, 390, 406, 422, 438, 454, 470, 486, 502, 518, 534, 550, 566, and 582, or a substantially similar sequence thereof having at least 90%, at least 95%, at least 98% or at least 99% sequence identity; a LCDR1 domain having an amino acid sequence selected from the group consisting of SEQ ID NO: 12, 28, 44, 60, 76, 92, 108, 124, 140, 156, 172, 188, 204, 220, 236, 252, 268, 284, 300, 316, 332, 348, 364, 380, 396, 412, 428, 444, 460, 476, 492, 508, 524, 540, 556, 572, and 588, or a substantially similar sequence thereof having at least 90%, at least 95%, at least 98% or at least 99% sequence identity; and a LCDR2 domain having an amino acid sequence selected from the group consisting of SEQ ID NO: 14, 30, 46, 62, 78, 94, 110, 126, 142, 158, 174, 190, 206, 222, 238, 254, 270, 286, 302, 318, 334, 350, 366, 382, 398, 414, 430, 446, 462, 478, 494, 510, 526, 542, 558, 574, and 590, or a substantially similar sequence thereof having at least 90%, at least 95%, at least 98% or at least 99% sequence identity; (v) binds to GREM1 with a $K_D$ equal to or less than $10^{-7}$; (vi) blocks GREM1 binding to one of BMP2, BMP4 or BMP7; (vii) blocks GREM1 inhibition of BMP signaling and promotes cell differentiation; and (viii) blocks GREM1 binding to heparin.

Certain anti-GREM1 antibodies of the present invention are able to bind to and neutralize the activity of GREM1, as determined by in vitro or in vivo assays. The ability of the antibodies of the invention to bind to and neutralize the activity of GREM1 may be measured using any standard method known to those skilled in the art, including binding assays, or activity assays, as described herein.

Non-limiting, exemplary in vitro assays for measuring binding activity are illustrated in Example 4, herein. In Example 4, the binding affinities and kinetic constants of human anti-GREM1 antibodies were determined by surface plasmon resonance and the measurements were conducted on a T200 Biacore instrument. In Example 5, blocking assays were used to determine the ability of the anti-GREM1 antibodies to block the BMP4 binding ability of GREM1 in vitro. Examples 6 and 7 describe the activity of the anti-GREM1 antibodies in promoting BMP4 signaling and cell differentiation. In Example 6, the anti-GREM1 antibodies blocked the GREM1 inhibition of BMP4 signaling. In Example 7, the anti-GREM1 antibodies promoted BMP4 signaling and cell differentiation of osteoblast progenitor cells. Example 9 describes inhibition of the GREM1-heparin binding interaction using GREM1-specific antibodies.

The present invention also includes anti-GREM1 antibodies and antigen binding fragments thereof which bind to at least one biologically active fragment of any of the following proteins, or peptides: SEQ ID NO: 594 (full length native human GREM1), or SEQ ID NO: 595 (recombinant form of human GREM1). Any of the GREM1 peptides described herein, or fragments thereof, may be used to generate anti-GREM1 antibodies.

The peptides may be modified to include addition or substitution of certain residues for tagging or for purposes of conjugation to carrier molecules, such as, KLH. For example, a cysteine may be added at either the N terminal or C terminal end of a peptide, or a linker sequence may be added to prepare the peptide for conjugation to, for example, KLH for immunization.

The antibodies specific for GREM1 may contain no additional labels or moieties, or they may contain an N-terminal or C-terminal label or moiety. In one embodiment, the label or moiety is biotin. In a binding assay, the location of a label (if any) may determine the orientation of the peptide relative to the surface upon which the peptide is bound. For example, if a surface is coated with avidin, a peptide containing an N-terminal biotin will be oriented such that the C-terminal portion of the peptide will be distal to the surface. In one embodiment, the label may be a radionuclide, a fluorescent dye or a MRI-detectable label. In certain embodiments, such labeled antibodies may be used in diagnostic assays including imaging assays.

Epitope Mapping and Related Technologies

The present invention includes anti-GREM1 antibodies which interact with one or more amino acids found within one or more regions of GREM1. The epitope to which the antibodies bind may consist of a single contiguous sequence of 3 or more (e.g., 3, 4, 5, 6, 7, 8, 9, 10, 11, 12, 13, 14, 15, 16, 17, 18, 19, 20 or more) amino acids located within any of the aforementioned regions of the GREM1 molecule (e.g. a linear epitope in a domain). Alternatively, the epitope may consist of a plurality of non-contiguous amino acids (or amino acid sequences) located within either or both of the aforementioned regions of the GREM1 molecule (e.g. a conformational epitope).

Various techniques known to persons of ordinary skill in the art can be used to determine whether an antibody "interacts with one or more amino acids" within a polypeptide or protein. Exemplary techniques include, for example, routine cross-blocking assays, such as that described in Antibodies, Harlow and Lane (Cold Spring Harbor Press, Cold Spring Harbor, N.Y.). Other methods include alanine scanning mutational analysis, peptide blot analysis (Reineke (2004) Methods Mol Biol 248:443-63), peptide cleavage analysis crystallographic studies and NMR analysis. In addition, methods such as epitope excision, epitope extraction and chemical modification of antigens can be employed (Tomer (2000) Protein Science 9: 487-496). Another method that can be used to identify the amino acids within a polypeptide with which an antibody interacts is hydrogen/deuterium exchange detected by mass spectrometry. In general terms, the hydrogen/deuterium exchange method involves deuterium-labeling the protein of interest, followed by binding the antibody to the deuterium-labeled protein. Next, the protein/antibody complex is transferred to water and exchangeable protons within amino acids that are protected by the antibody complex undergo deuterium-to-hydrogen back-exchange at a slower rate than exchangeable protons within amino acids that are not part of the interface. As a result, amino acids that form part of the protein/antibody interface may retain deuterium and therefore exhibit relatively higher mass compared to amino acids not included in the interface. After dissociation of the antibody, the target protein is subjected to protease cleavage and mass spectrometry analysis, thereby revealing the deuterium-labeled residues which correspond to the specific amino acids with which the antibody interacts. See, e.g., Ehring (1999) *Analytical Biochemistry* 267(2):252-259; Engen and Smith (2001) *Anal. Chem.* 73: 256A-265A.

The term "epitope" refers to a site on an antigen to which B and/or T cells respond. B-cell epitopes can be formed both from contiguous amino acids or noncontiguous amino acids juxtaposed by tertiary folding of a protein. Epitopes formed from contiguous amino acids are typically retained on exposure to denaturing solvents, whereas epitopes formed by tertiary folding are typically lost on treatment with denaturing solvents. An epitope typically includes at least 3, and more usually, at least 5 or 8-10 amino acids in a unique spatial conformation.

Modification-Assisted Profiling (MAP), also known as Antigen Structure-based Antibody Profiling (ASAP) is a method that categorizes large numbers of monoclonal antibodies (mAbs) directed against the same antigen according to the similarities of the binding profile of each antibody to chemically or enzymatically modified antigen surfaces (see US 2004/0101920, herein specifically incorporated by reference in its entirety). Each category may reflect a unique epitope either distinctly different from or partially overlapping with epitope represented by another category. This technology allows rapid filtering of genetically identical antibodies, such that characterization can be focused on genetically distinct antibodies. When applied to hybridoma screening, MAP may facilitate identification of rare hybridoma clones that produce mAbs having the desired characteristics. MAP may be used to sort the antibodies of the invention into groups of antibodies binding different epitopes.

In certain embodiments, the anti-GREM1 antibodies or antigen-binding fragments thereof bind an epitope within any one or more of the regions exemplified in GREM1, either in natural form, as exemplified in SEQ ID NO: 594, or recombinantly produced, as exemplified in SEQ ID NO: 595, or to a fragment thereof. In certain embodiments, the antibodies of the invention, as shown in Table 1, interact with at least one amino acid sequence selected from the group consisting of amino acid residues ranging from about position 1 to about position 24 of SEQ ID NO: 594; or amino acid residues ranging from about position 25 to about position 184 of SEQ ID NO: 594. These regions are further exemplified in SEQ ID NO: 595.

The present invention includes anti-human GREM1 antibodies that bind to the same epitope, or a portion of the epitope, as any of the specific exemplary antibodies described herein in Table 1, or an antibody having the CDR sequences of any of the exemplary antibodies described in Table 1. Likewise, the present invention also includes anti-human GREM1 antibodies that compete for binding to GREM1 or a GREM1 fragment with any of the specific exemplary antibodies described herein in Table 1, or an antibody having the CDR sequences of any of the exemplary antibodies described in Table 1.

One can easily determine whether an antibody binds to the same epitope as, or competes for binding with, a reference anti-GREM1 antibody by using routine methods known in the art. For example, to determine if a test antibody binds to the same epitope as a reference anti-GREM1 antibody of the invention, the reference antibody is allowed to bind to a GREM1 protein or peptide under saturating conditions. Next, the ability of a test antibody to bind to the GREM1 molecule is assessed. If the test antibody is able to bind to GREM1 following saturation binding with the reference anti-GREM1 antibody, it can be concluded that the test antibody binds to a different epitope than the reference anti-GREM1 antibody. On the other hand, if the test antibody is not able to bind to the GREM1 protein following saturation binding with the reference anti-GREM1 antibody, then the test antibody may bind to the same epitope as the epitope bound by the reference anti-GREM1 antibody of the invention.

To determine if an antibody competes for binding with a reference anti-GREM1 antibody, the above-described binding methodology is performed in two orientations: In a first orientation, the reference antibody is allowed to bind to a GREM1 protein under saturating conditions followed by assessment of binding of the test antibody to the GREM1 molecule. In a second orientation, the test antibody is allowed to bind to a GREM1 molecule under saturating conditions followed by assessment of binding of the reference antibody to the GREM1 molecule. If, in both orientations, only the first (saturating) antibody is capable of binding to the GREM1 molecule, then it is concluded that the test antibody and the reference antibody compete for binding to GREM1. As will be appreciated by a person of ordinary skill in the art, an antibody that competes for binding with a reference antibody may not necessarily bind to the identical epitope as the reference antibody, but may sterically block binding of the reference antibody by binding an overlapping or adjacent epitope.

Two antibodies bind to the same or overlapping epitope if each competitively inhibits (blocks) binding of the other to the antigen. That is, a 1-, 5-, 10-, 20- or 100-fold excess of one antibody inhibits binding of the other by at least 50% but preferably 75%, 90% or even 99% as measured in a competitive binding assay (see, e.g., Junghans et al., Cancer Res. 1990 50:1495-1502). Alternatively, two antibodies have the same epitope if essentially all amino acid mutations in the antigen that reduce or eliminate binding of one antibody reduce or eliminate binding of the other. Two antibodies have overlapping epitopes if some amino acid mutations that reduce or eliminate binding of one antibody reduce or eliminate binding of the other.

Additional routine experimentation (e.g., peptide mutation and binding analyses) can then be carried out to confirm whether the observed lack of binding of the test antibody is in fact due to binding to the same epitope as the reference antibody or if steric blocking (or another phenomenon) is responsible for the lack of observed binding. Experiments of this sort can be performed using ELISA, RIA, surface plasmon resonance, flow cytometry or any other quantitative or qualitative antibody-binding assay available in the art.

Immunoconjugates

The invention encompasses a human anti-GREM1 monoclonal antibody conjugated to a therapeutic moiety ("immunoconjugate"), such as an agent that is capable of reducing the severity of fibrosis, or to ameliorate at least one symptom associated with fibrosis, including dry persistent cough and/or difficulty in breathing, or the severity thereof. As used herein, the term "immunoconjugate" refers to an antibody which is chemically or biologically linked to a radioactive agent, a cytokine, an interferon, a target or reporter moiety, an enzyme, a toxin, or a therapeutic agent. The antibody may be linked to the radioactive agent, cytokine, interferon, target or reporter moiety, enzyme, toxin, or therapeutic agent at any location along the molecule so long as it is able to bind its target. An example of immunoconjugate is antibody drug conjugate. In some embodiments, the agent may be a second different antibody to human GREM1, or to a cytokine such as IL-1, IL-6, or a chemokine such as TGF-β. The type of therapeutic moiety that may be conjugated to the anti-GREM1 antibody and will take into account the condition to be treated and the desired therapeutic effect to be achieved. For example, if the desired therapeutic effect is to treat the sequelae or symptoms associated with fibrosis, or any other condition resulting from fibrosis, such as, but not limited to, inflammation or weight loss, it may be advantageous to conjugate an agent appropriate to treat the sequelae or symptoms of the condition, or to alleviate any side effects of the antibodies of the invention. Examples of suitable agents for forming immunoconjugates are known in the art; see for example, WO 05/103081. The preparation of immunoconjugates and immunotoxins is generally well known in the art (see, e.g., U.S. Pat. No. 4,340,535). Immunoconjugates are described in detail, for example, in U.S. Pat. Nos. 7,250,492, 7,420,040 and 7,411,046, each of which is incorporated herein in their entirety.

Multi-Specific Antibodies

The antibodies of the present invention may be mono-specific, bi-specific, or multi-specific. Multi-specific antibodies may be specific for different epitopes of one target polypeptide or may contain antigen-binding domains specific for more than one target polypeptide. See, e.g., Tutt et al., 1991, J. Immunol. 147:60-69; Kufer et al., 2004, Trends Biotechnol. 22:238-244. The antibodies of the present invention can be linked to or co-expressed with another functional molecule, e.g., another peptide or protein. For example, an antibody or fragment thereof can be functionally linked (e.g., by chemical coupling, genetic fusion, noncovalent association or otherwise) to one or more other molecular entities, such as another antibody or antibody fragment to produce a bi-specific or a multi-specific antibody with a second binding specificity. For example, the present invention includes bi-specific antibodies wherein one arm of an immunoglobulin is specific for the N-terminal region of GREM1, or a fragment thereof, and the other arm of the immunoglobulin is specific for the C-terminal region of GREM1, or a second therapeutic target, or is conjugated to a therapeutic moiety. An exemplary bi-specific antibody format that can be used in the context of the present invention involves the use of a first immunoglobulin (Ig) $C_{H3}$ domain and a second Ig $C_{H3}$ domain, wherein the first and second Ig $C_{H3}$ domains differ from one another by at least one amino acid, and wherein at least one amino acid difference reduces binding of the bi-specific antibody to Protein A as compared to a bi-specific antibody lacking the amino acid difference. In one embodiment, the first Ig $C_{H3}$ domain binds Protein A and the second Ig $C_{H3}$ domain contains a mutation that reduces or abolishes Protein A binding such as an H95R modification (by IMGT exon numbering; H435R by EU numbering). The second $C_{H3}$ may further comprise a Y96F modification (by IMGT; Y436F by EU). Further modifications that may be found within the second $C_{H3}$ include: D16E, L18M, N44S, K52N, V57M, and V82I (by IMGT; D356E, L358M, N384S, K392N, V397M, and V422I by EU) in the case of IgG1 antibodies; N44S, K52N, and V82I (IMGT; N384S, K392N, and V422I by EU) in the case of IgG2 antibodies; and Q15R, N44S, K52N, V57M, R69K, E79Q, and V82I (by IMGT; Q355R, N384S, K392N, V397M, R409K, E419Q, and V422I by EU) in the case of IgG4 antibodies. Variations on the bi-specific antibody format described above are contemplated within the scope of the present invention.

Other exemplary bispecific formats that can be used in the context of the present invention include, without limitation, e.g., scFv-based or diabody bispecific formats, IgG-scFv fusions, dual variable domain (DVD)-Ig, Quadroma, knobs-into-holes, common light chain (e.g., common light chain with knobs-into-holes, etc.), CrossMab, CrossFab, (SEED) body, leucine zipper, Duobody, IgG1/IgG2, dual acting Fab (DAF)-IgG, and Mab$^2$ bispecific formats (see, e.g., Klein et al. 2012, mAbs 4:6, 1-11, and references cited therein, for a review of the foregoing formats). Bispecific antibodies can also be constructed using peptide/nucleic acid conjugation, e.g., wherein unnatural amino acids with orthogonal chemical reactivity are used to generate site-specific antibody-oligonucleotide conjugates which then self-assemble into multimeric complexes with defined composition, valency and geometry. (See, e.g., Kazane et al., *J. Am. Chem. Soc.* [Epub: Dec. 4, 2012]).

Therapeutic Administration and Formulations

The invention provides therapeutic compositions comprising the anti-GREM1 antibodies or antigen-binding fragments thereof of the present invention. The administration of therapeutic compositions in accordance with the invention will be administered with suitable carriers, excipients, and other agents that are incorporated into formulations to provide improved transfer, delivery, tolerance, and the like. A multitude of appropriate formulations can be found in the formulary known to all pharmaceutical chemists: Remington's Pharmaceutical Sciences, Mack Publishing Company, Easton, Pa. These formulations include, for example, powders, pastes, ointments, jellies, waxes, oils, lipids, lipid (cationic or anionic) containing vesicles (such as LIPOFECTIN™), DNA conjugates, anhydrous absorption pastes, oil-in-water and water-in-oil emulsions, emulsions carbowax (polyethylene glycols of various molecular weights), semi-solid gels, and semi-solid mixtures containing carbowax. See also Powell et al. "Compendium of excipients for parenteral formulations" PDA (1998) J Pharm Sci Technol 52:238-311.

The dose of antibody may vary depending upon the age and the size of a subject to be administered, target disease, conditions, route of administration, and the like. When the antibody of the present invention is used for treating fibrosis in an adult patient, or for treating pulmonary hypertension, or for lessening the severity of the disease, it is advantageous to intravenously administer the antibody of the present invention normally at a single dose of about 0.1 to about 100 mg/kg body weight, more preferably about 5 to about 100, about 10 to about 90, or about 20 to about 70 mg/kg body weight. Depending on the severity of the condition, the frequency and the duration of the treatment can be adjusted. In certain embodiments, the antibody or antigen-binding fragment thereof of the invention can be administered as an initial dose of at least about 0.1 mg to about 800 mg, about 1 to about 500 mg, about 5 to about 300 mg, or about 10 to about 200 mg, to about 100 mg, or to about 50 mg. In certain embodiments, the initial dose may be followed by administration of a second or a plurality of subsequent doses of the antibody or antigen-binding fragment thereof in an amount that can be approximately the same or less than that of the initial dose, wherein the subsequent doses are separated by at least 1 day to 3 days; at least one week, at least 2 weeks; at least 3 weeks; at least 4 weeks; at least 5 weeks; at least 6 weeks; at least 7 weeks; at least 8 weeks; at least 9 weeks; at least 10 weeks; at least 12 weeks; or at least 14 weeks.

Various delivery systems are known and can be used to administer the pharmaceutical composition of the invention, e.g., encapsulation in liposomes, microparticles, microcapsules, recombinant cells capable of expressing the mutant viruses, receptor mediated endocytosis (see, e.g., Wu et al. (1987) J. Biol. Chem. 262:4429-4432). Methods of introduction include, but are not limited to, intradermal, transdermal, intramuscular, intraperitoneal, intravenous, subcutaneous, intranasal, epidural and oral routes. The composition may be administered by any convenient route, for example by infusion or bolus injection, by absorption through epithelial or mucocutaneous linings (e.g., oral mucosa, rectal and intestinal mucosa, etc.) and may be administered together with other biologically active agents. Administration can be systemic or local. The pharmaceutical composition can be also delivered in a vesicle, in particular a liposome (see, for example, Langer (1990) Science 249: 1527-1533).

The use of nanoparticles to deliver the antibodies of the present invention is also contemplated herein. Antibody-conjugated nanoparticles may be used both for therapeutic and diagnostic applications. Antibody-conjugated nanoparticles and methods of preparation and use are described in detail by Arruebo, M., et al. 2009 ("Antibody-conjugated nanoparticles for biomedical applications" in J. Nanomat. Volume 2009, Article ID 439389, 24 pages, doi: 10.1155/2009/439389), incorporated herein by reference. Nanoparticles for drug delivery have also been described in, for example, U.S. Pat. Nos. 8,277,812, 8,258,256, 8,257,740, 8,246,995, 8,236,330, each incorporated herein in its entirety.

In certain situations, the pharmaceutical composition can be delivered in a controlled release system. In one embodiment, a pump may be used. In another embodiment, polymeric materials can be used. In yet another embodiment, a controlled release system can be placed in proximity of the composition's target, thus requiring only a fraction of the systemic dose.

The injectable preparations may include dosage forms for intravenous, subcutaneous, intracutaneous and intramuscular injections, drip infusions, etc. These injectable preparations may be prepared by methods publicly known. For example, the injectable preparations may be prepared, e.g., by dissolving, suspending or emulsifying the antibody or its salt described above in a sterile aqueous medium or an oily medium conventionally used for injections. As the aqueous medium for injections, there are, for example, physiological saline, an isotonic solution containing glucose and other auxiliary agents, etc., which may be used in combination with an appropriate solubilizing agent such as an alcohol (e.g., ethanol), a polyalcohol (e.g., propylene glycol, polyethylene glycol), a nonionic surfactant [e.g., polysorbate 80, HCO-50 (polyoxyethylene (50 mol) adduct of hydrogenated castor oil)], etc. As the oily medium, there are employed, e.g., sesame oil, soybean oil, etc., which may be used in combination with a solubilizing agent such as benzyl benzoate, benzyl alcohol, etc. The injection thus prepared is preferably filled in an appropriate ampoule.

A pharmaceutical composition of the present invention can be delivered subcutaneously or intravenously with a standard needle and syringe. In addition, with respect to subcutaneous delivery, a pen delivery device readily has applications in delivering a pharmaceutical composition of the present invention. Such a pen delivery device can be reusable or disposable. A reusable pen delivery device generally utilizes a replaceable cartridge that contains a pharmaceutical composition. Once all of the pharmaceutical composition within the cartridge has been administered and the cartridge is empty, the empty cartridge can readily be discarded and replaced with a new cartridge that contains the pharmaceutical composition. The pen delivery device can then be reused. In a disposable pen delivery device, there is no replaceable cartridge. Rather, the disposable pen delivery device comes prefilled with the pharmaceutical composition held in a reservoir within the device. Once the reservoir is emptied of the pharmaceutical composition, the entire device is discarded.

Numerous reusable pen and autoinjector delivery devices have applications in the subcutaneous delivery of a pharmaceutical composition of the present invention. Examples include, but certainly are not limited to AUTOPEN™ (Owen Mumford, Inc., Woodstock, UK), DISETRONIC™ pen (Disetronic Medical Systems, Burghdorf, Switzerland), HUMALOG MIX 75/25™ pen, HUMALOG™ pen, HUMALIN 70/30™ pen (Eli Lilly and Co., Indianapolis, Ind.), NOVOPEN™ I, II and III (Novo Nordisk, Copenhagen, Denmark), NOVOPEN JUNIOR™ (Novo Nordisk, Copenhagen, Denmark), BD™ pen (Becton Dickinson, Franklin Lakes, N.J.), OPTIPEN™, OPTIPEN PRO™, OPTIPEN STARLET™, and OPTICLIK™ (Sanofi-aventis, Frankfurt, Germany), to name only a few. Examples of disposable pen delivery devices having applications in subcutaneous delivery of a pharmaceutical composition of the present invention include, but certainly are not limited to the SOLOSTAR™ pen (Sanofi-aventis), the FLEXPEN™ (Novo Nordisk), and the KWIKPEN™ (Eli Lilly), the SURECLICK™ Autoinjector (Amgen, Thousand Oaks, Calif.), the PENLET™ (Haselmeier, Stuttgart, Germany), the EPIPEN (Dey, L. P.) and the HUMIRA™ Pen (Abbott Labs, Abbott Park, Ill.), to name only a few.

Advantageously, the pharmaceutical compositions for oral or parenteral use described above are prepared into dosage forms in a unit dose suited to fit a dose of the active ingredients. Such dosage forms in a unit dose include, for example, tablets, pills, capsules, injections (ampoules), suppositories, etc. The amount of the aforesaid antibody contained is generally about 5 to about 500 mg per dosage form in a unit dose; especially in the form of injection, it is preferred that the aforesaid antibody is contained in about 5 to about 100 mg and in about 10 to about 250 mg for the other dosage forms.

Therapeutic Uses of the Antibodies

In certain embodiments of the invention, the present antibodies are useful for treating a disease or condition associated with fibrosis, or at least one symptom associated with the disease or condition, such as persistent cough, breathlessness, weight loss or loss of appetite, or for lessening the severity of the disease. In some embodiments, the antibodies may be useful for treating a condition or symptom of fibrosis at a later stage in the disease. The antibodies of the invention are also contemplated for prophylactic use in patients at risk for developing fibrosis. These patients include the elderly, or patients with a family history, or patients immunocompromised due to illness or treatment with immunosuppressive therapeutics, or patients who may have an underlying medical condition such as diabetes that predisposes them to fibrosis, or patients who may be predisposed to fibrosis due to lifestyle choices such as smoking or alcohol abuse. It is contemplated that the antibodies of the invention may be used alone, or in conjunction with a second agent, or third agent for treating fibrosis, or for alleviating at least one symptom or complication associated with fibrosis, such loss of kidney function or liver function associated with, or resulting from fibrosis. The second or third agents may be delivered concurrently with the antibodies of the invention, or they may be administered separately, either before or after the antibodies of the invention.

Symptoms for fibrosis disorders include, but are not limited to, dry cough, difficulty in breathing, loss of appetite, weight loss, fatigue, nausea, swelling and fluid accumulation, liver damage, liver failure, hypertension, and loss of renal function. Other signs or symptoms include, but are not limited to, malaise, poor sleep, or complications such as pneumonia or urinary tract infection, hyperglycemia, and proteinuria. The antibodies of the present invention may be used to relieve or to prevent or to decrease the severity of one or more of the symptoms or conditions listed above.

In certain embodiments, the present antibodies are useful for treating a condition or indication associated with cancer including, but not limited to sarcoma, or carcinoma of lung, ovary, kidney, breast, colon, pancreas and uterine cervix.

In certain embodiments, one or more antibodies of the present invention may be used alone or in combination to block GREM1 binding to heparin and/or heparin-mediated angiogenesis.

In a further embodiment of the invention the present antibodies are used for the preparation of a pharmaceutical composition for treating patients suffering from fibrosis or cancer, or a symptom associated with fibrosis or cancer. In yet another embodiment of the invention the present antibodies are used for the preparation of a pharmaceutical composition for reducing the tissue damage or for preventing progressive degeneration or for protecting kidney function or liver function in fibrosis. In one embodiment of the invention the present antibodies are used as adjunct therapy with any other agent useful for treating fibrosis or cancer, including an analgesic, a NSAID, an anti-tumor drug, chemotherapy, radiotherapy, a glucocorticoid, a vascular endothelial growth factor (VEGF) antagonist [e.g., a "VEGF-Trap" such as aflibercept or other VEGF-inhibiting fusion protein as set forth in U.S. Pat. No. 7,087,411, or an anti-VEGF antibody or antigen binding fragment thereof (e.g., bevacizumab, or ranibizumab)], a second antibody to GREM1, an antibody to GREM2 or to an inflammatory cytokine such as IL-1, IL-6, or TGF-β, or any other palliative therapy known to those skilled in the art.

Combination Therapies

Combination therapies may include an anti-GREM1 antibody of the invention and any additional therapeutic agent that may be advantageously combined with an antibody of the invention, or with a biologically active fragment of an antibody of the invention.

For example, a second or third therapeutic agent such as a non-steroidal anti-inflammatory agent (NSAID) or an analgesic may be employed to aid in alleviating the symptoms of fibrosis such as dry cough or difficulty in breathing. An example of a common analgesic is acetaminophen. Exemplary NSAIDs include aspirin, ibuprofen, and naproxen. The additional therapeutic agent may be an antibiotic to treat a complication such as urinary tract infection. The antibodies of the present invention may be combined with an antihypertensive agent to slow down the development of fibrosis. For example, for patients suffering from diabetic nephropathy, the antibodies may be combined with treatment such as angiotensin-converting enzyme inhibitors to reduce blood pressure and protect kidney function.

The antibodies may be used in conjunction with other therapies, such as corticosteroids, or nutritional supplements in fibrosis treatment. Anti-fibrotic drugs such as pirfenidone have been found both to produce durable symptomatic remissions and to delay or halt progression of fibrosis. This is important as such damage is usually irreversible. Anti-inflammatories and analgesics improve pain but do not prevent tissue damage or slow the disease progression. In some embodiments, second or third therapeutic agents may be used to minimize clinical symptoms such as nausea and swelling, as well as prevent fibrotic tissue damage. An additional therapeutic agent may comprise cortisone therapy, e.g., a low dosage of prednisone or prednisolone may be used in conjunction with one or more antibodies of the present invention in a long term treatment plan for fibrosis. The use of one or more antibodies directed to a cytokine such as IL-1, IL-6, or TGF-β in fibrosis treatments are also envisaged within the scope of the present invention. The antibodies of the present invention may be combined with additional therapeutic agents to minimize or prevent complications such as urinary tract infection, hyperglycemia or blood pressure.

The antibodies of the present invention may also be administered in combination with other treatment options for fibrosis including physical therapy, lifestyle changes (including exercise and weight control), pulmonary rehabilitation, oxygen therapy, and dietary changes. Transplant surgery of liver, lungs or kidney may be required in advanced forms of fibrosis.

The antibodies of the present invention may be combined synergistically with one or more anti-cancer drugs or therapy used to treat cancer. Examples of anti-cancer drugs and therapy that may be used include, but are not limited to, cytotoxins, chemotherapeutic agents, radiation and surgery. In some embodiments, one or more antibodies of the present invention may be used in combination with an anti-inflammatory drug (e.g., corticosteroids, and non-steroidal anti-inflammatory drugs), an antibody to a tumor-specific antigen (e.g., CA9, CA125, melanoma-associated antigen (MAGE), carcinoembryonic antigen (CEA), vimentin, tumor-M2-PK, prostate-specific antigen (PSA), MART-1, and CA19-9), a vascular endothelial growth factor (VEGF) antagonist [e.g., a "VEGF-Trap" such as aflibercept or other VEGF-inhibiting fusion protein as set forth in U.S. Pat. No. 7,087,411, or an anti-VEGF antibody or antigen binding fragment thereof (e.g., bevacizumab, or ranibizumab)], a dietary supplement such as anti-oxidants or any palliative care to treat cancer.

The additional therapeutically active component(s) may be administered prior to, concurrent with, or after the administration of the anti-GREM1 antibody of the present invention. For purposes of the present disclosure, such administration regimens are considered the administration of an anti-GREM1 antibody "in combination with" a second therapeutically active component.

Diagnostic Uses of the Antibodies

The anti-GREM1 antibodies of the present invention may also be used to detect and/or measure GREM1 in a sample, e.g., for diagnostic purposes. It is envisioned that any one or more of the antibodies of the invention may be used to detect severity of tissue damage in fibrosis. Exemplary diagnostic assays for GREM1 may comprise, e.g., contacting a sample, obtained from a patient, with an anti-GREM1 antibody of the invention, wherein the anti-GREM1 antibody is labeled with a detectable label or reporter molecule or used as a capture ligand to selectively isolate GREM1 from patient samples. Alternatively, an unlabeled anti-GREM1 antibody can be used in diagnostic applications in combination with a secondary antibody which is itself detectably labeled. The detectable label or reporter molecule can be a radioisotope, such as $^3H$, $^{14}C$, $^{32}P$, $^{35}S$, or $^{125}I$; a fluorescent or chemiluminescent moiety such as fluorescein isothiocyanate, or rhodamine; or an enzyme such as alkaline phosphatase, β-galactosidase, horseradish peroxidase, or luciferase. Specific exemplary assays that can be used to detect or measure GREM1 in a sample include enzyme-linked immunosorbent assay (ELISA), radioimmunoassay (RIA), and fluorescence-activated cell sorting (FACS).

Samples that can be used in GREM1 diagnostic assays according to the present invention include any tissue or fluid sample obtainable from a patient, which contains detectable quantities of either GREM1 protein, or fragments thereof, under normal or pathological conditions. Generally, levels of GREM1 in a particular sample obtained from a healthy patient (e.g., a patient not afflicted with fibrosis) will be measured to initially establish a baseline, or standard, level of GREM1. This baseline level of GREM1 can then be compared against the levels of GREM1 measured in samples obtained from individuals suspected of having fibrosis related condition, or symptoms associated with such condition.

The antibodies specific for GREM1 may contain no additional labels or moieties, or they may contain an N-terminal or C-terminal label or moiety. In one embodiment, the label or moiety is biotin. In a binding assay, the location of a label (if any) may determine the orientation of the peptide relative to the surface upon which the peptide is bound. For example, if a surface is coated with avidin, a peptide containing an N-terminal biotin will be oriented such that the C-terminal portion of the peptide will be distal to the surface. In some embodiments, the label may be detectable label such as a radionuclide, a fluorescent dye or a MRI-detectable label. Detectable labels may be linked to the antibodies wherein such antibodies may be used in imaging assays. Methods using imaging assays may be useful for fibrosis diagnosis and prognosis, or monitoring fibrotic activity.

Aspects of the invention relate to use of the disclosed antibodies as markers for predicting prognosis of fibrosis in patients. GREM1 has been found to be upregulated in fibrotic tissues in, for example, lung or liver or kidneys. Elevated levels of GREM1 have been correlated to diabetic nephropathy or pulmonary hypertension and could be used for evaluation of patient's prognosis. Antibodies of the present invention may be used in diagnostic assays to evaluate prognosis of fibrotic disease in a patient and to predict survival.

EXAMPLES

The following examples are put forth so as to provide those of ordinary skill in the art with a complete disclosure and description of how to make and use the methods and compositions of the invention, and are not intended to limit the scope of what the inventors regard as their invention. Efforts have been made to ensure accuracy with respect to numbers used (e.g., amounts, temperature, etc.) but some experimental errors and deviations should be accounted for. Unless indicated otherwise, parts are parts by weight, molecular weight is average molecular weight, temperature is in degrees Centigrade, and pressure is at or near atmospheric.

Example 1. Generation of Human Antibodies to Human GREM1

In certain embodiments, the immunogen may be a peptide from the N terminal or C terminal end of human GREM1. In certain embodiments of the invention, the immunogen is the mature protein of human GREM1 that ranges from about amino acid residues 25-184 of SEQ ID NO: 594. In one embodiment, the antibodies of the invention were obtained from mice immunized with full length recombinant human GREM1.

In certain embodiments, antibodies that bind specifically to human GREM1 may be prepared using fragments of the above-noted regions, or peptides that extend beyond the designated regions by about 5 to about 20 amino acid residues from either, or both, the N or C terminal ends of the regions described herein. In certain embodiments, any combination of the above-noted regions or fragments thereof may be used in the preparation of GREM1 specific antibodies. In certain embodiments, any one or more of the above-noted domains of hGREM1, or fragments thereof may be used for preparing monospecific, bispecific, or multispecific antibodies (see Example 8 below for details).

The full length proteins, or fragments thereof, that were used as immunogens, as noted above, were administered directly, with an adjuvant to stimulate the immune response, to a VELOCIMMUNE® mouse comprising DNA encoding human Immunoglobulin heavy and kappa light chain variable regions. The antibody immune response was monitored by a GREM1-specific immunoassay. When a desired immune response was achieved splenocytes were harvested and fused with mouse myeloma cells to preserve their viability and form hybridoma cell lines. The hybridoma cell lines were screened and selected to identify cell lines that produce GREM1-specific antibodies. Using this technique, and the various immunogens described above, several anti-GREM1, as well as cross-reactive, chimeric antibodies (i.e., antibodies possessing human variable domains and mouse constant domains) were obtained; exemplary antibodies generated in this manner were designated as H1M2907N, H2M2780N, H2M2782N, H2M2783N, H4H2783N2, H2M2784N, H2M2785N, H2M2786N, H2M2889N, H2M2890N, H2M2891N, H2M2892N, H2M2895N, H2M2897N, H2M2898N, H2M2899N, H2M2901N, H2M2906N, H2M2926N, H3M2788N, and H3M2929N.

Anti-GREM1 antibodies were also isolated directly from antigen-positive B cells without fusion to myeloma cells, as described in U.S. 2007/0280945A1, herein specifically incorporated by reference in its entirety. Using this method, several fully human anti-GREM1 antibodies (i.e., antibodies possessing human variable domains and human constant domains) were obtained; exemplary antibodies generated in this manner were designated as follows: H4H6232P, H4H6233P, H4H6236P, H4H6238P, H4H6240P, H4H6243P, H4H6245P, H4H6246P, H4H6248P, H4H6250P, H4H6251P, H4H6252S, H4H6256P, H4H6260P, H4H6269P, and H4H6270P.

The biological properties of the exemplary antibodies generated in accordance with the methods of this Example are described in detail in the Examples set forth below.

Example 2. Heavy and Light Chain Variable Region Amino Acid Sequences

Table 1 sets forth the heavy and light chain variable region amino acid sequence pairs of selected antibodies specific for human GREM1 and their corresponding antibody identifiers. Antibodies are typically referred to herein according to the following nomenclature: Fc prefix (e.g. "H4H", "H1 M, "H2M"), followed by a numerical identifier (e.g. "2907" as shown in Table 1), followed by a "P" or "N" suffix. Thus, according to this nomenclature, an antibody may be referred to as, e.g. "H1H2907". The H4H, H1M, and H2M prefixes on the antibody designations used herein indicate the particular Fc region of the antibody. For example, an "H2M" antibody has a mouse IgG2 Fc, whereas an "H4H" antibody has a human IgG4 Fc. As will be appreciated by a person of ordinary skill in the art, an H1M or H2M antibody can be converted to an H4H antibody, and vice versa, but in any event, the variable domains (including the CDRs), which are indicated by the numerical identifiers shown in Table 1, will remain the same. Antibodies having the same numerical antibody designation, but differing by a letter suffix of N, B or P refer to antibodies having heavy and light chains with identical CDR sequences but with sequence variations in regions that fall outside of the CDR sequences (i.e., in the framework regions). Thus, N, B and P variants of a particular antibody have identical CDR sequences within their heavy and light chain variable regions but differ from one another within their framework regions.

TABLE 1

| Antibody Designation | SEQ ID NOs: | | | | | | | |
|---|---|---|---|---|---|---|---|---|
| | HCVR | HCDR1 | HCDR2 | HCDR3 | LCVR | LCDR1 | LCDR2 | LCDR3 |
| 2907N | 2 | 4 | 6 | 8 | 10 | 12 | 14 | 16 |
| 2780N | 18 | 20 | 22 | 24 | 26 | 28 | 30 | 32 |
| 2782N | 34 | 36 | 38 | 40 | 42 | 44 | 46 | 48 |
| 2783N | 50 | 52 | 54 | 56 | 58 | 60 | 62 | 64 |
| 2783N2 | 66 | 68 | 70 | 72 | 74 | 76 | 78 | 80 |
| 2784N | 82 | 84 | 86 | 88 | 90 | 92 | 94 | 96 |
| 2785N | 98 | 100 | 102 | 104 | 106 | 108 | 110 | 112 |
| 2786N | 114 | 116 | 118 | 120 | 122 | 124 | 126 | 128 |
| 2889N | 130 | 132 | 134 | 136 | 138 | 140 | 142 | 144 |
| 2890N | 146 | 148 | 150 | 152 | 154 | 156 | 158 | 160 |
| 2891N | 162 | 164 | 166 | 168 | 170 | 172 | 174 | 176 |
| 2892N | 178 | 180 | 182 | 184 | 186 | 188 | 190 | 192 |
| 2895N | 194 | 196 | 198 | 200 | 202 | 204 | 206 | 208 |
| 2897N | 210 | 212 | 214 | 216 | 218 | 220 | 222 | 224 |
| 2898N | 226 | 228 | 230 | 232 | 234 | 236 | 238 | 240 |
| 2899N | 242 | 244 | 246 | 248 | 250 | 252 | 254 | 256 |
| 2901N | 258 | 260 | 262 | 264 | 266 | 268 | 270 | 272 |
| 2906N | 274 | 276 | 278 | 280 | 282 | 284 | 286 | 288 |
| 2926N | 290 | 292 | 294 | 296 | 298 | 300 | 302 | 304 |
| 2788N | 306 | 308 | 310 | 312 | 314 | 316 | 318 | 320 |
| 2929N | 322 | 324 | 326 | 328 | 330 | 332 | 334 | 336 |
| 6232P | 338 | 340 | 342 | 344 | 346 | 348 | 350 | 352 |
| 6233P | 354 | 356 | 358 | 360 | 362 | 364 | 366 | 368 |
| 6236P | 370 | 372 | 374 | 376 | 378 | 380 | 382 | 384 |
| 6238P | 386 | 388 | 390 | 392 | 394 | 396 | 398 | 400 |
| 6240P | 402 | 404 | 406 | 408 | 410 | 412 | 414 | 416 |
| 6243P | 418 | 420 | 422 | 424 | 426 | 428 | 430 | 432 |
| 6245P | 434 | 436 | 438 | 440 | 442 | 444 | 446 | 448 |
| 6246P | 450 | 452 | 454 | 456 | 458 | 460 | 462 | 464 |
| 6248P | 466 | 468 | 470 | 472 | 474 | 476 | 478 | 480 |
| 6250P | 482 | 484 | 486 | 488 | 490 | 492 | 494 | 496 |
| 6251P | 498 | 500 | 502 | 504 | 506 | 508 | 510 | 512 |
| 6252P | 514 | 516 | 518 | 520 | 522 | 524 | 526 | 528 |
| 6256P | 530 | 532 | 534 | 536 | 538 | 540 | 542 | 544 |
| 6260P | 546 | 548 | 550 | 552 | 554 | 556 | 558 | 560 |
| 6269P | 562 | 564 | 566 | 568 | 570 | 572 | 574 | 576 |
| 6270P | 578 | 580 | 582 | 584 | 586 | 588 | 590 | 592 |

Example 3. Variable Gene Utilization Analysis

To analyze the structure of antibodies produced, the nucleic acids encoding antibody variable regions were cloned and sequenced. From the nucleic acid sequence and predicted amino acid sequence of the antibodies, gene usage was identified for each Heavy Chain Variable Region (HCVR) and Light Chain Variable Region (LCVR). Table 2 sets forth the gene usage for selected antibodies in accordance with the invention.

TABLE 2

| Antibody | HCVR | | | LCVR | |
|---|---|---|---|---|---|
| | $V_H$ | $D_H$ | $J_H$ | $V_K$ | $J_K$ |
| H4H2780N | 3-21 | 1-26 | 6 | 1-27 | 3 |
| H2bM2782N | 3-21 | 1-7 | 4 | 1-27 | 3 |
| H4H2784N | 3-33 | 3-10 | 4 | 3-15 | 2 |
| H2bM2785N | 3-23 | 6-13 | 3 | 1-33 | 2 |
| H2bM2786N | 3-23 | 2-8 | 3 | 1-33 | 2 |
| H2M2783N | 3-23 | 6-13 | 3 | 1-33 | 2 |
| H4H2783N2 | 3-23 | 6-13 | 3 | 1-33 | 2 |
| H3M2788N | 3-33 | 4-23 | 4 | 1-17 | 1 |
| H4H2897N | 3-30 | 2-21 | 4 | 2-28 | 3 |
| H2bM2891N | 3-7 | 3-3 | 4 | 1-12 | 2 |
| H2AM2898N | 3-13 | 2-2 | 6 | 1-6 | 1 |
| H2BM2906N | 3-7 | 3-3 | 4 | 1-12 | 2 |
| H4H2892N | 3-33 | 1-1 | 2 | 1-9 | 1 |
| H1M2907N | 3-33 | 1-1 | 3 | 3-11 | 2 |
| H2BM2890N | 3-33 | 1-14 | 4 | 3-11 | 4 |
| H2AM2899N | 1-8 | 6-6 | 4 | 1-33 | 3 |
| H4H2895N | 3-53 | 3-9 | 4 | 6-21 | 1 |
| H4H2926N | 3-9 | 6-13 | 4 | 1-33 | 4 |
| H3M2929N | 3-33 | 3-10 | 4 | 3-15 | 1 |
| H2AM2901N | 3-21 | 2-12 | 4 | 1-27 | 3 |
| H4H2889N | 4-59 | 4-4 | 6 | 1-6 | 1 |
| H4H6232P | 1-24 | 3-9 | 6 | 1-39 | 3 |
| H4H6233P | 3-33 | 1-7 | 4 | 3-11 | 2 |
| H4H6236P | 1-24 | 3-9 | 6 or 3 | 1-39 | 3 |
| H4H6238P | 3-11 | 1-1 | 4 | 3-15 | 2 |
| H4H6240P | 3-33 | 1-7 | 4 | 3D-15 | 3 |
| H4H6243P | 1-24 | 3-9 | 6 or 4 | 1-39 | 3 |
| H4H6245P | 3-7 | 2-15 | 4 | 1-33 | 2 |
| H4H6246P | 3-33 | 4-17 | 4 | 1-17 | 3 |
| H4H6248P | 3-33 | 4-17 | 4 | 3-15 | 1 |
| H4H6250P | 3-33 | 4-17 | 4 | 1-17 | 3 |
| H4H6251P | 3-33 | 4-17 | 4 | 3-15 | 1 |
| H4H6252P | 3-33 | 4-17 | 4 | 1-17 | 3 |
| H4H6256P | 3-33 | 4-17 | 5 or 4 | 3-15 | 1 |
| H4H6260P | 3-33 | 1-1 | 3 | 3-11 | 5 |
| H4H6269P | 4-31 | 1-1 | 4 | 1-6 | 4 |
| H4H6270P | 3-33 | 3-10 | 4 | 3-15 | 2 |

Example 4. Antibody Binding to Human GREM1 as Determined by Surface Plasmon Resonance Binding associative and dissociative rate constants ($k_a$ and $k_d$, respectively) and calculated equilibrium dissociation constants and dissociative half-lives ($K_D$ and $t_{1/2}$, respectively) for antigen binding to purified anti-Gremlin1 (GREM1) antibodies were determined using a real-time surface plasmon resonance biosensor (Biacore T200) assay at 25° C. and at 37° C.

Anti-GREM1 antibodies were captured on either a goat anti-mouse IgG polyclonal antibody (GE Healthcare, #BR-1008-38) or a mouse anti-human IgG monoclonal antibody (GE Healthcare, #BR-1008-39) surface created through direct amine coupling to a Biacore CM5 sensor chip. Kinetic experiments were carried out using HBS-EP+heparin [10 mM HEPES, 150 mM NaCl, 3 mM EDTA, 0.05% (v/v) surfactant P20, 10 µg/ml heparin sodium salt, pH 7.4] as both the running buffer and the sample buffer. Antigen-antibody association rates were measured by injecting various concentrations (ranging from 11 to 100 nM, 3-fold dilutions) of human GREM1 (hGREM1-His; SEQ ID NO: 595) over the captured anti-GREM1 antibody surface. Antigen-antibody association was monitored for 150 seconds while dissociation in buffer was monitored for 420 seconds. Kinetic analysis was performed using Scrubber software version 2.0a or Biacore T200 evaluation software v1.0 to determine $k_a$ and $k_d$ values. $K_D$ and $t_{1/2}$ were then calculated from the experimentally determined $k_a$ and $k_d$ values as $K_D = k_d/k_a$ and $t_{1/2} = \ln(2)/k_d$.

As shown in Table 3, thirty-five anti-GREM1 antibodies when captured on the Biacore sensor exhibited binding to hGREM1-His protein injected over the surface at 25° C., with $K_D$ values ranging from 625 pM to 270 nM. Two of the antibodies tested, H2aM2898N and H2bM2785N, did not bind hGREM1-His under these experimental conditions. A subset of the 37 anti-GREM1 antibodies was tested again at 37° C. As shown in Table 4, twenty-four anti-GREM1 antibodies when captured on the Biacore sensor exhibited binding to hGREM1-His protein injected over the surface at 37° C., with $K_D$ values ranging from 1.23 nM to 275 nM.

TABLE 3

Biacore affinities at 25° C. for hGREM1-His binding to captured anti-GREM1 monoclonal antibodies

| mAb captured | $K_a$(1/Ms) | $k_d$(1/s) | $K_D$ (M) | $t_{1/2}$ (min) |
|---|---|---|---|---|
| H4H2895N | 1.70E+05 | 1.32E−04 | 7.78E−10 | 88 |
| H4H2780N | 7.12E+04 | 8.80E−04 | 1.24E−08 | 13 |
| H4H2783N2 | 3.04E+04 | 4.76E−04 | 1.57E−08 | 24 |
| H4H2784N | 6.18E+04 | 1.05E−03 | 1.70E−08 | 11 |
| H4H2897N | 2.77E+03 | 4.10E−04 | 1.48E−07 | 28 |
| H4H2889N | 6.27E+04 | 1.18E−04 | 1.89E−09 | 98 |
| H4H2892N | 1.42E+05 | 1.73E−04 | 1.22E−09 | 67 |
| H4H2926N | 9.10E+04 | 5.02E−04 | 5.52E−09 | 23 |
| H4H6232P | 7.68E+04 | 9.60E−05 | 1.25E−09 | 120 |
| H4H6233P | 9.13E+04 | 1.72E−04 | 1.88E−09 | 67 |
| H4H6236P | 4.20E+04 | 1.25E−04 | 2.99E−09 | 92 |
| H4H6238P | 2.41E+04 | 2.25E−04 | 9.32E−09 | 51 |
| H4H6240P | 7.97E+04 | 3.19E−04 | 4.00E−09 | 36 |
| H4H6243P | 1.58E+04 | 1.78E−04 | 1.13E−08 | 65 |
| H4H6245P | 7.79E+04 | 1.17E−04 | 1.51E−09 | 98 |
| H4H6246P | 7.39E+04 | 1.92E−04 | 2.59E−09 | 60 |
| H4H6248P | 5.03E+04 | 7.73E−05 | 1.54E−09 | 149 |
| H4H6250P | 9.01E+04 | 2.97E−04 | 3.30E−09 | 39 |
| H4H6251P | 2.82E+04 | 6.52E−04 | 2.31E−08 | 18 |
| H4H6252P | 7.46E+04 | 7.58E−05 | 1.02E−09 | 152 |
| H4H6256P | 9.00E+04 | 1.07E−04 | 1.19E−09 | 108 |
| H4H6260P | 9.74E+04 | 6.51E−05 | 6.69E−10 | 177 |
| H4H6269P | 1.01E+05 | 6.32E−05 | 6.25E−10 | 183 |
| H4H6270P | 4.29E+04 | 1.75E−04 | 4.08E−09 | 66 |
| H1M2907N | 6.20E+04 | 2.81E−03 | 4.53E−08 | 4.1 |
| H2aM2898N | NB | NB | NB | NB |
| H2aM2899N | 8.00E+03 | 2.00E−03 | 2.70E−07 | 5.8 |
| H2aM2901N | 1.64E+05 | 1.45E−03 | 8.80E−09 | 8.0 |
| H2bM2782N | 1.23E+05 | 1.89E−03 | 1.53E−08 | 6.1 |
| H2bM2785N | NB | NB | NB | NB |
| H2bM2786N | 1.80E+05 | 6.00E−03 | 3.30E−08 | 1.9 |
| H2bM2890N | 1.00E+04 | 1.00E−03 | 1.30E−07 | 11.6 |
| H2bM2891N | 2.00E+04 | 1.20E−03 | 6.00E−08 | 9.6 |
| H2bM2906N | 8.00E+04 | 1.30E−03 | 1.50E−08 | 8.9 |
| H3M2788N | 8.00E+04 | 3.50E−04 | 4.20E−09 | 33.0 |
| H2bM2783N | 2.02E+05 | 1.50E−03 | 7.40E−09 | 7.7 |
| H3M2929N | 1.25E+05 | 3.62E−03 | 2.90E−08 | 3 |

NB = no binding under the conditions tested

TABLE 4

Biacore affinities at 37° C. for hGREM1-His binding to captured anti-GREM1 monoclonal antibodies

| mAb captured | $k_a$(1/Ms) | $k_d$(1/s) | $K_D$ (M) | $t_{1/2}$ (min) |
|---|---|---|---|---|
| H4H2895N | 1.75E+05 | 2.15E−04 | 1.23E−09 | 54 |
| H4H2780N | 5.74E+04 | 1.61E−03 | 2.80E−08 | 7 |
| H4H2783N2 | 1.39E+04 | 8.49E−04 | 6.11E−08 | 14 |
| H4H2784N | 1.42E+05 | 1.97E−04 | 1.38E−08 | 6 |
| H4H2897N | 7.03E+04 | 2.02E−04 | 2.88E−08 | 6 |
| H4H2889N | 1.04E+05 | 4.22E−04 | 4.06E−09 | 27 |
| H4H2892N | 1.71E+05 | 4.00E−04 | 2.35E−09 | 29 |
| H4H2926N | 1.26E+05 | 1.40E−03 | 1.11E−08 | 8 |
| H4H6232P | 1.13E+05 | 1.95E−04 | 1.73E−09 | 59 |
| H4H6233P | 1.57E+05 | 5.12E−04 | 3.26E−09 | 23 |
| H4H6236P | 9.30E+04 | 2.45E−04 | 2.63E−09 | 47 |
| H4H6238P | 5.69E+04 | 9.31E−04 | 1.64E−08 | 12 |
| H4H6240P | 1.21E+05 | 1.18E−03 | 9.75E−09 | 10 |
| H4H6243P | 7.05E+03 | 4.84E−04 | 6.87E−08 | 24 |
| H4H6245P | 1.03E+05 | 2.62E−04 | 2.53E−09 | 44 |
| H4H6246P | 1.27E+05 | 4.44E−04 | 3.50E−09 | 26 |
| H4H6248P | 8.55E+04 | 4.87E−04 | 5.69E−09 | 24 |
| H4H6250P | 1.49E+05 | 8.82E−04 | 5.93E−09 | 13 |
| H4H6251P | 2.53E+04 | 6.94E−03 | 2.75E−07 | 2 |
| H4H6252P | 1.11E+05 | 4.59E−04 | 4.14E−09 | 25 |
| H4H6256P | 1.14E+05 | 4.66E−04 | 4.08E−09 | 25 |
| H4H6260P | 1.66E+05 | 2.85E−04 | 1.71E−09 | 41 |
| H4H6269P | 1.28E+05 | 2.54E−04 | 1.98E−09 | 46 |
| H4H6270P | 9.58E+04 | 6.50E−04 | 6.79E−09 | 18 |

Example 5. Determination of the GREM1 Inhibitory Activity of the Anti-hGREM1 Antibodies To further characterize the anti-human Gremlin 1 (GREM1) antibodies, their ability to block GREM1 binding to human bone morphogenetic protein 4 (BMP4) was examined via ELISA. Plates were coated with recombinant human BMP4 (2 ug/mL) (hBMP4; R&D, #314-BP/CF, residues S293-R408 of accession #Q53XC5, expressed in NS0 cells) overnight and then serial dilutions of antibodies were incubated with a constant amount (100 pM) of recombinant human GREM1 protein (hGREM1-His; SEQ ID NO: 595) modified with a biotin tag for 1 hour at 25° C. before this complex was added to coated plates and allowed to incubate for an additional hour at 25° C. The plates were then washed and plate bound biotin-hGREM1-His was detected with streptavidin conjugated with horseradish peroxidase (Pierce, #N200). Plates were then developed with a TMB solution (BD Biosciences, #555214) to produce a colorimetric reaction and the reaction was quenched by acidification with sulfuric acid before reading absorbance at 450 nm on a Perkin Elmer Victor X5 plate reader. Data were analyzed using a sigmoidal dose-response model within Prism™ software. The calculated $IC_{50}$ value, defined as the antibody concentration required to achieve 50% of maximum blocking, was used as an indicator of blocking potency. The $IC_{50}$ value for several samples was reported at a fixed, lower-bound value of 2.5E−11M, which represents the theoretical lower-limit of this assay, given the fixed concentration of biotin-hGREM1-His used in the assay. Percent blockade was calculated as the ratio of the reduction in signal observed in the presence of antibody relative to the difference between the signal with GREM1 alone and background (signal from HRP-conjugated secondary antibody alone). The absorbance measured for the constant concentration of 100 pM biotin-hGREM1-His alone is defined as 0% blocking and the absorbance measured for no added GREM1 is defined as 100% blocking. The absorbance values of the wells containing the highest concentration for each antibody were used to determine the percent maximum blocking. All 24 anti-GREM1 antibodies tested in this assay blocked biotin-hGREM1-His with $IC_{50}$ values ranging from <25 pM to 1.9 nM. At a concentration of 20 nM of antibody, the 24 antibodies exhibited from 42 to 96-percent blockade of biotin-hGREM1-His binding to hBMP4.

TABLE 5

Anti-GREM1 antibodies blocking bone morphogenic protein 4 (HBMP4) binding to biotin-hGREM1-His

| Ab PID | $IC_{50}$ (M) | % blocked at maximum Ab tested (20 nM) |
|---|---|---|
| H4H2780N | 1.0E−10 | 69 |
| H4H2783N2 | <2.5E−11 | 76 |
| H4H2784N | 4.5E−10 | 59 |
| H4H2889N | <2.5E−11 | 86 |
| H4H2892N | 1.7E−10 | 82 |
| H4H2895N | 3.6E−11 | 94 |
| H4H2897N | 4.2E−11 | 73 |
| H4H2926N | 5.2E−11 | 93 |
| H4H6232P | <2.5E−11 | 93 |
| H4H6233P | 6.9E−10 | 66 |
| H4H6236P | <2.5E−11 | 95 |
| H4H6238P | 9.7E−10 | 64 |
| H4H6240P | 6.5E−10 | 60 |
| H4H6243P | 7.2E−12 | 92 |
| H4H6245P | 3.6E−11 | 96 |
| H4H6246P | 1.5E−09 | 62 |
| H4H6248P | 2.1E−10 | 62 |
| H4H6250P | 1.1E−10 | 42 |
| H4H6251P | 1.1E−10 | 62 |
| H4H6252P | 1.9E−10 | 53 |
| H4H6256P | 8.7E−11 | 75 |
| H4H6260P | <2.5E−11 | 87 |
| H4H6269P | 2.6E−11 | 73 |
| H4H6270P | 1.9E−09 | 62 |
| H4H121N isotype control | >2.00E−08 | 5.9 |

Calculated IC50 values <2.50E−11 below theoretical assay bottom and reported as <2.50E−11

Example 6. Effect of GREM1 on BMP4 Signaling

Gremlin 1 (GREM1) is a negative regulator of bone morphogenetic protein (BMP) signaling (Walsh et al. 2010). BMPs belong to the TGF-β superfamily and are involved in regulation of many physiological processes including proliferation, differentiation, and cell-fate determination during embryonic and postnatal development (Hogan, 1996). Activation of BMP receptors leads to phosphorylation of SMAD proteins and transcriptional activation of BMP-responsive genes. GREM1 binds to BMP2, BMP4, and BMP7 and blocks binding to their receptors. A bioassay was developed to detect the regulation of BMP4 signaling by GREM1 in a mammalian cell line, W-20-17, a mouse bone marrow stromal cell line previously shown to be responsive to BMP2 (Thies et al. 1992). This cell line was modified to stably express a BMP-responsive luciferase reporter. The resulting stable cell line (W-20-17/BRE-luc cells) was isolated and maintained in 10% fetal bovine serum, DMEM, NEAA, penicillin/streptomycin, and 200 µg/ml G418.

For the bioassay, the W-20-17/BRE-luc cells were seeded onto 96-well assay plates at 10,000 cells/well and incubated at 37° C. and 5% $CO_2$ overnight. The next day, recombinant human BMP4 (hBMP4; R&D, #314-BP/CF, residues S293-R408 of accession #Q53XC5, expressed in NS0 cells) was serially diluted at 1:3 and added to cells starting from 100 nM to 0.002 nM including no hBMP4 control for dose response. For inhibition of hBMP4 by GREM1, recombinant human GREM1 (hGREM1-His; C-terminal 10His tagged, R&D, #5190-GR, residues K25-D184 of accession #O60565, expressed in NS0 cells) was serially diluted at 1:2 starting from 400 nM to 0.4 nM including no hGREM1-His control and added to cells along with 200 pM or 100 pM hBMP4. For inhibition of hGREM1-His, antibodies were serially diluted at 1:3 starting from 100 nM to 0.002 nM including no antibody control and added to cells along with hBMP4 and hGREM1-His at final concentrations of either 200 pM and 20 nM or 100 pM and 10 nM, respectively. Luciferase activity was detected after 5.5 hours of incubation in 37° C. and 5% $CO_2$.

Thirty-four of the 36 anti-GREM1 antibodies tested in the W-20-17/BRE-luc bioassay fully blocked hGREM1-His inhibition of hBMP signaling at 10 nM hGREM1-His and 100 pM hBMP4 or 20 nM hGREM1-His and 200 pM hBMP4. One antibody, H4H2780N, showed partial blocking of hGREM1-His and another antibody, H4H6269P, did not inhibit hGREM1-His. Isotype control antibodies (Control mAb1 and Control mAb2) were also included. $IC_{50}$ values are shown in Tables 6 and 7. hBMP4 activated the W-20-17/BRE-luc cells with $EC_{50}$ values of 39 to 116 pM. hGREM1-His inhibited 200 pM hBMP4 with an $IC_{50}$ value of 10.3 nM and 100 pM hBMP4 with an $IC_{50}$ value of 2.9-6.0 nM.

TABLE 6

Inhibition of hGREM-His by anti-human GREM1-antibodies in a cell based assay

| MBMP4 $EC_{50}$ (pM) | 116 | 56 | 75 | 73 | 39 |
|---|---|---|---|---|---|
| hGrem1-His $IC_{50}$ (nM) | 10.3 | 6.0 | 4.3 | 4.2 | 5.4 |
| hBMP4 Constant | 200 pM | | 100 pM | | |
| hGrem1-His Constant | 20 nM | | 10 nM | | |

| AbPID | $IC_{50}$ [M] | $IC_{50}$ [M] | $IC_{50}$ [M] | $IC_{50}$ [M] | $IC_{50}$ [M] |
|---|---|---|---|---|---|
| H2bM2782N | 3.5E−09 | | | | |
| H2bM2785N | 2.7E−08 | | | | |
| H2bM2786N | 1.9E−08 | | | | |
| H3M2788N | 2.5E−08 | | | | |
| H2bM2890N | | 2.1E−09 | | | |
| H2bM2891N | | 1.1E−09 | | | |
| H2aM2898N | | 1.4E−09 | | | |
| H2aM2899N | | 2.1E−09 | | | |
| H2aM2901N | | | | 1.7E−09 | |
| H2bM2906N | | | 1.6E−09 | | |
| H1M2907N | | 1.8E−09 | | | |
| H3M2929N | | | | | 2.2E−09 |
| Control mAb1 | Not Block | Not Block | Not Block | Not Block | Not Block |

TABLE 7

Inhibition of hGREM-His by anti-human GREM1-antibodies in a cell based assay

| | |
|---|---|
| MBMP4 EC$_{50}$ (pM) | 60 |
| hGrem1-His IC$_{50}$ (nM) | 2.9 |
| hBMP4 Constant | 100 pM |
| hGrem1-His Constant | 10 nM |

| AbPID | IC$_{50}$ [M] |
|---|---|
| H4H2780N | 49% Inhibition |
| H4H2783N2 | 1.3E−09 |
| H4H2784N | 9.5E−10 |
| H4H2889N | 1.2E−09 |
| H4H2892N | 9.5E−10 |
| H4H2895N | 5.8E−10 |
| H4H2897N | 4.5E−10 |
| H4H2926N | 1.2E−09 |
| H4H6232P | 7.8E−10 |
| H4H6233P | 4.1E−10 |
| H4H6236P | 5.4E−10 |
| H4H6238P | 1.1E−09 |
| H4H6240P | 8.1E−10 |
| H4H6243P | 5.4E−10 |
| H4H6245P | 5.3E−10 |
| H4H6246P | 5.6E−10 |
| H4H6248P | 5.3E−10 |
| H4H6250P | 4.4E−10 |
| H4H6251P | 6.3E−10 |
| H4H6252P | 8.2E−10 |
| H4H6256P | 5.4E−10 |
| H4H6260P | 4.6E−10 |
| H4H6269P | Not Block |
| H4H6270P | 5.4E−10 |
| Control mAb2 | Not Block |

Example 7. Effect of Anti-GREM1 on BMP Signaling and Cell Differentiation

In order to determine the potency of anti-human Gremlin 1 (GREM1) antibodies, their ability to block GREM1 induced inhibition of bone morphogenetic protein 4 (BMP4) signaling was investigated. W-20-17 cells are an osteoblast progenitor cell line and can differentiate in response to BMP4 signaling. GREM1, a known BMP inhibitor, blocks this differentiation. Blocking of GREM1 results in a reversal of BMP4 inhibition in this assay. Differentiation can be measured colorimetrically by using a substrate to detect endogenous expression of alkaline phosphatase, an early marker of osteoblast differentiation. A total of 24 anti-GREM1 antibodies were tested.

W-20-17 cells were grown in DMEM/10% fetal bovine serum/glutamine/penicillin/streptomycin (complete media) to 100% confluency at 37° C. in 5% CO$_2$. Cells were washed in 1×PBS, trypsinized (trypsin containing EDTA), plated at 3000 cells/well in clear plastic 96 well plates, an\\d grown overnight in complete media at a volume of 100 uL/well. The next day recombinant human GREM1 protein (hGREM1-His; C-terminal 10His tagged, R&D, #5190-GR, residues K25-D184 of accession #060565, expressed in NS0 cells) was mixed with anti-GREM1 antibodies in complete media and incubated at room temperature (RT) for 40 minutes. Recombinant human BMP4 (hBMP4; R&D, #314-BP/CF, residues S293-R408 of accession #Q53XC5, expressed in NS0 cells), also diluted in complete media, was added to the hGREM1-His/GREM1 antibody mixtures and then incubated at RT for an additional 30 minutes. After incubation, 50 uL of these mixtures was added to W-20-17 cells plated in 100 uL of complete media. The final concentration of hBMP4 and hGREM1-His on W-20-17 cells in each well was 1.5 nM and 6 nM, respectively, and the antibody concentration varied over an 11-point, 2-fold dilution series (maximum antibody concentration of 200 nM). After 3 days of growth at 37° C. in 5% CO$_2$, media was aspirated and 50 uL of water was added to each well. Ninety-six well plates were frozen at −80° C. for 2 hours and then thawed on ice. Alkaline phosphatase was measured using p-nitrophenyl phosphate substrate prepared as directed (Sigma, #N2770-50SET). Absorbance at 405 nm was measured on a Victor plate reader seven minutes after addition of 50 uL of substrate. Graphs were plotted in Prism as mean+/−SEM (4 replicates for each condition).

Twenty-two of the 24 anti-GREM1 antibodies tested blocked hGREM1-His inhibition of hBMP4 in this assay with IC$_{50}$ values as shown in Table 8. Two antibodies, H4H6269P and H4H2780N, did not exhibit any measurable blocking of hGREM1-His activity in this assay.

TABLE 8

Gremlin 1 blocking antibodies in W-20-17 cell differentiation assay

| AbPID | HGREM1-His Inhibition IC$_{50}$, M |
|---|---|
| H4H2895N | 1.9E−09 |
| H4H2889N | 5.4E−09 |
| H4H2892N | 4.4E−09 |
| H4H2783N2 | 5.6E−09 |
| H4H2784N | 2.4E−08 |
| H4H2897N | 1.8E−08 |
| H4H2926N | 1.3E−08 |
| H4H6232P | 4.5E−09 |
| H4H6233P | 2.3E−08 |
| H4H6236P | 3.9E−09 |
| H4H6238P | 2.2E−08 |
| H4H6240P | 7.8E−09 |
| H4H6243P | 5.9E−09 |
| H4H6245P | 6.1E−09 |
| H4H6246P | 6.2E−09 |
| H4H6248P | 5.6E−09 |
| H4H6250P | 1.2E−08 |
| H4H6251P | 1.1E−08 |
| H4H6252P | 6.1E−09 |
| H4H6256P | 5.7E−09 |
| H4H6260P | 3.3E−09 |
| H4H6270P | 3.1E−09 |
| hBMP4 and hGREM1-His activity in W-20-17 cell differentiation assay: | |
| hBMP4 EC$_{50}$ (M) | 5.6E−10 |
| hGREMI-His, IC$_{50}$ (M) | 4.4E−09 |

Example 8. Generation of a Bi-Specific Antibody

Various bi-specific antibodies are generated for use in practicing the methods of the invention. For example, hGREM1-specific antibodies are generated in a bi-specific format (a "bi-specific") in which variable regions binding to distinct regions of hGREM1 are linked together to confer dual-domain specificity within a single binding molecule. Appropriately designed bi-specifics may enhance overall GREM1 inhibitory efficacy through increasing both specificity and binding avidity. Variable regions with specificity for individual regions or epitopes of GREM1 are paired on a structural scaffold that allows each region to bind simultaneously to the separate epitopes. In one example for a bi-specific, heavy chain variable regions (V$_H$) from a binder with specificity for one region are recombined with light chain variable regions (V$_L$) from a series of binders with specificity for a second region to identify non-cognate V$_L$ partners that can be paired with an original V$_H$ without disrupting the original specificity for that V$_H$. In this way, a single $V_L$ segment (e.g., $V_L1$) can be combined with two different $V_H$ domains (e.g., $V_H1$ and $V_H2$) to generate a bi-specific comprised of two binding "arms" ($V_H1$-$V_L1$ and $V_H2$-$V_L1$). Use of a single $V_L$ segment reduces the complexity of the system and thereby simplifies and increases efficiency in cloning, expression, and purification processes used to generate the bi-specific (See, for example, U.S. Ser. No. 13/022,759 and US2010/0331527).

Alternatively, antibodies that bind to GREM1 and a second target, such as, but not limited to, for example, a second different anti-GREM1 antibody, or a drug specific for fibrosis, may be prepared in a bi-specific format using techniques described herein, or other techniques known to those skilled in the art. Antibody variable regions binding to distinct catalytic domain regions may be linked together with variable regions that bind to relevant sites on, for example, the signal peptide domain, to confer dual-antigen specificity within a single binding molecule. Appropriately designed bi-specifics of this nature serve a dual function. For example, in the case of a bi-specific antibody that binds both the domains, one may be able to better neutralize both the domains concurrently, without the need for administration of a composition containing two separate antibodies. Variable regions with specificity for the catalytic domain are combined with a variable region with specificity for the signal peptide domain and are paired on a structural scaffold that allows each variable region to bind to the separate antigens.

Example 9. Inhibition of the GREM1-Heparin Binding Interaction Using GREM1-Specific Antibodies In the present study, Bio-Layer Interferometry was used to confirm previous results showing GREM1 binding to heparin and to evaluate the ability of GREM1 specific monoclonal antibodies to interfere with this binding interaction. GREM1 and other structurally related cysteine knot-containing proteins including GREM2 and cerberus were also tested for their ability to bind to heparin. Using these observations, amino acid residues involved in the binding of GREM1 to heparin were hypothesized by comparing the sequences and known heparin-binding properties of other cysteine-knot containing DAN family proteins. The binding of GREM1 to heparin was competed by different GAGs including heparin, HS, and dermatan sulfate (DS) to varying degrees, demonstrating the specificity of the interaction. Finally, individual antibodies were tested for their ability to interfere with the binding of GREM1 to heparin. Of the twenty-four antibodies tested, four were demonstrated to partially affect aspects of this binding interaction. In an attempt to completely block the interaction, the four antibodies that promoted partial blockade of the GREM1 and heparin binding interaction when tested alone were tested in combination. Some of the combinations including three of the antibodies and the mixture containing all four antibodies were able to completely inhibit the GREM1 and heparin binding interaction. These results give more insight into the binding mechanics of GREM1 and heparin and demonstrate a possible method using combinations of antibodies for inhibiting the angiogenic interaction of GREM1 with HS for therapeutic treatment.

Reagents and Instrumentation

Carrier free recombinant human GREM1 with a C-terminal decahistidine tag was obtained from R&D Systems (Minneapolis, Minn.). Heparin-biotin sodium salt from porcine intestinal mucosa and heparin sodium salt from porcine intestinal mucosa were obtained from Millipore (Billerica, Mass.). Heparan sulfate (HS) sodium salt from porcine intestinal mucosa and dermatan sulfate (DS) sodium salt from porcine intestinal mucosa were obtained from Celsus (Cincinnati, Ohio).

Binding measurements were conducted using an Octet Red96 label-free biomolecular interaction instrument (ForteBio). All experiments were performed at 25° C. using plate agitation at 1000 rpm. Solutions were made in an aqueous buffer containing 10 mM HEPES, 150 mM NaCl, 3 mM EDTA 0.05% P20, 0.1 mg/mL BSA and adjusted to pH of 7.4 (HBST buffer).

Binding Kinetics of GREM1 Interacting with Captured Heparin

Super Streptavidin biosensors were loaded with 10 µg/mL heparin-biotin solutions for 90 seconds. Following a 120 second wash, the heparin-captured biosensors were submerged in wells containing 11.1 nM, 33.3 nM, 100 nM, and 300 nM GREM1 solutions to measure association for 240 seconds. The biosensors were then submerged in HBST buffer to measure dissociation for 240 seconds. The measured association and dissociation rate constants ($k_{on}$=1.17× $10^6$ $M^{-1}s^{-1}$ and $k_{off}$=3.27×$10^{-3}$ $s^{-1}$) demonstrate that GREM1 binds to heparin with high affinity ($K_D$=$k_{off}$/$k_{on}$=2.8×$10^{-6}$ M).

Inhibition of GREM1 Binding to Captured Heparin by Glycosaminoglycans

Super Streptavidin biosensors were loaded with 10 µg/mL heparin-biotin solutions for 90 seconds. Following a 120 second wash, the heparin-captured biosensors were submerged in wells containing 100 nM GREM1 solution premixed with increasing concentrations (0 nM, 20 nM, 100 nM, 2 µM) of heparin, heparan sulfate (HS), or dermatan sulfate (DS) to measure association for 240 seconds.

GREM1 exhibited reduced binding to captured heparin-biotin in the presence of increasing concentrations of heparin, HS, and DS, as reflected in the binding signals observed after 240 seconds of association (Table 9). Exogenously added heparin was most effective in blocking the binding 100 nM GREM1 to captured heparin-biotin, exhibiting complete inhibition at 100 nM. Nearly complete inhibition of GREM1 binding to captured heparin-biotin was observed when GREM1 was mixed with 2 µM of HS and DS. The complete inhibition of 100 nM GREM1 binding to captured heparin-biotin with soluble heparin at 100 nM supports the specificity of this binding. Partial inhibition with the other glycosaminoglycans, which are all negatively charged, suggests that electrostatic interactions may be important in the GREM1-heparin binding interaction.

TABLE 9

The effect of soluble glycosaminoglycans on the GREM1-heparin binding interaction

| Concentration of Glycosaminoglycan | Binding Response (nm) for 100 nM GREM1 Binding to Captured Biotin-Heparin in the Presence of Increasing Concentrations of Glycosaminoglycans | | |
|---|---|---|---|
| | Heparin | Heparan Sulfate | Dermatan Sulfate |
| 0 nM | 0.12 | 0.11 | 0.09 |
| 20 nM | 0.07 | 0.11 | 0.08 |
| 100 nM | 0 | 0.07 | 0.05 |
| 2 µM | 0 | 0.04 | 0.02 |

Inhibition of GREM1 Binding to GREM1 Specific Monoclonal Antibodies by Heparin

Anti-Human IgG Fc Capture biosensors (ForteBio) were separately loaded with 50 μg/mL solutions of 24 different anti-GREM1 antibodies for 60 seconds. Following a 30 second wash, duplicate biosensors for each antibody were submerged into wells containing either 100 nM GREM1 solutions or 100 nM GREM1 solutions containing 5 μM of heparin, measuring association for 300 seconds. The presence or absence of heparin for some of the antibodies influenced the association rate, and this effect is summarized in Table 10 where observed signals at both 30 seconds and 300 seconds are provided. The binding of antibodies H4H2895N, H4H2780N, H4H6269P, and H4H2892N to GREM1 was minimally affected by the presence of heparin (the binding signals at 30 seconds were reduced by 0.05 nm or less). The binding of eight antibodies (H4H2897N, H4H6252P, H4H6245P, H4H6251P, H4H6232P, H4H2783N2, H4H6236P, and H4H6243P) exhibited the greatest reduction in binding to GREM1 in the presence of heparin (binding signals reduced by 0.19 nm or greater at 30 seconds). The other antibodies tested showed intermediate levels of binding inhibition to GREM1 in the presence of heparin.

H4H6243P, H4H6245P) chosen from the group in the previous experiment that exhibited the strongest inhibition of GREM1-heparin binding when tested alone. The mixtures included single antibodies and combinations of two, three, or four antibodies. Each antibody had a concentration of 600 nM in the mixtures. Also included were a negative isotype control antibody known not to bind to GREM1, two antibodies (H4H2892N and H4H2780N) whose binding to GREM1 was minimally affected by the presence of heparin, and the reference condition of GREM1 alone. As shown in Table 11, the individual antibodies only partially reduced binding of GREM1 to captured heparin in this binding format. Combinations of antibodies decreased binding of GREM1 to captured heparin more effectively. The solution containing H4H2897N, H4H6243P, and H4H6245P and the solution containing all four antibodies completely inhibited GREM1 from binding to captured heparin.

The GREM1 and heparin binding interaction was completely inhibited using combinations of antibodies that were each individually identified to be effective at partially interfering with this binding interaction. Given the highly negatively charged nature of heparin, the results suggest that

TABLE 10

The inhibitory effect of soluble glycosaminoglycans on GREM1-antibody binding interactions

| mAb Captured | 100 nM GREM1 | | 100 nM GREM1 + 5 uM Heparin | | | |
|---|---|---|---|---|---|---|
| | Binding Signal with 30 sec Association (nm) | Binding Signal with 300 sec Association (nm) | Binding Signal with 30 sec Association (nm) | Binding Signal with 300 sec Association (nm) | Reduction in Signal from Heparin at 30 sec | Reduction in Signal from Heparin at 300 sec |
| H4H2895N | 0.15 | 0.5 | 0.22 | 0.54 | −0.07 | −0.04 |
| H4H2780N | 0.13 | 0.58 | 0.13 | 0.58 | 0.00 | 0.00 |
| H4H6269P | 0.15 | 0.6 | 0.14 | 0.52 | 0.01 | 0.08 |
| H4H2892N | 0.2 | 0.49 | 0.15 | 0.49 | 0.05 | 0.00 |
| H4H6233P | 0.19 | 0.47 | 0.08 | 0.41 | 0.11 | 0.06 |
| H4H6238P | 0.13 | 0.41 | 0.02 | 0.33 | 0.11 | 0.08 |
| H4H6246P | 0.19 | 0.38 | 0.06 | 0.34 | 0.13 | 0.04 |
| H4H6256P | 0.2 | 0.4 | 0.07 | 0.38 | 0.13 | 0.02 |
| H4H6250P | 0.2 | 0.37 | 0.06 | 0.32 | 0.14 | 0.05 |
| H4H2889N | 0.2 | 0.46 | 0.05 | 0.44 | 0.15 | 0.02 |
| H4H6270P | 0.2 | 0.39 | 0.05 | 0.33 | 0.15 | 0.06 |
| H4H2926N | 0.23 | 0.49 | 0.07 | 0.42 | 0.16 | 0.07 |
| H4H6248P | 0.21 | 0.42 | 0.04 | 0.37 | 0.17 | 0.05 |
| H4H6260P | 0.24 | 0.42 | 0.07 | 0.37 | 0.17 | 0.05 |
| H4H2784N | 0.24 | 0.52 | 0.06 | 0.46 | 0.18 | 0.06 |
| H4H6240P | 0.23 | 0.53 | 0.05 | 0.37 | 0.18 | 0.16 |
| H4H2897N | 0.2 | 0.68 | 0.01 | 0.26 | 0.19 | 0.42 |
| H4H6252P | 0.23 | 0.44 | 0.04 | 0.35 | 0.19 | 0.09 |
| H4H6245P | 0.23 | 0.41 | 0.02 | 0.22 | 0.21 | 0.19 |
| H4H6251P | 0.27 | 0.45 | 0.03 | 0.36 | 0.24 | 0.09 |
| H4H6232P | 0.33 | 0.48 | 0.06 | 0.46 | 0.27 | 0.02 |
| H4H2783N2 | 0.29 | 0.47 | 0.01 | 0.29 | 0.28 | 0.18 |
| H4H6236P | 0.33 | 0.45 | 0.05 | 0.43 | 0.28 | 0.02 |
| H4H6243P | 0.3 | 0.47 | 0 | 0.21 | 0.30 | 0.26 |

Inhibition of GREM1 Binding to Heparin by Combinations of GREM1 Antibodies

Super Streptavidin biosensors were loaded with 10 μg/mL solutions of heparin-biotin for 60 seconds. Following a 30 second wash, the biosensors were submerged into separate GREM1 solutions, each containing all 15 possible combinations of four antibodies (H4H2783N2, H4H2897N, heparin binds to GREM1 at multiple positively charged surface residues on GREM1. With this insight, it is proposed that in order to completely inhibit the angiogenesis-inducing HS and GREM1 binding interaction, multiple antibodies are required that have diverse epitopes overlapping with multiple heparin-binding sites in the structure of GREM1.

TABLE 11

The inhibitory effect of GREM1-specific antibodies on the GREM1-heparin binding interaction

| PID | Binding Response (nm) at 300 sec of 100 nM GREM1 binding to captured heparin in the presence of 600 nM of each antibody alone or as a combination |
|---|---|
| H4H2783N2 | 0.08 |
| H4H2897N | 0.20 |
| H4H6243P | 0.13 |
| H4H6245P | 0.19 |
| H4H2783N2 + H4H2897N | 0.06 |
| H4H2783N2 + H4H6243P | 0.06 |
| H4H2783N2 + H4H6245P | 0.04 |
| H4H2897N + H4H6243P | 0.07 |
| H4H2897N + H4H6245P | 0.19 |
| H4H6243P + H4H6245P | 0.05 |
| H4H2783N2 + H4H2897N + H4H6243P | 0.04 |
| H4H2897N + H4H6243P + H4H6245P | −0.01 |
| H4H2783N2 + H4H6243P + H4H6245P | 0.02 |
| H4H2783N2 + H4H2897N + H4H6245P | 0.10 |
| H4H2783N2 + H4H2897N + H4H6243P + H4H6245P | −0.01 |
| H4H2892N | 0.40 |
| H4H2780N | 0.29 |
| no antibody | 0.13 |
| negative control antibody | 0.12 |

The present invention is not to be limited in scope by the specific embodiments described herein. Indeed, various modifications of the invention in addition to those described herein will become apparent to those skilled in the art from the foregoing description and the accompanying figures. Such modifications are intended to fall within the scope of the appended claims.

What is claimed is:

1. An isolated human monoclonal antibody or antigen-binding fragment thereof that binds specifically to human gremlin-1 (GREM1), and blocks GREM1-mediated inhibition of bone morphogenetic protein (BMP) signaling, wherein the antibody or antigen-binding fragment comprises the six complementarity determining regions (HCDR1, HCDR2, HCDR3, LCDR1, LCDR2, and LCDR3) contained within the HCVR/LCVR amino acid sequence pair of SEQ ID NOs: 434/442.

2. The isolated human monoclonal antibody or antigen-binding fragment of claim 1, wherein HCDR1, HCDR2, HCDR3, LCDR1, LCDR2, and LCDR3 comprise, respectively, the amino acid sequences of SEQ ID NOs: 436-438-440-444-446-448.

3. The isolated human monoclonal antibody or antigen-binding fragment of claim 2, comprising a HCVR/LCVR amino acid sequence pair of SEQ ID NOs: 434/442.

4. The isolated human monoclonal antibody or antigen-binding fragment of claim 1, wherein the antibody or antigen-binding fragment thereof blocks GREM1 binding to bone morphogenetic-protein 2 (BMP2), or BMP4.

5. The isolated human monoclonal antibody or antigen-binding fragment thereof of claim 1, wherein the antibody or antigen-binding fragment thereof exhibits one or more properties selected from the group consisting of:

(a) binds GREM1 at 37° C. with a binding dissociation equilibrium constant ($K_D$) of less than about 275 nM as measured by surface plasmon resonance;

(b) binds to GREM1 at 37° C. with a dissociative half-life ($t^{1/2}$) of greater than about 3 minutes as measured by surface plasmon resonance;

(c) binds GREM1 at 25° C. with a $K_D$ of less than about 280 nM as measured by surface plasmon resonance;

(d) binds to GREM1 at 25° C. with a $t^{1/2}$ of greater than about 2 minutes as measured by surface plasmon resonance; and (e) blocks GREM1 binding to BMP4 with an $IC_{50}$ of less than about 1.9 nM as measured in a competition ELISA assay at 25° C.

6. The isolated human monoclonal antibody or antigen-binding fragment of claim 1 that blocks GREM1-mediated inhibition of BMP4 signaling.

7. A pharmaceutical composition comprising the antibody or antigen-binding fragment thereof of claim 3, and a pharmaceutically acceptable carrier or diluent.

8. A pharmaceutical composition comprising the antibody or antigen-binding fragment thereof of claim 1, and a pharmaceutically acceptable carrier or diluent.

9. A pharmaceutical composition comprising the antibody or antigen-binding fragment thereof of claim 2, and a pharmaceutically acceptable carrier or diluent.

10. The isolated human monoclonal antibody or antigen-binding fragment thereof of claim 3 that is a full length IgG1 antibody.

11. The isolated human monoclonal antibody or antigen-binding fragment thereof of claim 3 that is a full length IgG4 antibody.

12. A pharmaceutical composition comprising the antibody of claim 10, and a pharmaceutically acceptable carrier or diluent.

13. A pharmaceutical composition comprising the antibody of claim 11, and a pharmaceutically acceptable carrier or diluent.

* * * * *

SEQUENCE LISTING

```
<160> NUMBER OF SEQ ID NOS: 595

<210> SEQ ID NO 1
<211> LENGTH: 357
<212> TYPE: DNA
<213> ORGANISM: Artificial Sequence
<220> FEATURE:
<223> OTHER INFORMATION: Synthetic

<400> SEQUENCE: 1
caggtgcagc tggtggagtc tgggggaggc gtggtccagc ctgggaggtc cctgagactc      60
tcctgtgcag cgtctggatt caccttcagc agctatggca tgcactgggt ccgccaggct     120
ccaggcaagg ggctggagtg ggtggcaatt atatggaatg atggaagtaa taaatactat     180
gtagactccg tgaagggccg attcaccatc tccagagcca attccaagaa cacgctgtat     240
ctgcaaatga acagcctgag agccgaagac acggctgtgt attactgtgc gagagacgga     300
ctggaacctg atgcttttga tatctggggc caagggacaa tggtcaccgt ttcttca       357

<210> SEQ ID NO 2
<211> LENGTH: 119
<212> TYPE: PRT
<213> ORGANISM: Artificial Sequence
<220> FEATURE:
<223> OTHER INFORMATION: Synthetic

<400> SEQUENCE: 2

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
                20                  25                  30

Gly Met His Trp Val Arg Gln Ala Pro Gly Lys Gly Leu Glu Trp Val
            35                  40                  45

Ala Ile Ile Trp Asn Asp Gly Ser Asn Lys Tyr Tyr Val Asp Ser Val
        50                  55                  60

Lys Gly Arg Phe Thr Ile Ser Arg Ala Asn Ser Lys Asn Thr Leu Tyr
65                  70                  75                  80
```

```
Leu Gln Met Asn Ser Leu Arg Ala Glu Asp Thr Ala Val Tyr Tyr Cys
            85                  90                  95

Ala Arg Asp Gly Leu Glu Pro Asp Ala Phe Asp Ile Trp Gly Gln Gly
        100                 105                 110

Thr Met Val Thr Val Ser Ser
        115

<210> SEQ ID NO 3
<211> LENGTH: 24
<212> TYPE: DNA
<213> ORGANISM: Artificial Sequence
<220> FEATURE:
<223> OTHER INFORMATION: Synthetic

<400> SEQUENCE: 3
ggattcacct tcagcagcta tggc                                          24

<210> SEQ ID NO 4
<211> LENGTH: 8
<212> TYPE: PRT
<213> ORGANISM: Artificial Sequence
<220> FEATURE:
<223> OTHER INFORMATION: Synthetic

<400> SEQUENCE: 4

Gly Phe Thr Phe Ser Ser Tyr Gly
1               5

<210> SEQ ID NO 5
<211> LENGTH: 24
<212> TYPE: DNA
<213> ORGANISM: Artificial Sequence
<220> FEATURE:
<223> OTHER INFORMATION: Synthetic

<400> SEQUENCE: 5
atatggaatg atggaagtaa taaa                                          24

<210> SEQ ID NO 6
<211> LENGTH: 8
<212> TYPE: PRT
<213> ORGANISM: Artificial Sequence
<220> FEATURE:
<223> OTHER INFORMATION: Synthetic

<400> SEQUENCE: 6

Ile Trp Asn Asp Gly Ser Asn Lys
1               5

<210> SEQ ID NO 7
<211> LENGTH: 36
<212> TYPE: DNA
<213> ORGANISM: Artificial Sequence
<220> FEATURE:
<223> OTHER INFORMATION: Synthetic

<400> SEQUENCE: 7
gcgagagacg gactggaacc tgatgctttt gatatc                             36

<210> SEQ ID NO 8
<211> LENGTH: 12
<212> TYPE: PRT
<213> ORGANISM: Artificial Sequence
<220> FEATURE:
<223> OTHER INFORMATION: Synthetic
```

-continued

<400> SEQUENCE: 8

Ala Arg Asp Gly Leu Glu Pro Asp Ala Phe Asp Ile
1               5                   10

<210> SEQ ID NO 9
<211> LENGTH: 324
<212> TYPE: DNA
<213> ORGANISM: Artificial Sequence
<220> FEATURE:
<223> OTHER INFORMATION: Synthetic

<400> SEQUENCE: 9

```
gaaattgtgt tgacacagtc tccagccacc ctgtctttgt ctccagggga aagagccacc    60
ctctcctgca gggccagtca gagtgttagc agcttcttag cctggtacca acagaaacct   120
ggccaggctc ccaggctcct catctatgat gcatccaaca gggccactgg catcccagcc   180
aggttcagtg gcagtgggtc tgggacagac ttcactctca ccatcagcag cctagagcct   240
gaagattttg cagtttatta ctgtcagcag cgtagcaact ggcctccgta cacttttggc   300
caggggacca agctggagat caaa                                          324
```

<210> SEQ ID NO 10
<211> LENGTH: 108
<212> TYPE: PRT
<213> ORGANISM: Artificial Sequence
<220> FEATURE:
<223> OTHER INFORMATION: Synthetic

<400> SEQUENCE: 10

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Phe
            20                  25                  30

Leu Ala Trp Tyr Gln Gln Lys Pro Gly Gln Ala Pro Arg Leu Leu Ile
        35                  40                  45

Tyr Asp Ala Ser Asn Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Arg Ser Asn Trp Pro Pro
                85                  90                  95

Tyr Thr Phe Gly Gln Gly Thr Lys Leu Glu Ile Lys
            100                 105

<210> SEQ ID NO 11
<211> LENGTH: 18
<212> TYPE: DNA
<213> ORGANISM: Artificial Sequence
<220> FEATURE:
<223> OTHER INFORMATION: Synthetic

<400> SEQUENCE: 11

```
cagagtgtta gcagcttc                                                  18
```

<210> SEQ ID NO 12
<211> LENGTH: 6
<212> TYPE: PRT
<213> ORGANISM: Artificial Sequence
<220> FEATURE:
<223> OTHER INFORMATION: Synthetic

<400> SEQUENCE: 12

```
Gln Ser Val Ser Ser Phe
1               5
```

<210> SEQ ID NO 13
<211> LENGTH: 9
<212> TYPE: DNA
<213> ORGANISM: Artificial Sequence
<220> FEATURE:
<223> OTHER INFORMATION: Synthetic

<400> SEQUENCE: 13 gatgcatcc                                                              9

<210> SEQ ID NO 14
<211> LENGTH: 3
<212> TYPE: PRT
<213> ORGANISM: Artificial Sequence
<220> FEATURE:
<223> OTHER INFORMATION: Synthetic

<400> SEQUENCE: 14

```
Asp Ala Ser
1
```

<210> SEQ ID NO 15
<211> LENGTH: 30
<212> TYPE: DNA
<213> ORGANISM: Artificial Sequence
<220> FEATURE:
<223> OTHER INFORMATION: Synthetic

<400> SEQUENCE: 15
cagcagcgta gcaactggcc tccgtacact                                       30

<210> SEQ ID NO 16
<211> LENGTH: 10
<212> TYPE: PRT
<213> ORGANISM: Artificial Sequence
<220> FEATURE:
<223> OTHER INFORMATION: Synthetic

<400> SEQUENCE: 16

```
Gln Gln Arg Ser Asn Trp Pro Pro Tyr Thr
1               5                   10
```

<210> SEQ ID NO 17
<211> LENGTH: 360
<212> TYPE: DNA
<213> ORGANISM: Artificial Sequence
<220> FEATURE:
<223> OTHER INFORMATION: Synthetic

<400> SEQUENCE: 17
gaggtgcagc tggtggagtc tgggggcggc ctggtcaagc ctggggggtc cctgagactc       60
tcctgtgcag cctctggatt caccttcagt acctacagca tgaactgggt ccgccaggct      120
ccagggaagg ggctggagtg ggtctcatcc attagtagtg gtagtagtta catatactac      180
acagactcag tgaagggccg attcaccatc tccagagaca cgccaagaa ctcactgtat      240 ctgcaaatga acagcctgag agccgaggac acggctgtgt attactgtgc gagattcggg      300
agctactact acttcggttt cgacgtctgg ggccaaggga ccacggtcac cgtctcctca      360

<210> SEQ ID NO 18
<211> LENGTH: 120

<212> TYPE: PRT
<213> ORGANISM: Artificial Sequence
<220> FEATURE:
<223> OTHER INFORMATION: Synthetic

<400> SEQUENCE: 18

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Thr Tyr
            20                  25                  30

Ser Met Asn Trp Val Arg Gln Ala Pro Gly Lys Gly Leu Glu Trp Val
        35                  40                  45

Ser Ser Ile Ser Ser Gly Ser Ser Tyr Ile Tyr Tyr Thr Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Phe Gly Ser Tyr Tyr Phe Gly Phe Asp Val Trp Gly Gln
            100                 105                 110

Gly Thr Thr Val Thr Val Ser Ser
        115                 120

<210> SEQ ID NO 19
<211> LENGTH: 24
<212> TYPE: DNA
<213> ORGANISM: Artificial Sequence
<220> FEATURE:
<223> OTHER INFORMATION: Synthetic

<400> SEQUENCE: 19
ggattcacct tcagtaccta cagc                                          24

<210> SEQ ID NO 20
<211> LENGTH: 8
<212> TYPE: PRT
<213> ORGANISM: Artificial Sequence
<220> FEATURE:
<223> OTHER INFORMATION: Synthetic

<400> SEQUENCE: 20

Gly Phe Thr Phe Ser Thr Tyr Ser
1               5

<210> SEQ ID NO 21
<211> LENGTH: 24
<212> TYPE: DNA
<213> ORGANISM: Artificial Sequence
<220> FEATURE:
<223> OTHER INFORMATION: Synthetic

<400> SEQUENCE: 21
attagtagtg gtagtagtta cata                                          24

<210> SEQ ID NO 22
<211> LENGTH: 8
<212> TYPE: PRT
<213> ORGANISM: Artificial Sequence
<220> FEATURE:
<223> OTHER INFORMATION: Synthetic

<400> SEQUENCE: 22

Ile Ser Ser Gly Ser Ser Tyr Ile

<210> SEQ ID NO 23
<211> LENGTH: 39
<212> TYPE: DNA
<213> ORGANISM: Artificial Sequence
<220> FEATURE:
<223> OTHER INFORMATION: Synthetic

<400> SEQUENCE: 23
gcgagattcg ggagctacta ctacttcggt ttcgacgtc                    39

<210> SEQ ID NO 24
<211> LENGTH: 13
<212> TYPE: PRT
<213> ORGANISM: Artificial Sequence
<220> FEATURE:
<223> OTHER INFORMATION: Synthetic

<400> SEQUENCE: 24

Ala Arg Phe Gly Ser Tyr Tyr Tyr Phe Gly Phe Asp Val
1               5                   10

<210> SEQ ID NO 25
<211> LENGTH: 321
<212> TYPE: DNA
<213> ORGANISM: Artificial Sequence
<220> FEATURE:
<223> OTHER INFORMATION: Synthetic

<400> SEQUENCE: 25
gacatccaga tgacccagtc tccatcctcc ctgtctgcat ctgtaggaga cagagtcacc    60
atcacttgcc gggcgagtca gggcattagc aattatttag cctggtatca gcagaaacca   120
gggaaagttc ctaaactcct gatctttttct gcatccactt tgcaatcagg ggtcccatct   180
cggttcagtg gcagtggatc tgggccagat tcactctca ccgtcagcag cctgcagcct    240
gaagatgttg caacttatta ctgtcaaaag tataacagtg ccccattcgc tttcggccct   300
gggaccaaag tggatatcaa a                                             321

<210> SEQ ID NO 26
<211> LENGTH: 107
<212> TYPE: PRT
<213> ORGANISM: Artificial Sequence
<220> FEATURE:
<223> OTHER INFORMATION: Synthetic

<400> SEQUENCE: 26

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Ser Asn Tyr
            20                  25                  30

Leu Ala Trp Tyr Gln Gln Lys Pro Gly Lys Val Pro Lys Leu Leu Ile
        35                  40                  45

Phe Ser Ala Ser Thr Leu Gln Ser Gly Val Pro Ser Arg Phe Ser Gly
    50                  55                  60

Ser Gly Ser Gly Pro Asp Phe Thr Leu Thr Val Ser Ser Leu Gln Pro
65                  70                  75                  80

Glu Asp Val Ala Thr Tyr Tyr Cys Gln Lys Tyr Asn Ser Ala Pro Phe
                85                  90                  95

Ala Phe Gly Pro Gly Thr Lys Val Asp Ile Lys
            100                 105

<210> SEQ ID NO 27
<211> LENGTH: 18
<212> TYPE: DNA
<213> ORGANISM: Artificial Sequence
<220> FEATURE:
<223> OTHER INFORMATION: Synthetic

<400> SEQUENCE: 27
cagggcatta gcaattat                                                   18

<210> SEQ ID NO 28
<211> LENGTH: 6
<212> TYPE: PRT
<213> ORGANISM: Artificial Sequence
<220> FEATURE:
<223> OTHER INFORMATION: Synthetic

<400> SEQUENCE: 28

Gln Gly Ile Ser Asn Tyr
1               5

<210> SEQ ID NO 29
<211> LENGTH: 9
<212> TYPE: DNA
<213> ORGANISM: Artificial Sequence
<220> FEATURE:
<223> OTHER INFORMATION: Synthetic

<400> SEQUENCE: 29 tctgcatcc                                                              9

<210> SEQ ID NO 30
<211> LENGTH: 3
<212> TYPE: PRT
<213> ORGANISM: Artificial Sequence
<220> FEATURE:
<223> OTHER INFORMATION: Synthetic

<400> SEQUENCE: 30

Ser Ala Ser
1

<210> SEQ ID NO 31
<211> LENGTH: 27
<212> TYPE: DNA
<213> ORGANISM: Artificial Sequence
<220> FEATURE:
<223> OTHER INFORMATION: Synthetic

<400> SEQUENCE: 31
caaaagtata acagtgcccc attcgct                                         27

<210> SEQ ID NO 32
<211> LENGTH: 9
<212> TYPE: PRT
<213> ORGANISM: Artificial Sequence
<220> FEATURE:
<223> OTHER INFORMATION: Synthetic

<400> SEQUENCE: 32

Gln Lys Tyr Asn Ser Ala Pro Phe Ala
1               5

<210> SEQ ID NO 33
<211> LENGTH: 354

```
<212> TYPE: DNA
<213> ORGANISM: Artificial Sequence
<220> FEATURE:
<223> OTHER INFORMATION: Synthetic

<400> SEQUENCE: 33
gaggtgcagc tggtggagtc tgggggaggc ctggtccagc ctgggggtc cctgagactc        60 tcctgtgcag cctctggatt caccttcagt agttatagca tgaactgggt ccgccaggct      120
ccagggaagg ggctggagtg gtctcatcc ataagtagta gtagtaatta cataaactac       180
gcagactcta ttaagggccg attcaccatc tccagagaca acgccaagaa ctcactatat      240
ctacaaatga acagcctgag agccgaggat acggctgtgt attactgtgc gagagttaat      300
tgggactacc cctttgactg ctggggccgg ggaaccctgg tcaccgtctc ctca            354

<210> SEQ ID NO 34
<211> LENGTH: 118
<212> TYPE: PRT
<213> ORGANISM: Artificial Sequence
<220> FEATURE:
<223> OTHER INFORMATION: Synthetic

<400> SEQUENCE: 34

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ser Met Asn Trp Val Arg Gln Ala Pro Gly Lys Gly Leu Glu Trp Val
        35                  40                  45

Ser Ser Ile Ser Ser Ser Ser Asn Tyr Ile Asn Tyr Ala Asp Ser Ile
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Val Asn Trp Asp Tyr Pro Phe Asp Cys Trp Gly Arg Gly Thr
            100                 105                 110

Leu Val Thr Val Ser Ser
        115

<210> SEQ ID NO 35
<211> LENGTH: 24
<212> TYPE: DNA
<213> ORGANISM: Artificial Sequence
<220> FEATURE:
<223> OTHER INFORMATION: Synthetic

<400> SEQUENCE: 35
ggattcacct tcagtagtta tagc                                              24

<210> SEQ ID NO 36
<211> LENGTH: 8
<212> TYPE: PRT
<213> ORGANISM: Artificial Sequence
<220> FEATURE:
<223> OTHER INFORMATION: Synthetic

<400> SEQUENCE: 36

Gly Phe Thr Phe Ser Ser Tyr Ser
1               5
```

```
<210> SEQ ID NO 37
<211> LENGTH: 24
<212> TYPE: DNA
<213> ORGANISM: Artificial Sequence
<220> FEATURE:
<223> OTHER INFORMATION: Synthetic

<400> SEQUENCE: 37
ataagtagta gtagtaatta cata                                              24

<210> SEQ ID NO 38
<211> LENGTH: 8
<212> TYPE: PRT
<213> ORGANISM: Artificial Sequence
<220> FEATURE:
<223> OTHER INFORMATION: Synthetic

<400> SEQUENCE: 38

Ile Ser Ser Ser Ser Asn Tyr Ile
1               5

<210> SEQ ID NO 39
<211> LENGTH: 33
<212> TYPE: DNA
<213> ORGANISM: Artificial Sequence
<220> FEATURE:
<223> OTHER INFORMATION: Synthetic

<400> SEQUENCE: 39
gcgagagtta attgggacta cccctttgac tgc                                    33

<210> SEQ ID NO 40
<211> LENGTH: 11
<212> TYPE: PRT
<213> ORGANISM: Artificial Sequence
<220> FEATURE:
<223> OTHER INFORMATION: Synthetic

<400> SEQUENCE: 40

Ala Arg Val Asn Trp Asp Tyr Pro Phe Asp Cys
1               5                   10

<210> SEQ ID NO 41
<211> LENGTH: 321
<212> TYPE: DNA
<213> ORGANISM: Artificial Sequence
<220> FEATURE:
<223> OTHER INFORMATION: Synthetic

<400> SEQUENCE: 41
gacatccaga tgacccagtc tccatcctcc ctgtctgcat ctgtaggaga cagagtcacc        60
atcacttgcc gggcgagtca ggacattaga cattatttag tctggtatca gcagaaacca      120
gggaaagttc ctaagctcct gatctatgct gcatccactt tgcaatcagg ggtcccatct      180
cggttcagtg gcagtggatc tgggacagat ttcattctca ccatcagcag cctgcagcct      240
gaagatgttg caactatta ctgtcaaaag tataacagtg ccccattcac tttcggccct      300
gggaccaaag tggatatcaa a                                                321

<210> SEQ ID NO 42
<211> LENGTH: 107
<212> TYPE: PRT
<213> ORGANISM: Artificial Sequence
<220> FEATURE:
<223> OTHER INFORMATION: Synthetic
```

-continued

<400> SEQUENCE: 42

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile Arg His Tyr
            20                  25                  30

Leu Val Trp Tyr Gln Gln Lys Pro Gly Lys Val Pro Lys Leu Leu Ile
        35                  40                  45

Tyr Ala Ala Ser Thr Leu Gln Ser Gly Val Pro Ser Arg Phe Ser Gly
50                  55                  60

Ser Gly Ser Gly Thr Asp Phe Ile Leu Thr Ile Ser Ser Leu Gln Pro
65                  70                  75                  80

Glu Asp Val Ala Thr Tyr Tyr Cys Gln Lys Tyr Asn Ser Ala Pro Phe
                85                  90                  95

Thr Phe Gly Pro Gly Thr Lys Val Asp Ile Lys
            100                 105

<210> SEQ ID NO 43
<211> LENGTH: 18
<212> TYPE: DNA
<213> ORGANISM: Artificial Sequence
<220> FEATURE:
<223> OTHER INFORMATION: Synthetic

<400> SEQUENCE: 43
caggacatta gacattat                                                   18

<210> SEQ ID NO 44
<211> LENGTH: 6
<212> TYPE: PRT
<213> ORGANISM: Artificial Sequence
<220> FEATURE:
<223> OTHER INFORMATION: Synthetic

<400> SEQUENCE: 44

Gln Asp Ile Arg His Tyr
1               5

<210> SEQ ID NO 45
<211> LENGTH: 9
<212> TYPE: DNA
<213> ORGANISM: Artificial Sequence
<220> FEATURE:
<223> OTHER INFORMATION: Synthetic

<400> SEQUENCE: 45 gctgcatcc                                                              9

<210> SEQ ID NO 46
<211> LENGTH: 3
<212> TYPE: PRT
<213> ORGANISM: Artificial Sequence
<220> FEATURE:
<223> OTHER INFORMATION: Synthetic

<400> SEQUENCE: 46

Ala Ala Ser
1

<210> SEQ ID NO 47
<211> LENGTH: 27
<212> TYPE: DNA
<213> ORGANISM: Artificial Sequence
<220> FEATURE:

<223> OTHER INFORMATION: Synthetic

<400> SEQUENCE: 47
caaaagtata acagtgcccc attcact                                               27

<210> SEQ ID NO 48
<211> LENGTH: 9
<212> TYPE: PRT
<213> ORGANISM: Artificial Sequence
<220> FEATURE:
<223> OTHER INFORMATION: Synthetic

<400> SEQUENCE: 48

Gln Lys Tyr Asn Ser Ala Pro Phe Thr
1               5

<210> SEQ ID NO 49
<211> LENGTH: 366
<212> TYPE: DNA
<213> ORGANISM: Artificial Sequence
<220> FEATURE:
<223> OTHER INFORMATION: Synthetic

<400> SEQUENCE: 49
gaggtgcagc tgttggagtc tgggggaggc ttggtacagc cggggggtc cctgagactc            60 tcctgtgcag cctctggatt cacctttagc agctatgtca tgaactgggt ccgccaggct          120
ccagggaagg ggctggagtg ggtctcagct attagcggaa gtggtggtag cacatactac          180
gcagactccg tgaagggccg gtccaccatc tccagagaca attccaagaa cacactgtat          240
ctgcaaatga atagcctgag agccgaggac acggccatat attattgtgc gaaaggggat          300
atagcagcaa ttgtctttga tgcttttgat atctggggcc aagggacagt ggtcaccgtc          360
tcttca                                                                    366

<210> SEQ ID NO 50
<211> LENGTH: 122
<212> TYPE: PRT
<213> ORGANISM: Artificial Sequence
<220> FEATURE:
<223> OTHER INFORMATION: Synthetic

<400> SEQUENCE: 50

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Val Met Asn Trp Val Arg Gln Ala Pro Gly Lys Gly Leu Glu Trp Val
        35                  40                  45

Ser Ala Ile Ser Gly Ser Gly Ser Thr Tyr Tyr Ala Asp Ser Val
    50                  55                  60

Lys Gly Arg Ser Thr Ile Ser Arg Asp Asn Ser Lys Asn Thr Leu Tyr
65                  70                  75                  80

Leu Gln Met Asn Ser Leu Arg Ala Glu Asp Thr Ala Ile Tyr Tyr Cys
                85                  90                  95

Ala Lys Gly Asp Ile Ala Ala Ile Val Phe Asp Ala Phe Asp Ile Trp
            100                 105                 110

Gly Gln Gly Thr Val Val Thr Val Ser Ser
        115                 120

<210> SEQ ID NO 51

```
<211> LENGTH: 24
<212> TYPE: DNA
<213> ORGANISM: Artificial Sequence
<220> FEATURE:
<223> OTHER INFORMATION: Synthetic

<400> SEQUENCE: 51
ggattcacct ttagcagcta tgtc                                    24

<210> SEQ ID NO 52
<211> LENGTH: 8
<212> TYPE: PRT
<213> ORGANISM: Artificial Sequence
<220> FEATURE:
<223> OTHER INFORMATION: Synthetic

<400> SEQUENCE: 52

Gly Phe Thr Phe Ser Ser Tyr Val
1               5

<210> SEQ ID NO 53
<211> LENGTH: 24
<212> TYPE: DNA
<213> ORGANISM: Artificial Sequence
<220> FEATURE:
<223> OTHER INFORMATION: Synthetic

<400> SEQUENCE: 53
attagcggaa gtggtggtag caca                                    24

<210> SEQ ID NO 54
<211> LENGTH: 8
<212> TYPE: PRT
<213> ORGANISM: Artificial Sequence
<220> FEATURE:
<223> OTHER INFORMATION: Synthetic

<400> SEQUENCE: 54

Ile Ser Gly Ser Gly Gly Ser Thr
1               5

<210> SEQ ID NO 55
<211> LENGTH: 45
<212> TYPE: DNA
<213> ORGANISM: Artificial Sequence
<220> FEATURE:
<223> OTHER INFORMATION: Synthetic

<400> SEQUENCE: 55
gcgaaagggg atatagcagc aattgtcttt gatgcttttg atatc              45

<210> SEQ ID NO 56
<211> LENGTH: 15
<212> TYPE: PRT
<213> ORGANISM: Artificial Sequence
<220> FEATURE:
<223> OTHER INFORMATION: Synthetic

<400> SEQUENCE: 56

Ala Lys Gly Asp Ile Ala Ala Ile Val Phe Asp Ala Phe Asp Ile
1               5                   10                  15

<210> SEQ ID NO 57
<211> LENGTH: 321
<212> TYPE: DNA
<213> ORGANISM: Artificial Sequence
<220> FEATURE:
```

<223> OTHER INFORMATION: Synthetic

<400> SEQUENCE: 57

```
gacatccaga tgacccagtc tccatcctcc ctgtctgcat ctgtaggaga cagagtcacc    60
atcacttgcc aggcgagtca ggacattagc agctgtttaa attggtatca acacaaacca   120
gggaaagccc ctaagctcct gatctacgat gcatcctatt tggaaacagg ggtcccatca   180
aggttcagtg aagtggatc tgggacagat tttactttca ccatcagcag cctgcagcct   240
gaagatattg caacatatta ctgtcaacag tatgataatc tcccgtacac ttttggccag   300
gggaccaagc tggagatcaa a                                             321
```

<210> SEQ ID NO 58
<211> LENGTH: 107
<212> TYPE: PRT
<213> ORGANISM: Artificial Sequence
<220> FEATURE:
<223> OTHER INFORMATION: Synthetic

<400> SEQUENCE: 58

```
Asp Ile Gln Met Thr Gln Ser Pro Ser Ser Leu Ser Ala Ser Val Gly
1               5                   10                  15
Asp Arg Val Thr Ile Thr Cys Gln Ala Ser Gln Asp Ile Ser Ser Cys
            20                  25                  30
Leu Asn Trp Tyr Gln His Lys Pro Gly Lys Ala Pro Lys Leu Leu Ile
        35                  40                  45
Tyr Asp Ala Ser Tyr Leu Glu Thr Gly Val Pro Ser Arg Phe Ser Gly
    50                  55                  60
Ser Gly Ser Gly Thr Asp Phe Thr Phe Thr Ile Ser Ser Leu Gln Pro
65                  70                  75                  80
Glu Asp Ile Ala Thr Tyr Tyr Cys Gln Gln Tyr Asp Asn Leu Pro Tyr
                85                  90                  95
Thr Phe Gly Gln Gly Thr Lys Leu Glu Ile Lys
            100                 105
```

<210> SEQ ID NO 59
<211> LENGTH: 18
<212> TYPE: DNA
<213> ORGANISM: Artificial Sequence
<220> FEATURE:
<223> OTHER INFORMATION: Synthetic

<400> SEQUENCE: 59

```
caggacatta gcagctgt                                                  18
```

<210> SEQ ID NO 60
<211> LENGTH: 6
<212> TYPE: PRT
<213> ORGANISM: Artificial Sequence
<220> FEATURE:
<223> OTHER INFORMATION: Synthetic

<400> SEQUENCE: 60

```
Gln Asp Ile Ser Ser Cys
1               5
```

<210> SEQ ID NO 61
<211> LENGTH: 9
<212> TYPE: DNA
<213> ORGANISM: Artificial Sequence
<220> FEATURE:
<223> OTHER INFORMATION: Synthetic -continued

<400> SEQUENCE: 61 gatgcatcc                                                                 9

<210> SEQ ID NO 62
<211> LENGTH: 3
<212> TYPE: PRT
<213> ORGANISM: Artificial Sequence
<220> FEATURE:
<223> OTHER INFORMATION: Synthetic

<400> SEQUENCE: 62

Asp Ala Ser
1

<210> SEQ ID NO 63
<211> LENGTH: 27
<212> TYPE: DNA
<213> ORGANISM: Artificial Sequence
<220> FEATURE:
<223> OTHER INFORMATION: Synthetic

<400> SEQUENCE: 63
caacagtatg ataatctccc gtacact                                            27

<210> SEQ ID NO 64
<211> LENGTH: 9
<212> TYPE: PRT
<213> ORGANISM: Artificial Sequence
<220> FEATURE:
<223> OTHER INFORMATION: Synthetic

<400> SEQUENCE: 64

Gln Gln Tyr Asp Asn Leu Pro Tyr Thr
1               5

<210> SEQ ID NO 65
<211> LENGTH: 366
<212> TYPE: DNA
<213> ORGANISM: Artificial Sequence
<220> FEATURE:
<223> OTHER INFORMATION: Synthetic

<400> SEQUENCE: 65
gaggtgcagc tgttggagtc tggggggaggc ttggtacagc cggggggggtc cctgagactc      60 tcctgtgcag cctctggatt cacctttagc agctatgtca tgaactgggt ccgccaggct     120
ccagggaagg ggctggagtg ggtctcagct attagcggaa gtggtggtag cacatactac     180
gcagactccg tgaagggccg gtccaccatc tccagagaca attccaagaa cacactgtat     240
ctgcaaatga atagcctgag agccgaggac acggccatat attattgtgc gaaaggggat     300
atagcagcaa ttgtctttga tgcttttgat atctggggcc aagggacagt ggtcaccgtc     360
tcttca                                                                366

<210> SEQ ID NO 66
<211> LENGTH: 122
<212> TYPE: PRT
<213> ORGANISM: Artificial Sequence
<220> FEATURE:
<223> OTHER INFORMATION: Synthetic

<400> SEQUENCE: 66

Glu Val Gln Leu Leu Glu Ser Gly Gly Gly Leu Val Gln Pro Gly Gly
1               5                   10                  15

```
Ser Leu Arg Leu Ser Cys Ala Ala Ser Gly Phe Thr Phe Ser Ser Tyr
         20                  25                  30

Val Met Asn Trp Val Arg Gln Ala Pro Gly Lys Gly Leu Glu Trp Val
         35                  40                  45

Ser Ala Ile Ser Gly Ser Gly Gly Ser Thr Tyr Tyr Ala Asp Ser Val
         50                  55                  60

Lys Gly Arg Ser Thr Ile Ser Arg Asp Asn Ser Lys Asn Thr Leu Tyr
65                   70                  75                  80

Leu Gln Met Asn Ser Leu Arg Ala Glu Asp Thr Ala Ile Tyr Tyr Cys
                 85                  90                  95

Ala Lys Gly Asp Ile Ala Ala Ile Val Phe Asp Ala Phe Asp Ile Trp
            100                 105                 110

Gly Gln Gly Thr Val Val Thr Val Ser Ser
        115                 120
```

<210> SEQ ID NO 67
<211> LENGTH: 24
<212> TYPE: DNA
<213> ORGANISM: Artificial Sequence
<220> FEATURE:
<223> OTHER INFORMATION: Synthetic

<400> SEQUENCE: 67
ggattcacct ttagcagcta tgtc          24

<210> SEQ ID NO 68
<211> LENGTH: 8
<212> TYPE: PRT
<213> ORGANISM: Artificial Sequence
<220> FEATURE:
<223> OTHER INFORMATION: Synthetic

<400> SEQUENCE: 68

```
Gly Phe Thr Phe Ser Ser Tyr Val
1               5
```

<210> SEQ ID NO 69
<211> LENGTH: 24
<212> TYPE: DNA
<213> ORGANISM: Artificial Sequence
<220> FEATURE:
<223> OTHER INFORMATION: Synthetic

<400> SEQUENCE: 69
attagcggaa gtggtggtag caca          24

<210> SEQ ID NO 70
<211> LENGTH: 8
<212> TYPE: PRT
<213> ORGANISM: Artificial Sequence
<220> FEATURE:
<223> OTHER INFORMATION: Synthetic

<400> SEQUENCE: 70

```
Ile Ser Gly Ser Gly Gly Ser Thr
1               5
```

<210> SEQ ID NO 71
<211> LENGTH: 45
<212> TYPE: DNA
<213> ORGANISM: Artificial Sequence
<220> FEATURE:
<223> OTHER INFORMATION: Synthetic

<400> SEQUENCE: 71
gcgaaagggg atatagcagc aattgtcttt gatgcttttg atatc    45

<210> SEQ ID NO 72
<211> LENGTH: 15
<212> TYPE: PRT
<213> ORGANISM: Artificial Sequence
<220> FEATURE:
<223> OTHER INFORMATION: Synthetic

<400> SEQUENCE: 72

Ala Lys Gly Asp Ile Ala Ala Ile Val Phe Asp Ala Phe Asp Ile
1               5                   10                  15

<210> SEQ ID NO 73
<211> LENGTH: 321
<212> TYPE: DNA
<213> ORGANISM: Artificial Sequence
<220> FEATURE:
<223> OTHER INFORMATION: Synthetic

<400> SEQUENCE: 73
gacatccaga tgacccagtc tccatcctcc ctgtctgcat ctgtaggaga cagagtcacc    60
atcacttgcc aggcgagtca ggacattagc agcgctttaa attggtatca acacaaacca   120
gggaaagccc ctaagctcct gatctacgat gcatcctatt tggaaacagg ggtcccatca   180
aggttcagtg aagtggatc tgggacagat tttactttca ccatcagcag cctgcagcct    240
gaagatattg caacatatta ctgtcaacag tatgataatc tcccgtacac ttttggccag   300
gggaccaagc tggagatcaa a                                             321

<210> SEQ ID NO 74
<211> LENGTH: 107
<212> TYPE: PRT
<213> ORGANISM: Artificial Sequence
<220> FEATURE:
<223> OTHER INFORMATION: Synthetic

<400> SEQUENCE: 74

Asp Ile Gln Met Thr Gln Ser Pro Ser Ser Leu Ser Ala Ser Val Gly
1               5                   10                  15

Asp Arg Val Thr Ile Thr Cys Gln Ala Ser Gln Asp Ile Ser Ser Ala
            20                  25                  30

Leu Asn Trp Tyr Gln His Lys Pro Gly Lys Ala Pro Lys Leu Leu Ile
        35                  40                  45

Tyr Asp Ala Ser Tyr Leu Glu Thr Gly Val Pro Ser Arg Phe Ser Gly
    50                  55                  60

Ser Gly Ser Gly Thr Asp Phe Thr Phe Thr Ile Ser Ser Leu Gln Pro
65                  70                  75                  80

Glu Asp Ile Ala Thr Tyr Tyr Cys Gln Gln Tyr Asp Asn Leu Pro Tyr
                85                  90                  95

Thr Phe Gly Gln Gly Thr Lys Leu Glu Ile Lys
            100                 105

<210> SEQ ID NO 75
<211> LENGTH: 18
<212> TYPE: DNA
<213> ORGANISM: Artificial Sequence
<220> FEATURE:
<223> OTHER INFORMATION: Synthetic

<400> SEQUENCE: 75
caggacatta gcagcgct                                                    18

<210> SEQ ID NO 76
<211> LENGTH: 6
<212> TYPE: PRT
<213> ORGANISM: Artificial Sequence
<220> FEATURE:
<223> OTHER INFORMATION: Synthetic

<400> SEQUENCE: 76

Gln Asp Ile Ser Ser Ala
1               5

<210> SEQ ID NO 77
<211> LENGTH: 9
<212> TYPE: DNA
<213> ORGANISM: Artificial Sequence
<220> FEATURE:
<223> OTHER INFORMATION: Synthetic

<400> SEQUENCE: 77 gatgcatcc                                                               9

<210> SEQ ID NO 78
<211> LENGTH: 3
<212> TYPE: PRT
<213> ORGANISM: Artificial Sequence
<220> FEATURE:
<223> OTHER INFORMATION: Synthetic

<400> SEQUENCE: 78

Asp Ala Ser
1

<210> SEQ ID NO 79
<211> LENGTH: 27
<212> TYPE: DNA
<213> ORGANISM: Artificial Sequence
<220> FEATURE:
<223> OTHER INFORMATION: Synthetic

<400> SEQUENCE: 79
caacagtatg ataatctccc gtacact                                          27

<210> SEQ ID NO 80
<211> LENGTH: 9
<212> TYPE: PRT
<213> ORGANISM: Artificial Sequence
<220> FEATURE:
<223> OTHER INFORMATION: Synthetic

<400> SEQUENCE: 80

Gln Gln Tyr Asp Asn Leu Pro Tyr Thr
1               5

<210> SEQ ID NO 81
<211> LENGTH: 348
<212> TYPE: DNA
<213> ORGANISM: Artificial Sequence
<220> FEATURE:
<223> OTHER INFORMATION: Synthetic

<400> SEQUENCE: 81
caggtgcagc tggtggagtc tgggggaggc gtggtccagc ctggggaggtc cctgagactc     60

```
tcctgtgcag cgtctggatt caccttcagt agctatggca tgcactgggt ccgccaggct    120
ccaggcaagg ggctggagtg ggtgacaatt atatggcatg atggaagtaa taaatactat    180
gcagactccg tgaagggccg attcaccatc tccagagaca attccaagaa cacgctgtat    240
ctgcaaatga acagtgtgag agccgaggac acggctgtgt attactgtgc gagagacgaa    300
gatttttttg actactgggg ccagggaacc ctggtcaccg tctcctca                 348
```

```
<210> SEQ ID NO 82
<211> LENGTH: 116
<212> TYPE: PRT
<213> ORGANISM: Artificial Sequence
<220> FEATURE:
<223> OTHER INFORMATION: Synthetic

<400> SEQUENCE: 82
```

```
Gln Val Gln Leu Val Glu Ser Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Thr Ile Ile Trp His Asp Gly Ser Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Val Arg Ala Glu Asp Thr Ala Val Tyr Tyr Cys
                85                  90                  95

Ala Arg Asp Glu Asp Phe Phe Asp Tyr Trp Gly Gln Gly Thr Leu Val
            100                 105                 110

Thr Val Ser Ser
        115
```

```
<210> SEQ ID NO 83
<211> LENGTH: 24
<212> TYPE: DNA
<213> ORGANISM: Artificial Sequence
<220> FEATURE:
<223> OTHER INFORMATION: Synthetic

<400> SEQUENCE: 83
ggattcacct tcagtagcta tggc                                             24
```

```
<210> SEQ ID NO 84
<211> LENGTH: 8
<212> TYPE: PRT
<213> ORGANISM: Artificial Sequence
<220> FEATURE:
<223> OTHER INFORMATION: Synthetic

<400> SEQUENCE: 84
```

```
Gly Phe Thr Phe Ser Ser Tyr Gly
1               5
```

```
<210> SEQ ID NO 85
<211> LENGTH: 24
<212> TYPE: DNA
<213> ORGANISM: Artificial Sequence
<220> FEATURE:
<223> OTHER INFORMATION: Synthetic

<400> SEQUENCE: 85
```
atatggcatg atggaagtaa taaa                                              24

<210> SEQ ID NO 86
<211> LENGTH: 8
<212> TYPE: PRT
<213> ORGANISM: Artificial Sequence
<220> FEATURE:
<223> OTHER INFORMATION: Synthetic

<400> SEQUENCE: 86

Ile Trp His Asp Gly Ser Asn Lys
1               5

<210> SEQ ID NO 87
<211> LENGTH: 27
<212> TYPE: DNA
<213> ORGANISM: Artificial Sequence
<220> FEATURE:
<223> OTHER INFORMATION: Synthetic

<400> SEQUENCE: 87
gcgagagacg aagattttt tgactac                                            27

<210> SEQ ID NO 88
<211> LENGTH: 9
<212> TYPE: PRT
<213> ORGANISM: Artificial Sequence
<220> FEATURE:
<223> OTHER INFORMATION: Synthetic

<400> SEQUENCE: 88

Ala Arg Asp Glu Asp Phe Phe Asp Tyr
1               5

<210> SEQ ID NO 89
<211> LENGTH: 324
<212> TYPE: DNA
<213> ORGANISM: Artificial Sequence
<220> FEATURE:
<223> OTHER INFORMATION: Synthetic

<400> SEQUENCE: 89
gaaattgtga tgacgcagtc tccagccacc ctgtctgtgt ctccagggga aaaagccacc        60
ctctcctgca gggccagtca gagtgttagt atcaacttag cctggtacca acagaaacct       120
ggccaggctc ccaggctcct catctatgat gcatccacca gggccactgg tatcccagcc       180
aggttcagtg gcagtgggtc tgggacagag ttcactctca ccatcagcag cctgcagtct       240
gaagattttg cagtttatta ctgtcagcag tataataact ggcctccgta cactttggc       300 caggggacta agctggagat caaa                                             324

<210> SEQ ID NO 90
<211> LENGTH: 108
<212> TYPE: PRT
<213> ORGANISM: Artificial Sequence
<220> FEATURE:
<223> OTHER INFORMATION: Synthetic

<400> SEQUENCE: 90

Glu Ile Val Met Thr Gln Ser Pro Ala Thr Leu Ser Val Ser Pro Gly
1               5                   10                  15

Glu Lys Ala Thr Leu Ser Cys Arg Ala Ser Gln Ser Val Ser Ile Asn
            20                  25                  30

Leu Ala Trp Tyr Gln Gln Lys Pro Gly Gln Ala Pro Arg Leu Leu Ile

```
                35                  40                  45
Tyr Asp Ala Ser Thr Arg Ala Thr Gly Ile Pro Ala Arg Phe Ser Gly
     50                  55                  60

Ser Gly Ser Gly Thr Glu Phe Thr Leu Thr Ile Ser Ser Leu Gln Ser
 65                  70                  75                  80

Glu Asp Phe Ala Val Tyr Tyr Cys Gln Gln Tyr Asn Asn Trp Pro Pro
                 85                  90                  95

Tyr Thr Phe Gly Gln Gly Thr Lys Leu Glu Ile Lys
            100                 105
```

<210> SEQ ID NO 91
<211> LENGTH: 18
<212> TYPE: DNA
<213> ORGANISM: Artificial Sequence
<220> FEATURE:
<223> OTHER INFORMATION: Synthetic

<400> SEQUENCE: 91
cagagtgtta gtatcaac                                            18

<210> SEQ ID NO 92
<211> LENGTH: 6
<212> TYPE: PRT
<213> ORGANISM: Artificial Sequence
<220> FEATURE:
<223> OTHER INFORMATION: Synthetic

<400> SEQUENCE: 92

Gln Ser Val Ser Ile Asn
1               5

<210> SEQ ID NO 93
<211> LENGTH: 9
<212> TYPE: DNA
<213> ORGANISM: Artificial Sequence
<220> FEATURE:
<223> OTHER INFORMATION: Synthetic

<400> SEQUENCE: 93 gatgcatcc                                                       9

<210> SEQ ID NO 94
<211> LENGTH: 3
<212> TYPE: PRT
<213> ORGANISM: Artificial Sequence
<220> FEATURE:
<223> OTHER INFORMATION: Synthetic

<400> SEQUENCE: 94

Asp Ala Ser
1

<210> SEQ ID NO 95
<211> LENGTH: 30
<212> TYPE: DNA
<213> ORGANISM: Artificial Sequence
<220> FEATURE:
<223> OTHER INFORMATION: Synthetic

<400> SEQUENCE: 95
cagcagtata taactggcc tccgtacact                                30

<210> SEQ ID NO 96
<211> LENGTH: 10

```
<212> TYPE: PRT
<213> ORGANISM: Artificial Sequence
<220> FEATURE:
<223> OTHER INFORMATION: Synthetic

<400> SEQUENCE: 96

Gln Gln Tyr Asn Asn Trp Pro Pro Tyr Thr
1               5                   10

<210> SEQ ID NO 97
<211> LENGTH: 366
<212> TYPE: DNA
<213> ORGANISM: Artificial Sequence
<220> FEATURE:
<223> OTHER INFORMATION: Synthetic

<400> SEQUENCE: 97
gaggtgcagc tgttggagtc tgggggaggc ttggtacagc cggggggggtc cctgagactc      60 tcctgtgcag cctctggatt cacctttagc agctatgtca tgaactgggt ccgccaggct     120
ccagggaagg ggctggagtg ggtctcagct attagcggaa gtggtggtag cacatcctac     180
gcagactccg tgaagggccg gtccaccatc tccagagaca attccaagaa cacactgtat     240
ctgcaaatga atagcctgag agccgaggac acggccgtat attattgtgc gaaaggggat     300
atagcagcaa ttgttttttga tgcttttgat atctggggcc aagggacaat ggtcaccgtc     360
tcttca                                                                366

<210> SEQ ID NO 98
<211> LENGTH: 122
<212> TYPE: PRT
<213> ORGANISM: Artificial Sequence
<220> FEATURE:
<223> OTHER INFORMATION: Synthetic

<400> SEQUENCE: 98

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Val Met Asn Trp Val Arg Gln Ala Pro Gly Lys Gly Leu Glu Trp Val
        35                  40                  45

Ser Ala Ile Ser Gly Ser Gly Gly Ser Thr Ser Tyr Ala Asp Ser Val
    50                  55                  60

Lys Gly Arg Ser Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Gly Asp Ile Ala Ala Ile Val Phe Asp Ala Phe Asp Ile Trp
            100                 105                 110

Gly Gln Gly Thr Met Val Thr Val Ser Ser
        115                 120

<210> SEQ ID NO 99
<211> LENGTH: 24
<212> TYPE: DNA
<213> ORGANISM: Artificial Sequence
<220> FEATURE:
<223> OTHER INFORMATION: Synthetic

<400> SEQUENCE: 99
ggattcacct ttagcagcta tgtc                                              24
```

<210> SEQ ID NO 100
<211> LENGTH: 8
<212> TYPE: PRT
<213> ORGANISM: Artificial Sequence
<220> FEATURE:
<223> OTHER INFORMATION: Synthetic

<400> SEQUENCE: 100

Gly Phe Thr Phe Ser Ser Tyr Val
1               5

<210> SEQ ID NO 101
<211> LENGTH: 24
<212> TYPE: DNA
<213> ORGANISM: Artificial Sequence
<220> FEATURE:
<223> OTHER INFORMATION: Synthetic

<400> SEQUENCE: 101
attagcggaa gtggtggtag caca                                          24

<210> SEQ ID NO 102
<211> LENGTH: 8
<212> TYPE: PRT
<213> ORGANISM: Artificial Sequence
<220> FEATURE:
<223> OTHER INFORMATION: Synthetic

<400> SEQUENCE: 102

Ile Ser Gly Ser Gly Gly Ser Thr
1               5

<210> SEQ ID NO 103
<211> LENGTH: 45
<212> TYPE: DNA
<213> ORGANISM: Artificial Sequence
<220> FEATURE:
<223> OTHER INFORMATION: Synthetic

<400> SEQUENCE: 103
gcgaaagggg atatagcagc aattgttttt gatgcttttg atatc                   45

<210> SEQ ID NO 104
<211> LENGTH: 15
<212> TYPE: PRT
<213> ORGANISM: Artificial Sequence
<220> FEATURE:
<223> OTHER INFORMATION: Synthetic

<400> SEQUENCE: 104

Ala Lys Gly Asp Ile Ala Ala Ile Val Phe Asp Ala Phe Asp Ile
1               5                   10                  15

<210> SEQ ID NO 105
<211> LENGTH: 321
<212> TYPE: DNA
<213> ORGANISM: Artificial Sequence
<220> FEATURE:
<223> OTHER INFORMATION: Synthetic

<400> SEQUENCE: 105
gacatccaga tgacccagtc tccatcctcc ctgtctgcat ctgtaggaga cagagtcacc    60
atcacttgcc aggcgagtca ggacattagc aactgtttaa attggtatca acacaaacca   120
gggaaagccc ctaagctcct gatctacgat gcatcctatt tggaaacagg ggcccatca   180 aggttcagtg gaagtggatc tgggacagat tttactttca ccatcagaag cctgcagcct        240
gaagattttg caacatatta ctgtcaacag tatgataatc tcccgtacac ttttggccag        300
gggaccaagc tggagatcaa a        321

<210> SEQ ID NO 106
<211> LENGTH: 107
<212> TYPE: PRT
<213> ORGANISM: Artificial Sequence
<220> FEATURE:
<223> OTHER INFORMATION: Synthetic

<400> SEQUENCE: 106

Asp Ile Gln Met Thr Gln Ser Pro Ser Ser Leu Ser Ala Ser Val Gly
1               5                   10                  15

Asp Arg Val Thr Ile Thr Cys Gln Ala Ser Gln Asp Ile Ser Asn Cys
            20                  25                  30

Leu Asn Trp Tyr Gln His Lys Pro Gly Lys Ala Pro Lys Leu Leu Ile
        35                  40                  45

Tyr Asp Ala Ser Tyr Leu Glu Thr Gly Gly Pro Ser Arg Phe Ser Gly
    50                  55                  60

Ser Gly Ser Gly Thr Asp Phe Thr Phe Thr Ile Arg Ser Leu Gln Pro
65                  70                  75                  80

Glu Asp Phe Ala Thr Tyr Tyr Cys Gln Gln Tyr Asp Asn Leu Pro Tyr
                85                  90                  95

Thr Phe Gly Gln Gly Thr Lys Leu Glu Ile Lys
                100                 105

<210> SEQ ID NO 107
<211> LENGTH: 18
<212> TYPE: DNA
<213> ORGANISM: Artificial Sequence
<220> FEATURE:
<223> OTHER INFORMATION: Synthetic

<400> SEQUENCE: 107
caggacatta gcaactgt        18

<210> SEQ ID NO 108
<211> LENGTH: 6
<212> TYPE: PRT
<213> ORGANISM: Artificial Sequence
<220> FEATURE:
<223> OTHER INFORMATION: Synthetic

<400> SEQUENCE: 108

Gln Asp Ile Ser Asn Cys
1               5

<210> SEQ ID NO 109
<211> LENGTH: 9
<212> TYPE: DNA
<213> ORGANISM: Artificial Sequence
<220> FEATURE:
<223> OTHER INFORMATION: Synthetic

<400> SEQUENCE: 109 gatgcatcc        9

<210> SEQ ID NO 110
<211> LENGTH: 3
<212> TYPE: PRT

```
<213> ORGANISM: Artificial Sequence
<220> FEATURE:
<223> OTHER INFORMATION: Synthetic

<400> SEQUENCE: 110

Asp Ala Ser
1

<210> SEQ ID NO 111
<211> LENGTH: 27
<212> TYPE: DNA
<213> ORGANISM: Artificial Sequence
<220> FEATURE:
<223> OTHER INFORMATION: Synthetic

<400> SEQUENCE: 111
caacagtatg ataatctccc gtacact                                           27

<210> SEQ ID NO 112
<211> LENGTH: 9
<212> TYPE: PRT
<213> ORGANISM: Artificial Sequence
<220> FEATURE:
<223> OTHER INFORMATION: Synthetic

<400> SEQUENCE: 112

Gln Gln Tyr Asp Asn Leu Pro Tyr Thr
1               5

<210> SEQ ID NO 113
<211> LENGTH: 366
<212> TYPE: DNA
<213> ORGANISM: Artificial Sequence
<220> FEATURE:
<223> OTHER INFORMATION: Synthetic

<400> SEQUENCE: 113
gaggtgcact tgttggagtc tgggggaggc ttggtacagc cggggggtc cctgagactc         60 tcctgtgcag cctctggatt cacctttagc agctatgtca tgaactgggt ccgccaggct       120
ccagggaagg ggctggagtg gtctcagct attagcggaa gtggtggtag cacatactac        180
ggagactccg tgaagggccg gtccaccatc tccagagaca attccaagaa cacactgtat       240
ctgcaaatga aagcctgag agccgaggac acggccgtat attattgtgc gaaaggggat       300
atagcaccaa ttgtctttga tgcttttgat atctggggcc aagggacaat ggtcaccgtc      360
tcttca                                                                 366

<210> SEQ ID NO 114
<211> LENGTH: 122
<212> TYPE: PRT
<213> ORGANISM: Artificial Sequence
<220> FEATURE:
<223> OTHER INFORMATION: Synthetic

<400> SEQUENCE: 114

Glu Val His Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Val Met Asn Trp Val Arg Gln Ala Pro Gly Lys Gly Leu Glu Trp Val
        35                  40                  45

Ser Ala Ile Ser Gly Ser Gly Gly Ser Thr Tyr Tyr Gly Asp Ser Val
    50                  55                  60
```

```
Lys Gly Arg Ser Thr Ile Ser Arg Asp Asn Ser Lys Asn Thr Leu Tyr
 65                  70                  75                  80

Leu Gln Met Lys Ser Leu Arg Ala Glu Asp Thr Ala Val Tyr Tyr Cys
                 85                  90                  95

Ala Lys Gly Asp Ile Ala Pro Ile Val Phe Asp Ala Phe Asp Ile Trp
            100                 105                 110

Gly Gln Gly Thr Met Val Thr Val Ser Ser
        115                 120
```

<210> SEQ ID NO 115
<211> LENGTH: 24
<212> TYPE: DNA
<213> ORGANISM: Artificial Sequence
<220> FEATURE:
<223> OTHER INFORMATION: Synthetic

<400> SEQUENCE: 115
ggattcacct ttagcagcta tgtc                                          24

<210> SEQ ID NO 116
<211> LENGTH: 8
<212> TYPE: PRT
<213> ORGANISM: Artificial Sequence
<220> FEATURE:
<223> OTHER INFORMATION: Synthetic

<400> SEQUENCE: 116

```
Gly Phe Thr Phe Ser Ser Tyr Val
 1               5
```

<210> SEQ ID NO 117
<211> LENGTH: 24
<212> TYPE: DNA
<213> ORGANISM: Artificial Sequence
<220> FEATURE:
<223> OTHER INFORMATION: Synthetic

<400> SEQUENCE: 117
attagcggaa gtggtggtag caca                                          24

<210> SEQ ID NO 118
<211> LENGTH: 8
<212> TYPE: PRT
<213> ORGANISM: Artificial Sequence
<220> FEATURE:
<223> OTHER INFORMATION: Synthetic

<400> SEQUENCE: 118

```
Ile Ser Gly Ser Gly Gly Ser Thr
 1               5
```

<210> SEQ ID NO 119
<211> LENGTH: 45
<212> TYPE: DNA
<213> ORGANISM: Artificial Sequence
<220> FEATURE:
<223> OTHER INFORMATION: Synthetic

<400> SEQUENCE: 119
gcgaaagggg atatagcacc aattgtcttt gatgcttttg atatc                   45

<210> SEQ ID NO 120
<211> LENGTH: 15
<212> TYPE: PRT

<213> ORGANISM: Artificial Sequence
<220> FEATURE:
<223> OTHER INFORMATION: Synthetic

<400> SEQUENCE: 120

| Ala | Lys | Gly | Asp | Ile | Ala | Pro | Ile | Val | Phe | Asp | Ala | Phe | Asp | Ile |
|-----|-----|-----|-----|-----|-----|-----|-----|-----|-----|-----|-----|-----|-----|-----|
| 1   |     |     |     | 5   |     |     |     |     | 10  |     |     |     |     | 15  |

<210> SEQ ID NO 121
<211> LENGTH: 321
<212> TYPE: DNA
<213> ORGANISM: Artificial Sequence
<220> FEATURE:
<223> OTHER INFORMATION: Synthetic

<400> SEQUENCE: 121

```
gacatccaga tgacccagtc tccatcctcc ctgtctgcat ctgtaggaga cagagtcacc    60
atcacttgcc aggcgagtca ggacattagc aactgtttaa attggtatca acacaaacca   120
gggaaagccc ctaaactcct gatctacgat gcatcctatt tggaaacagg ggtcccatca   180
aggttcagtg aagtggatc  tgggacagat tttactttca ccatcagcag cctgcagcct   240
gaagatattg caacatatta ctgtcaacag tatgataatc tcccgtacac ttttggccag   300
gggaccaagc tggagatcaa a                                              321
```

<210> SEQ ID NO 122
<211> LENGTH: 107
<212> TYPE: PRT
<213> ORGANISM: Artificial Sequence
<220> FEATURE:
<223> OTHER INFORMATION: Synthetic

<400> SEQUENCE: 122

| Asp | Ile | Gln | Met | Thr | Gln | Ser | Pro | Ser | Ser | Leu | Ser | Ala | Ser | Val | Gly |
|-----|-----|-----|-----|-----|-----|-----|-----|-----|-----|-----|-----|-----|-----|-----|-----|
| 1   |     |     |     | 5   |     |     |     |     | 10  |     |     |     |     | 15  |     |

| Asp | Arg | Val | Thr | Ile | Thr | Cys | Gln | Ala | Ser | Gln | Asp | Ile | Ser | Asn | Cys |
|-----|-----|-----|-----|-----|-----|-----|-----|-----|-----|-----|-----|-----|-----|-----|-----|
|     |     |     | 20  |     |     |     |     | 25  |     |     |     |     | 30  |     |     |

| Leu | Asn | Trp | Tyr | Gln | His | Lys | Pro | Gly | Lys | Ala | Pro | Lys | Leu | Leu | Ile |
|-----|-----|-----|-----|-----|-----|-----|-----|-----|-----|-----|-----|-----|-----|-----|-----|
|     |     |     | 35  |     |     |     |     | 40  |     |     |     |     | 45  |     |     |

| Tyr | Asp | Ala | Ser | Tyr | Leu | Glu | Thr | Gly | Val | Pro | Ser | Arg | Phe | Ser | Gly |
|-----|-----|-----|-----|-----|-----|-----|-----|-----|-----|-----|-----|-----|-----|-----|-----|
|     | 50  |     |     |     |     | 55  |     |     |     |     | 60  |     |     |     |     |

| Ser | Gly | Ser | Gly | Thr | Asp | Phe | Thr | Phe | Thr | Ile | Ser | Ser | Leu | Gln | Pro |
|-----|-----|-----|-----|-----|-----|-----|-----|-----|-----|-----|-----|-----|-----|-----|-----|
| 65  |     |     |     |     | 70  |     |     |     |     | 75  |     |     |     |     | 80  |

| Glu | Asp | Ile | Ala | Thr | Tyr | Tyr | Cys | Gln | Gln | Tyr | Asp | Asn | Leu | Pro | Tyr |
|-----|-----|-----|-----|-----|-----|-----|-----|-----|-----|-----|-----|-----|-----|-----|-----|
|     |     |     |     | 85  |     |     |     |     | 90  |     |     |     |     | 95  |     |

| Thr | Phe | Gly | Gln | Gly | Thr | Lys | Leu | Glu | Ile | Lys |
|-----|-----|-----|-----|-----|-----|-----|-----|-----|-----|-----|
|     |     |     | 100 |     |     |     |     | 105 |     |     |

<210> SEQ ID NO 123
<211> LENGTH: 18
<212> TYPE: DNA
<213> ORGANISM: Artificial Sequence
<220> FEATURE:
<223> OTHER INFORMATION: Synthetic

<400> SEQUENCE: 123

```
caggacatta gcaactgt                                                   18
```

<210> SEQ ID NO 124
<211> LENGTH: 6
<212> TYPE: PRT
<213> ORGANISM: Artificial Sequence
<220> FEATURE:
<223> OTHER INFORMATION: Synthetic

<400> SEQUENCE: 124

Gln Asp Ile Ser Asn Cys
1               5

<210> SEQ ID NO 125
<211> LENGTH: 9
<212> TYPE: DNA
<213> ORGANISM: Artificial Sequence
<220> FEATURE:
<223> OTHER INFORMATION: Synthetic

<400> SEQUENCE: 125 gatgcatcc                                                                   9

<210> SEQ ID NO 126
<211> LENGTH: 3
<212> TYPE: PRT
<213> ORGANISM: Artificial Sequence
<220> FEATURE:
<223> OTHER INFORMATION: Synthetic

<400> SEQUENCE: 126

Asp Ala Ser
1

<210> SEQ ID NO 127
<211> LENGTH: 27
<212> TYPE: DNA
<213> ORGANISM: Artificial Sequence
<220> FEATURE:
<223> OTHER INFORMATION: Synthetic

<400> SEQUENCE: 127
caacagtatg ataatctccc gtacact                                              27

<210> SEQ ID NO 128
<211> LENGTH: 9
<212> TYPE: PRT
<213> ORGANISM: Artificial Sequence
<220> FEATURE:
<223> OTHER INFORMATION: Synthetic

<400> SEQUENCE: 128

Gln Gln Tyr Asp Asn Leu Pro Tyr Thr
1               5

<210> SEQ ID NO 129
<211> LENGTH: 372
<212> TYPE: DNA
<213> ORGANISM: Artificial Sequence
<220> FEATURE:
<223> OTHER INFORMATION: Synthetic

<400> SEQUENCE: 129
caggtgcagc tgcaggagtc gggcccagga ctggtgaagc cttcggagac cctgtccctc      60
acctgcactg tctctggtgg ctccatcagt aattcctact ggagctggat ccggcagccc     120
ccagggaagg gactggagtg gattgggtat atctattaca gtgggaacac caactacaac     180
ccctccctca agagtcgagt caccatatca gtggacacgt ccaagaacca gttctccctg     240
aagctgagct ctgtgaccgc cgcagacacg gccgtgtatt actgtgcgag agtcaatgac     300
tacagtaatt atgactccta ctattacggt atggacgtct ggggccaagg gaccacggtc     360
accgtctcct ca                                                        372

<210> SEQ ID NO 130
<211> LENGTH: 124
<212> TYPE: PRT
<213> ORGANISM: Artificial Sequence
<220> FEATURE:
<223> OTHER INFORMATION: Synthetic

<400> SEQUENCE: 130

Gln Val Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Ser Asn Ser
            20                  25                  30

Tyr Trp Ser Trp Ile Arg Gln Pro Pro Gly Lys Gly Leu Glu Trp Ile
        35                  40                  45

Gly Tyr Ile Tyr Tyr Ser Gly Asn Thr Asn Tyr Asn Pro Ser Leu Lys
    50                  55                  60

Ser Arg Val Thr Ile Ser Val Asp Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95

Arg Val Asn Asp Tyr Ser Asn Tyr Asp Ser Tyr Tyr Tyr Gly Met Asp
            100                 105                 110

Val Trp Gly Gln Gly Thr Thr Val Thr Val Ser Ser
        115                 120

<210> SEQ ID NO 131
<211> LENGTH: 24
<212> TYPE: DNA
<213> ORGANISM: Artificial Sequence
<220> FEATURE:
<223> OTHER INFORMATION: Synthetic

<400> SEQUENCE: 131
ggtggctcca tcagtaattc ctac                                            24

<210> SEQ ID NO 132
<211> LENGTH: 8
<212> TYPE: PRT
<213> ORGANISM: Artificial Sequence
<220> FEATURE:
<223> OTHER INFORMATION: Synthetic

<400> SEQUENCE: 132

Gly Gly Ser Ile Ser Asn Ser Tyr
1               5

<210> SEQ ID NO 133
<211> LENGTH: 21
<212> TYPE: DNA
<213> ORGANISM: Artificial Sequence
<220> FEATURE:
<223> OTHER INFORMATION: Synthetic

<400> SEQUENCE: 133
atctattaca gtgggaacac c                                               21

<210> SEQ ID NO 134
<211> LENGTH: 7
<212> TYPE: PRT
<213> ORGANISM: Artificial Sequence

```
<220> FEATURE:
<223> OTHER INFORMATION: Synthetic

<400> SEQUENCE: 134

Ile Tyr Tyr Ser Gly Asn Thr
1               5

<210> SEQ ID NO 135
<211> LENGTH: 54
<212> TYPE: DNA
<213> ORGANISM: Artificial Sequence
<220> FEATURE:
<223> OTHER INFORMATION: Synthetic

<400> SEQUENCE: 135
gcgagagtca atgactacag taattatgac tcctactatt acggtatgga cgtc         54

<210> SEQ ID NO 136
<211> LENGTH: 18
<212> TYPE: PRT
<213> ORGANISM: Artificial Sequence
<220> FEATURE:
<223> OTHER INFORMATION: Synthetic

<400> SEQUENCE: 136

Ala Arg Val Asn Asp Tyr Ser Asn Tyr Asp Ser Tyr Tyr Gly Met
1               5                   10                  15

Asp Val

<210> SEQ ID NO 137
<211> LENGTH: 321
<212> TYPE: DNA
<213> ORGANISM: Artificial Sequence
<220> FEATURE:
<223> OTHER INFORMATION: Synthetic

<400> SEQUENCE: 137
gccatccaga tgacccagtc tccatcctcc ctgtctgcat ctgtgggaga cagagtcacc    60
atcacttgcc gggcaagtca gggcattaga aatgatttag ctggtatca gcagaaacca   120 gggaaagccc ctaaactcct gatctatgct gcatccagtt tacaaagtgg ggtcccatca   180
aggttcagcg gcagtggatc tggcacagat ttcactctca ccatcagcag cctgcagcct   240
gaagattttg caacttatta ctgtctacaa gattacaatt accctccgac gttcggccaa   300
gggaccaagg tggacatcaa g                                             321

<210> SEQ ID NO 138
<211> LENGTH: 107
<212> TYPE: PRT
<213> ORGANISM: Artificial Sequence
<220> FEATURE:
<223> OTHER INFORMATION: Synthetic

<400> SEQUENCE: 138

Ala Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Arg Asn Asp
            20                  25                  30

Leu Gly Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60
```

```
Ser Gly Ser Gly Thr Asp Phe Thr Leu Thr Ile Ser Ser Leu Gln Pro
 65                  70                  75                  80

Glu Asp Phe Ala Thr Tyr Tyr Cys Leu Gln Asp Tyr Asn Tyr Pro Pro
                 85                  90                  95

Thr Phe Gly Gln Gly Thr Lys Val Asp Ile Lys
            100                 105
```

<210> SEQ ID NO 139
<211> LENGTH: 18
<212> TYPE: DNA
<213> ORGANISM: Artificial Sequence
<220> FEATURE:
<223> OTHER INFORMATION: Synthetic

<400> SEQUENCE: 139
cagggcatta gaaatgat                                             18

<210> SEQ ID NO 140
<211> LENGTH: 6
<212> TYPE: PRT
<213> ORGANISM: Artificial Sequence
<220> FEATURE:
<223> OTHER INFORMATION: Synthetic

<400> SEQUENCE: 140

```
Gln Gly Ile Arg Asn Asp
1               5
```

<210> SEQ ID NO 141
<211> LENGTH: 9
<212> TYPE: DNA
<213> ORGANISM: Artificial Sequence
<220> FEATURE:
<223> OTHER INFORMATION: Synthetic

<400> SEQUENCE: 141 gctgcatcc                                                        9

<210> SEQ ID NO 142
<211> LENGTH: 3
<212> TYPE: PRT
<213> ORGANISM: Artificial Sequence
<220> FEATURE:
<223> OTHER INFORMATION: Synthetic

<400> SEQUENCE: 142

```
Ala Ala Ser
1
```

<210> SEQ ID NO 143
<211> LENGTH: 27
<212> TYPE: DNA
<213> ORGANISM: Artificial Sequence
<220> FEATURE:
<223> OTHER INFORMATION: Synthetic

<400> SEQUENCE: 143
ctacaagatt acaattaccc tccgacg                                   27

<210> SEQ ID NO 144
<211> LENGTH: 9
<212> TYPE: PRT
<213> ORGANISM: Artificial Sequence
<220> FEATURE:
<223> OTHER INFORMATION: Synthetic

<400> SEQUENCE: 144

Leu Gln Asp Tyr Asn Tyr Pro Pro Thr
1               5

<210> SEQ ID NO 145
<211> LENGTH: 360
<212> TYPE: DNA
<213> ORGANISM: Artificial Sequence
<220> FEATURE:
<223> OTHER INFORMATION: Synthetic

<400> SEQUENCE: 145

```
caggtgcagc tggtggagtc tgggggaggc gtggtccagc ctgggaggtc cctgagactc    60
acctgtgcag cgtctggatt caccttcagt agctttggca tgcactgggt ccgacaggct   120
ccaggcaagg gctggagtg gtggcaatt atatggtatg atggaagtaa taaatactat    180
gcagattccg tgaagggccg attcaccatc tccagagaca attccaagaa cacgctgtat   240
ctgcaaatga acagcctgcg agccgaggac acggctgtgt attactgtgc gagagaggat   300
aactggaccc gggattactt tgactactgg ggccaggaa ccctggtcac cgtctcctca    360
```

<210> SEQ ID NO 146
<211> LENGTH: 120
<212> TYPE: PRT
<213> ORGANISM: Artificial Sequence
<220> FEATURE:
<223> OTHER INFORMATION: Synthetic

<400> SEQUENCE: 146

Gln Val Gln Leu Val Glu Ser Gly Gly Gly Val Val Gln Pro Gly Arg
1               5                   10                  15

Ser Leu Arg Leu Thr Cys Ala Ala Ser Gly Phe Thr Phe Ser Ser Phe
            20                  25                  30

Gly Met His Trp Val Arg Gln Ala Pro Gly Lys Gly Leu Glu Trp Val
        35                  40                  45

Ala Ile Ile Trp Tyr Asp Gly Ser Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Glu Asp Asn Trp Thr Arg Asp Tyr Phe Asp Tyr Trp Gly Gln
            100                 105                 110

Gly Thr Leu Val Thr Val Ser Ser
        115                 120

<210> SEQ ID NO 147
<211> LENGTH: 24
<212> TYPE: DNA
<213> ORGANISM: Artificial Sequence
<220> FEATURE:
<223> OTHER INFORMATION: Synthetic

<400> SEQUENCE: 147
ggattcacct tcagtagctt tggc                                           24

<210> SEQ ID NO 148
<211> LENGTH: 8
<212> TYPE: PRT
<213> ORGANISM: Artificial Sequence
<220> FEATURE:

<223> OTHER INFORMATION: Synthetic

<400> SEQUENCE: 148

Gly Phe Thr Phe Ser Ser Phe Gly
1               5

<210> SEQ ID NO 149
<211> LENGTH: 24
<212> TYPE: DNA
<213> ORGANISM: Artificial Sequence
<220> FEATURE:
<223> OTHER INFORMATION: Synthetic

<400> SEQUENCE: 149
atatggtatg atggaagtaa taaa                                          24

<210> SEQ ID NO 150
<211> LENGTH: 8
<212> TYPE: PRT
<213> ORGANISM: Artificial Sequence
<220> FEATURE:
<223> OTHER INFORMATION: Synthetic

<400> SEQUENCE: 150

Ile Trp Tyr Asp Gly Ser Asn Lys
1               5

<210> SEQ ID NO 151
<211> LENGTH: 39
<212> TYPE: DNA
<213> ORGANISM: Artificial Sequence
<220> FEATURE:
<223> OTHER INFORMATION: Synthetic

<400> SEQUENCE: 151
gcgagagagg ataactggac ccgggattac tttgactac                          39

<210> SEQ ID NO 152
<211> LENGTH: 13
<212> TYPE: PRT
<213> ORGANISM: Artificial Sequence
<220> FEATURE:
<223> OTHER INFORMATION: Synthetic

<400> SEQUENCE: 152

Ala Arg Glu Asp Asn Trp Thr Arg Asp Tyr Phe Asp Tyr
1               5                   10

<210> SEQ ID NO 153
<211> LENGTH: 324
<212> TYPE: DNA
<213> ORGANISM: Artificial Sequence
<220> FEATURE:
<223> OTHER INFORMATION: Synthetic

<400> SEQUENCE: 153
gaaattgtgt tgacacagtc tccagccacc ctgtctttgt ctccagggga aagagccacc    60
ctctcctgca gggccagtca gagtgttagc aacttcttag cctggtatca acagaagcct   120
ggccaggctc ccaggctcct catctatgat gcatccaaca gggccactgg catcccagcc   180
aggttcagtg gcagtgggtc tgggacagac ttcactctca ccatcagcag cctagagcct   240
gaagattttg cagtttatta ctgtcagcag cgtagcaact ggcctccgct ccctttcggc   300
ggagggacca aggtggagat caaa                                         324

<210> SEQ ID NO 154
<211> LENGTH: 108
<212> TYPE: PRT
<213> ORGANISM: Artificial Sequence
<220> FEATURE:
<223> OTHER INFORMATION: Synthetic

<400> SEQUENCE: 154

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Asn Phe
            20                  25                  30

Leu Ala Trp Tyr Gln Gln Lys Pro Gly Gln Ala Pro Arg Leu Leu Ile
        35                  40                  45

Tyr Asp Ala Ser Asn Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Arg Ser Asn Trp Pro Pro
                85                  90                  95

Leu Pro Phe Gly Gly Gly Thr Lys Val Glu Ile Lys
            100                 105

<210> SEQ ID NO 155
<211> LENGTH: 18
<212> TYPE: DNA
<213> ORGANISM: Artificial Sequence
<220> FEATURE:
<223> OTHER INFORMATION: Synthetic

<400> SEQUENCE: 155
cagagtgtta gcaacttc                                                   18

<210> SEQ ID NO 156
<211> LENGTH: 6
<212> TYPE: PRT
<213> ORGANISM: Artificial Sequence
<220> FEATURE:
<223> OTHER INFORMATION: Synthetic

<400> SEQUENCE: 156

Gln Ser Val Ser Asn Phe
1               5

<210> SEQ ID NO 157
<211> LENGTH: 9
<212> TYPE: DNA
<213> ORGANISM: Artificial Sequence
<220> FEATURE:
<223> OTHER INFORMATION: Synthetic

<400> SEQUENCE: 157 gatgcatcc                                                              9

<210> SEQ ID NO 158
<211> LENGTH: 3
<212> TYPE: PRT
<213> ORGANISM: Artificial Sequence
<220> FEATURE:
<223> OTHER INFORMATION: Synthetic

<400> SEQUENCE: 158

Asp Ala Ser

<210> SEQ ID NO 159
<211> LENGTH: 30
<212> TYPE: DNA
<213> ORGANISM: Artificial Sequence
<220> FEATURE:
<223> OTHER INFORMATION: Synthetic

<400> SEQUENCE: 159
cagcagcgta gcaactggcc tccgctccct                                      30

<210> SEQ ID NO 160
<211> LENGTH: 10
<212> TYPE: PRT
<213> ORGANISM: Artificial Sequence
<220> FEATURE:
<223> OTHER INFORMATION: Synthetic

<400> SEQUENCE: 160

Gln Gln Arg Ser Asn Trp Pro Pro Leu Pro
1               5                   10

<210> SEQ ID NO 161
<211> LENGTH: 357
<212> TYPE: DNA
<213> ORGANISM: Artificial Sequence
<220> FEATURE:
<223> OTHER INFORMATION: Synthetic

<400> SEQUENCE: 161
gaggtacaga tggtggagtc tgggggaggc ttggtccagc ctggggggtc cctgagactc       60
tcctgtgcag cctctagatt caccctttagt aactattgga tgggctgggt ccgccaggct     120
ccagggaagg ggctggagtg ggtggccaac ataaagcaag atgggagtga aaatactat      180 gtggactctg tgaggggccg attcaccatc tccagagaca acgccaagaa ctctctatat     240
ctgcaaatga acagcctgag agccgaggac acggctgtgt attactgtgc gagggattac     300 gattttttgga ggtcctttga ctactggggc cagggaaccc tggtcaccgt cccctca       357

<210> SEQ ID NO 162
<211> LENGTH: 119
<212> TYPE: PRT
<213> ORGANISM: Artificial Sequence
<220> FEATURE:
<223> OTHER INFORMATION: Synthetic

<400> SEQUENCE: 162

Glu Val Gln Met Val Glu Ser Gly Gly Gly Leu Val Gln Pro Gly Gly
1               5                   10                  15

Ser Leu Arg Leu Ser Cys Ala Ala Ser Arg Phe Thr Leu Ser Asn Tyr
            20                  25                  30

Trp Met Gly Trp Val Arg Gln Ala Pro Gly Lys Gly Leu Glu Trp Val
        35                  40                  45

Ala Asn Ile Lys Gln Asp Gly Ser Glu Lys Tyr Tyr Val Asp Ser Val
    50                  55                  60

Arg Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Asp Tyr Asp Phe Trp Arg Ser Phe Asp Tyr Trp Gly Gln Gly
            100                 105                 110

Thr Leu Val Thr Val Pro Ser
        115

<210> SEQ ID NO 163
<211> LENGTH: 24
<212> TYPE: DNA
<213> ORGANISM: Artificial Sequence
<220> FEATURE:
<223> OTHER INFORMATION: Synthetic

<400> SEQUENCE: 163
agattcaccc ttagtaacta ttgg                                              24

<210> SEQ ID NO 164
<211> LENGTH: 8
<212> TYPE: PRT
<213> ORGANISM: Artificial Sequence
<220> FEATURE:
<223> OTHER INFORMATION: Synthetic

<400> SEQUENCE: 164

Arg Phe Thr Leu Ser Asn Tyr Trp
1               5

<210> SEQ ID NO 165
<211> LENGTH: 24
<212> TYPE: DNA
<213> ORGANISM: Artificial Sequence
<220> FEATURE:
<223> OTHER INFORMATION: Synthetic

<400> SEQUENCE: 165
ataaagcaag atgggagtga gaaa                                              24

<210> SEQ ID NO 166
<211> LENGTH: 8
<212> TYPE: PRT
<213> ORGANISM: Artificial Sequence
<220> FEATURE:
<223> OTHER INFORMATION: Synthetic

<400> SEQUENCE: 166

Ile Lys Gln Asp Gly Ser Glu Lys
1               5

<210> SEQ ID NO 167
<211> LENGTH: 36
<212> TYPE: DNA
<213> ORGANISM: Artificial Sequence
<220> FEATURE:
<223> OTHER INFORMATION: Synthetic

<400> SEQUENCE: 167
gcgagggatt acgatttttg gaggtcnttt gactac                                 36

<210> SEQ ID NO 168
<211> LENGTH: 12
<212> TYPE: PRT
<213> ORGANISM: Artificial Sequence
<220> FEATURE:
<223> OTHER INFORMATION: Synthetic

<400> SEQUENCE: 168

Ala Arg Asp Tyr Asp Phe Trp Arg Ser Phe Asp Tyr
1               5                   10

<210> SEQ ID NO 169
<211> LENGTH: 322
<212> TYPE: DNA
<213> ORGANISM: Artificial Sequence
<220> FEATURE:
<223> OTHER INFORMATION: Synthetic

<400> SEQUENCE: 169

```
gacatccaga tgacccagtc tccatcttcc gtgtctgcat ctgtaggaga cagagtcacc    60
atcacctgtc gggcgagtca gggtgttagc agctggttag cctggtatca gcagacacca   120
gggaaagccc ctaagctcct gatctatgtt gtatcaagtt tgcaaagtgg ggtcccatca   180
agattcagcg gcagtggatc tgggacagat ttcactctca ccatcaacag cctgcagcct   240
gaagattttg caacttacta ttgtcaacag ggtaacagtt tcccgtacac ttttggccag   300
gggaccaagc tggagatcaa ak                                             322
```

<210> SEQ ID NO 170
<211> LENGTH: 107
<212> TYPE: PRT
<213> ORGANISM: Artificial Sequence
<220> FEATURE:
<223> OTHER INFORMATION: Synthetic

<400> SEQUENCE: 170

```
Asp Ile Gln Met Thr Gln Ser Pro Ser Ser Val Ser Ala Ser Val Gly
1               5                   10                  15

Asp Arg Val Thr Ile Thr Cys Arg Ala Ser Gln Gly Val Ser Ser Trp
            20                  25                  30

Leu Ala Trp Tyr Gln Gln Thr Pro Gly Lys Ala Pro Lys Leu Leu Ile
        35                  40                  45

Tyr Val Val Ser Ser Leu Gln Ser Gly Val Pro Ser Arg Phe Ser Gly
    50                  55                  60

Ser Gly Ser Gly Thr Asp Phe Thr Leu Thr Ile Asn Ser Leu Gln Pro
65                  70                  75                  80

Glu Asp Phe Ala Thr Tyr Tyr Cys Gln Gln Gly Asn Ser Phe Pro Tyr
                85                  90                  95

Thr Phe Gly Gln Gly Thr Lys Leu Glu Ile Lys
            100                 105
```

<210> SEQ ID NO 171
<211> LENGTH: 18
<212> TYPE: DNA
<213> ORGANISM: Artificial Sequence
<220> FEATURE:
<223> OTHER INFORMATION: Synthetic

<400> SEQUENCE: 171

```
cagggtgtta gcagctgg                                                   18
```

<210> SEQ ID NO 172
<211> LENGTH: 6
<212> TYPE: PRT
<213> ORGANISM: Artificial Sequence
<220> FEATURE:
<223> OTHER INFORMATION: Synthetic

<400> SEQUENCE: 172

```
Gln Gly Val Ser Ser Trp
1               5
```

```
<210> SEQ ID NO 173
<211> LENGTH: 9
<212> TYPE: DNA
<213> ORGANISM: Artificial Sequence
<220> FEATURE:
<223> OTHER INFORMATION: Synthetic

<400> SEQUENCE: 173 gttgtatca                                                                   9

<210> SEQ ID NO 174
<211> LENGTH: 3
<212> TYPE: PRT
<213> ORGANISM: Artificial Sequence
<220> FEATURE:
<223> OTHER INFORMATION: Synthetic

<400> SEQUENCE: 174

Val Val Ser
1

<210> SEQ ID NO 175
<211> LENGTH: 27
<212> TYPE: DNA
<213> ORGANISM: Artificial Sequence
<220> FEATURE:
<223> OTHER INFORMATION: Synthetic

<400> SEQUENCE: 175
caacagggta acagtttccc gtacact                                              27

<210> SEQ ID NO 176
<211> LENGTH: 9
<212> TYPE: PRT
<213> ORGANISM: Artificial Sequence
<220> FEATURE:
<223> OTHER INFORMATION: Synthetic

<400> SEQUENCE: 176

Gln Gln Gly Asn Ser Phe Pro Tyr Thr
1               5

<210> SEQ ID NO 177
<211> LENGTH: 357
<212> TYPE: DNA
<213> ORGANISM: Artificial Sequence
<220> FEATURE:
<223> OTHER INFORMATION: Synthetic

<400> SEQUENCE: 177
caggtgcagc tggtggagtc tgggggaggc gtggtccagc ctggggaggtc cctgagactc          60 tcctgtgcag cgtctggatt caccttcagt agctatggca tacactgggt ccgccaggct         120
ccaggcaagg ggctggagtg ggtggcaatt ctatggtatg atggaagtaa taaatactat         180
gccgactccg tgaagggccg attcaccatc tccagagaca attccaaaac cacgctgtat         240
ctgcaaatga acagcctgag agccgaggac acggctgtgt attactgtgc gagagaaaac         300
tataacgact tgaacttcga tctctggggc cgtggcaccc tggtcactgt ctcctca            357

<210> SEQ ID NO 178
<211> LENGTH: 119
<212> TYPE: PRT
<213> ORGANISM: Artificial Sequence
<220> FEATURE:
<223> OTHER INFORMATION: Synthetic
```

<400> SEQUENCE: 178

```
Gln Val Gln Leu Val Glu Ser Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Gly Ile His Trp Val Arg Gln Ala Pro Gly Lys Gly Leu Glu Trp Val
        35                  40                  45

Ala Ile Leu Trp Tyr Asp Gly Ser Asn Lys Tyr Tyr Ala Asp Ser Val
    50                  55                  60

Lys Gly Arg Phe Thr Ile Ser Arg Asp Asn Ser Lys Thr Thr Leu Tyr
65                  70                  75                  80

Leu Gln Met Asn Ser Leu Arg Ala Glu Asp Thr Ala Val Tyr Tyr Cys
                85                  90                  95

Ala Arg Glu Asn Tyr Asn Asp Leu Asn Phe Asp Leu Trp Gly Arg Gly
            100                 105                 110

Thr Leu Val Thr Val Ser Ser
        115
```

<210> SEQ ID NO 179
<211> LENGTH: 24
<212> TYPE: DNA
<213> ORGANISM: Artificial Sequence
<220> FEATURE:
<223> OTHER INFORMATION: Synthetic

<400> SEQUENCE: 179
ggattcacct tcagtagcta tggc                                        24

<210> SEQ ID NO 180
<211> LENGTH: 8
<212> TYPE: PRT
<213> ORGANISM: Artificial Sequence
<220> FEATURE:
<223> OTHER INFORMATION: Synthetic

<400> SEQUENCE: 180

```
Gly Phe Thr Phe Ser Ser Tyr Gly
1               5
```

<210> SEQ ID NO 181
<211> LENGTH: 24
<212> TYPE: DNA
<213> ORGANISM: Artificial Sequence
<220> FEATURE:
<223> OTHER INFORMATION: Synthetic

<400> SEQUENCE: 181
ctatggtatg atggaagtaa taaa                                        24

<210> SEQ ID NO 182
<211> LENGTH: 8
<212> TYPE: PRT
<213> ORGANISM: Artificial Sequence
<220> FEATURE:
<223> OTHER INFORMATION: Synthetic

<400> SEQUENCE: 182

```
Leu Trp Tyr Asp Gly Ser Asn Lys
1               5
```

<210> SEQ ID NO 183
<211> LENGTH: 36

<212> TYPE: DNA
<213> ORGANISM: Artificial Sequence
<220> FEATURE:
<223> OTHER INFORMATION: Synthetic

<400> SEQUENCE: 183
gcgagagaaa actataacga cttgaacttc gatctc                              36

<210> SEQ ID NO 184
<211> LENGTH: 12
<212> TYPE: PRT
<213> ORGANISM: Artificial Sequence
<220> FEATURE:
<223> OTHER INFORMATION: Synthetic

<400> SEQUENCE: 184

Ala Arg Glu Asn Tyr Asn Asp Leu Asn Phe Asp Leu
1               5                   10

<210> SEQ ID NO 185
<211> LENGTH: 324
<212> TYPE: DNA
<213> ORGANISM: Artificial Sequence
<220> FEATURE:
<223> OTHER INFORMATION: Synthetic

<400> SEQUENCE: 185
gacatccagt tgacccagtc tccatccttc ctgtctgcat ctgtaggaga cagagtcacc    60
atcacttgct gggccagtca gggcattagc agttatttag cctggtatca gcacaaacca   120
gggaaagccc ctaagctcct gatctatgct gcatccactt tgcaaagtgg ggtcccatca   180
cggttcagcg gcagtggatc tgggatagaa ttcactctca caatcagcag cctgcagcct   240
gaagattttg caacttatta ctgtcaacag cttaaaagtt accctccgtg gacgttcggc   300
caagggacca aggtggaaat caga                                          324

<210> SEQ ID NO 186
<211> LENGTH: 108
<212> TYPE: PRT
<213> ORGANISM: Artificial Sequence
<220> FEATURE:
<223> OTHER INFORMATION: Synthetic

<400> SEQUENCE: 186

Asp Ile Gln Leu Thr Gln Ser Pro Ser Phe Leu Ser Ala Ser Val Gly
1               5                   10                  15

Asp Arg Val Thr Ile Thr Cys Trp Ala Ser Gln Gly Ile Ser Ser Tyr
            20                  25                  30

Leu Ala Trp Tyr Gln His Lys Pro Gly Lys Ala Pro Lys Leu Leu Ile
        35                  40                  45

Tyr Ala Ala Ser Thr Leu Gln Ser Gly Val Pro Ser Arg Phe Ser Gly
    50                  55                  60

Ser Gly Ser Gly Ile Glu Phe Thr Leu Thr Ile Ser Ser Leu Gln Pro
65                  70                  75                  80

Glu Asp Phe Ala Thr Tyr Tyr Cys Gln Gln Leu Lys Ser Tyr Pro Pro
                85                  90                  95

Trp Thr Phe Gly Gln Gly Thr Lys Val Glu Ile Arg
            100                 105

<210> SEQ ID NO 187
<211> LENGTH: 18
<212> TYPE: DNA

```
<213> ORGANISM: Artificial Sequence
<220> FEATURE:
<223> OTHER INFORMATION: Synthetic

<400> SEQUENCE: 187
cagggcatta gcagttat                                                  18

<210> SEQ ID NO 188
<211> LENGTH: 6
<212> TYPE: PRT
<213> ORGANISM: Artificial Sequence
<220> FEATURE:
<223> OTHER INFORMATION: Synthetic

<400> SEQUENCE: 188

Gln Gly Ile Ser Ser Tyr
1               5

<210> SEQ ID NO 189
<211> LENGTH: 9
<212> TYPE: DNA
<213> ORGANISM: Artificial Sequence
<220> FEATURE:
<223> OTHER INFORMATION: Synthetic

<400> SEQUENCE: 189 gctgcatcc                                                             9

<210> SEQ ID NO 190
<211> LENGTH: 3
<212> TYPE: PRT
<213> ORGANISM: Artificial Sequence
<220> FEATURE:
<223> OTHER INFORMATION: Synthetic

<400> SEQUENCE: 190

Ala Ala Ser
1

<210> SEQ ID NO 191
<211> LENGTH: 30
<212> TYPE: DNA
<213> ORGANISM: Artificial Sequence
<220> FEATURE:
<223> OTHER INFORMATION: Synthetic

<400> SEQUENCE: 191
caacagctta aaagttaccc tccgtggacg                                     30

<210> SEQ ID NO 192
<211> LENGTH: 10
<212> TYPE: PRT
<213> ORGANISM: Artificial Sequence
<220> FEATURE:
<223> OTHER INFORMATION: Synthetic

<400> SEQUENCE: 192

Gln Gln Leu Lys Ser Tyr Pro Pro Trp Thr
1               5                   10

<210> SEQ ID NO 193
<211> LENGTH: 348
<212> TYPE: DNA
<213> ORGANISM: Artificial Sequence
<220> FEATURE:
<223> OTHER INFORMATION: Synthetic
```

<400> SEQUENCE: 193

```
gaggtgcagc tggtggagtc tggaggaggc ttggtccagc ctggggggtc cctgagactc      60
tcatgtgcag cctctggttt caccgtcagt agcaactaca tgagctgggt ccgccaggct     120
ccagggaagg gctggagtg gtctcagtt atttatagcg gtggtaacac atactacgca      180
gactccgtga agggccgatt caccatctcc agacacaatt ccaagaacac gctgtatctt     240
caaatgaaca gcctgagagc tgaggacacg gccgtgtact actgtgcgcg agatctaggc     300
attaagtctg actattgggg ccagggaacc ctggtcaccg tctcctca                 348
```

<210> SEQ ID NO 194
<211> LENGTH: 116
<212> TYPE: PRT
<213> ORGANISM: Artificial Sequence
<220> FEATURE:
<223> OTHER INFORMATION: Synthetic

<400> SEQUENCE: 194

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Val Ser Ser Asn
            20                  25                  30

Tyr Met Ser Trp Val Arg Gln Ala Pro Gly Lys Gly Leu Glu Trp Val
        35                  40                  45

Ser Val Ile Tyr Ser Gly Gly Asn Thr Tyr Tyr Ala Asp Ser Val Lys
    50                  55                  60

Gly Arg Phe Thr Ile Ser Arg His Asn Ser Lys Asn Thr Leu Tyr Leu
65                  70                  75                  80

Gln Met Asn Ser Leu Arg Ala Glu Asp Thr Ala Val Tyr Tyr Cys Ala
                85                  90                  95

Arg Asp Leu Gly Ile Lys Ser Asp Tyr Trp Gly Gln Gly Thr Leu Val
            100                 105                 110

Thr Val Ser Ser
        115
```

<210> SEQ ID NO 195
<211> LENGTH: 24
<212> TYPE: DNA
<213> ORGANISM: Artificial Sequence
<220> FEATURE:
<223> OTHER INFORMATION: Synthetic

<400> SEQUENCE: 195

```
ggtttcaccg tcagtagcaa ctac                                            24
```

<210> SEQ ID NO 196
<211> LENGTH: 8
<212> TYPE: PRT
<213> ORGANISM: Artificial Sequence
<220> FEATURE:
<223> OTHER INFORMATION: Synthetic

<400> SEQUENCE: 196

```
Gly Phe Thr Val Ser Ser Asn Tyr
1               5
```

<210> SEQ ID NO 197
<211> LENGTH: 21
<212> TYPE: DNA
<213> ORGANISM: Artificial Sequence
<220> FEATURE:

<223> OTHER INFORMATION: Synthetic

<400> SEQUENCE: 197
atttatagcg gtggtaacac a                                             21

<210> SEQ ID NO 198
<211> LENGTH: 7
<212> TYPE: PRT
<213> ORGANISM: Artificial Sequence
<220> FEATURE:
<223> OTHER INFORMATION: Synthetic

<400> SEQUENCE: 198

Ile Tyr Ser Gly Gly Asn Thr
1               5

<210> SEQ ID NO 199
<211> LENGTH: 30
<212> TYPE: DNA
<213> ORGANISM: Artificial Sequence
<220> FEATURE:
<223> OTHER INFORMATION: Synthetic

<400> SEQUENCE: 199
gcgcgagatc taggcattaa gtctgactat                                    30

<210> SEQ ID NO 200
<211> LENGTH: 10
<212> TYPE: PRT
<213> ORGANISM: Artificial Sequence
<220> FEATURE:
<223> OTHER INFORMATION: Synthetic

<400> SEQUENCE: 200

Ala Arg Asp Leu Gly Ile Lys Ser Asp Tyr
1               5                   10

<210> SEQ ID NO 201
<211> LENGTH: 321
<212> TYPE: DNA
<213> ORGANISM: Artificial Sequence
<220> FEATURE:
<223> OTHER INFORMATION: Synthetic

<400> SEQUENCE: 201
gaaattgtgc tgactcagtc tccagacttt cagtctgtga ctccaaagga gaaagtcacc    60
atcacctgcc gggccagtca gagcattggt actaccttac actggtacca gcagaaacca   120
gatcagtctc caaaactcct catcaagtat gtttcccagt ccctctcagg ggtcccctcg   180
aggttcagtg gcagtggatc tgggacagat ttcaccctca ccatcaatag cctggaagct   240
gaagatgctg caacgtatta ctgtcatcag agtagtagtt taccgtggac gttcggccaa   300
gggaccaagg tggaaatcaa a                                             321

<210> SEQ ID NO 202
<211> LENGTH: 107
<212> TYPE: PRT
<213> ORGANISM: Artificial Sequence
<220> FEATURE:
<223> OTHER INFORMATION: Synthetic

<400> SEQUENCE: 202

Glu Ile Val Leu Thr Gln Ser Pro Asp Phe Gln Ser Val Thr Pro Lys
1               5                   10                  15

```
Glu Lys Val Thr Ile Thr Cys Arg Ala Ser Gln Ser Ile Gly Thr Thr
            20                  25                  30

Leu His Trp Tyr Gln Gln Lys Pro Asp Gln Ser Pro Lys Leu Leu Ile
        35                  40                  45

Lys Tyr Val Ser Gln Ser Leu Ser Gly Val Pro Ser Arg Phe Ser Gly
    50                  55                  60

Ser Gly Ser Gly Thr Asp Phe Thr Leu Thr Ile Asn Ser Leu Glu Ala
65                  70                  75                  80

Glu Asp Ala Ala Thr Tyr Tyr Cys His Gln Ser Ser Ser Leu Pro Trp
                85                  90                  95

Thr Phe Gly Gln Gly Thr Lys Val Glu Ile Lys
            100                 105
```

<210> SEQ ID NO 203
<211> LENGTH: 18
<212> TYPE: DNA
<213> ORGANISM: Artificial Sequence
<220> FEATURE:
<223> OTHER INFORMATION: Synthetic

<400> SEQUENCE: 203
cagagcattg gtactacc                                                 18

<210> SEQ ID NO 204
<211> LENGTH: 6
<212> TYPE: PRT
<213> ORGANISM: Artificial Sequence
<220> FEATURE:
<223> OTHER INFORMATION: Synthetic

<400> SEQUENCE: 204

Gln Ser Ile Gly Thr Thr
1               5

<210> SEQ ID NO 205
<211> LENGTH: 9
<212> TYPE: DNA
<213> ORGANISM: Artificial Sequence
<220> FEATURE:
<223> OTHER INFORMATION: Synthetic

<400> SEQUENCE: 205 tatgtttcc                                                            9

<210> SEQ ID NO 206
<211> LENGTH: 3
<212> TYPE: PRT
<213> ORGANISM: Artificial Sequence
<220> FEATURE:
<223> OTHER INFORMATION: Synthetic

<400> SEQUENCE: 206

Tyr Val Ser
1

<210> SEQ ID NO 207
<211> LENGTH: 27
<212> TYPE: DNA
<213> ORGANISM: Artificial Sequence
<220> FEATURE:
<223> OTHER INFORMATION: Synthetic

<400> SEQUENCE: 207
catcagagta gtagtttacc gtggacg                                       27

<210> SEQ ID NO 208
<211> LENGTH: 9
<212> TYPE: PRT
<213> ORGANISM: Artificial Sequence
<220> FEATURE:
<223> OTHER INFORMATION: Synthetic

<400> SEQUENCE: 208

His Gln Ser Ser Ser Leu Pro Trp Thr
1               5

<210> SEQ ID NO 209
<211> LENGTH: 360
<212> TYPE: DNA
<213> ORGANISM: Artificial Sequence
<220> FEATURE:
<223> OTHER INFORMATION: Synthetic

<400> SEQUENCE: 209
caggtgcagc tggtggagtc tgggggaggc gtggtccagc ctggagggtc cctgagactc      60
tcctgtgcag cctctggatt caccttcact aactatggca tgcactgggt ccgccaggct     120
ccaggcaagg ggctggagtg ggtggcagct atatcatatg atggaactaa taaatactat     180
gcagactccg tgaagggccg attcaccatc tccagagacg attccaagaa cacgctgtgt     240
ctgcaaatga acagcctgag agctgaggac acggctgtgt attactgtgc gaaagagggg     300
actggtgaag gtttctcctt tgactactgg ggccagggaa ccctggtcac cgtctcctca     360

<210> SEQ ID NO 210
<211> LENGTH: 120
<212> TYPE: PRT
<213> ORGANISM: Artificial Sequence
<220> FEATURE:
<223> OTHER INFORMATION: Synthetic

<400> SEQUENCE: 210

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Thr Asn Tyr
            20                  25                  30

Gly Met His Trp Val Arg Gln Ala Pro Gly Lys Gly Leu Glu Trp Val
        35                  40                  45

Ala Ala Ile Ser Tyr Asp Gly Thr Asn Lys Tyr Tyr Ala Asp Ser Val
    50                  55                  60

Lys Gly Arg Phe Thr Ile Ser Arg Asp Asp Ser Lys Asn Thr Leu Cys
65                  70                  75                  80

Leu Gln Met Asn Ser Leu Arg Ala Glu Asp Thr Ala Val Tyr Tyr Cys
                85                  90                  95

Ala Lys Glu Gly Thr Gly Glu Gly Phe Ser Phe Asp Tyr Trp Gly Gln
            100                 105                 110

Gly Thr Leu Val Thr Val Ser Ser
        115                 120

<210> SEQ ID NO 211
<211> LENGTH: 24
<212> TYPE: DNA
<213> ORGANISM: Artificial Sequence
<220> FEATURE:
<223> OTHER INFORMATION: Synthetic

<400> SEQUENCE: 211

```
ggattcacct tcactaacta tggc                                              24
```

<210> SEQ ID NO 212
<211> LENGTH: 8
<212> TYPE: PRT
<213> ORGANISM: Artificial Sequence
<220> FEATURE:
<223> OTHER INFORMATION: Synthetic

<400> SEQUENCE: 212

```
Gly Phe Thr Phe Thr Asn Tyr Gly
1               5
```

<210> SEQ ID NO 213
<211> LENGTH: 24
<212> TYPE: DNA
<213> ORGANISM: Artificial Sequence
<220> FEATURE:
<223> OTHER INFORMATION: Synthetic

<400> SEQUENCE: 213

```
atatcatatg atggaactaa taaa                                              24
```

<210> SEQ ID NO 214
<211> LENGTH: 8
<212> TYPE: PRT
<213> ORGANISM: Artificial Sequence
<220> FEATURE:
<223> OTHER INFORMATION: Synthetic

<400> SEQUENCE: 214

```
Ile Ser Tyr Asp Gly Thr Asn Lys
1               5
```

<210> SEQ ID NO 215
<211> LENGTH: 39
<212> TYPE: DNA
<213> ORGANISM: Artificial Sequence
<220> FEATURE:
<223> OTHER INFORMATION: Synthetic

<400> SEQUENCE: 215

```
gcgaaagagg ggactggtga aggtttctcc tttgactac                              39
```

<210> SEQ ID NO 216
<211> LENGTH: 13
<212> TYPE: PRT
<213> ORGANISM: Artificial Sequence
<220> FEATURE:
<223> OTHER INFORMATION: Synthetic

<400> SEQUENCE: 216

```
Ala Lys Glu Gly Thr Gly Glu Gly Phe Ser Phe Asp Tyr
1               5                   10
```

<210> SEQ ID NO 217
<211> LENGTH: 336
<212> TYPE: DNA
<213> ORGANISM: Artificial Sequence
<220> FEATURE:
<223> OTHER INFORMATION: Synthetic

<400> SEQUENCE: 217

```
gatattgtga tgactcagtc tccactctcc ctgcccgtca cccctggaga gccggcctcc       60
atctcctgca ggtctagtca gagcctccta cattttaatg gatacaacta tttggattgg      120
```

```
tacctgcaga agccagggca gtctccacag ctcctgatct atttgggttc taatcgggcc    180 tccgggtcc ctgacaggtt cagtggcagt ggatcaggca cagattttac actgaaagtc     240
agcagagtgg aggctgagga tgttggggtt tattactgca tgcaagctct acaaactcca    300
ttcactttcg gccctgggac caaagtggat atcaaa                              336
```

<210> SEQ ID NO 218
<211> LENGTH: 112
<212> TYPE: PRT
<213> ORGANISM: Artificial Sequence
<220> FEATURE:
<223> OTHER INFORMATION: Synthetic

<400> SEQUENCE: 218

```
Asp Ile Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Leu His Phe
            20                  25                  30

Asn Gly Tyr Asn Tyr Leu Asp Trp Tyr Leu Gln Lys Pro Gly Gln Ser
        35                  40                  45

Pro Gln Leu Leu Ile Tyr Leu Gly Ser Asn Arg Ala Ser Gly Val Pro
    50                  55                  60

Asp Arg Phe Ser Gly Ser Gly Ser Gly Thr Asp Phe Thr Leu Lys Val
65                  70                  75                  80

Ser Arg Val Glu Ala Glu Asp Val Gly Val Tyr Tyr Cys Met Gln Ala
                85                  90                  95

Leu Gln Thr Pro Phe Thr Phe Gly Pro Gly Thr Lys Val Asp Ile Lys
            100                 105                 110
```

<210> SEQ ID NO 219
<211> LENGTH: 33
<212> TYPE: DNA
<213> ORGANISM: Artificial Sequence
<220> FEATURE:
<223> OTHER INFORMATION: Synthetic

<400> SEQUENCE: 219

```
cagagcctcc tacattttaa tggatacaac tat                                 33
```

<210> SEQ ID NO 220
<211> LENGTH: 11
<212> TYPE: PRT
<213> ORGANISM: Artificial Sequence
<220> FEATURE:
<223> OTHER INFORMATION: Synthetic

<400> SEQUENCE: 220

```
Gln Ser Leu Leu His Phe Asn Gly Tyr Asn Tyr
1               5                   10
```

<210> SEQ ID NO 221
<211> LENGTH: 9
<212> TYPE: DNA
<213> ORGANISM: Artificial Sequence
<220> FEATURE:
<223> OTHER INFORMATION: Synthetic

<400> SEQUENCE: 221

```
ttgggttct                                                            9
```

<210> SEQ ID NO 222

<211> LENGTH: 3
<212> TYPE: PRT
<213> ORGANISM: Artificial Sequence
<220> FEATURE:
<223> OTHER INFORMATION: Synthetic

<400> SEQUENCE: 222

Leu Gly Ser
1

<210> SEQ ID NO 223
<211> LENGTH: 27
<212> TYPE: DNA
<213> ORGANISM: Artificial Sequence
<220> FEATURE:
<223> OTHER INFORMATION: Synthetic

<400> SEQUENCE: 223
atgcaagctc tacaaactcc attcact                                            27

<210> SEQ ID NO 224
<211> LENGTH: 9
<212> TYPE: PRT
<213> ORGANISM: Artificial Sequence
<220> FEATURE:
<223> OTHER INFORMATION: Synthetic

<400> SEQUENCE: 224

Met Gln Ala Leu Gln Thr Pro Phe Thr
1               5

<210> SEQ ID NO 225
<211> LENGTH: 360
<212> TYPE: DNA
<213> ORGANISM: Artificial Sequence
<220> FEATURE:
<223> OTHER INFORMATION: Synthetic

<400> SEQUENCE: 225
gaggtgcagc tggtggagtc tgggggaggc ttggtacagc ctggggggtc cctgagactc        60
tcctgtgcag cctctggatt caccttcagt atctacgaca tgcactgggt ccgccaagct       120
acaggaaaag gtctggagtg ggtctcaggt attggtaatg ctggtgacac atactatgca       180
ggctccgtga agggccgatt caccatctcc agagaaaatg ccaagaactc cttgtatctt       240
caaatgaaca gcctgagagc cggggacacg gctgtatatt actgtgcaag agagggtccc       300
aactactact actatggtat ggacgtctgg ggccaaggga ccacggtcac cgtctcctca       360

<210> SEQ ID NO 226
<211> LENGTH: 120
<212> TYPE: PRT
<213> ORGANISM: Artificial Sequence
<220> FEATURE:
<223> OTHER INFORMATION: Synthetic

<400> SEQUENCE: 226

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ile Tyr
            20                  25                  30

Asp Met His Trp Val Arg Gln Ala Thr Gly Lys Gly Leu Glu Trp Val
        35                  40                  45

Ser Gly Ile Gly Asn Ala Gly Asp Thr Tyr Tyr Ala Gly Ser Val Lys
    50                  55                  60

Gly Arg Phe Thr Ile Ser Arg Glu Asn Ala Lys Asn Ser Leu Tyr Leu
65                  70                  75                  80

Gln Met Asn Ser Leu Arg Ala Gly Asp Thr Ala Val Tyr Tyr Cys Ala
                85                  90                  95

Arg Glu Gly Pro Asn Tyr Tyr Tyr Gly Met Asp Val Trp Gly Gln
            100                 105                 110

Gly Thr Thr Val Thr Val Ser Ser
        115                 120

<210> SEQ ID NO 227
<211> LENGTH: 24
<212> TYPE: DNA
<213> ORGANISM: Artificial Sequence
<220> FEATURE:
<223> OTHER INFORMATION: Synthetic

<400> SEQUENCE: 227
ggattcacct tcagtatcta cgac                                    24

<210> SEQ ID NO 228
<211> LENGTH: 8
<212> TYPE: PRT
<213> ORGANISM: Artificial Sequence
<220> FEATURE:
<223> OTHER INFORMATION: Synthetic

<400> SEQUENCE: 228

Gly Phe Thr Phe Ser Ile Tyr Asp
1               5

<210> SEQ ID NO 229
<211> LENGTH: 21
<212> TYPE: DNA
<213> ORGANISM: Artificial Sequence
<220> FEATURE:
<223> OTHER INFORMATION: Synthetic

<400> SEQUENCE: 229
attggtaatg ctggtgacac a                                       21

<210> SEQ ID NO 230
<211> LENGTH: 7
<212> TYPE: PRT
<213> ORGANISM: Artificial Sequence
<220> FEATURE:
<223> OTHER INFORMATION: Synthetic

<400> SEQUENCE: 230

Ile Gly Asn Ala Gly Asp Thr
1               5

<210> SEQ ID NO 231
<211> LENGTH: 42
<212> TYPE: DNA
<213> ORGANISM: Artificial Sequence
<220> FEATURE:
<223> OTHER INFORMATION: Synthetic

<400> SEQUENCE: 231
gcaagagagg gtcccaacta ctactactat ggtatggacg tc                42

<210> SEQ ID NO 232
<211> LENGTH: 14
<212> TYPE: PRT

<213> ORGANISM: Artificial Sequence
<220> FEATURE:
<223> OTHER INFORMATION: Synthetic

<400> SEQUENCE: 232

Ala Arg Glu Gly Pro Asn Tyr Tyr Tyr Gly Met Asp Val
1               5                   10

<210> SEQ ID NO 233
<211> LENGTH: 321
<212> TYPE: DNA
<213> ORGANISM: Artificial Sequence
<220> FEATURE:
<223> OTHER INFORMATION: Synthetic

<400> SEQUENCE: 233

```
gccatccaga tgacccagtc tccatcctcc ctgtctgcat ctgtaggaga cagagtcacc      60
atcacttgcc gggcaagtca gggcattaga gatgatttag gctggtatca gcagaaacca     120
gggaaagccc ctaagctcct gatctatgct gcatccagtt tacaaagtgg ggtcccatca     180
aggttcagcg gcagtggatc tggcacagat ttcactctca ccatcagcag cctgcagcct     240
gaagattttg caacttatta ctgtctacaa gattacaatt acccgtggac gttcggccaa     300
gggaccaagg tggagatcaa a                                               321
```

<210> SEQ ID NO 234
<211> LENGTH: 107
<212> TYPE: PRT
<213> ORGANISM: Artificial Sequence
<220> FEATURE:
<223> OTHER INFORMATION: Synthetic

<400> SEQUENCE: 234

Ala Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Arg Asp Asp
            20                  25                  30

Leu Gly Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Leu Gln Asp Tyr Asn Tyr Pro Trp
                85                  90                  95

Thr Phe Gly Gln Gly Thr Lys Val Glu Ile Lys
            100                 105

<210> SEQ ID NO 235
<211> LENGTH: 18
<212> TYPE: DNA
<213> ORGANISM: Artificial Sequence
<220> FEATURE:
<223> OTHER INFORMATION: Synthetic

<400> SEQUENCE: 235
cagggcatta gagatgat                                                    18

<210> SEQ ID NO 236
<211> LENGTH: 6
<212> TYPE: PRT
<213> ORGANISM: Artificial Sequence
<220> FEATURE:
<223> OTHER INFORMATION: Synthetic

<400> SEQUENCE: 236

Gln Gly Ile Arg Asp Asp
1               5

<210> SEQ ID NO 237
<211> LENGTH: 9
<212> TYPE: DNA
<213> ORGANISM: Artificial Sequence
<220> FEATURE:
<223> OTHER INFORMATION: Synthetic

<400> SEQUENCE: 237 gctgcatcc                                                                                      9

<210> SEQ ID NO 238
<211> LENGTH: 3
<212> TYPE: PRT
<213> ORGANISM: Artificial Sequence
<220> FEATURE:
<223> OTHER INFORMATION: Synthetic

<400> SEQUENCE: 238

Ala Ala Ser
1

<210> SEQ ID NO 239
<211> LENGTH: 27
<212> TYPE: DNA
<213> ORGANISM: Artificial Sequence
<220> FEATURE:
<223> OTHER INFORMATION: Synthetic

<400> SEQUENCE: 239
ctacaagatt acaattaccc gtggacg                                                                  27

<210> SEQ ID NO 240
<211> LENGTH: 9
<212> TYPE: PRT
<213> ORGANISM: Artificial Sequence
<220> FEATURE:
<223> OTHER INFORMATION: Synthetic

<400> SEQUENCE: 240

Leu Gln Asp Tyr Asn Tyr Pro Trp Thr
1               5

<210> SEQ ID NO 241
<211> LENGTH: 351
<212> TYPE: DNA
<213> ORGANISM: Artificial Sequence
<220> FEATURE:
<223> OTHER INFORMATION: Synthetic

<400> SEQUENCE: 241
caggtgcagc tggtgcagtc tggggctgag gtgaagaagc ctggggcctc agtgaaggtc      60
tcctgcaagg cttctggatt caccttcacc agttatgata tcaactgggt gcgacaggcc     120
actggacagg ggcttgagtg gatgggatgg atgaacccta agagtggtaa cacagactat     180
gcacaaaagt tcctgggcag agtcaccctg accaggaaca cctccaaaag cacagcctac     240
atggagctga gcagcctgag atctgaggac acggccgtgt actactgtgc gagaggaaag     300
cagctcgtct ttgactactg gggccaggga accctggtca ccgtctccgc a              351

<210> SEQ ID NO 242
<211> LENGTH: 117
<212> TYPE: PRT
<213> ORGANISM: Artificial Sequence
<220> FEATURE:
<223> OTHER INFORMATION: Synthetic

<400> SEQUENCE: 242

Gln Val Gln Leu Val Gln Ser Gly Ala Glu Val Lys Lys Pro Gly Ala
1               5                   10                  15

Ser Val Lys Val Ser Cys Lys Ala Ser Gly Phe Thr Phe Thr Ser Tyr
            20                  25                  30

Asp Ile Asn Trp Val Arg Gln Ala Thr Gly Gln Gly Leu Glu Trp Met
        35                  40                  45

Gly Trp Met Asn Pro Lys Ser Gly Asn Thr Asp Tyr Ala Gln Lys Phe
    50                  55                  60

Leu Gly Arg Val Thr Leu Thr Arg Asn Thr Ser Lys Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Gly Lys Gln Leu Val Phe Asp Tyr Trp Gly Gln Gly Thr Leu
            100                 105                 110

Val Thr Val Ser Ala
        115

<210> SEQ ID NO 243
<211> LENGTH: 24
<212> TYPE: DNA
<213> ORGANISM: Artificial Sequence
<220> FEATURE:
<223> OTHER INFORMATION: Synthetic

<400> SEQUENCE: 243
ggattcacct tcaccagtta tgat                                          24

<210> SEQ ID NO 244
<211> LENGTH: 8
<212> TYPE: PRT
<213> ORGANISM: Artificial Sequence
<220> FEATURE:
<223> OTHER INFORMATION: Synthetic

<400> SEQUENCE: 244

Gly Phe Thr Phe Thr Ser Tyr Asp
1               5

<210> SEQ ID NO 245
<211> LENGTH: 24
<212> TYPE: DNA
<213> ORGANISM: Artificial Sequence
<220> FEATURE:
<223> OTHER INFORMATION: Synthetic

<400> SEQUENCE: 245 atgaaccctaagagtggtaacaca                                          24

<210> SEQ ID NO 246
<211> LENGTH: 8
<212> TYPE: PRT
<213> ORGANISM: Artificial Sequence
<220> FEATURE:
<223> OTHER INFORMATION: Synthetic

<400> SEQUENCE: 246

Met Asn Pro Lys Ser Gly Asn Thr
1               5

<210> SEQ ID NO 247
<211> LENGTH: 30
<212> TYPE: DNA
<213> ORGANISM: Artificial Sequence
<220> FEATURE:
<223> OTHER INFORMATION: Synthetic

<400> SEQUENCE: 247
gcgagaggaa agcagctcgt ctttgactac                                        30

<210> SEQ ID NO 248
<211> LENGTH: 10
<212> TYPE: PRT
<213> ORGANISM: Artificial Sequence
<220> FEATURE:
<223> OTHER INFORMATION: Synthetic

<400> SEQUENCE: 248

Ala Arg Gly Lys Gln Leu Val Phe Asp Tyr
1               5                   10

<210> SEQ ID NO 249
<211> LENGTH: 321
<212> TYPE: DNA
<213> ORGANISM: Artificial Sequence
<220> FEATURE:
<223> OTHER INFORMATION: Synthetic

<400> SEQUENCE: 249
gacatccaga tgacccagtc tccatcctcc ctgtctgcat ctgtaggaga cagagtcacc        60
atcacttgcc aggcgaatca ggacattact aactatttaa attggtatca gaagaaacca      120
gggaaagccc ctaagctcct gatctacgat gcatccaatt tggaaacagg ggtcccatca      180
aggttcagtg gaagtggata tgggacagat tttactttca ccatcagcag cctgcagcct      240
gaagatattg caacatatta ctgtcaacag tatgataatc tcccattcac tttcggccct      300
gggaccaaag tggatatcaa a                                                321

<210> SEQ ID NO 250
<211> LENGTH: 107
<212> TYPE: PRT
<213> ORGANISM: Artificial Sequence
<220> FEATURE:
<223> OTHER INFORMATION: Synthetic

<400> SEQUENCE: 250

Asp Ile Gln Met Thr Gln Ser Pro Ser Ser Leu Ser Ala Ser Val Gly
1               5                   10                  15

Asp Arg Val Thr Ile Thr Cys Gln Ala Asn Gln Asp Ile Thr Asn Tyr
            20                  25                  30

Leu Asn Trp Tyr Gln Lys Lys Pro Gly Lys Ala Pro Lys Leu Leu Ile
        35                  40                  45

Tyr Asp Ala Ser Asn Leu Glu Thr Gly Val Pro Ser Arg Phe Ser Gly
    50                  55                  60

Ser Gly Tyr Gly Thr Asp Phe Thr Phe Thr Ile Ser Ser Leu Gln Pro
65                  70                  75                  80

Glu Asp Ile Ala Thr Tyr Tyr Cys Gln Gln Tyr Asp Asn Leu Pro Phe

```
                    85                  90                  95
Thr Phe Gly Pro Gly Thr Lys Val Asp Ile Lys
            100                 105

<210> SEQ ID NO 251
<211> LENGTH: 18
<212> TYPE: DNA
<213> ORGANISM: Artificial Sequence
<220> FEATURE:
<223> OTHER INFORMATION: Synthetic

<400> SEQUENCE: 251
caggacatta ctaactat                                                 18

<210> SEQ ID NO 252
<211> LENGTH: 6
<212> TYPE: PRT
<213> ORGANISM: Artificial Sequence
<220> FEATURE:
<223> OTHER INFORMATION: Synthetic

<400> SEQUENCE: 252

Gln Asp Ile Thr Asn Tyr
1               5

<210> SEQ ID NO 253
<211> LENGTH: 9
<212> TYPE: DNA
<213> ORGANISM: Artificial Sequence
<220> FEATURE:
<223> OTHER INFORMATION: Synthetic

<400> SEQUENCE: 253 gatgcatcc                                                            9

<210> SEQ ID NO 254
<211> LENGTH: 3
<212> TYPE: PRT
<213> ORGANISM: Artificial Sequence
<220> FEATURE:
<223> OTHER INFORMATION: Synthetic

<400> SEQUENCE: 254

Asp Ala Ser
1

<210> SEQ ID NO 255
<211> LENGTH: 27
<212> TYPE: DNA
<213> ORGANISM: Artificial Sequence
<220> FEATURE:
<223> OTHER INFORMATION: Synthetic

<400> SEQUENCE: 255
caacagtatg ataatctccc attcact                                       27

<210> SEQ ID NO 256
<211> LENGTH: 9
<212> TYPE: PRT
<213> ORGANISM: Artificial Sequence
<220> FEATURE:
<223> OTHER INFORMATION: Synthetic

<400> SEQUENCE: 256

Gln Gln Tyr Asp Asn Leu Pro Phe Thr
1               5
```

<210> SEQ ID NO 257
<211> LENGTH: 348
<212> TYPE: DNA
<213> ORGANISM: Artificial Sequence
<220> FEATURE:
<223> OTHER INFORMATION: Synthetic

<400> SEQUENCE: 257

```
gaggtgcagc tggtggagtc tgggggaggc ctggtcaagc ctggggggtc cctgagactc      60
tcctgtgcag cctctggatt caccttcagt tactatagca tgatctgggt ccgccaggct     120
ccagggaagg ggctggagtg gtctcatcc atcagtagta gtagtagtta catatactac     180
gcagactcag tgaagggccg attcaccatc tccagagaca acgccaagaa atcaatgtat    240
ctgcaaatga acagcctgag agccgaggac acggctgtgt attactgtgc gagaggtagt    300
ggctaccctg actactgggg ccagggaacc ctggtcaccg tctcctca                 348
```

<210> SEQ ID NO 258
<211> LENGTH: 116
<212> TYPE: PRT
<213> ORGANISM: Artificial Sequence
<220> FEATURE:
<223> OTHER INFORMATION: Synthetic

<400> SEQUENCE: 258

```
Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Tyr Tyr
            20                  25                  30

Ser Met Ile Trp Val Arg Gln Ala Pro Gly Lys Gly Leu Glu Trp Val
        35                  40                  45

Ser Ser Ile Ser Ser Ser Ser Tyr Ile Tyr Tyr Ala Asp Ser Val
    50                  55                  60

Lys Gly Arg Phe Thr Ile Ser Arg Asp Asn Ala Lys Lys Ser Met Tyr
65                  70                  75                  80

Leu Gln Met Asn Ser Leu Arg Ala Glu Asp Thr Ala Val Tyr Tyr Cys
                85                  90                  95

Ala Arg Gly Ser Gly Tyr Pro Asp Tyr Trp Gly Gln Gly Thr Leu Val
            100                 105                 110

Thr Val Ser Ser
        115
```

<210> SEQ ID NO 259
<211> LENGTH: 24
<212> TYPE: DNA
<213> ORGANISM: Artificial Sequence
<220> FEATURE:
<223> OTHER INFORMATION: Synthetic

<400> SEQUENCE: 259

```
ggattcacct tcagttacta tagc                                            24
```

<210> SEQ ID NO 260
<211> LENGTH: 8
<212> TYPE: PRT
<213> ORGANISM: Artificial Sequence
<220> FEATURE:
<223> OTHER INFORMATION: Synthetic

<400> SEQUENCE: 260

Gly Phe Thr Phe Ser Tyr Tyr Ser
1               5

<210> SEQ ID NO 261
<211> LENGTH: 24
<212> TYPE: DNA
<213> ORGANISM: Artificial Sequence
<220> FEATURE:
<223> OTHER INFORMATION: Synthetic

<400> SEQUENCE: 261
atcagtagta gtagtagtta cata                                          24

<210> SEQ ID NO 262
<211> LENGTH: 8
<212> TYPE: PRT
<213> ORGANISM: Artificial Sequence
<220> FEATURE:
<223> OTHER INFORMATION: Synthetic

<400> SEQUENCE: 262

Ile Ser Ser Ser Ser Ser Tyr Ile
1               5

<210> SEQ ID NO 263
<211> LENGTH: 27
<212> TYPE: DNA
<213> ORGANISM: Artificial Sequence
<220> FEATURE:
<223> OTHER INFORMATION: Synthetic

<400> SEQUENCE: 263
gcgagaggta gtggctaccc tgactac                                       27

<210> SEQ ID NO 264
<211> LENGTH: 9
<212> TYPE: PRT
<213> ORGANISM: Artificial Sequence
<220> FEATURE:
<223> OTHER INFORMATION: Synthetic

<400> SEQUENCE: 264

Ala Arg Gly Ser Gly Tyr Pro Asp Tyr
1               5

<210> SEQ ID NO 265
<211> LENGTH: 321
<212> TYPE: DNA
<213> ORGANISM: Artificial Sequence
<220> FEATURE:
<223> OTHER INFORMATION: Synthetic

<400> SEQUENCE: 265
gacatccaga tgacccagtc tccatcctcc ctgtctgcat ctgtaggaga cagagtcacc    60
atcacttgcc gggcgagtca gggcattaac aattatttag cctggtatca gcagaaacca   120
gggaaagttc ctaagctcct gatctatgct gcatccactt tacgatcagg ggtcccatct   180
cggttcagtg gcagtggatc tgggacagat ttcactctca ccatcagcag cctgcagcct   240
gaagatgttg caacttatta ctgtcaaaag tataacagtg ccccattcac tttcggccct   300
gggaccaaag tggatatcaa a                                            321

<210> SEQ ID NO 266
<211> LENGTH: 107
<212> TYPE: PRT

-continued

<213> ORGANISM: Artificial Sequence
<220> FEATURE:
<223> OTHER INFORMATION: Synthetic

<400> SEQUENCE: 266

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Asn Asn Tyr
            20                  25                  30

Leu Ala Trp Tyr Gln Gln Lys Pro Gly Lys Val Pro Lys Leu Leu Ile
        35                  40                  45

Tyr Ala Ala Ser Thr Leu Arg Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Val Ala Thr Tyr Tyr Cys Gln Lys Tyr Asn Ser Ala Pro Phe
                85                  90                  95

Thr Phe Gly Pro Gly Thr Lys Val Asp Ile Lys
            100                 105

<210> SEQ ID NO 267
<211> LENGTH: 18
<212> TYPE: DNA
<213> ORGANISM: Artificial Sequence
<220> FEATURE:
<223> OTHER INFORMATION: Synthetic

<400> SEQUENCE: 267
cagggcatta acaattat                                                 18

<210> SEQ ID NO 268
<211> LENGTH: 6
<212> TYPE: PRT
<213> ORGANISM: Artificial Sequence
<220> FEATURE:
<223> OTHER INFORMATION: Synthetic

<400> SEQUENCE: 268

Gln Gly Ile Asn Asn Tyr
1               5

<210> SEQ ID NO 269
<211> LENGTH: 9
<212> TYPE: DNA
<213> ORGANISM: Artificial Sequence
<220> FEATURE:
<223> OTHER INFORMATION: Synthetic

<400> SEQUENCE: 269 gctgcatcc                                                            9

<210> SEQ ID NO 270
<211> LENGTH: 3
<212> TYPE: PRT
<213> ORGANISM: Artificial Sequence
<220> FEATURE:
<223> OTHER INFORMATION: Synthetic

<400> SEQUENCE: 270

Ala Ala Ser
1

<210> SEQ ID NO 271

```
<211> LENGTH: 27
<212> TYPE: DNA
<213> ORGANISM: Artificial Sequence
<220> FEATURE:
<223> OTHER INFORMATION: Synthetic

<400> SEQUENCE: 271
caaaagtata acagtgcccc attcact                                                27

<210> SEQ ID NO 272
<211> LENGTH: 9
<212> TYPE: PRT
<213> ORGANISM: Artificial Sequence
<220> FEATURE:
<223> OTHER INFORMATION: Synthetic

<400> SEQUENCE: 272

Gln Lys Tyr Asn Ser Ala Pro Phe Thr
 1               5

<210> SEQ ID NO 273
<211> LENGTH: 357
<212> TYPE: DNA
<213> ORGANISM: Artificial Sequence
<220> FEATURE:
<223> OTHER INFORMATION: Synthetic

<400> SEQUENCE: 273
gaggtacaga tggtggagtc tgggggaggc ttggtccagc ctggggggtc cctgagactc            60
tcctgtgcag cctctggatt caccttagt aactattgga tgggctgggt ccgccaggct           120
ccagggaagg ggctggagtg ggtggccaac ataaagcaag atgggagtga aaatactat           180 gtggactctg tgaggggccg attcaccatc tccagagaca acgccaagaa ctcactgtat          240
ctgcaaatga acagcctgag agccgaggac acggctgttt attactgtgc gagggattac         300 gattttttgga ggtcctttga ctactggggc cagggaaccc tggtcaccgt ctcctca           357

<210> SEQ ID NO 274
<211> LENGTH: 119
<212> TYPE: PRT
<213> ORGANISM: Artificial Sequence
<220> FEATURE:
<223> OTHER INFORMATION: Synthetic

<400> SEQUENCE: 274

Glu Val Gln Met Val Glu Ser Gly Gly Gly Leu Val Gln Pro Gly Gly
 1               5                  10                  15

Ser Leu Arg Leu Ser Cys Ala Ala Ser Gly Phe Thr Leu Ser Asn Tyr
                20                  25                  30

Trp Met Gly Trp Val Arg Gln Ala Pro Gly Lys Gly Leu Glu Trp Val
            35                  40                  45

Ala Asn Ile Lys Gln Asp Gly Ser Glu Lys Tyr Tyr Val Asp Ser Val
        50                  55                  60

Arg Gly Arg Phe Thr Ile Ser Arg Asp Asn Ala Lys Asn Ser Leu Tyr
 65                  70                  75                  80

Leu Gln Met Asn Ser Leu Arg Ala Glu Asp Thr Ala Val Tyr Tyr Cys
                85                  90                  95

Ala Arg Asp Tyr Asp Phe Trp Arg Ser Phe Asp Tyr Trp Gly Gln Gly
               100                 105                 110

Thr Leu Val Thr Val Ser Ser
           115
```

<210> SEQ ID NO 275
<211> LENGTH: 24
<212> TYPE: DNA
<213> ORGANISM: Artificial Sequence
<220> FEATURE:
<223> OTHER INFORMATION: Synthetic

<400> SEQUENCE: 275
ggattcaccc ttagtaacta ttgg                                          24

<210> SEQ ID NO 276
<211> LENGTH: 8
<212> TYPE: PRT
<213> ORGANISM: Artificial Sequence
<220> FEATURE:
<223> OTHER INFORMATION: Synthetic

<400> SEQUENCE: 276

Gly Phe Thr Leu Ser Asn Tyr Trp
1               5

<210> SEQ ID NO 277
<211> LENGTH: 24
<212> TYPE: DNA
<213> ORGANISM: Artificial Sequence
<220> FEATURE:
<223> OTHER INFORMATION: Synthetic

<400> SEQUENCE: 277
ataaagcaag atgggagtga gaaa                                          24

<210> SEQ ID NO 278
<211> LENGTH: 8
<212> TYPE: PRT
<213> ORGANISM: Artificial Sequence
<220> FEATURE:
<223> OTHER INFORMATION: Synthetic

<400> SEQUENCE: 278

Ile Lys Gln Asp Gly Ser Glu Lys
1               5

<210> SEQ ID NO 279
<211> LENGTH: 36
<212> TYPE: DNA
<213> ORGANISM: Artificial Sequence
<220> FEATURE:
<223> OTHER INFORMATION: Synthetic

<400> SEQUENCE: 279
gcgagggatt acgatttttg gaggtccttt gactac                             36

<210> SEQ ID NO 280
<211> LENGTH: 12
<212> TYPE: PRT
<213> ORGANISM: Artificial Sequence
<220> FEATURE:
<223> OTHER INFORMATION: Synthetic

<400> SEQUENCE: 280

Ala Arg Asp Tyr Asp Phe Trp Arg Ser Phe Asp Tyr
1               5                   10

<210> SEQ ID NO 281
<211> LENGTH: 321
<212> TYPE: DNA

<213> ORGANISM: Artificial Sequence
<220> FEATURE:
<223> OTHER INFORMATION: Synthetic

<400> SEQUENCE: 281

```
gacatccaga tgacccagtc tccatcttcc gtgtctgcat ctgtaggaga cagagtcacc    60
atcacctgtc gggcgagtca gggtgttagc agctggttag cctggtatca gcagaaacca   120
gggaaaaccc ctaagctcct gatctatgtt gtatccagtt tgcaaagtgg ggtcccatca   180
aggttcagcg gccgtggatc tgggacagat ttcactctca ccatcaacag cctgcagcct   240
gaagattttg caacttacta ttgtcaacag ggtaacagtt tcccgtacac ttttggccag   300
gggaccaagc tggagatcaa a                                              321
```

<210> SEQ ID NO 282
<211> LENGTH: 107
<212> TYPE: PRT
<213> ORGANISM: Artificial Sequence
<220> FEATURE:
<223> OTHER INFORMATION: Synthetic

<400> SEQUENCE: 282

```
Asp Ile Gln Met Thr Gln Ser Pro Ser Ser Val Ser Ala Ser Val Gly
1               5                   10                  15
Asp Arg Val Thr Ile Thr Cys Arg Ala Ser Gln Gly Val Ser Ser Trp
            20                  25                  30
Leu Ala Trp Tyr Gln Gln Lys Pro Gly Lys Thr Pro Lys Leu Leu Ile
        35                  40                  45
Tyr Val Val Ser Ser Leu Gln Ser Gly Val Pro Ser Arg Phe Ser Gly
    50                  55                  60
Arg Gly Ser Gly Thr Asp Phe Thr Leu Thr Ile Asn Ser Leu Gln Pro
65                  70                  75                  80
Glu Asp Phe Ala Thr Tyr Tyr Cys Gln Gln Gly Asn Ser Phe Pro Tyr
                85                  90                  95
Thr Phe Gly Gln Gly Thr Lys Leu Glu Ile Lys
            100                 105
```

<210> SEQ ID NO 283
<211> LENGTH: 18
<212> TYPE: DNA
<213> ORGANISM: Artificial Sequence
<220> FEATURE:
<223> OTHER INFORMATION: Synthetic

<400> SEQUENCE: 283

```
cagggtgtta gcagctgg                                                   18
```

<210> SEQ ID NO 284
<211> LENGTH: 6
<212> TYPE: PRT
<213> ORGANISM: Artificial Sequence
<220> FEATURE:
<223> OTHER INFORMATION: Synthetic

<400> SEQUENCE: 284

```
Gln Gly Val Ser Ser Trp
1               5
```

<210> SEQ ID NO 285
<211> LENGTH: 9
<212> TYPE: DNA
<213> ORGANISM: Artificial Sequence
<220> FEATURE:
<223> OTHER INFORMATION: Synthetic

<400> SEQUENCE: 285 gttgtatcc                                                                 9

<210> SEQ ID NO 286
<211> LENGTH: 3
<212> TYPE: PRT
<213> ORGANISM: Artificial Sequence
<220> FEATURE:
<223> OTHER INFORMATION: Synthetic

<400> SEQUENCE: 286

Val Val Ser
1

<210> SEQ ID NO 287
<211> LENGTH: 27
<212> TYPE: DNA
<213> ORGANISM: Artificial Sequence
<220> FEATURE:
<223> OTHER INFORMATION: Synthetic

<400> SEQUENCE: 287
caacagggta acagtttccc gtacact                                            27

<210> SEQ ID NO 288
<211> LENGTH: 9
<212> TYPE: PRT
<213> ORGANISM: Artificial Sequence
<220> FEATURE:
<223> OTHER INFORMATION: Synthetic

<400> SEQUENCE: 288

Gln Gln Gly Asn Ser Phe Pro Tyr Thr
1               5

<210> SEQ ID NO 289
<211> LENGTH: 366
<212> TYPE: DNA
<213> ORGANISM: Artificial Sequence
<220> FEATURE:
<223> OTHER INFORMATION: Synthetic

<400> SEQUENCE: 289
gaagtgcagc tggtggagtc tgggggaggc ttggtacaga ctggcaggtc cctgagactc         60
tcctgtgcag cctctggatt cacgtttgat gattatgcca tgaactgggt ccggcaagct       120
ccagggaagg gcctggagtg ggtctcaggt attagttgga atagtggtaa cataggctat       180
gcggactctg tgaagggccg attcaccatc tccagagaca cgccaagaa ttccctgtat       240 ctgcaaatga acagtctgag agctgaggac acggccttgt attactgtgt aaaatatata       300
gggcagcagc tggtacagga ctactttgac tactggggcc agggaaccct ggtcaccgtc       360
tcctca                                                                  366

<210> SEQ ID NO 290
<211> LENGTH: 122
<212> TYPE: PRT
<213> ORGANISM: Artificial Sequence
<220> FEATURE:
<223> OTHER INFORMATION: Synthetic

<400> SEQUENCE: 290

-continued

Glu Val Gln Leu Val Glu Ser Gly Gly Gly Leu Val Gln Thr Gly Arg
1               5                   10                  15

Ser Leu Arg Leu Ser Cys Ala Ala Ser Gly Phe Thr Phe Asp Asp Tyr
            20                  25                  30

Ala Met Asn Trp Val Arg Gln Ala Pro Gly Lys Gly Leu Glu Trp Val
        35                  40                  45

Ser Gly Ile Ser Trp Asn Ser Gly Asn Ile Gly Tyr Ala Asp Ser Val
    50                  55                  60

Lys Gly Arg Phe Thr Ile Ser Arg Asp Asn Lys Asn Ser Leu Tyr
65                  70                  75                  80

Leu Gln Met Asn Ser Leu Arg Ala Glu Asp Thr Ala Leu Tyr Tyr Cys
                85                  90                  95

Val Lys Tyr Ile Gly Gln Gln Leu Val Gln Asp Tyr Phe Asp Tyr Trp
            100                 105                 110

Gly Gln Gly Thr Leu Val Thr Val Ser Ser
        115                 120

<210> SEQ ID NO 291
<211> LENGTH: 24
<212> TYPE: DNA
<213> ORGANISM: Artificial Sequence
<220> FEATURE:
<223> OTHER INFORMATION: Synthetic

<400> SEQUENCE: 291
ggattcacgt ttgatgatta tgcc          24

<210> SEQ ID NO 292
<211> LENGTH: 8
<212> TYPE: PRT
<213> ORGANISM: Artificial Sequence
<220> FEATURE:
<223> OTHER INFORMATION: Synthetic

<400> SEQUENCE: 292

Gly Phe Thr Phe Asp Asp Tyr Ala
1               5

<210> SEQ ID NO 293
<211> LENGTH: 24
<212> TYPE: DNA
<213> ORGANISM: Artificial Sequence
<220> FEATURE:
<223> OTHER INFORMATION: Synthetic

<400> SEQUENCE: 293
attagttgga atagtggtaa cata          24

<210> SEQ ID NO 294
<211> LENGTH: 8
<212> TYPE: PRT
<213> ORGANISM: Artificial Sequence
<220> FEATURE:
<223> OTHER INFORMATION: Synthetic

<400> SEQUENCE: 294

Ile Ser Trp Asn Ser Gly Asn Ile
1               5

<210> SEQ ID NO 295
<211> LENGTH: 45
<212> TYPE: DNA
<213> ORGANISM: Artificial Sequence
<220> FEATURE:
<223> OTHER INFORMATION: Synthetic

<400> SEQUENCE: 295
gtaaaatata tagggcagca gctggtacag gactactttg actac                    45

<210> SEQ ID NO 296
<211> LENGTH: 15
<212> TYPE: PRT
<213> ORGANISM: Artificial Sequence
<220> FEATURE:
<223> OTHER INFORMATION: Synthetic

<400> SEQUENCE: 296

Val Lys Tyr Ile Gly Gln Gln Leu Val Gln Asp Tyr Phe Asp Tyr
1               5                   10                  15

<210> SEQ ID NO 297
<211> LENGTH: 321
<212> TYPE: DNA
<213> ORGANISM: Artificial Sequence
<220> FEATURE:
<223> OTHER INFORMATION: Synthetic

<400> SEQUENCE: 297
gacatccaga tgacccagtc tccatcctcc ctgtctgcat ctgtaggaga cagagtcacc     60
atcacttgcc aggcgagtca ggacattacc aattatttaa attggtatca gcagagacca    120
gggaaagccc ctaagctcct gatctacgat gcattcaatt tggaaagagg ggtcccatca    180
aggttcagtg gaagtggata tgggacatat tttactttca ccatcagcag cctgcagcct    240
gaagatattg caatatatta ctgtcaacag tatgataatc tcccgctcac tttcggcgga    300
gggaccaagg tggagatcga a                                              321

<210> SEQ ID NO 298
<211> LENGTH: 107
<212> TYPE: PRT
<213> ORGANISM: Artificial Sequence
<220> FEATURE:
<223> OTHER INFORMATION: Synthetic

<400> SEQUENCE: 298

Asp Ile Gln Met Thr Gln Ser Pro Ser Ser Leu Ser Ala Ser Val Gly
1               5                   10                  15

Asp Arg Val Thr Ile Thr Cys Gln Ala Ser Gln Asp Ile Thr Asn Tyr
                20                  25                  30

Leu Asn Trp Tyr Gln Gln Arg Pro Gly Lys Ala Pro Lys Leu Leu Ile
            35                  40                  45

Tyr Asp Ala Phe Asn Leu Glu Arg Gly Val Pro Ser Arg Phe Ser Gly
        50                  55                  60

Ser Gly Tyr Gly Thr Tyr Phe Thr Phe Thr Ile Ser Ser Leu Gln Pro
65                  70                  75                  80

Glu Asp Ile Ala Ile Tyr Tyr Cys Gln Gln Tyr Asp Asn Leu Pro Leu
                85                  90                  95

Thr Phe Gly Gly Gly Thr Lys Val Glu Ile Glu
            100                 105

<210> SEQ ID NO 299
<211> LENGTH: 18
<212> TYPE: DNA
<213> ORGANISM: Artificial Sequence
<220> FEATURE:

<223> OTHER INFORMATION: Synthetic

<400> SEQUENCE: 299
caggacatta ccaattat                                                           18

<210> SEQ ID NO 300
<211> LENGTH: 6
<212> TYPE: PRT
<213> ORGANISM: Artificial Sequence
<220> FEATURE:
<223> OTHER INFORMATION: Synthetic

<400> SEQUENCE: 300

Gln Asp Ile Thr Asn Tyr
1               5

<210> SEQ ID NO 301
<211> LENGTH: 9
<212> TYPE: DNA
<213> ORGANISM: Artificial Sequence
<220> FEATURE:
<223> OTHER INFORMATION: Synthetic

<400> SEQUENCE: 301 gatgcattc                                                                      9

<210> SEQ ID NO 302
<211> LENGTH: 3
<212> TYPE: PRT
<213> ORGANISM: Artificial Sequence
<220> FEATURE:
<223> OTHER INFORMATION: Synthetic

<400> SEQUENCE: 302

Asp Ala Phe
1

<210> SEQ ID NO 303
<211> LENGTH: 27
<212> TYPE: DNA
<213> ORGANISM: Artificial Sequence
<220> FEATURE:
<223> OTHER INFORMATION: Synthetic

<400> SEQUENCE: 303
caacagtatg ataatctccc gctcact                                                 27

<210> SEQ ID NO 304
<211> LENGTH: 9
<212> TYPE: PRT
<213> ORGANISM: Artificial Sequence
<220> FEATURE:
<223> OTHER INFORMATION: Synthetic

<400> SEQUENCE: 304

Gln Gln Tyr Asp Asn Leu Pro Leu Thr
1               5

<210> SEQ ID NO 305
<211> LENGTH: 357
<212> TYPE: DNA
<213> ORGANISM: Artificial Sequence
<220> FEATURE:
<223> OTHER INFORMATION: Synthetic

<400> SEQUENCE: 305

```
caggtgcagc tggtggagtc tgggggaggc gtggtccagc ctgggaggtc cctgagactc      60
tcctgtgcag cgtctggatt caccttcagt agtcatggca tgcattgggt ccgccaggct     120
ccaggcaagg ggctggagtg ggtggcagtc atatggtatg atggaagtaa taaataccat     180
gcagactccg tgaagggccg attcaccatc tacagagaca attccaagaa cacgctggat     240
ctgcaaatga acagcctgag agtcgaggac acggctatgt attactgtgc gagagaagac     300
agtaataacg aagatcttga ctattggggc cagggaaccc tggtcaccgt ttcctca       357
```

<210> SEQ ID NO 306
<211> LENGTH: 119
<212> TYPE: PRT
<213> ORGANISM: Artificial Sequence
<220> FEATURE:
<223> OTHER INFORMATION: Synthetic

<400> SEQUENCE: 306

```
Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser His
            20                  25                  30

Gly Met His Trp Val Arg Gln Ala Pro Gly Lys Gly Leu Glu Trp Val
        35                  40                  45

Ala Val Ile Trp Tyr Asp Gly Ser Asn Lys Tyr His Ala Asp Ser Val
    50                  55                  60

Lys Gly Arg Phe Thr Ile Tyr Arg Asp Asn Ser Lys Asn Thr Leu Asp
65                  70                  75                  80

Leu Gln Met Asn Ser Leu Arg Val Glu Asp Thr Ala Met Tyr Tyr Cys
                85                  90                  95

Ala Arg Glu Asp Ser Asn Asn Glu Asp Leu Asp Tyr Trp Gly Gln Gly
            100                 105                 110

Thr Leu Val Thr Val Ser Ser
        115
```

<210> SEQ ID NO 307
<211> LENGTH: 24
<212> TYPE: DNA
<213> ORGANISM: Artificial Sequence
<220> FEATURE:
<223> OTHER INFORMATION: Synthetic

<400> SEQUENCE: 307

```
ggattcacct tcagtagtca tggc                                              24
```

<210> SEQ ID NO 308
<211> LENGTH: 8
<212> TYPE: PRT
<213> ORGANISM: Artificial Sequence
<220> FEATURE:
<223> OTHER INFORMATION: Synthetic

<400> SEQUENCE: 308

```
Gly Phe Thr Phe Ser Ser His Gly
1               5
```

<210> SEQ ID NO 309
<211> LENGTH: 24
<212> TYPE: DNA
<213> ORGANISM: Artificial Sequence
<220> FEATURE:
<223> OTHER INFORMATION: Synthetic

<400> SEQUENCE: 309
atatggtatg atggaagtaa taaa                                         24

<210> SEQ ID NO 310
<211> LENGTH: 8
<212> TYPE: PRT
<213> ORGANISM: Artificial Sequence
<220> FEATURE:
<223> OTHER INFORMATION: Synthetic

<400> SEQUENCE: 310

Ile Trp Tyr Asp Gly Ser Asn Lys
1               5

<210> SEQ ID NO 311
<211> LENGTH: 36
<212> TYPE: DNA
<213> ORGANISM: Artificial Sequence
<220> FEATURE:
<223> OTHER INFORMATION: Synthetic

<400> SEQUENCE: 311
gcgagagaag acagtaataa cgaagatctt gactat                            36

<210> SEQ ID NO 312
<211> LENGTH: 12
<212> TYPE: PRT
<213> ORGANISM: Artificial Sequence
<220> FEATURE:
<223> OTHER INFORMATION: Synthetic

<400> SEQUENCE: 312

Ala Arg Glu Asp Ser Asn Asn Glu Asp Leu Asp Tyr
1               5                   10

<210> SEQ ID NO 313
<211> LENGTH: 324
<212> TYPE: DNA
<213> ORGANISM: Artificial Sequence
<220> FEATURE:
<223> OTHER INFORMATION: Synthetic

<400> SEQUENCE: 313
gacatccaga tgacccagtc tccatcctcc ctgtctgcat ctgtaggaga cagagtcacc    60
atcacttgcc gggcaagtca gggcattaga aatgatttag gctggtttca gcagaaacca   120
ggaaaagccc ctaagcgcct gatctatgtt gcatccaatt tacaaagtgg ggtcccatca   180
aggttcagcg gcagtggatc tgggacagaa ttcactctca caatcagcag cctgcagcct   240
gaagattttg caacttatta ctgtctacag catagtaatt accctccgtg acgttcggc    300 caagggacca aggtggaaat caaa                                         324

<210> SEQ ID NO 314
<211> LENGTH: 108
<212> TYPE: PRT
<213> ORGANISM: Artificial Sequence
<220> FEATURE:
<223> OTHER INFORMATION: Synthetic

<400> SEQUENCE: 314

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Arg Asn Asp
            20                  25                  30

Leu Gly Trp Phe Gln Gln Lys Pro Gly Lys Ala Pro Lys Arg Leu Ile
            35                  40                  45

Tyr Val Ala Ser Asn Leu Gln Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Glu Asp Phe Ala Thr Tyr Tyr Cys Leu Gln His Ser Asn Tyr Pro Pro
                85                  90                  95

Trp Thr Phe Gly Gln Gly Thr Lys Val Glu Ile Lys
            100                 105

<210> SEQ ID NO 315
<211> LENGTH: 18
<212> TYPE: DNA
<213> ORGANISM: Artificial Sequence
<220> FEATURE:
<223> OTHER INFORMATION: Synthetic

<400> SEQUENCE: 315
cagggcatta gaaatgat                                                       18

<210> SEQ ID NO 316
<211> LENGTH: 6
<212> TYPE: PRT
<213> ORGANISM: Artificial Sequence
<220> FEATURE:
<223> OTHER INFORMATION: Synthetic

<400> SEQUENCE: 316

Gln Gly Ile Arg Asn Asp
1               5

<210> SEQ ID NO 317
<211> LENGTH: 9
<212> TYPE: DNA
<213> ORGANISM: Artificial Sequence
<220> FEATURE:
<223> OTHER INFORMATION: Synthetic

<400> SEQUENCE: 317 gttgcatcc                                                                  9

<210> SEQ ID NO 318
<211> LENGTH: 3
<212> TYPE: PRT
<213> ORGANISM: Artificial Sequence
<220> FEATURE:
<223> OTHER INFORMATION: Synthetic

<400> SEQUENCE: 318

Val Ala Ser
1

<210> SEQ ID NO 319
<211> LENGTH: 30
<212> TYPE: DNA
<213> ORGANISM: Artificial Sequence
<220> FEATURE:
<223> OTHER INFORMATION: Synthetic

<400> SEQUENCE: 319
ctacagcata gtaattaccc tccgtggacg                                          30

```
<210> SEQ ID NO 320
<211> LENGTH: 10
<212> TYPE: PRT
<213> ORGANISM: Artificial Sequence
<220> FEATURE:
<223> OTHER INFORMATION: Synthetic

<400> SEQUENCE: 320

Leu Gln His Ser Asn Tyr Pro Pro Trp Thr
1               5                   10

<210> SEQ ID NO 321
<211> LENGTH: 354
<212> TYPE: DNA
<213> ORGANISM: Artificial Sequence
<220> FEATURE:
<223> OTHER INFORMATION: Synthetic

<400> SEQUENCE: 321
caggtgcagc tggtggagtc tgggggaggc gtggtccagc ctgggaggtc cctgagactc      60
tcctgtgcag cgtctggatt catttttcagt agctatggca tgcactgggt ccgccaggct   120
ccaggcaagg gctggagtg gtggcagtt atatggaatg atggaagtaa taaatactct      180
gcagactccg tgaagggccg attcaccgtc tccaggaca attccaagaa cacccctgtat   240 ctgcaaatga acagtctgaa agccgaggac acggctgtgt attactgtgc gagagacggg   300
gagtgggagg tttttgacta ctggggccag ggaaccctgg tcaccgtctc ctca          354

<210> SEQ ID NO 322
<211> LENGTH: 118
<212> TYPE: PRT
<213> ORGANISM: Artificial Sequence
<220> FEATURE:
<223> OTHER INFORMATION: Synthetic

<400> SEQUENCE: 322

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Ile Phe Ser Ser Tyr
            20                  25                  30

Gly Met His Trp Val Arg Gln Ala Pro Gly Lys Gly Leu Glu Trp Val
        35                  40                  45

Ala Val Ile Trp Asn Asp Gly Ser Asn Lys Tyr Ser Ala Asp Ser Val
    50                  55                  60

Lys Gly Arg Phe Thr Val Ser Arg Asp Asn Ser Lys Asn Thr Leu Tyr
65                  70                  75                  80

Leu Gln Met Asn Ser Leu Lys Ala Glu Asp Thr Ala Val Tyr Tyr Cys
                85                  90                  95

Ala Arg Asp Gly Glu Trp Glu Val Phe Asp Tyr Trp Gly Gln Gly Thr
            100                 105                 110

Leu Val Thr Val Ser Ser
        115

<210> SEQ ID NO 323
<211> LENGTH: 24
<212> TYPE: DNA
<213> ORGANISM: Artificial Sequence
<220> FEATURE:
<223> OTHER INFORMATION: Synthetic

<400> SEQUENCE: 323
ggattcattt tcagtagcta tggc                                            24
```

<210> SEQ ID NO 324
<211> LENGTH: 8
<212> TYPE: PRT
<213> ORGANISM: Artificial Sequence
<220> FEATURE:
<223> OTHER INFORMATION: Synthetic

<400> SEQUENCE: 324

Gly Phe Ile Phe Ser Ser Tyr Gly
1               5

<210> SEQ ID NO 325
<211> LENGTH: 24
<212> TYPE: DNA
<213> ORGANISM: Artificial Sequence
<220> FEATURE:
<223> OTHER INFORMATION: Synthetic

<400> SEQUENCE: 325
atatggaatg atggaagtaa taaa                                              24

<210> SEQ ID NO 326
<211> LENGTH: 8
<212> TYPE: PRT
<213> ORGANISM: Artificial Sequence
<220> FEATURE:
<223> OTHER INFORMATION: Synthetic

<400> SEQUENCE: 326

Ile Trp Asn Asp Gly Ser Asn Lys
1               5

<210> SEQ ID NO 327
<211> LENGTH: 33
<212> TYPE: DNA
<213> ORGANISM: Artificial Sequence
<220> FEATURE:
<223> OTHER INFORMATION: Synthetic

<400> SEQUENCE: 327
gcgagagacg gggagtggga ggtttttgac tac                                    33

<210> SEQ ID NO 328
<211> LENGTH: 11
<212> TYPE: PRT
<213> ORGANISM: Artificial Sequence
<220> FEATURE:
<223> OTHER INFORMATION: Synthetic

<400> SEQUENCE: 328

Ala Arg Asp Gly Glu Trp Glu Val Phe Asp Tyr
1               5                   10

<210> SEQ ID NO 329
<211> LENGTH: 324
<212> TYPE: DNA
<213> ORGANISM: Artificial Sequence
<220> FEATURE:
<223> OTHER INFORMATION: Synthetic

<400> SEQUENCE: 329
gacatagtga tgacgcagtc tccagtcacc ctgtctgcgt ctccagggga aagagccacc       60
ctctcctgca gggccagtca gagtgttcga agcaacttag cctggtacca ggagaaacct      120
ggccaggctc ccaggctcct catctatggt gcatccacca gggccactgg tatcccagcc      180

```
aggttcagtg gcagtgggtc tgggacagag ttcactctca ccatcagcag cctgcagtct    240
gaagattttg cagtttatta ctgtcagcag tataatgact ggcctccgtg gacgttcggc    300
caagggacca aggtggaaat caaa                                           324
```

<210> SEQ ID NO 330
<211> LENGTH: 108
<212> TYPE: PRT
<213> ORGANISM: Artificial Sequence
<220> FEATURE:
<223> OTHER INFORMATION: Synthetic

<400> SEQUENCE: 330

```
Asp Ile Val Met Thr Gln Ser Pro Val Thr Leu Ser Ala Ser Pro Gly
1               5                   10                  15

Glu Arg Ala Thr Leu Ser Cys Arg Ala Ser Gln Ser Val Arg Ser Asn
            20                  25                  30

Leu Ala Trp Tyr Gln Glu Lys Pro Gly Gln Ala Pro Arg Leu Leu Ile
        35                  40                  45

Tyr Gly Ala Ser Thr Arg Ala Thr Gly Ile Pro Ala Arg Phe Ser Gly
    50                  55                  60

Ser Gly Ser Gly Thr Glu Phe Thr Leu Thr Ile Ser Ser Leu Gln Ser
65                  70                  75                  80

Glu Asp Phe Ala Val Tyr Tyr Cys Gln Gln Tyr Asn Asp Trp Pro Pro
                85                  90                  95

Trp Thr Phe Gly Gln Gly Thr Lys Val Glu Ile Lys
            100                 105
```

<210> SEQ ID NO 331
<211> LENGTH: 18
<212> TYPE: DNA
<213> ORGANISM: Artificial Sequence
<220> FEATURE:
<223> OTHER INFORMATION: Synthetic

<400> SEQUENCE: 331

```
cagagtgttc gaagcaac                                                   18
```

<210> SEQ ID NO 332
<211> LENGTH: 6
<212> TYPE: PRT
<213> ORGANISM: Artificial Sequence
<220> FEATURE:
<223> OTHER INFORMATION: Synthetic

<400> SEQUENCE: 332

```
Gln Ser Val Arg Ser Asn
1               5
```

<210> SEQ ID NO 333
<211> LENGTH: 9
<212> TYPE: DNA
<213> ORGANISM: Artificial Sequence
<220> FEATURE:
<223> OTHER INFORMATION: Synthetic

<400> SEQUENCE: 333

```
ggtgcatcc                                                              9
```

<210> SEQ ID NO 334
<211> LENGTH: 3
<212> TYPE: PRT

```
<213> ORGANISM: Artificial Sequence
<220> FEATURE:
<223> OTHER INFORMATION: Synthetic

<400> SEQUENCE: 334

Gly Ala Ser
1

<210> SEQ ID NO 335
<211> LENGTH: 30
<212> TYPE: DNA
<213> ORGANISM: Artificial Sequence
<220> FEATURE:
<223> OTHER INFORMATION: Synthetic

<400> SEQUENCE: 335
cagcagtata atgactggcc tccgtggacg                                          30

<210> SEQ ID NO 336
<211> LENGTH: 10
<212> TYPE: PRT
<213> ORGANISM: Artificial Sequence
<220> FEATURE:
<223> OTHER INFORMATION: Synthetic

<400> SEQUENCE: 336

Gln Gln Tyr Asn Asp Trp Pro Pro Trp Thr
1               5                   10

<210> SEQ ID NO 337
<211> LENGTH: 372
<212> TYPE: DNA
<213> ORGANISM: Artificial Sequence
<220> FEATURE:
<223> OTHER INFORMATION: Synthetic

<400> SEQUENCE: 337
caggtgcagc tggtgcagtc tggggctgag gtgaagaagc ctggggcctc agtgaaggtc        60
tcctgcaaag tttccggata caccctcact gaattatcca tgcactgggt gcgacaggct      120
cctggaaaag ggcttgagtg gatgggaggt tttgatcctg aagatggtga acaatctac       180 gcacagaagt tccagggcag actcaccatg accgaggaca catctacaga cacagcctac      240
atggagctga gcagcctgag atctgaggac acggccgtgt attactgtgc aacagacgat      300
tacgatattt tgacttctta tccttacaat atggacgtct ggggccaagg gaccacggtc      360
accgtctcct ca                                                          372

<210> SEQ ID NO 338
<211> LENGTH: 124
<212> TYPE: PRT
<213> ORGANISM: Artificial Sequence
<220> FEATURE:
<223> OTHER INFORMATION: Synthetic

<400> SEQUENCE: 338

Gln Val Gln Leu Val Gln Ser Gly Ala Glu Val Lys Lys Pro Gly Ala
1               5                   10                  15

Ser Val Lys Val Ser Cys Lys Val Ser Gly Tyr Thr Leu Thr Glu Leu
            20                  25                  30

Ser Met His Trp Val Arg Gln Ala Pro Gly Lys Gly Leu Glu Trp Met
        35                  40                  45

Gly Gly Phe Asp Pro Glu Asp Gly Glu Thr Ile Tyr Ala Gln Lys Phe
    50                  55                  60
```

Gln Gly Arg Leu Thr Met Thr Glu Asp Thr Ser Thr Asp Thr Ala Tyr
65                  70                  75                  80

Met Glu Leu Ser Ser Leu Arg Ser Glu Asp Thr Ala Val Tyr Tyr Cys
                85                  90                  95

Ala Thr Asp Asp Tyr Asp Ile Leu Thr Ser Tyr Pro Tyr Asn Met Asp
            100                 105                 110

Val Trp Gly Gln Gly Thr Thr Val Thr Val Ser Ser
        115                 120

<210> SEQ ID NO 339
<211> LENGTH: 24
<212> TYPE: DNA
<213> ORGANISM: Artificial Sequence
<220> FEATURE:
<223> OTHER INFORMATION: Synthetic

<400> SEQUENCE: 339
ggatacaccc tcactgaatt atcc                                         24

<210> SEQ ID NO 340
<211> LENGTH: 8
<212> TYPE: PRT
<213> ORGANISM: Artificial Sequence
<220> FEATURE:
<223> OTHER INFORMATION: Synthetic

<400> SEQUENCE: 340

Gly Tyr Thr Leu Thr Glu Leu Ser
1               5

<210> SEQ ID NO 341
<211> LENGTH: 24
<212> TYPE: DNA
<213> ORGANISM: Artificial Sequence
<220> FEATURE:
<223> OTHER INFORMATION: Synthetic

<400> SEQUENCE: 341
tttgatcctg aagatggtga aaca                                         24

<210> SEQ ID NO 342
<211> LENGTH: 8
<212> TYPE: PRT
<213> ORGANISM: Artificial Sequence
<220> FEATURE:
<223> OTHER INFORMATION: Synthetic

<400> SEQUENCE: 342

Phe Asp Pro Glu Asp Gly Glu Thr
1               5

<210> SEQ ID NO 343
<211> LENGTH: 51
<212> TYPE: DNA
<213> ORGANISM: Artificial Sequence
<220> FEATURE:
<223> OTHER INFORMATION: Synthetic

<400> SEQUENCE: 343
gcaacagacg attacgatat tttgacttct tatccttaca atatggacgt c            51

<210> SEQ ID NO 344
<211> LENGTH: 17
<212> TYPE: PRT

<213> ORGANISM: Artificial Sequence
<220> FEATURE:
<223> OTHER INFORMATION: Synthetic

<400> SEQUENCE: 344

Ala Thr Asp Asp Tyr Asp Ile Leu Thr Ser Tyr Pro Tyr Asn Met Asp
1               5                   10                  15
Val

<210> SEQ ID NO 345
<211> LENGTH: 321
<212> TYPE: DNA
<213> ORGANISM: Artificial Sequence
<220> FEATURE:
<223> OTHER INFORMATION: Synthetic

<400> SEQUENCE: 345

```
gacatccaga tgacccagtc tccatcctcc ctgtctgcat ctgtaggaga cagagtcacc    60
atcacttgcc gggcaagtca gagcattaac aactatttaa attggtatca gcagaaacca   120
gggaaagccc ctaagctcct gatctatgct gcatccagtt tgcaaagtgg ggtcccatca   180
aggttcagtg gcagtggatc tgggacagat ttcactctca ccatcagcag ccttcaacct   240
gaagattttg aacttactac tgtcaacag agtgacagta ccccattcac tttcggccct   300
gggaccaaag tggatatcaa a                                             321
```

<210> SEQ ID NO 346
<211> LENGTH: 107
<212> TYPE: PRT
<213> ORGANISM: Artificial Sequence
<220> FEATURE:
<223> OTHER INFORMATION: Synthetic

<400> SEQUENCE: 346

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Asn Asn Tyr
                20                  25                  30

Leu Asn Trp Tyr Gln Gln Lys Pro Gly Lys Ala Pro Lys Leu Leu Ile
            35                  40                  45

Tyr Ala Ala Ser Ser Leu Gln Ser Gly Val Pro Ser Arg Phe Ser Gly
        50                  55                  60

Ser Gly Ser Gly Thr Asp Phe Thr Leu Thr Ile Ser Ser Leu Gln Pro
65                  70                  75                  80

Glu Asp Phe Gly Thr Tyr Tyr Cys Gln Gln Ser Asp Ser Thr Pro Phe
                85                  90                  95

Thr Phe Gly Pro Gly Thr Lys Val Asp Ile Lys
            100                 105

<210> SEQ ID NO 347
<211> LENGTH: 18
<212> TYPE: DNA
<213> ORGANISM: Artificial Sequence
<220> FEATURE:
<223> OTHER INFORMATION: Synthetic

<400> SEQUENCE: 347

```
cagagcatta acaactat                                                  18
```

<210> SEQ ID NO 348
<211> LENGTH: 6

<212> TYPE: PRT
<213> ORGANISM: Artificial Sequence
<220> FEATURE:
<223> OTHER INFORMATION: Synthetic

<400> SEQUENCE: 348

Gln Ser Ile Asn Asn Tyr
1               5

<210> SEQ ID NO 349
<211> LENGTH: 9
<212> TYPE: DNA
<213> ORGANISM: Artificial Sequence
<220> FEATURE:
<223> OTHER INFORMATION: Synthetic

<400> SEQUENCE: 349 gctgcatcc                                                            9

<210> SEQ ID NO 350
<211> LENGTH: 3
<212> TYPE: PRT
<213> ORGANISM: Artificial Sequence
<220> FEATURE:
<223> OTHER INFORMATION: Synthetic

<400> SEQUENCE: 350

Ala Ala Ser
1

<210> SEQ ID NO 351
<211> LENGTH: 27
<212> TYPE: DNA
<213> ORGANISM: Artificial Sequence
<220> FEATURE:
<223> OTHER INFORMATION: Synthetic

<400> SEQUENCE: 351
caacagagtg acagtacccc attcact                                       27

<210> SEQ ID NO 352
<211> LENGTH: 9
<212> TYPE: PRT
<213> ORGANISM: Artificial Sequence
<220> FEATURE:
<223> OTHER INFORMATION: Synthetic

<400> SEQUENCE: 352

Gln Gln Ser Asp Ser Thr Pro Phe Thr
1               5

<210> SEQ ID NO 353
<211> LENGTH: 363
<212> TYPE: DNA
<213> ORGANISM: Artificial Sequence
<220> FEATURE:
<223> OTHER INFORMATION: Synthetic

<400> SEQUENCE: 353
caggtgcagc tggtggagtc tgggggaggc gtggtccagc ctggggaggtc cctgagactc    60 tcctgtgcag cgtctggatt caccttcagt agctatggca tgcactgggt ccgccaggct   120
ccaggcaagg ggctggagtg ggtggcagtt atatggtatg atggaagtaa ttattactat   180
gcagcctccg tgaagggccg attcaccatc tccagagaca attccgagaa cacgctgtat   240
ctgcaaatga acagactgag agccgaggac acggctgtgt attactgtgc gagagagggg   300

```
actggaagta cggaggacta ctttgactac tggggccagg gaaccctggt caccgtctcc    360
tca                                                                  363
```

<210> SEQ ID NO 354
<211> LENGTH: 121
<212> TYPE: PRT
<213> ORGANISM: Artificial Sequence
<220> FEATURE:
<223> OTHER INFORMATION: Synthetic

<400> SEQUENCE: 354

```
Gln Val Gln Leu Val Glu Ser Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ala Val Ile Trp Tyr Asp Gly Ser Asn Tyr Tyr Ala Ala Ser Val
    50                  55                  60

Lys Gly Arg Phe Thr Ile Ser Arg Asp Asn Ser Glu Asn Thr Leu Tyr
65                  70                  75                  80

Leu Gln Met Asn Arg Leu Arg Ala Glu Asp Thr Ala Val Tyr Tyr Cys
                85                  90                  95

Ala Arg Glu Gly Thr Gly Ser Thr Glu Asp Tyr Phe Asp Tyr Trp Gly
            100                 105                 110

Gln Gly Thr Leu Val Thr Val Ser Ser
        115                 120
```

<210> SEQ ID NO 355
<211> LENGTH: 24
<212> TYPE: DNA
<213> ORGANISM: Artificial Sequence
<220> FEATURE:
<223> OTHER INFORMATION: Synthetic

<400> SEQUENCE: 355

```
ggattcacct tcagtagcta tggc                                           24
```

<210> SEQ ID NO 356
<211> LENGTH: 8
<212> TYPE: PRT
<213> ORGANISM: Artificial Sequence
<220> FEATURE:
<223> OTHER INFORMATION: Synthetic

<400> SEQUENCE: 356

```
Gly Phe Thr Phe Ser Ser Tyr Gly
1               5
```

<210> SEQ ID NO 357
<211> LENGTH: 24
<212> TYPE: DNA
<213> ORGANISM: Artificial Sequence
<220> FEATURE:
<223> OTHER INFORMATION: Synthetic

<400> SEQUENCE: 357

```
atatggtatg atggaagtaa ttat                                           24
```

<210> SEQ ID NO 358
<211> LENGTH: 8

```
<212> TYPE: PRT
<213> ORGANISM: Artificial Sequence
<220> FEATURE:
<223> OTHER INFORMATION: Synthetic

<400> SEQUENCE: 358

Ile Trp Tyr Asp Gly Ser Asn Tyr
1               5

<210> SEQ ID NO 359
<211> LENGTH: 42
<212> TYPE: DNA
<213> ORGANISM: Artificial Sequence
<220> FEATURE:
<223> OTHER INFORMATION: Synthetic

<400> SEQUENCE: 359
gcgagagagg ggactggaag tacggaggac tactttgact ac                    42

<210> SEQ ID NO 360
<211> LENGTH: 14
<212> TYPE: PRT
<213> ORGANISM: Artificial Sequence
<220> FEATURE:
<223> OTHER INFORMATION: Synthetic

<400> SEQUENCE: 360

Ala Arg Glu Gly Thr Gly Ser Thr Glu Asp Tyr Phe Asp Tyr
1               5                   10

<210> SEQ ID NO 361
<211> LENGTH: 324
<212> TYPE: DNA
<213> ORGANISM: Artificial Sequence
<220> FEATURE:
<223> OTHER INFORMATION: Synthetic

<400> SEQUENCE: 361
gaaattgtgt tgacacagtc tccagccacc ctgtctttgt ctccagggga aagagccacc    60
ctctcctgca gggccagtca gagtgttagc agcttcttag cctggtatca acagaaacct   120
ggccaggctc ccaggctcct catctatgat gcatccaaca gggccactgg catcccagtc   180
aggttcagtg gcagtgggtc tgggacagac ttcactctca ccatcagcag cctagagcct   240
gaagattttg cagtttatta ctgtcagcag cgtagcaact ggcctccgta cacttttggc   300
caggggacca agctggagat caaa                                          324

<210> SEQ ID NO 362
<211> LENGTH: 108
<212> TYPE: PRT
<213> ORGANISM: Artificial Sequence
<220> FEATURE:
<223> OTHER INFORMATION: Synthetic

<400> SEQUENCE: 362

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Phe
            20                  25                  30

Leu Ala Trp Tyr Gln Gln Lys Pro Gly Gln Ala Pro Arg Leu Leu Ile
        35                  40                  45

Tyr Asp Ala Ser Asn Arg Ala Thr Gly Ile Pro Val Arg Phe Ser Gly
    50                  55                  60
```

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Arg Ser Asn Trp Pro Pro
                85                  90                  95

Tyr Thr Phe Gly Gln Gly Thr Lys Leu Glu Ile Lys
            100                 105

<210> SEQ ID NO 363
<211> LENGTH: 18
<212> TYPE: DNA
<213> ORGANISM: Artificial Sequence
<220> FEATURE:
<223> OTHER INFORMATION: Synthetic

<400> SEQUENCE: 363
cagagtgtta gcagcttc                                                 18

<210> SEQ ID NO 364
<211> LENGTH: 6
<212> TYPE: PRT
<213> ORGANISM: Artificial Sequence
<220> FEATURE:
<223> OTHER INFORMATION: Synthetic

<400> SEQUENCE: 364

Gln Ser Val Ser Ser Phe
1               5

<210> SEQ ID NO 365
<211> LENGTH: 9
<212> TYPE: DNA
<213> ORGANISM: Artificial Sequence
<220> FEATURE:
<223> OTHER INFORMATION: Synthetic

<400> SEQUENCE: 365 gatgcatcc                                                            9

<210> SEQ ID NO 366
<211> LENGTH: 3
<212> TYPE: PRT
<213> ORGANISM: Artificial Sequence
<220> FEATURE:
<223> OTHER INFORMATION: Synthetic

<400> SEQUENCE: 366

Asp Ala Ser
1

<210> SEQ ID NO 367
<211> LENGTH: 30
<212> TYPE: DNA
<213> ORGANISM: Artificial Sequence
<220> FEATURE:
<223> OTHER INFORMATION: Synthetic

<400> SEQUENCE: 367
cagcagcgta gcaactggcc tccgtacact                                    30

<210> SEQ ID NO 368
<211> LENGTH: 10
<212> TYPE: PRT
<213> ORGANISM: Artificial Sequence
<220> FEATURE:
<223> OTHER INFORMATION: Synthetic

<400> SEQUENCE: 368

Gln Gln Arg Ser Asn Trp Pro Pro Tyr Thr
1               5                   10

<210> SEQ ID NO 369
<211> LENGTH: 372
<212> TYPE: DNA
<213> ORGANISM: Artificial Sequence
<220> FEATURE:
<223> OTHER INFORMATION: Synthetic

<400> SEQUENCE: 369
caggtccagc tggtacagtc tggggctgag gtgaagaagc ctggggcctc agtgaaggtc     60
tcctgcaagg tttccggata caccctcact gaattatcca tgcactgggt gcgacaggct    120
cctggaaaag gcttgagtg gatgggaggt tttgatcctg aagatgggga aacaatctac    180
gcacagaagt tccagggcag agtcaccatg accgaggaca catctacaga aacagcctac    240
atggagctga gcagcctgag atctgaggac acggccgtgt attactgtgc aacagacgat    300
tacgatattt tgactgatta ccttacaat atggacgtct ggggccaagg gaccacggtc    360
accgtctcct ca                                                        372

<210> SEQ ID NO 370
<211> LENGTH: 124
<212> TYPE: PRT
<213> ORGANISM: Artificial Sequence
<220> FEATURE:
<223> OTHER INFORMATION: Synthetic

<400> SEQUENCE: 370

Gln Val Gln Leu Val Gln Ser Gly Ala Glu Val Lys Lys Pro Gly Ala
1               5                   10                  15

Ser Val Lys Val Ser Cys Lys Val Ser Gly Tyr Thr Leu Thr Glu Leu
            20                  25                  30

Ser Met His Trp Val Arg Gln Ala Pro Gly Lys Gly Leu Glu Trp Met
        35                  40                  45

Gly Gly Phe Asp Pro Glu Asp Gly Glu Thr Ile Tyr Ala Gln Lys Phe
    50                  55                  60

Gln Gly Arg Val Thr Met Thr Glu Asp Thr Ser Thr Glu Thr Ala Tyr
65                  70                  75                  80

Met Glu Leu Ser Ser Leu Arg Ser Glu Asp Thr Ala Val Tyr Tyr Cys
                85                  90                  95

Ala Thr Asp Asp Tyr Asp Ile Leu Thr Asp Tyr Pro Tyr Asn Met Asp
            100                 105                 110

Val Trp Gly Gln Gly Thr Thr Val Thr Val Ser Ser
        115                 120

<210> SEQ ID NO 371
<211> LENGTH: 24
<212> TYPE: DNA
<213> ORGANISM: Artificial Sequence
<220> FEATURE:
<223> OTHER INFORMATION: Synthetic

<400> SEQUENCE: 371
ggatacaccc tcactgaatt atcc                                            24

<210> SEQ ID NO 372
<211> LENGTH: 8
<212> TYPE: PRT

```
<213> ORGANISM: Artificial Sequence
<220> FEATURE:
<223> OTHER INFORMATION: Synthetic

<400> SEQUENCE: 372

Gly Tyr Thr Leu Thr Glu Leu Ser
1               5

<210> SEQ ID NO 373
<211> LENGTH: 24
<212> TYPE: DNA
<213> ORGANISM: Artificial Sequence
<220> FEATURE:
<223> OTHER INFORMATION: Synthetic

<400> SEQUENCE: 373
tttgatcctg aagatgggga aaca                                          24

<210> SEQ ID NO 374
<211> LENGTH: 8
<212> TYPE: PRT
<213> ORGANISM: Artificial Sequence
<220> FEATURE:
<223> OTHER INFORMATION: Synthetic

<400> SEQUENCE: 374

Phe Asp Pro Glu Asp Gly Glu Thr
1               5

<210> SEQ ID NO 375
<211> LENGTH: 51
<212> TYPE: DNA
<213> ORGANISM: Artificial Sequence
<220> FEATURE:
<223> OTHER INFORMATION: Synthetic

<400> SEQUENCE: 375
gcaacagacg attacgatat tttgactgat tatccttaca atatggacgt c            51

<210> SEQ ID NO 376
<211> LENGTH: 17
<212> TYPE: PRT
<213> ORGANISM: Artificial Sequence
<220> FEATURE:
<223> OTHER INFORMATION: Synthetic

<400> SEQUENCE: 376

Ala Thr Asp Asp Tyr Asp Ile Leu Thr Asp Tyr Pro Tyr Asn Met Asp
1               5                   10                  15

Val

<210> SEQ ID NO 377
<211> LENGTH: 321
<212> TYPE: DNA
<213> ORGANISM: Artificial Sequence
<220> FEATURE:
<223> OTHER INFORMATION: Synthetic

<400> SEQUENCE: 377
gacatccaga tgacccagtc tccatcctcc ctgtctgcat ctgtaggaga cagagtcacc    60
atcacttgcc gggcaagtca gagcattagc agctatttaa attggtatca gcagaaacca   120
gggaaagccc ctaagctcct gatctatgct gcatccagtt tgcaaagtgg ggtcccatca   180
aggttcagtg gcagtggatc tgggacagat ttcactctca ccatcagcag tctgcaacct   240
```

```
gaagatcttg caacttacta ctgtcaacag agttccagta ccccattcac tttcggccct      300
gggaccaaag tggatatcaa a                                                321
```

<210> SEQ ID NO 378
<211> LENGTH: 107
<212> TYPE: PRT
<213> ORGANISM: Artificial Sequence
<220> FEATURE:
<223> OTHER INFORMATION: Synthetic

<400> SEQUENCE: 378

```
Asp Ile Gln Met Thr Gln Ser Pro Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Leu Ala Thr Tyr Tyr Cys Gln Gln Ser Ser Ser Thr Pro Phe
                85                  90                  95

Thr Phe Gly Pro Gly Thr Lys Val Asp Ile Lys
            100                 105
```

<210> SEQ ID NO 379
<211> LENGTH: 18
<212> TYPE: DNA
<213> ORGANISM: Artificial Sequence
<220> FEATURE:
<223> OTHER INFORMATION: Synthetic

<400> SEQUENCE: 379

```
cagagcatta gcagctat                                                     18
```

<210> SEQ ID NO 380
<211> LENGTH: 6
<212> TYPE: PRT
<213> ORGANISM: Artificial Sequence
<220> FEATURE:
<223> OTHER INFORMATION: Synthetic

<400> SEQUENCE: 380

```
Gln Ser Ile Ser Ser Tyr
1               5
```

<210> SEQ ID NO 381
<211> LENGTH: 9
<212> TYPE: DNA
<213> ORGANISM: Artificial Sequence
<220> FEATURE:
<223> OTHER INFORMATION: Synthetic

<400> SEQUENCE: 381

```
gctgcatcc                                                                9
```

<210> SEQ ID NO 382
<211> LENGTH: 3
<212> TYPE: PRT
<213> ORGANISM: Artificial Sequence
<220> FEATURE:
<223> OTHER INFORMATION: Synthetic

<400> SEQUENCE: 382

Ala Ala Ser
1

<210> SEQ ID NO 383
<211> LENGTH: 27
<212> TYPE: DNA
<213> ORGANISM: Artificial Sequence
<220> FEATURE:
<223> OTHER INFORMATION: Synthetic

<400> SEQUENCE: 383
caacagagtt ccagtacccc attcact                                              27

<210> SEQ ID NO 384
<211> LENGTH: 9
<212> TYPE: PRT
<213> ORGANISM: Artificial Sequence
<220> FEATURE:
<223> OTHER INFORMATION: Synthetic

<400> SEQUENCE: 384

Gln Gln Ser Ser Ser Thr Pro Phe Thr
1               5

<210> SEQ ID NO 385
<211> LENGTH: 357
<212> TYPE: DNA
<213> ORGANISM: Artificial Sequence
<220> FEATURE:
<223> OTHER INFORMATION: Synthetic

<400> SEQUENCE: 385
caggtgcagc tggtggagtc ggggggaggc ttggtcaaac ctggagggtc cctgagactc          60
tcctgtgcag cctctggatt caccttcagt gactactaca tgagctggat ccgccaggct         120
ccagggaagg ggctggagtg ggtttcatac attggtactc gtggtagttc catatactac         180
gcagactctt tgaagggccg attcaccatc tccaggaca acgccaagaa ctcactatat          240
ctgcaaatga acagcctgag agccgaggac acggccgtgt attactgtgc gagagaccca         300
actggaacct cctactttga ctactggggc cagggtaccc tggtcaccgt ctcctca           357

<210> SEQ ID NO 386
<211> LENGTH: 119
<212> TYPE: PRT
<213> ORGANISM: Artificial Sequence
<220> FEATURE:
<223> OTHER INFORMATION: Synthetic

<400> SEQUENCE: 386

Gln Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Asp Tyr
            20                  25                  30

Tyr Met Ser Trp Ile Arg Gln Ala Pro Gly Lys Gly Leu Glu Trp Val
        35                  40                  45

Ser Tyr Ile Gly Thr Arg Gly Ser Ser Ile Tyr Tyr Ala Asp Ser Leu
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys 85                  90                  95
Ala Arg Asp Pro Thr Gly Thr Ser Tyr Phe Asp Tyr Trp Gly Gln Gly
                100                 105                 110
Thr Leu Val Thr Val Ser Ser
        115

<210> SEQ ID NO 387
<211> LENGTH: 24
<212> TYPE: DNA
<213> ORGANISM: Artificial Sequence
<220> FEATURE:
<223> OTHER INFORMATION: Synthetic

<400> SEQUENCE: 387
ggattcacct tcagtgacta ctac                                      24

<210> SEQ ID NO 388
<211> LENGTH: 8
<212> TYPE: PRT
<213> ORGANISM: Artificial Sequence
<220> FEATURE:
<223> OTHER INFORMATION: Synthetic

<400> SEQUENCE: 388

Gly Phe Thr Phe Ser Asp Tyr Tyr
1               5

<210> SEQ ID NO 389
<211> LENGTH: 24
<212> TYPE: DNA
<213> ORGANISM: Artificial Sequence
<220> FEATURE:
<223> OTHER INFORMATION: Synthetic

<400> SEQUENCE: 389
attggtactc gtggtagttc cata                                      24

<210> SEQ ID NO 390
<211> LENGTH: 8
<212> TYPE: PRT
<213> ORGANISM: Artificial Sequence
<220> FEATURE:
<223> OTHER INFORMATION: Synthetic

<400> SEQUENCE: 390

Ile Gly Thr Arg Gly Ser Ser Ile
1               5

<210> SEQ ID NO 391
<211> LENGTH: 36
<212> TYPE: DNA
<213> ORGANISM: Artificial Sequence
<220> FEATURE:
<223> OTHER INFORMATION: Synthetic

<400> SEQUENCE: 391
gcgagagacc caactggaac ctcctacttt gactac                         36

<210> SEQ ID NO 392
<211> LENGTH: 12
<212> TYPE: PRT
<213> ORGANISM: Artificial Sequence
<220> FEATURE:
<223> OTHER INFORMATION: Synthetic

<400> SEQUENCE: 392

Ala Arg Asp Pro Thr Gly Thr Ser Tyr Phe Asp Tyr
1               5                   10

<210> SEQ ID NO 393
<211> LENGTH: 324
<212> TYPE: DNA
<213> ORGANISM: Artificial Sequence
<220> FEATURE:
<223> OTHER INFORMATION: Synthetic

<400> SEQUENCE: 393
gaaatagtga tgacacagtc tccagccacc ctgtctgtgt ctccagggga aagagccacc      60
ctctcctgca gggccagtca gagtcttagc agcaacttag cctggtacca gcagaaacct     120
ggccaggctc ccaggctcct catctatggt gcatccacca gggccactgg tatcccagcc     180
aggttcagtg gcagtgggtc tgggacagag ttcactctca ccatcaacag cctgcagtct     240
gaagactttg cagttttatta ctgtcagcag tataataact ggcctccgta cacttttggc    300
caggggacca agctggagat caaa                                            324

<210> SEQ ID NO 394
<211> LENGTH: 108
<212> TYPE: PRT
<213> ORGANISM: Artificial Sequence
<220> FEATURE:
<223> OTHER INFORMATION: Synthetic

<400> SEQUENCE: 394

Glu Ile Val Met Thr Gln Ser Pro Ala Thr Leu Ser Val Ser Pro Gly
1               5                   10                  15

Glu Arg Ala Thr Leu Ser Cys Arg Ala Ser Gln Ser Leu Ser Ser Asn
            20                  25                  30

Leu Ala Trp Tyr Gln Gln Lys Pro Gly Gln Ala Pro Arg Leu Leu Ile
        35                  40                  45

Tyr Gly Ala Ser Thr Arg Ala Thr Gly Ile Pro Ala Arg Phe Ser Gly
    50                  55                  60

Ser Gly Ser Gly Thr Glu Phe Thr Leu Thr Ile Asn Ser Leu Gln Ser
65                  70                  75                  80

Glu Asp Phe Ala Val Tyr Tyr Cys Gln Gln Tyr Asn Asn Trp Pro Pro
                85                  90                  95

Tyr Thr Phe Gly Gln Gly Thr Lys Leu Glu Ile Lys
            100                 105

<210> SEQ ID NO 395
<211> LENGTH: 18
<212> TYPE: DNA
<213> ORGANISM: Artificial Sequence
<220> FEATURE:
<223> OTHER INFORMATION: Synthetic

<400> SEQUENCE: 395
cagagtctta gcagcaac                                                    18

<210> SEQ ID NO 396
<211> LENGTH: 6
<212> TYPE: PRT
<213> ORGANISM: Artificial Sequence
<220> FEATURE:
<223> OTHER INFORMATION: Synthetic

<400> SEQUENCE: 396

Gln Ser Leu Ser Ser Asn
1               5

<210> SEQ ID NO 397
<211> LENGTH: 9
<212> TYPE: DNA
<213> ORGANISM: Artificial Sequence
<220> FEATURE:
<223> OTHER INFORMATION: Synthetic

<400> SEQUENCE: 397 ggtgcatcc                                                                9

<210> SEQ ID NO 398
<211> LENGTH: 3
<212> TYPE: PRT
<213> ORGANISM: Artificial Sequence
<220> FEATURE:
<223> OTHER INFORMATION: Synthetic

<400> SEQUENCE: 398

Gly Ala Ser
1

<210> SEQ ID NO 399
<211> LENGTH: 30
<212> TYPE: DNA
<213> ORGANISM: Artificial Sequence
<220> FEATURE:
<223> OTHER INFORMATION: Synthetic

<400> SEQUENCE: 399
cagcagtata ataactggcc tccgtacact                                         30

<210> SEQ ID NO 400
<211> LENGTH: 10
<212> TYPE: PRT
<213> ORGANISM: Artificial Sequence
<220> FEATURE:
<223> OTHER INFORMATION: Synthetic

<400> SEQUENCE: 400

Gln Gln Tyr Asn Asn Trp Pro Pro Tyr Thr
1               5                   10

<210> SEQ ID NO 401
<211> LENGTH: 357
<212> TYPE: DNA
<213> ORGANISM: Artificial Sequence
<220> FEATURE:
<223> OTHER INFORMATION: Synthetic

<400> SEQUENCE: 401
caggtgcagc tggtggagtc tgggggaggc gtggtccagc ctggaggtc cctgagactc         60 tcctgtgcag cgtctggatt caccttcagt agttatggaa tgcactgggt ccgccaggct       120
ccaggcaagg ggctggagtg ggtggcagtt atatggtatg atggaagtaa taaatactat       180
gcagactccg tgaagggccg attcatcatc tccagagaca attccaagaa catgatgtat       240
ctgcaaatga acagcctgag agccgaggac acggctgtgt attactgtgc gagagaagat       300
aactggaact acgcctttga ctactggggc cagggaaccc tggtcaccgt ctcctca         357

<210> SEQ ID NO 402
<211> LENGTH: 119
<212> TYPE: PRT

<213> ORGANISM: Artificial Sequence
<220> FEATURE:
<223> OTHER INFORMATION: Synthetic

<400> SEQUENCE: 402

```
Gln Val Gln Leu Val Glu Ser Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ala Val Ile Trp Tyr Asp Gly Ser Asn Lys Tyr Tyr Ala Asp Ser Val
    50                  55                  60

Lys Gly Arg Phe Ile Ile Ser Arg Asp Asn Ser Lys Asn Met Met Tyr
65                  70                  75                  80

Leu Gln Met Asn Ser Leu Arg Ala Glu Asp Thr Ala Val Tyr Tyr Cys
                85                  90                  95

Ala Arg Glu Asp Asn Trp Asn Tyr Ala Phe Asp Tyr Trp Gly Gln Gly
            100                 105                 110

Thr Leu Val Thr Val Ser Ser
        115
```

<210> SEQ ID NO 403
<211> LENGTH: 24
<212> TYPE: DNA
<213> ORGANISM: Artificial Sequence
<220> FEATURE:
<223> OTHER INFORMATION: Synthetic

<400> SEQUENCE: 403
ggattcacct tcagtagtta tgga                                24

<210> SEQ ID NO 404
<211> LENGTH: 8
<212> TYPE: PRT
<213> ORGANISM: Artificial Sequence
<220> FEATURE:
<223> OTHER INFORMATION: Synthetic

<400> SEQUENCE: 404

```
Gly Phe Thr Phe Ser Ser Tyr Gly
1               5
```

<210> SEQ ID NO 405
<211> LENGTH: 24
<212> TYPE: DNA
<213> ORGANISM: Artificial Sequence
<220> FEATURE:
<223> OTHER INFORMATION: Synthetic

<400> SEQUENCE: 405
atatggtatg atggaagtaa taaa                                24

<210> SEQ ID NO 406
<211> LENGTH: 8
<212> TYPE: PRT
<213> ORGANISM: Artificial Sequence
<220> FEATURE:
<223> OTHER INFORMATION: Synthetic

<400> SEQUENCE: 406

```
Ile Trp Tyr Asp Gly Ser Asn Lys
1               5
```

<210> SEQ ID NO 407
<211> LENGTH: 36
<212> TYPE: DNA
<213> ORGANISM: Artificial Sequence
<220> FEATURE:
<223> OTHER INFORMATION: Synthetic

<400> SEQUENCE: 407
gcgagagaag ataactggaa ctacgccttt gactac                         36

<210> SEQ ID NO 408
<211> LENGTH: 12
<212> TYPE: PRT
<213> ORGANISM: Artificial Sequence
<220> FEATURE:
<223> OTHER INFORMATION: Synthetic

<400> SEQUENCE: 408

Ala Arg Glu Asp Asn Trp Asn Tyr Ala Phe Asp Tyr
 1               5                  10

<210> SEQ ID NO 409
<211> LENGTH: 324
<212> TYPE: DNA
<213> ORGANISM: Artificial Sequence
<220> FEATURE:
<223> OTHER INFORMATION: Synthetic

<400> SEQUENCE: 409
gaaatagtga tgacgcagtc tccagccacc ctgtctgtgt ctccagggga aagagccacc     60
ctctcctgca gggccagtca gagtattagc agcaacttag cctggtacca gcagaaacct    120
ggccaggctc ccaggctcct catctatgat tcatccacca gggccactgg aatcccagcc    180
aggttcagtg gcagtgggtc tggaacacaa ttcactctca ccatcagcag cctgcagtct    240
gaagattttg cactttatta ctgtcagcag tatagtaact ggcctccatt cacttttcggc   300 cctgggacca aagtggatat caaa                                          324

<210> SEQ ID NO 410
<211> LENGTH: 108
<212> TYPE: PRT
<213> ORGANISM: Artificial Sequence
<220> FEATURE:
<223> OTHER INFORMATION: Synthetic

<400> SEQUENCE: 410

Glu Ile Val Met Thr Gln Ser Pro Ala Thr Leu Ser Val Ser Pro Gly
 1               5                  10                  15

Glu Arg Ala Thr Leu Ser Cys Arg Ala Ser Gln Ser Ile Ser Ser Asn
                20                  25                  30

Leu Ala Trp Tyr Gln Gln Lys Pro Gly Gln Ala Pro Arg Leu Leu Ile
            35                  40                  45

Tyr Asp Ser Ser Thr Arg Ala Thr Gly Ile Pro Ala Arg Phe Ser Gly
        50                  55                  60

Ser Gly Ser Gly Thr Gln Phe Thr Leu Thr Ile Ser Ser Leu Gln Ser
65                  70                  75                  80

Glu Asp Phe Ala Leu Tyr Tyr Cys Gln Gln Tyr Ser Asn Trp Pro Pro
                85                  90                  95

Phe Thr Phe Gly Pro Gly Thr Lys Val Asp Ile Lys
            100                 105

<210> SEQ ID NO 411
<211> LENGTH: 18
<212> TYPE: DNA
<213> ORGANISM: Artificial Sequence
<220> FEATURE:
<223> OTHER INFORMATION: Synthetic

<400> SEQUENCE: 411
cagagtatta gcagcaac                                                       18

<210> SEQ ID NO 412
<211> LENGTH: 6
<212> TYPE: PRT
<213> ORGANISM: Artificial Sequence
<220> FEATURE:
<223> OTHER INFORMATION: Synthetic

<400> SEQUENCE: 412

Gln Ser Ile Ser Ser Asn
1               5

<210> SEQ ID NO 413
<211> LENGTH: 9
<212> TYPE: DNA
<213> ORGANISM: Artificial Sequence
<220> FEATURE:
<223> OTHER INFORMATION: Synthetic

<400> SEQUENCE: 413 gattcatcc                                                                  9

<210> SEQ ID NO 414
<211> LENGTH: 3
<212> TYPE: PRT
<213> ORGANISM: Artificial Sequence
<220> FEATURE:
<223> OTHER INFORMATION: Synthetic

<400> SEQUENCE: 414

Asp Ser Ser
1

<210> SEQ ID NO 415
<211> LENGTH: 30
<212> TYPE: DNA
<213> ORGANISM: Artificial Sequence
<220> FEATURE:
<223> OTHER INFORMATION: Synthetic

<400> SEQUENCE: 415
cagcagtata gtaactggcc tccattcact                                           30

<210> SEQ ID NO 416
<211> LENGTH: 10
<212> TYPE: PRT
<213> ORGANISM: Artificial Sequence
<220> FEATURE:
<223> OTHER INFORMATION: Synthetic

<400> SEQUENCE: 416

Gln Gln Tyr Ser Asn Trp Pro Pro Phe Thr
1               5                   10

<210> SEQ ID NO 417
<211> LENGTH: 372
<212> TYPE: DNA

```
<213> ORGANISM: Artificial Sequence
<220> FEATURE:
<223> OTHER INFORMATION: Synthetic

<400> SEQUENCE: 417
caggtccagc tggtacagtc tggggctgag gtgaagaagc ctggggcctc agtgaaggtc      60
tcctgcaagg tttccggata caccctcact gaattatcca tgcactgggt gcgacaggct     120
cctggaaaag ggcttgagtg gatgggaggt tttgatcctg aagatggtga gacaatctac     180
gcacagaagt tccaggacag agtcaccatg accgaggaca catctacaga cacagcctac     240
atggagctga gcagcctgag atctgaggac acggccgtgt attactgtgt aacagacgat     300
tacgaaattt tgcctgaata tccttacaac atggacgtct ggggccaagg gaccacggtc     360
accgtctcct ca                                                         372

<210> SEQ ID NO 418
<211> LENGTH: 124
<212> TYPE: PRT
<213> ORGANISM: Artificial Sequence
<220> FEATURE:
<223> OTHER INFORMATION: Synthetic

<400> SEQUENCE: 418

Gln Val Gln Leu Val Gln Ser Gly Ala Glu Val Lys Lys Pro Gly Ala
1               5                   10                  15

Ser Val Lys Val Ser Cys Lys Val Ser Gly Tyr Thr Leu Thr Glu Leu
            20                  25                  30

Ser Met His Trp Val Arg Gln Ala Pro Gly Lys Gly Leu Glu Trp Met
        35                  40                  45

Gly Gly Phe Asp Pro Glu Asp Gly Glu Thr Ile Tyr Ala Gln Lys Phe
    50                  55                  60

Gln Asp Arg Val Thr Met Thr Glu Asp Thr Ser Thr Asp Thr Ala Tyr
65                  70                  75                  80

Met Glu Leu Ser Ser Leu Arg Ser Glu Asp Thr Ala Val Tyr Tyr Cys
                85                  90                  95

Val Thr Asp Asp Tyr Glu Ile Leu Pro Glu Tyr Pro Tyr Asn Met Asp
            100                 105                 110

Val Trp Gly Gln Gly Thr Thr Val Thr Val Ser Ser
        115                 120

<210> SEQ ID NO 419
<211> LENGTH: 24
<212> TYPE: DNA
<213> ORGANISM: Artificial Sequence
<220> FEATURE:
<223> OTHER INFORMATION: Synthetic

<400> SEQUENCE: 419
ggatacaccc tcactgaatt atcc                                             24

<210> SEQ ID NO 420
<211> LENGTH: 8
<212> TYPE: PRT
<213> ORGANISM: Artificial Sequence
<220> FEATURE:
<223> OTHER INFORMATION: Synthetic

<400> SEQUENCE: 420

Gly Tyr Thr Leu Thr Glu Leu Ser
1               5
```

<210> SEQ ID NO 421
<211> LENGTH: 24
<212> TYPE: DNA
<213> ORGANISM: Artificial Sequence
<220> FEATURE:
<223> OTHER INFORMATION: Synthetic

<400> SEQUENCE: 421
tttgatcctg aagatggtga gaca                                              24

<210> SEQ ID NO 422
<211> LENGTH: 8
<212> TYPE: PRT
<213> ORGANISM: Artificial Sequence
<220> FEATURE:
<223> OTHER INFORMATION: Synthetic

<400> SEQUENCE: 422

Phe Asp Pro Glu Asp Gly Glu Thr
1               5

<210> SEQ ID NO 423
<211> LENGTH: 51
<212> TYPE: DNA
<213> ORGANISM: Artificial Sequence
<220> FEATURE:
<223> OTHER INFORMATION: Synthetic

<400> SEQUENCE: 423
gtaacagacg attacgaaat tttgcctgaa tatccttaca acatggacgt c                51

<210> SEQ ID NO 424
<211> LENGTH: 17
<212> TYPE: PRT
<213> ORGANISM: Artificial Sequence
<220> FEATURE:
<223> OTHER INFORMATION: Synthetic

<400> SEQUENCE: 424

Val Thr Asp Asp Tyr Glu Ile Leu Pro Glu Tyr Pro Tyr Asn Met Asp
1               5                   10                  15

Val

<210> SEQ ID NO 425
<211> LENGTH: 321
<212> TYPE: DNA
<213> ORGANISM: Artificial Sequence
<220> FEATURE:
<223> OTHER INFORMATION: Synthetic

<400> SEQUENCE: 425
gacatccaga tgacccagtc tccatcctcc ctgtctgcat ctgtaggaga cagagtcacc        60
atcacttgcc gggcaagtca gagcattagt acctatttaa attggtatca gcagaaacca       120
gggaaagccc ctaagctcct gatctatgct gcatccagtt tgcaaagtgg ggtcccatca       180
aggttcagtg gcagtggatc tgggacagat ttcactctca ccatccgcag tctgcaacct      240
gaagattttg caacttacta ctgtcaacag agtcacatta ccccattcac tttcggccct      300
gggaccaaag tggatatcaa a                                               321

<210> SEQ ID NO 426
<211> LENGTH: 107
<212> TYPE: PRT
<213> ORGANISM: Artificial Sequence
<220> FEATURE:
<223> OTHER INFORMATION: Synthetic

<400> SEQUENCE: 426

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Thr Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Arg Ser Leu Gln Pro
65                  70                  75                  80

Glu Asp Phe Ala Thr Tyr Tyr Cys Gln Gln Ser His Ile Thr Pro Phe
                85                  90                  95

Thr Phe Gly Pro Gly Thr Lys Val Asp Ile Lys
            100                 105

<210> SEQ ID NO 427
<211> LENGTH: 18
<212> TYPE: DNA
<213> ORGANISM: Artificial Sequence
<220> FEATURE:
<223> OTHER INFORMATION: Synthetic

<400> SEQUENCE: 427
cagagcatta gtacctat                                                18

<210> SEQ ID NO 428
<211> LENGTH: 6
<212> TYPE: PRT
<213> ORGANISM: Artificial Sequence
<220> FEATURE:
<223> OTHER INFORMATION: Synthetic

<400> SEQUENCE: 428

Gln Ser Ile Ser Thr Tyr
1               5

<210> SEQ ID NO 429
<211> LENGTH: 9
<212> TYPE: DNA
<213> ORGANISM: Artificial Sequence
<220> FEATURE:
<223> OTHER INFORMATION: Synthetic

<400> SEQUENCE: 429 gctgcatcc                                                           9

<210> SEQ ID NO 430
<211> LENGTH: 3
<212> TYPE: PRT
<213> ORGANISM: Artificial Sequence
<220> FEATURE:
<223> OTHER INFORMATION: Synthetic

<400> SEQUENCE: 430

Ala Ala Ser
1

<210> SEQ ID NO 431
<211> LENGTH: 27

<212> TYPE: DNA
<213> ORGANISM: Artificial Sequence
<220> FEATURE:
<223> OTHER INFORMATION: Synthetic

<400> SEQUENCE: 431
caacagagtc acattacccc attcact                                    27

<210> SEQ ID NO 432
<211> LENGTH: 9
<212> TYPE: PRT
<213> ORGANISM: Artificial Sequence
<220> FEATURE:
<223> OTHER INFORMATION: Synthetic

<400> SEQUENCE: 432

Gln Gln Ser His Ile Thr Pro Phe Thr
1               5

<210> SEQ ID NO 433
<211> LENGTH: 351
<212> TYPE: DNA
<213> ORGANISM: Artificial Sequence
<220> FEATURE:
<223> OTHER INFORMATION: Synthetic

<400> SEQUENCE: 433
gaggtgcagc tggtggagtc tgggggaggc ttggtccagc ctggggggtc cctgagactc    60
tcctgtgcag cctctggatt cacgtttaat agcttttgga tgagctgggt ccgccaggct   120
ccagggaagg ggctggagtg ggtggccaac ataaagcagg atggaagtga aaatactat    180 gtggactctg tgaagggccg attcaccatc tccagagaca acgccaagaa ctcagtgtat   240
ctgcaaatga acagcctgag agccgaggac acggctgttt attactgtgc gagagatctg   300
gtaacttctt ttgactattg gggccaggga accctggtca ccgtctcctc a           351

<210> SEQ ID NO 434
<211> LENGTH: 117
<212> TYPE: PRT
<213> ORGANISM: Artificial Sequence
<220> FEATURE:
<223> OTHER INFORMATION: Synthetic

<400> SEQUENCE: 434

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Asn Ser Phe
            20                  25                  30

Trp Met Ser Trp Val Arg Gln Ala Pro Gly Lys Gly Leu Glu Trp Val
        35                  40                  45

Ala Asn Ile Lys Gln Asp Gly Ser Glu Lys Tyr Tyr Val Asp Ser Val
    50                  55                  60

Lys Gly Arg Phe Thr Ile Ser Arg Asp Asn Ala Lys Asn Ser Val Tyr
65                  70                  75                  80

Leu Gln Met Asn Ser Leu Arg Ala Glu Asp Thr Ala Val Tyr Tyr Cys
                85                  90                  95

Ala Arg Asp Leu Val Thr Ser Phe Asp Tyr Trp Gly Gln Gly Thr Leu
            100                 105                 110

Val Thr Val Ser Ser
        115

```
<210> SEQ ID NO 435
<211> LENGTH: 24
<212> TYPE: DNA
<213> ORGANISM: Artificial Sequence
<220> FEATURE:
<223> OTHER INFORMATION: Synthetic

<400> SEQUENCE: 435
ggattcacgt ttaatagctt ttgg                                         24

<210> SEQ ID NO 436
<211> LENGTH: 8
<212> TYPE: PRT
<213> ORGANISM: Artificial Sequence
<220> FEATURE:
<223> OTHER INFORMATION: Synthetic

<400> SEQUENCE: 436

Gly Phe Thr Phe Asn Ser Phe Trp
1               5

<210> SEQ ID NO 437
<211> LENGTH: 24
<212> TYPE: DNA
<213> ORGANISM: Artificial Sequence
<220> FEATURE:
<223> OTHER INFORMATION: Synthetic

<400> SEQUENCE: 437
ataaagcagg atggaagtga gaaa                                         24

<210> SEQ ID NO 438
<211> LENGTH: 8
<212> TYPE: PRT
<213> ORGANISM: Artificial Sequence
<220> FEATURE:
<223> OTHER INFORMATION: Synthetic

<400> SEQUENCE: 438

Ile Lys Gln Asp Gly Ser Glu Lys
1               5

<210> SEQ ID NO 439
<211> LENGTH: 30
<212> TYPE: DNA
<213> ORGANISM: Artificial Sequence
<220> FEATURE:
<223> OTHER INFORMATION: Synthetic

<400> SEQUENCE: 439
gcgagagatc tggtaacttc ttttgactat                                   30

<210> SEQ ID NO 440
<211> LENGTH: 10
<212> TYPE: PRT
<213> ORGANISM: Artificial Sequence
<220> FEATURE:
<223> OTHER INFORMATION: Synthetic

<400> SEQUENCE: 440

Ala Arg Asp Leu Val Thr Ser Phe Asp Tyr
1               5                   10

<210> SEQ ID NO 441
<211> LENGTH: 321
<212> TYPE: DNA
<213> ORGANISM: Artificial Sequence
```

<220> FEATURE:
<223> OTHER INFORMATION: Synthetic

<400> SEQUENCE: 441

```
gacatccaga tgacccagtc tccatcctcc ctgtctgcat ctgtaggaga cagagtcacc    60
atcacttgcc aggcgagtca ggacattaac aactatttaa attggtatca gcagaaacca   120
gggaaagccc ctaagctcct gatctacgat gcatcctatt tggaaacagg ggtcccatca   180
gggttcagtg aagtggatc tgggacagat tttactttca ccatcagcag cctgcagcct   240
gaggatattg caacatatta ctgtcaacag tatgatagtc tcccgtacac ttttggccag   300
gggaccaagc tggagatcaa a                                             321
```

<210> SEQ ID NO 442
<211> LENGTH: 107
<212> TYPE: PRT
<213> ORGANISM: Artificial Sequence
<220> FEATURE:
<223> OTHER INFORMATION: Synthetic

<400> SEQUENCE: 442

```
Asp Ile Gln Met Thr Gln Ser Pro Ser Ser Leu Ser Ala Ser Val Gly
1               5                   10                  15
Asp Arg Val Thr Ile Thr Cys Gln Ala Ser Gln Asp Ile Asn Asn Tyr
            20                  25                  30
Leu Asn Trp Tyr Gln Gln Lys Pro Gly Lys Ala Pro Lys Leu Leu Ile
        35                  40                  45
Tyr Asp Ala Ser Tyr Leu Glu Thr Gly Val Pro Ser Gly Phe Ser Gly
    50                  55                  60
Ser Gly Ser Gly Thr Asp Phe Thr Phe Thr Ile Ser Ser Leu Gln Pro
65                  70                  75                  80
Glu Asp Ile Ala Thr Tyr Tyr Cys Gln Gln Tyr Asp Ser Leu Pro Tyr
                85                  90                  95
Thr Phe Gly Gln Gly Thr Lys Leu Glu Ile Lys
            100                 105
```

<210> SEQ ID NO 443
<211> LENGTH: 18
<212> TYPE: DNA
<213> ORGANISM: Artificial Sequence
<220> FEATURE:
<223> OTHER INFORMATION: Synthetic

<400> SEQUENCE: 443

```
caggacatta acaactat                                                  18
```

<210> SEQ ID NO 444
<211> LENGTH: 6
<212> TYPE: PRT
<213> ORGANISM: Artificial Sequence
<220> FEATURE:
<223> OTHER INFORMATION: Synthetic

<400> SEQUENCE: 444

```
Gln Asp Ile Asn Asn Tyr
1               5
```

<210> SEQ ID NO 445
<211> LENGTH: 9
<212> TYPE: DNA
<213> ORGANISM: Artificial Sequence
<220> FEATURE:

<223> OTHER INFORMATION: Synthetic

<400> SEQUENCE: 445 gatgcatcc							9

<210> SEQ ID NO 446
<211> LENGTH: 3
<212> TYPE: PRT
<213> ORGANISM: Artificial Sequence
<220> FEATURE:
<223> OTHER INFORMATION: Synthetic

<400> SEQUENCE: 446

Asp Ala Ser
1

<210> SEQ ID NO 447
<211> LENGTH: 27
<212> TYPE: DNA
<213> ORGANISM: Artificial Sequence
<220> FEATURE:
<223> OTHER INFORMATION: Synthetic

<400> SEQUENCE: 447
caacagtatg atagtctccc gtacact							27

<210> SEQ ID NO 448
<211> LENGTH: 9
<212> TYPE: PRT
<213> ORGANISM: Artificial Sequence
<220> FEATURE:
<223> OTHER INFORMATION: Synthetic

<400> SEQUENCE: 448

Gln Gln Tyr Asp Ser Leu Pro Tyr Thr
1               5

<210> SEQ ID NO 449
<211> LENGTH: 363
<212> TYPE: DNA
<213> ORGANISM: Artificial Sequence
<220> FEATURE:
<223> OTHER INFORMATION: Synthetic

<400> SEQUENCE: 449
caggtgcagc tggtggagtc tgggggaggc gtggtccagc ctggagggtc cctgagactc    60
tcctgtgcag cgtctggatt caccttcagt agctatggca tgcactgggt ccgccaggct   120
ccaggcaagg ggctggagtg ggtggcgatt atatggtatg atggaagtaa tagatactat   180
gcagactccg tgaagggccg gttcaccatc tccagagaca attccaggaa cacgctgtat   240
ctgcaaatga acagcctgag agccgaggac acggctgtgt attactgtgc gcgagacgag   300
tacggtgact acgactaccc ttttgactac tggggccagg gaaccctggt caccgtctcc   360 tca									363

<210> SEQ ID NO 450
<211> LENGTH: 121
<212> TYPE: PRT
<213> ORGANISM: Artificial Sequence
<220> FEATURE:
<223> OTHER INFORMATION: Synthetic

<400> SEQUENCE: 450

Gln Val Gln Leu Val Glu Ser Gly Gly Gly Val Val Gln Pro Gly Arg

```
                1               5                  10                  15
Ser Leu Arg Leu Ser Cys Ala Ala Ser Gly Phe Thr Phe Ser Ser Tyr
                20                  25                  30

Gly Met His Trp Val Arg Gln Ala Pro Gly Lys Gly Leu Glu Trp Val
        35                  40                  45

Ala Ile Ile Trp Tyr Asp Gly Ser Asn Arg Tyr Tyr Ala Asp Ser Val
    50                  55                  60

Lys Gly Arg Phe Thr Ile Ser Arg Asp Asn Ser Arg Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asp Glu Tyr Gly Asp Tyr Asp Tyr Pro Phe Asp Tyr Trp Gly
            100                 105                 110

Gln Gly Thr Leu Val Thr Val Ser Ser
        115                 120
```

<210> SEQ ID NO 451
<211> LENGTH: 24
<212> TYPE: DNA
<213> ORGANISM: Artificial Sequence
<220> FEATURE:
<223> OTHER INFORMATION: Synthetic

<400> SEQUENCE: 451
ggattcacct tcagtagcta tggc                                          24

<210> SEQ ID NO 452
<211> LENGTH: 8
<212> TYPE: PRT
<213> ORGANISM: Artificial Sequence
<220> FEATURE:
<223> OTHER INFORMATION: Synthetic

<400> SEQUENCE: 452

Gly Phe Thr Phe Ser Ser Tyr Gly
1               5

<210> SEQ ID NO 453
<211> LENGTH: 24
<212> TYPE: DNA
<213> ORGANISM: Artificial Sequence
<220> FEATURE:
<223> OTHER INFORMATION: Synthetic

<400> SEQUENCE: 453
atatggtatg atggaagtaa taga                                          24

<210> SEQ ID NO 454
<211> LENGTH: 8
<212> TYPE: PRT
<213> ORGANISM: Artificial Sequence
<220> FEATURE:
<223> OTHER INFORMATION: Synthetic

<400> SEQUENCE: 454

Ile Trp Tyr Asp Gly Ser Asn Arg
1               5

<210> SEQ ID NO 455
<211> LENGTH: 42
<212> TYPE: DNA
<213> ORGANISM: Artificial Sequence
<220> FEATURE:

<223> OTHER INFORMATION: Synthetic

<400> SEQUENCE: 455
gcgcgagacg agtacggtga ctacgactac cctttgact ac                42

<210> SEQ ID NO 456
<211> LENGTH: 14
<212> TYPE: PRT
<213> ORGANISM: Artificial Sequence
<220> FEATURE:
<223> OTHER INFORMATION: Synthetic

<400> SEQUENCE: 456

Ala Arg Asp Glu Tyr Gly Asp Tyr Asp Tyr Pro Phe Asp Tyr
1               5                   10

<210> SEQ ID NO 457
<211> LENGTH: 324
<212> TYPE: DNA
<213> ORGANISM: Artificial Sequence
<220> FEATURE:
<223> OTHER INFORMATION: Synthetic

<400> SEQUENCE: 457
gacatccaga tgacccagtc tccatcctcc ctgtctgcat ctgtaggaga cagagtcacc    60
atcacttgcc gggcaagtca gggcattaga aatgatttag ctggtttca gcagaaacca    120 gggaaagccc ctaagcgcct gatctatgct gcatccagtt tgcaaagtgg ggtcccatca    180
aggttcagcg gcagtggatc tgggacagaa ttcactctca caatcagcag cctgcagcct    240
gaagattttg caacttatta ctgtctacag cataatactt accctccatt cactttcggc    300
cctgggacca agtggatat caaa                                           324

<210> SEQ ID NO 458
<211> LENGTH: 108
<212> TYPE: PRT
<213> ORGANISM: Artificial Sequence
<220> FEATURE:
<223> OTHER INFORMATION: Synthetic

<400> SEQUENCE: 458

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Arg Asn Asp
                20                  25                  30

Leu Gly Trp Phe Gln Gln Lys Pro Gly Lys Ala Pro Lys Arg Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Glu Asp Phe Ala Thr Tyr Tyr Cys Leu Gln His Asn Thr Tyr Pro Pro
                85                  90                  95

Phe Thr Phe Gly Pro Gly Thr Lys Val Asp Ile Lys
            100                 105

<210> SEQ ID NO 459
<211> LENGTH: 18
<212> TYPE: DNA
<213> ORGANISM: Artificial Sequence
<220> FEATURE:
<223> OTHER INFORMATION: Synthetic

<400> SEQUENCE: 459 caggggcatta gaaatgat                                                18

<210> SEQ ID NO 460
<211> LENGTH: 6
<212> TYPE: PRT
<213> ORGANISM: Artificial Sequence
<220> FEATURE:
<223> OTHER INFORMATION: Synthetic

<400> SEQUENCE: 460

Gln Gly Ile Arg Asn Asp
1               5

<210> SEQ ID NO 461
<211> LENGTH: 9
<212> TYPE: DNA
<213> ORGANISM: Artificial Sequence
<220> FEATURE:
<223> OTHER INFORMATION: Synthetic

<400> SEQUENCE: 461 gctgcatcc                                                            9

<210> SEQ ID NO 462
<211> LENGTH: 3
<212> TYPE: PRT
<213> ORGANISM: Artificial Sequence
<220> FEATURE:
<223> OTHER INFORMATION: Synthetic

<400> SEQUENCE: 462

Ala Ala Ser
1

<210> SEQ ID NO 463
<211> LENGTH: 30
<212> TYPE: DNA
<213> ORGANISM: Artificial Sequence
<220> FEATURE:
<223> OTHER INFORMATION: Synthetic

<400> SEQUENCE: 463
ctacagcata tacttaccc tccattcact                                     30

<210> SEQ ID NO 464
<211> LENGTH: 10
<212> TYPE: PRT
<213> ORGANISM: Artificial Sequence
<220> FEATURE:
<223> OTHER INFORMATION: Synthetic

<400> SEQUENCE: 464

Leu Gln His Asn Thr Tyr Pro Pro Phe Thr
1               5                   10

<210> SEQ ID NO 465
<211> LENGTH: 360
<212> TYPE: DNA
<213> ORGANISM: Artificial Sequence
<220> FEATURE:
<223> OTHER INFORMATION: Synthetic

<400> SEQUENCE: 465
caggtgcagc tggtggagtc tgggggaggc gtggtccagc ctggggaggtc cctgagactc    60

```
tcctgtgcag cgtctggatt caccttcagt aactatggca tgcactgggt ccgccaggtt    120
ccaggcaagg ggctggagtg ggtggcagtt atatggtatg atggaagtaa taaatactat    180
gcagactccg tgaagggccg attcaccatc tccagagaca attccaagaa cacgctgtat    240
ctgcaaatga acagtgtgag agccgaggac acggctgtat actactgtgc gagagatgac    300
tacggtgact ccccggggtt tgactactgg ggccagggaa ccctggtcac cgtctcctca    360
```

<210> SEQ ID NO 466
<211> LENGTH: 120
<212> TYPE: PRT
<213> ORGANISM: Artificial Sequence
<220> FEATURE:
<223> OTHER INFORMATION: Synthetic

<400> SEQUENCE: 466

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Asn Tyr
            20                  25                  30

Gly Met His Trp Val Arg Gln Val Pro Gly Lys Gly Leu Glu Trp Val
        35                  40                  45

Ala Val Ile Trp Tyr Asp Gly Ser Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Val Arg Ala Glu Asp Thr Ala Val Tyr Tyr Cys
                85                  90                  95

Ala Arg Asp Asp Tyr Gly Asp Ser Pro Gly Phe Asp Tyr Trp Gly Gln
            100                 105                 110

Gly Thr Leu Val Thr Val Ser Ser
        115                 120

<210> SEQ ID NO 467
<211> LENGTH: 24
<212> TYPE: DNA
<213> ORGANISM: Artificial Sequence
<220> FEATURE:
<223> OTHER INFORMATION: Synthetic

<400> SEQUENCE: 467

```
ggattcacct tcagtaacta tggc                                              24
```

<210> SEQ ID NO 468
<211> LENGTH: 8
<212> TYPE: PRT
<213> ORGANISM: Artificial Sequence
<220> FEATURE:
<223> OTHER INFORMATION: Synthetic

<400> SEQUENCE: 468

Gly Phe Thr Phe Ser Asn Tyr Gly
1               5

<210> SEQ ID NO 469
<211> LENGTH: 24
<212> TYPE: DNA
<213> ORGANISM: Artificial Sequence
<220> FEATURE:
<223> OTHER INFORMATION: Synthetic

<400> SEQUENCE: 469

```
atatggtatg atggaagtaa taaa                                            24

<210> SEQ ID NO 470
<211> LENGTH: 8
<212> TYPE: PRT
<213> ORGANISM: Artificial Sequence
<220> FEATURE:
<223> OTHER INFORMATION: Synthetic

<400> SEQUENCE: 470

Ile Trp Tyr Asp Gly Ser Asn Lys
1               5

<210> SEQ ID NO 471
<211> LENGTH: 39
<212> TYPE: DNA
<213> ORGANISM: Artificial Sequence
<220> FEATURE:
<223> OTHER INFORMATION: Synthetic

<400> SEQUENCE: 471
gcgagagatg actacggtga ctccccgggg tttgactac                             39

<210> SEQ ID NO 472
<211> LENGTH: 13
<212> TYPE: PRT
<213> ORGANISM: Artificial Sequence
<220> FEATURE:
<223> OTHER INFORMATION: Synthetic

<400> SEQUENCE: 472

Ala Arg Asp Asp Tyr Gly Asp Ser Pro Gly Phe Asp Tyr
1               5                   10

<210> SEQ ID NO 473
<211> LENGTH: 324
<212> TYPE: DNA
<213> ORGANISM: Artificial Sequence
<220> FEATURE:
<223> OTHER INFORMATION: Synthetic

<400> SEQUENCE: 473
gaaatagtga tgacgcagtc tccagccacc ctgtctgtgt ctccagggga aagagccacc      60
ctctcctgca gggccagtca gagtgttagc agcagcttag cctggtacca gcagaaacct    120
ggccaggctc ccaggctcct catctatgat gcatccacca gggccactgg tatcccagcc    180
aggttcagtg gcagtgggtc tgggacagag ttcactctca ccatcagcgg cctgcagtct    240
gaagattttg cagtttatta ctgtcagcag tataataact ggcctccgtg gacgttcggc    300
caagggacca aggtggaaat caaa                                           324

<210> SEQ ID NO 474
<211> LENGTH: 108
<212> TYPE: PRT
<213> ORGANISM: Artificial Sequence
<220> FEATURE:
<223> OTHER INFORMATION: Synthetic

<400> SEQUENCE: 474

Glu Ile Val Met Thr Gln Ser Pro Ala Thr Leu Ser Val Ser Pro Gly
1               5                   10                  15

Glu Arg Ala Thr Leu Ser Cys Arg Ala Ser Gln Ser Val Ser Ser Ser
            20                  25                  30
```

Leu Ala Trp Tyr Gln Gln Lys Pro Gly Gln Ala Pro Arg Leu Leu Ile
            35                  40                  45

Tyr Asp Ala Ser Thr Arg Ala Thr Gly Ile Pro Ala Arg Phe Ser Gly
 50                  55                  60

Ser Gly Ser Gly Thr Glu Phe Thr Leu Thr Ile Ser Gly Leu Gln Ser
 65                  70                  75                  80

Glu Asp Phe Ala Val Tyr Tyr Cys Gln Gln Tyr Asn Asn Trp Pro Pro
                 85                  90                  95

Trp Thr Phe Gly Gln Gly Thr Lys Val Glu Ile Lys
            100                 105

<210> SEQ ID NO 475
<211> LENGTH: 18
<212> TYPE: DNA
<213> ORGANISM: Artificial Sequence
<220> FEATURE:
<223> OTHER INFORMATION: Synthetic

<400> SEQUENCE: 475
cagagtgtta gcagcagc                                                    18

<210> SEQ ID NO 476
<211> LENGTH: 6
<212> TYPE: PRT
<213> ORGANISM: Artificial Sequence
<220> FEATURE:
<223> OTHER INFORMATION: Synthetic

<400> SEQUENCE: 476

Gln Ser Val Ser Ser Ser
1               5

<210> SEQ ID NO 477
<211> LENGTH: 9
<212> TYPE: DNA
<213> ORGANISM: Artificial Sequence
<220> FEATURE:
<223> OTHER INFORMATION: Synthetic

<400> SEQUENCE: 477 gatgcatcc                                                               9

<210> SEQ ID NO 478
<211> LENGTH: 3
<212> TYPE: PRT
<213> ORGANISM: Artificial Sequence
<220> FEATURE:
<223> OTHER INFORMATION: Synthetic

<400> SEQUENCE: 478

Asp Ala Ser
1

<210> SEQ ID NO 479
<211> LENGTH: 30
<212> TYPE: DNA
<213> ORGANISM: Artificial Sequence
<220> FEATURE:
<223> OTHER INFORMATION: Synthetic

<400> SEQUENCE: 479
cagcagtata ataactggcc tccgtggacg                                        30

<210> SEQ ID NO 480

```
<211> LENGTH: 10
<212> TYPE: PRT
<213> ORGANISM: Artificial Sequence
<220> FEATURE:
<223> OTHER INFORMATION: Synthetic

<400> SEQUENCE: 480

Gln Gln Tyr Asn Asn Trp Pro Pro Trp Thr
1               5                   10

<210> SEQ ID NO 481
<211> LENGTH: 363
<212> TYPE: DNA
<213> ORGANISM: Artificial Sequence
<220> FEATURE:
<223> OTHER INFORMATION: Synthetic

<400> SEQUENCE: 481
caggtgcagc tggtggagtc tgggggaggc gtggtccagc ctggggaggtc cctgagactc    60 tcctgtgcag cgtctggatt caccttcagt aactatggca tgcattgggt ccgccaggct   120
ccaggcaagg ggctggagtg ggtggcagtt atatggtatg atggaagtaa taaatactat   180
gcagactctg tgaagggccg attcaccatc tccagagaca attccaggaa aacgctgtat   240
ctgcaaatga acagcctgag agccgaggac acggctattt attactgtac gagagacgac   300
tacggtgact acgactaccc ttttgactac tggggccagg gaaccctggt caccgtctcc   360
tca                                                                 363

<210> SEQ ID NO 482
<211> LENGTH: 121
<212> TYPE: PRT
<213> ORGANISM: Artificial Sequence
<220> FEATURE:
<223> OTHER INFORMATION: Synthetic

<400> SEQUENCE: 482

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Asn Tyr
            20                  25                  30

Gly Met His Trp Val Arg Gln Ala Pro Gly Lys Gly Leu Glu Trp Val
        35                  40                  45

Ala Val Ile Trp Tyr Asp Gly Ser Asn Lys Tyr Tyr Ala Asp Ser Val
    50                  55                  60

Lys Gly Arg Phe Thr Ile Ser Arg Asp Asn Ser Arg Lys Thr Leu Tyr
65                  70                  75                  80

Leu Gln Met Asn Ser Leu Arg Ala Glu Asp Thr Ala Ile Tyr Tyr Cys
                85                  90                  95

Thr Arg Asp Asp Tyr Gly Asp Tyr Asp Tyr Pro Phe Asp Tyr Trp Gly
            100                 105                 110

Gln Gly Thr Leu Val Thr Val Ser Ser
        115                 120

<210> SEQ ID NO 483
<211> LENGTH: 24
<212> TYPE: DNA
<213> ORGANISM: Artificial Sequence
<220> FEATURE:
<223> OTHER INFORMATION: Synthetic

<400> SEQUENCE: 483
```

```
ggattcacct tcagtaacta tggc                                          24
```

<210> SEQ ID NO 484
<211> LENGTH: 8
<212> TYPE: PRT
<213> ORGANISM: Artificial Sequence
<220> FEATURE:
<223> OTHER INFORMATION: Synthetic

<400> SEQUENCE: 484

Gly Phe Thr Phe Ser Asn Tyr Gly
1               5

<210> SEQ ID NO 485
<211> LENGTH: 24
<212> TYPE: DNA
<213> ORGANISM: Artificial Sequence
<220> FEATURE:
<223> OTHER INFORMATION: Synthetic

<400> SEQUENCE: 485

```
atatggtatg atggaagtaa taaa                                          24
```

<210> SEQ ID NO 486
<211> LENGTH: 8
<212> TYPE: PRT
<213> ORGANISM: Artificial Sequence
<220> FEATURE:
<223> OTHER INFORMATION: Synthetic

<400> SEQUENCE: 486

Ile Trp Tyr Asp Gly Ser Asn Lys
1               5

<210> SEQ ID NO 487
<211> LENGTH: 42
<212> TYPE: DNA
<213> ORGANISM: Artificial Sequence
<220> FEATURE:
<223> OTHER INFORMATION: Synthetic

<400> SEQUENCE: 487

```
acgagagacg actacggtga ctacgactac ccttttgact ac                      42
```

<210> SEQ ID NO 488
<211> LENGTH: 14
<212> TYPE: PRT
<213> ORGANISM: Artificial Sequence
<220> FEATURE:
<223> OTHER INFORMATION: Synthetic

<400> SEQUENCE: 488

Thr Arg Asp Asp Tyr Gly Asp Tyr Asp Tyr Pro Phe Asp Tyr
1               5                   10

<210> SEQ ID NO 489
<211> LENGTH: 324
<212> TYPE: DNA
<213> ORGANISM: Artificial Sequence
<220> FEATURE:
<223> OTHER INFORMATION: Synthetic

<400> SEQUENCE: 489

```
gacatccaga tgacccagtc tccatcctcc ctgtctgcat ctgtaggaga cagagtcacc   60
atcacttgcc gggcaagtca gggcattaga aatgatttag gctggtatca gcagaaacca  120
```

```
gggaaagccc ctaagcgcct gatctatgct gcatccagtt tgcaaagtgg ggtcccatca    180
aggttcagcg gcactggatc tgggacagaa ttcactctca caatcagcag cctgcagcct    240
gaagattttg caacttatta ctgtctacaa cataatagtt accctccatt cactttcggc    300
cctgggacca aagtggatat caaa                                           324
```

<210> SEQ ID NO 490
<211> LENGTH: 108
<212> TYPE: PRT
<213> ORGANISM: Artificial Sequence
<220> FEATURE:
<223> OTHER INFORMATION: Synthetic

<400> SEQUENCE: 490

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Arg Asn Asp
            20                  25                  30

Leu Gly Trp Tyr Gln Gln Lys Pro Gly Lys Ala Pro Lys Arg Leu Ile
        35                  40                  45

Tyr Ala Ala Ser Ser Leu Gln Ser Gly Val Pro Ser Arg Phe Ser Gly
    50                  55                  60

Thr Gly Ser Gly Thr Glu Phe Thr Leu Thr Ile Ser Ser Leu Gln Pro
65                  70                  75                  80

Glu Asp Phe Ala Thr Tyr Tyr Cys Leu Gln His Asn Ser Tyr Pro Pro
                85                  90                  95

Phe Thr Phe Gly Pro Gly Thr Lys Val Asp Ile Lys
            100                 105
```

<210> SEQ ID NO 491
<211> LENGTH: 18
<212> TYPE: DNA
<213> ORGANISM: Artificial Sequence
<220> FEATURE:
<223> OTHER INFORMATION: Synthetic

<400> SEQUENCE: 491

```
cagggcatta gaaatgat                                                   18
```

<210> SEQ ID NO 492
<211> LENGTH: 6
<212> TYPE: PRT
<213> ORGANISM: Artificial Sequence
<220> FEATURE:
<223> OTHER INFORMATION: Synthetic

<400> SEQUENCE: 492

```
Gln Gly Ile Arg Asn Asp
1               5
```

<210> SEQ ID NO 493
<211> LENGTH: 9
<212> TYPE: DNA
<213> ORGANISM: Artificial Sequence
<220> FEATURE:
<223> OTHER INFORMATION: Synthetic

<400> SEQUENCE: 493

```
gctgcatcc                                                              9
```

<210> SEQ ID NO 494
<211> LENGTH: 3

```
<212> TYPE: PRT
<213> ORGANISM: Artificial Sequence
<220> FEATURE:
<223> OTHER INFORMATION: Synthetic

<400> SEQUENCE: 494

Ala Ala Ser
1

<210> SEQ ID NO 495
<211> LENGTH: 30
<212> TYPE: DNA
<213> ORGANISM: Artificial Sequence
<220> FEATURE:
<223> OTHER INFORMATION: Synthetic

<400> SEQUENCE: 495
ctacaacata atagttaccc tccattcact                                       30

<210> SEQ ID NO 496
<211> LENGTH: 10
<212> TYPE: PRT
<213> ORGANISM: Artificial Sequence
<220> FEATURE:
<223> OTHER INFORMATION: Synthetic

<400> SEQUENCE: 496

Leu Gln His Asn Ser Tyr Pro Pro Phe Thr
1               5                  10

<210> SEQ ID NO 497
<211> LENGTH: 360
<212> TYPE: DNA
<213> ORGANISM: Artificial Sequence
<220> FEATURE:
<223> OTHER INFORMATION: Synthetic

<400> SEQUENCE: 497
caggtgcagc tggtggagtc tgggggaggc gtggtccagc ctgggaagtc cctgagactc      60
tcctgtgcag cgtctggatt caccttcagt cgttatggca tgcactgggt ccgccaggct     120
ccaggcaagg ggctggagtg ggtggcagtt atatggtatg atggaagtaa taaatactat     180
gcagactccg tgaagggccg attcaccatc tccagagaca attccaagaa cacgctgtat     240
ctgcaaatga acagcctgag agccgacgac acggctatgt attactgtgc gagagatgac     300
tacggtgact ccccggggtt tgacttctgg ggccagggaa ccctggtcac cgtctcctca     360

<210> SEQ ID NO 498
<211> LENGTH: 120
<212> TYPE: PRT
<213> ORGANISM: Artificial Sequence
<220> FEATURE:
<223> OTHER INFORMATION: Synthetic

<400> SEQUENCE: 498

Gln Val Gln Leu Val Glu Ser Gly Gly Gly Val Val Gln Pro Gly Lys
1               5                  10                  15

Ser Leu Arg Leu Ser Cys Ala Ala Ser Gly Phe Thr Phe Ser Arg Tyr
            20                  25                  30

Gly Met His Trp Val Arg Gln Ala Pro Gly Lys Gly Leu Glu Trp Val
        35                  40                  45

Ala Val Ile Trp Tyr Asp Gly Ser Asn Lys Tyr Tyr Ala Asp Ser Val
    50                  55                  60
```

-continued

Lys Gly Arg Phe Thr Ile Ser Arg Asp Asn Ser Lys Asn Thr Leu Tyr
65                  70                  75                  80

Leu Gln Met Asn Ser Leu Arg Ala Asp Asp Thr Ala Met Tyr Tyr Cys
                85                  90                  95

Ala Arg Asp Asp Tyr Gly Asp Ser Pro Gly Phe Asp Phe Trp Gly Gln
            100                 105                 110

Gly Thr Leu Val Thr Val Ser Ser
        115                 120

<210> SEQ ID NO 499
<211> LENGTH: 24
<212> TYPE: DNA
<213> ORGANISM: Artificial Sequence
<220> FEATURE:
<223> OTHER INFORMATION: Synthetic

<400> SEQUENCE: 499
ggattcacct tcagtcgtta tggc                                              24

<210> SEQ ID NO 500
<211> LENGTH: 8
<212> TYPE: PRT
<213> ORGANISM: Artificial Sequence
<220> FEATURE:
<223> OTHER INFORMATION: Synthetic

<400> SEQUENCE: 500

Gly Phe Thr Phe Ser Arg Tyr Gly
1               5

<210> SEQ ID NO 501
<211> LENGTH: 24
<212> TYPE: DNA
<213> ORGANISM: Artificial Sequence
<220> FEATURE:
<223> OTHER INFORMATION: Synthetic

<400> SEQUENCE: 501
atatggtatg atggaagtaa taaa                                              24

<210> SEQ ID NO 502
<211> LENGTH: 8
<212> TYPE: PRT
<213> ORGANISM: Artificial Sequence
<220> FEATURE:
<223> OTHER INFORMATION: Synthetic

<400> SEQUENCE: 502

Ile Trp Tyr Asp Gly Ser Asn Lys
1               5

<210> SEQ ID NO 503
<211> LENGTH: 39
<212> TYPE: DNA
<213> ORGANISM: Artificial Sequence
<220> FEATURE:
<223> OTHER INFORMATION: Synthetic

<400> SEQUENCE: 503
gcgagagatg actacggtga ctccccgggg tttgacttc                              39

<210> SEQ ID NO 504
<211> LENGTH: 13
<212> TYPE: PRT
<213> ORGANISM: Artificial Sequence
<220> FEATURE:
<223> OTHER INFORMATION: Synthetic

<400> SEQUENCE: 504

Ala Arg Asp Asp Tyr Gly Asp Ser Pro Gly Phe Asp Phe
1               5                   10

<210> SEQ ID NO 505
<211> LENGTH: 324
<212> TYPE: DNA
<213> ORGANISM: Artificial Sequence
<220> FEATURE:
<223> OTHER INFORMATION: Synthetic

<400> SEQUENCE: 505
gaaatagtga tgacgcagtc tccagccacc ctgtctgtgt ctccagggga aagagccacc        60
ctctcctgca gggccagtca gagtgttagc agcaacttag cctggtacca gcagaaacct       120
ggccaggctc ccaggctcct catctatgat gcatccacca gggccactgg tatcccagcc       180
aggttcagtg gcactgggtc tgggacagag ttcactctca ccatcagcag cctgcagtct       240
gaagactttg cactttatta ctgtcagcag tatgatgact ggcctccgtg gacgttcggc       300
caagggacca aggtggaaat caaa                                              324

<210> SEQ ID NO 506
<211> LENGTH: 108
<212> TYPE: PRT
<213> ORGANISM: Artificial Sequence
<220> FEATURE:
<223> OTHER INFORMATION: Synthetic

<400> SEQUENCE: 506

Glu Ile Val Met Thr Gln Ser Pro Ala Thr Leu Ser Val Ser Pro Gly
1               5                   10                  15

Glu Arg Ala Thr Leu Ser Cys Arg Ala Ser Gln Ser Val Ser Ser Asn
            20                  25                  30

Leu Ala Trp Tyr Gln Gln Lys Pro Gly Gln Ala Pro Arg Leu Leu Ile
        35                  40                  45

Tyr Asp Ala Ser Thr Arg Ala Thr Gly Ile Pro Ala Arg Phe Ser Gly
    50                  55                  60

Thr Gly Ser Gly Thr Glu Phe Thr Leu Thr Ile Ser Ser Leu Gln Ser
65                  70                  75                  80

Glu Asp Phe Ala Leu Tyr Tyr Cys Gln Gln Tyr Asp Asp Trp Pro Pro
                85                  90                  95

Trp Thr Phe Gly Gln Gly Thr Lys Val Glu Ile Lys
            100                 105

<210> SEQ ID NO 507
<211> LENGTH: 18
<212> TYPE: DNA
<213> ORGANISM: Artificial Sequence
<220> FEATURE:
<223> OTHER INFORMATION: Synthetic

<400> SEQUENCE: 507
cagagtgtta gcagcaac                                                      18

<210> SEQ ID NO 508
<211> LENGTH: 6
<212> TYPE: PRT
<213> ORGANISM: Artificial Sequence
<220> FEATURE:

<223> OTHER INFORMATION: Synthetic

<400> SEQUENCE: 508

Gln Ser Val Ser Ser Asn
1               5

<210> SEQ ID NO 509
<211> LENGTH: 9
<212> TYPE: DNA
<213> ORGANISM: Artificial Sequence
<220> FEATURE:
<223> OTHER INFORMATION: Synthetic

<400> SEQUENCE: 509 gatgcatcc                                                                   9

<210> SEQ ID NO 510
<211> LENGTH: 3
<212> TYPE: PRT
<213> ORGANISM: Artificial Sequence
<220> FEATURE:
<223> OTHER INFORMATION: Synthetic

<400> SEQUENCE: 510

Asp Ala Ser
1

<210> SEQ ID NO 511
<211> LENGTH: 30
<212> TYPE: DNA
<213> ORGANISM: Artificial Sequence
<220> FEATURE:
<223> OTHER INFORMATION: Synthetic

<400> SEQUENCE: 511
cagcagtatg atgactggcc tccgtggacg                                           30

<210> SEQ ID NO 512
<211> LENGTH: 10
<212> TYPE: PRT
<213> ORGANISM: Artificial Sequence
<220> FEATURE:
<223> OTHER INFORMATION: Synthetic

<400> SEQUENCE: 512

Gln Gln Tyr Asp Asp Trp Pro Pro Trp Thr
1               5                   10

<210> SEQ ID NO 513
<211> LENGTH: 363
<212> TYPE: DNA
<213> ORGANISM: Artificial Sequence
<220> FEATURE:
<223> OTHER INFORMATION: Synthetic

<400> SEQUENCE: 513
caggtgcagc tggtggagtc tgggggaggc gtggtccagc ctggagggtc cctgagactc        60
tcctgtgcag cgtctggatt caccttcagt aactatggca tgcactgggt ccgccaggct       120
ccaggcaggg ggctggagtg ggtggcagtt atatggtttg atggaagtaa caaatactat       180
gcagactccg tgaagggccg attcaccatc tccagagaca attccaagaa cacgctgtat       240
ctgcaaatga acagtctgag atccgaggac acggctgtgt attactgtac gagagacgac       300
tacggtgact acgactaccc ttttgactac tggggccagg gaaccctggt caccgtctcc       360
tca                                                                    363

<210> SEQ ID NO 514
<211> LENGTH: 121
<212> TYPE: PRT
<213> ORGANISM: Artificial Sequence
<220> FEATURE:
<223> OTHER INFORMATION: Synthetic

<400> SEQUENCE: 514

Gln Val Gln Leu Val Glu Ser Gly Gly Val Val Gln Pro Gly Arg
1               5                   10                  15

Ser Leu Arg Leu Ser Cys Ala Ala Ser Gly Phe Thr Phe Ser Asn Tyr
            20                  25                  30

Gly Met His Trp Val Arg Gln Ala Pro Gly Arg Gly Leu Glu Trp Val
        35                  40                  45

Ala Val Ile Trp Phe Asp Gly Ser Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ser Glu Asp Thr Ala Val Tyr Tyr Cys
                85                  90                  95

Thr Arg Asp Asp Tyr Gly Asp Tyr Asp Tyr Pro Phe Asp Tyr Trp Gly
            100                 105                 110

Gln Gly Thr Leu Val Thr Val Ser Ser
        115                 120

<210> SEQ ID NO 515
<211> LENGTH: 24
<212> TYPE: DNA
<213> ORGANISM: Artificial Sequence
<220> FEATURE:
<223> OTHER INFORMATION: Synthetic

<400> SEQUENCE: 515
ggattcacct tcagtaacta tggc                                              24

<210> SEQ ID NO 516
<211> LENGTH: 8
<212> TYPE: PRT
<213> ORGANISM: Artificial Sequence
<220> FEATURE:
<223> OTHER INFORMATION: Synthetic

<400> SEQUENCE: 516

Gly Phe Thr Phe Ser Asn Tyr Gly
1               5

<210> SEQ ID NO 517
<211> LENGTH: 24
<212> TYPE: DNA
<213> ORGANISM: Artificial Sequence
<220> FEATURE:
<223> OTHER INFORMATION: Synthetic

<400> SEQUENCE: 517
atatggtttg atggaagtaa caaa                                              24

<210> SEQ ID NO 518
<211> LENGTH: 8
<212> TYPE: PRT
<213> ORGANISM: Artificial Sequence
<220> FEATURE:

<223> OTHER INFORMATION: Synthetic

<400> SEQUENCE: 518

Ile Trp Phe Asp Gly Ser Asn Lys
1               5

<210> SEQ ID NO 519
<211> LENGTH: 42
<212> TYPE: DNA
<213> ORGANISM: Artificial Sequence
<220> FEATURE:
<223> OTHER INFORMATION: Synthetic

<400> SEQUENCE: 519
acgagagacg actacggtga ctacgactac cctttttgact ac        42

<210> SEQ ID NO 520
<211> LENGTH: 14
<212> TYPE: PRT
<213> ORGANISM: Artificial Sequence
<220> FEATURE:
<223> OTHER INFORMATION: Synthetic

<400> SEQUENCE: 520

Thr Arg Asp Asp Tyr Gly Asp Tyr Asp Tyr Pro Phe Asp Tyr
1               5                   10

<210> SEQ ID NO 521
<211> LENGTH: 324
<212> TYPE: DNA
<213> ORGANISM: Artificial Sequence
<220> FEATURE:
<223> OTHER INFORMATION: Synthetic

<400> SEQUENCE: 521
gacatccaga tgacccagtc tccatcctcc ctgtctgcat ctgtaggaga cagagtcacc        60
atcacttgcc gggcaagtca gggcattaga aatgatttag gctggtatca gcagaaacca       120
gggaaagccc ctaagcgcct gatctatgct gcatccagtt tgcaaagtgg ggtcccatca       180
aggttcagcg gcagtggatc cgggacagaa ttcactctca caatcagcag cctgcagcct       240
gaagattttg caacttatta ctgtctacag tataatactt accctccatt cactttcggc       300
cctgggacca agtggatat caaa                                               324

<210> SEQ ID NO 522
<211> LENGTH: 108
<212> TYPE: PRT
<213> ORGANISM: Artificial Sequence
<220> FEATURE:
<223> OTHER INFORMATION: Synthetic

<400> SEQUENCE: 522

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Arg Asn Asp
            20                  25                  30

Leu Gly Trp Tyr Gln Gln Lys Pro Gly Lys Ala Pro Lys Arg Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Glu Asp Phe Ala Thr Tyr Tyr Cys Leu Gln Tyr Asn Thr Tyr Pro Pro
            85                  90                  95

Phe Thr Phe Gly Pro Gly Thr Lys Val Asp Ile Lys
            100                 105

<210> SEQ ID NO 523
<211> LENGTH: 18
<212> TYPE: DNA
<213> ORGANISM: Artificial Sequence
<220> FEATURE:
<223> OTHER INFORMATION: Synthetic

<400> SEQUENCE: 523
cagggcatta gaaatgat                                                 18

<210> SEQ ID NO 524
<211> LENGTH: 6
<212> TYPE: PRT
<213> ORGANISM: Artificial Sequence
<220> FEATURE:
<223> OTHER INFORMATION: Synthetic

<400> SEQUENCE: 524

Gln Gly Ile Arg Asn Asp
1               5

<210> SEQ ID NO 525
<211> LENGTH: 9
<212> TYPE: DNA
<213> ORGANISM: Artificial Sequence
<220> FEATURE:
<223> OTHER INFORMATION: Synthetic

<400> SEQUENCE: 525 gctgcatcc                                                            9

<210> SEQ ID NO 526
<211> LENGTH: 3
<212> TYPE: PRT
<213> ORGANISM: Artificial Sequence
<220> FEATURE:
<223> OTHER INFORMATION: Synthetic

<400> SEQUENCE: 526

Ala Ala Ser
1

<210> SEQ ID NO 527
<211> LENGTH: 30
<212> TYPE: DNA
<213> ORGANISM: Artificial Sequence
<220> FEATURE:
<223> OTHER INFORMATION: Synthetic

<400> SEQUENCE: 527
ctacagtata atacttaccc tccattcact                                    30

<210> SEQ ID NO 528
<211> LENGTH: 10
<212> TYPE: PRT
<213> ORGANISM: Artificial Sequence
<220> FEATURE:
<223> OTHER INFORMATION: Synthetic

<400> SEQUENCE: 528

Leu Gln Tyr Asn Thr Tyr Pro Pro Phe Thr

<210> SEQ ID NO 529
<211> LENGTH: 360
<212> TYPE: DNA
<213> ORGANISM: Artificial Sequence
<220> FEATURE:
<223> OTHER INFORMATION: Synthetic

<400> SEQUENCE: 529

```
caggtgcagc tggtggagtc tgggggaggc gtggtccagc ctggggaggtc cctgagactc    60
tcctgtgcag cgtctggatt caccttcagt gcctatggca tgcactgggt ccgccagggt   120
ccaggcaagg ggctggagtg ggtggcagtt atatggtatg atggaagtaa taaatactat   180
gcagactccg tgaagggccg attcaccatc tccagagaca attccaagaa cacgctgtat   240
ctgcaaatga atagactgag agccgaggac acggctgtgt attactgtgc gagagatgac   300
tacggtgact ccccggggtt tgaccactgg ggccagggaa ccctggtcac tgtctcctca   360
```

<210> SEQ ID NO 530
<211> LENGTH: 120
<212> TYPE: PRT
<213> ORGANISM: Artificial Sequence
<220> FEATURE:
<223> OTHER INFORMATION: Synthetic

<400> SEQUENCE: 530

```
Gln Val Gln Leu Val Glu Ser Gly Gly Gly Val Val Gln Pro Gly Arg
1               5                   10                  15
Ser Leu Arg Leu Ser Cys Ala Ala Ser Gly Phe Thr Phe Ser Ala Tyr
            20                  25                  30
Gly Met His Trp Val Arg Gln Gly Pro Gly Lys Gly Leu Glu Trp Val
        35                  40                  45
Ala Val Ile Trp Tyr Asp Gly Ser Asn Lys Tyr Tyr Ala Asp Ser Val
    50                  55                  60
Lys Gly Arg Phe Thr Ile Ser Arg Asp Asn Ser Lys Asn Thr Leu Tyr
65                  70                  75                  80
Leu Gln Met Asn Arg Leu Arg Ala Glu Asp Thr Ala Val Tyr Tyr Cys
                85                  90                  95
Ala Arg Asp Asp Tyr Gly Asp Ser Pro Gly Phe Asp His Trp Gly Gln
            100                 105                 110
Gly Thr Leu Val Thr Val Ser Ser
        115                 120
```

<210> SEQ ID NO 531
<211> LENGTH: 24
<212> TYPE: DNA
<213> ORGANISM: Artificial Sequence
<220> FEATURE:
<223> OTHER INFORMATION: Synthetic

<400> SEQUENCE: 531

```
ggattcacct tcagtgccta tggc                                            24
```

<210> SEQ ID NO 532
<211> LENGTH: 8
<212> TYPE: PRT
<213> ORGANISM: Artificial Sequence
<220> FEATURE:
<223> OTHER INFORMATION: Synthetic

<400> SEQUENCE: 532

```
Gly Phe Thr Phe Ser Ala Tyr Gly
1               5
```

<210> SEQ ID NO 533
<211> LENGTH: 24
<212> TYPE: DNA
<213> ORGANISM: Artificial Sequence
<220> FEATURE:
<223> OTHER INFORMATION: Synthetic

<400> SEQUENCE: 533
atatggtatg atggaagtaa taaa                                          24

<210> SEQ ID NO 534
<211> LENGTH: 8
<212> TYPE: PRT
<213> ORGANISM: Artificial Sequence
<220> FEATURE:
<223> OTHER INFORMATION: Synthetic

<400> SEQUENCE: 534

```
Ile Trp Tyr Asp Gly Ser Asn Lys
1               5
```

<210> SEQ ID NO 535
<211> LENGTH: 39
<212> TYPE: DNA
<213> ORGANISM: Artificial Sequence
<220> FEATURE:
<223> OTHER INFORMATION: Synthetic

<400> SEQUENCE: 535
gcgagagatg actacggtga ctccccgggg tttgaccac                           39

<210> SEQ ID NO 536
<211> LENGTH: 13
<212> TYPE: PRT
<213> ORGANISM: Artificial Sequence
<220> FEATURE:
<223> OTHER INFORMATION: Synthetic

<400> SEQUENCE: 536

```
Ala Arg Asp Asp Tyr Gly Asp Ser Pro Gly Phe Asp His
1               5                   10
```

<210> SEQ ID NO 537
<211> LENGTH: 324
<212> TYPE: DNA
<213> ORGANISM: Artificial Sequence
<220> FEATURE:
<223> OTHER INFORMATION: Synthetic

<400> SEQUENCE: 537
gaaatagtga tgacgcagtc tccagccacc ctgtctgtgt ctccagggga aagagccacc    60
ctctcctgca gggccagtca gagtgttagc agcgagttag cctggtatca gcagaaacct   120
ggccaggctc ccaggctcct cttgtatggt gcatccacca gggccactgg tatcccagcc   180
aggttcagtg gcagtgggtc tgggacagag ttcactctca ccatcagcag cctgcagtct   240
gaagattttg cagtttatta ctgtcagcag tatagtaact ggcctccgtg gacgttcggc   300
caagggacca aggtggaaat caaa                                         324

<210> SEQ ID NO 538
<211> LENGTH: 108

<212> TYPE: PRT
<213> ORGANISM: Artificial Sequence
<220> FEATURE:
<223> OTHER INFORMATION: Synthetic

<400> SEQUENCE: 538

Glu Ile Val Met Thr Gln Ser Pro Ala Thr Leu Ser Val Ser Pro Gly
1               5                   10                  15

Glu Arg Ala Thr Leu Ser Cys Arg Ala Ser Gln Ser Val Ser Ser Glu
            20                  25                  30

Leu Ala Trp Tyr Gln Gln Lys Pro Gly Gln Ala Pro Arg Leu Leu Leu
        35                  40                  45

Tyr Gly Ala Ser Thr Arg Ala Thr Gly Ile Pro Ala Arg Phe Ser Gly
    50                  55                  60

Ser Gly Ser Gly Thr Glu Phe Thr Leu Thr Ile Ser Ser Leu Gln Ser
65                  70                  75                  80

Glu Asp Phe Ala Val Tyr Tyr Cys Gln Gln Tyr Ser Asn Trp Pro Pro
                85                  90                  95

Trp Thr Phe Gly Gln Gly Thr Lys Val Glu Ile Lys
            100                 105

<210> SEQ ID NO 539
<211> LENGTH: 18
<212> TYPE: DNA
<213> ORGANISM: Artificial Sequence
<220> FEATURE:
<223> OTHER INFORMATION: Synthetic

<400> SEQUENCE: 539
cagagtgtta gcagcgag                                             18

<210> SEQ ID NO 540
<211> LENGTH: 6
<212> TYPE: PRT
<213> ORGANISM: Artificial Sequence
<220> FEATURE:
<223> OTHER INFORMATION: Synthetic

<400> SEQUENCE: 540

Gln Ser Val Ser Ser Glu
1               5

<210> SEQ ID NO 541
<211> LENGTH: 9
<212> TYPE: DNA
<213> ORGANISM: Artificial Sequence
<220> FEATURE:
<223> OTHER INFORMATION: Synthetic

<400> SEQUENCE: 541 ggtgcatcc                                                        9

<210> SEQ ID NO 542
<211> LENGTH: 3
<212> TYPE: PRT
<213> ORGANISM: Artificial Sequence
<220> FEATURE:
<223> OTHER INFORMATION: Synthetic

<400> SEQUENCE: 542

Gly Ala Ser
1

```
<210> SEQ ID NO 543
<211> LENGTH: 30
<212> TYPE: DNA
<213> ORGANISM: Artificial Sequence
<220> FEATURE:
<223> OTHER INFORMATION: Synthetic

<400> SEQUENCE: 543
cagcagtata gtaactggcc tccgtggacg                                          30

<210> SEQ ID NO 544
<211> LENGTH: 10
<212> TYPE: PRT
<213> ORGANISM: Artificial Sequence
<220> FEATURE:
<223> OTHER INFORMATION: Synthetic

<400> SEQUENCE: 544

Gln Gln Tyr Ser Asn Trp Pro Pro Trp Thr
1               5                   10

<210> SEQ ID NO 545
<211> LENGTH: 354
<212> TYPE: DNA
<213> ORGANISM: Artificial Sequence
<220> FEATURE:
<223> OTHER INFORMATION: Synthetic

<400> SEQUENCE: 545
caggtgcagc tggtggagtc tgggggaggc gtggtccagc ctggagggtc cctgagactc          60
tcctgtgcag cgtctggatt caccttcagt acctatggca tgcactgggt ccgccaggct         120
ccaggcaagg ggctggagtg ggtggcaatt atatggtatg atggaagtaa ttactactat         180
gcagactccg tgaagggccg attcaccatc tccagagaca attccaagaa cacgctgtat         240
ctgcaaatga acagcctgag agccgaggac acggctgtgt attactgtgc gagagaggac         300
aggaatgatg tttttgatat ctggggccaa gggacaatgg tcaccgtctc ttca              354

<210> SEQ ID NO 546
<211> LENGTH: 118
<212> TYPE: PRT
<213> ORGANISM: Artificial Sequence
<220> FEATURE:
<223> OTHER INFORMATION: Synthetic

<400> SEQUENCE: 546

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Thr Tyr
            20                  25                  30

Gly Met His Trp Val Arg Gln Ala Pro Gly Lys Gly Leu Glu Trp Val
        35                  40                  45

Ala Ile Ile Trp Tyr Asp Gly Ser Asn Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Glu Asp Arg Asn Asp Val Phe Asp Ile Trp Gly Gln Gly Thr
            100                 105                 110

Met Val Thr Val Ser Ser
        115
```

<210> SEQ ID NO 547
<211> LENGTH: 24
<212> TYPE: DNA
<213> ORGANISM: Artificial Sequence
<220> FEATURE:
<223> OTHER INFORMATION: Synthetic

<400> SEQUENCE: 547
ggattcacct tcagtaccta tggc                                          24

<210> SEQ ID NO 548
<211> LENGTH: 8
<212> TYPE: PRT
<213> ORGANISM: Artificial Sequence
<220> FEATURE:
<223> OTHER INFORMATION: Synthetic

<400> SEQUENCE: 548

Gly Phe Thr Phe Ser Thr Tyr Gly
1               5

<210> SEQ ID NO 549
<211> LENGTH: 24
<212> TYPE: DNA
<213> ORGANISM: Artificial Sequence
<220> FEATURE:
<223> OTHER INFORMATION: Synthetic

<400> SEQUENCE: 549
atatggtatg atggaagtaa ttac                                          24

<210> SEQ ID NO 550
<211> LENGTH: 8
<212> TYPE: PRT
<213> ORGANISM: Artificial Sequence
<220> FEATURE:
<223> OTHER INFORMATION: Synthetic

<400> SEQUENCE: 550

Ile Trp Tyr Asp Gly Ser Asn Tyr
1               5

<210> SEQ ID NO 551
<211> LENGTH: 33
<212> TYPE: DNA
<213> ORGANISM: Artificial Sequence
<220> FEATURE:
<223> OTHER INFORMATION: Synthetic

<400> SEQUENCE: 551
gcgagagagg acaggaatga tgtttttgat atc                                33

<210> SEQ ID NO 552
<211> LENGTH: 11
<212> TYPE: PRT
<213> ORGANISM: Artificial Sequence
<220> FEATURE:
<223> OTHER INFORMATION: Synthetic

<400> SEQUENCE: 552

Ala Arg Glu Asp Arg Asn Asp Val Phe Asp Ile
1               5                   10

<210> SEQ ID NO 553
<211> LENGTH: 324

<212> TYPE: DNA
<213> ORGANISM: Artificial Sequence
<220> FEATURE:
<223> OTHER INFORMATION: Synthetic

<400> SEQUENCE: 553

```
gaaattgtgt tgacacagtc tccagccacc ctgtctttgt ctccagggga aagagccacc      60
ctctcctgca gggccagtca gagtgttagc agcttcttag cctggtacca acagaaacct     120
ggccaggctc ccaggctcct catctatgat tcatccaaca gggccactgg catcccagcc     180
aggttcagtg gcagtgggtc tgggacagac ttcactctca ccatcagcag cctagagcct     240
gaagattttg cagtttatta ctgtcagcag cttagcaact ggcctccgat caccttcggc     300
caagggacac gactggagat taaa                                            324
```

<210> SEQ ID NO 554
<211> LENGTH: 108
<212> TYPE: PRT
<213> ORGANISM: Artificial Sequence
<220> FEATURE:
<223> OTHER INFORMATION: Synthetic

<400> SEQUENCE: 554

```
Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Phe
            20                  25                  30

Leu Ala Trp Tyr Gln Gln Lys Pro Gly Gln Ala Pro Arg Leu Leu Ile
        35                  40                  45

Tyr Asp Ser Ser Asn Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Leu Ser Asn Trp Pro Pro
                85                  90                  95

Ile Thr Phe Gly Gln Gly Thr Arg Leu Glu Ile Lys
            100                 105
```

<210> SEQ ID NO 555
<211> LENGTH: 18
<212> TYPE: DNA
<213> ORGANISM: Artificial Sequence
<220> FEATURE:
<223> OTHER INFORMATION: Synthetic

<400> SEQUENCE: 555

```
cagagtgtta gcagcttc                                                    18
```

<210> SEQ ID NO 556
<211> LENGTH: 6
<212> TYPE: PRT
<213> ORGANISM: Artificial Sequence
<220> FEATURE:
<223> OTHER INFORMATION: Synthetic

<400> SEQUENCE: 556

```
Gln Ser Val Ser Ser Phe
1               5
```

<210> SEQ ID NO 557
<211> LENGTH: 9
<212> TYPE: DNA

```
<213> ORGANISM: Artificial Sequence
<220> FEATURE:
<223> OTHER INFORMATION: Synthetic

<400> SEQUENCE: 557 gattcatcc                                                                  9

<210> SEQ ID NO 558
<211> LENGTH: 3
<212> TYPE: PRT
<213> ORGANISM: Artificial Sequence
<220> FEATURE:
<223> OTHER INFORMATION: Synthetic

<400> SEQUENCE: 558

Asp Ser Ser
1

<210> SEQ ID NO 559
<211> LENGTH: 30
<212> TYPE: DNA
<213> ORGANISM: Artificial Sequence
<220> FEATURE:
<223> OTHER INFORMATION: Synthetic

<400> SEQUENCE: 559
cagcagctta gcaactggcc tccgatcacc                                           30

<210> SEQ ID NO 560
<211> LENGTH: 10
<212> TYPE: PRT
<213> ORGANISM: Artificial Sequence
<220> FEATURE:
<223> OTHER INFORMATION: Synthetic

<400> SEQUENCE: 560

Gln Gln Leu Ser Asn Trp Pro Pro Ile Thr
1               5                   10

<210> SEQ ID NO 561
<211> LENGTH: 348
<212> TYPE: DNA
<213> ORGANISM: Artificial Sequence
<220> FEATURE:
<223> OTHER INFORMATION: Synthetic

<400> SEQUENCE: 561
caggtgcagc tgcaggagtc gggcccagga ctggtgaagc cttcacagac cctgtccctc          60
acctgcactg tctctggtgg ctccatcagc agtggtggtt actactggac ctggatccgc         120
cagcacccag ggaagggcct ggagtggatt gggtacatct attacagtgg gagcacctac         180
tacaacccgt ccctcaagag tcgagttacc atgtcagtag acacgtctaa gaaccagttc         240
tccctgaagc tgagctctgt gactgccgcg gacacggccg tgtattactg tgcgagacta         300
ctggattttg actactgggg ccagggaacc ctggtcactg tctcctca                      348

<210> SEQ ID NO 562
<211> LENGTH: 116
<212> TYPE: PRT
<213> ORGANISM: Artificial Sequence
<220> FEATURE:
<223> OTHER INFORMATION: Synthetic

<400> SEQUENCE: 562

Gln Val Gln Leu Gln Glu Ser Gly Pro Gly Leu Val Lys Pro Ser Gln
```

```
  1               5                   10                  15
Thr Leu Ser Leu Thr Cys Thr Val Ser Gly Gly Ser Ile Ser Ser Gly
                20                  25                  30
Gly Tyr Tyr Trp Thr Trp Ile Arg Gln His Pro Gly Lys Gly Leu Glu
                35                  40                  45
Trp Ile Gly Tyr Ile Tyr Tyr Ser Gly Ser Thr Tyr Tyr Asn Pro Ser
 50                  55                  60
Leu Lys Ser Arg Val Thr Met Ser Val Asp Thr Ser Lys Asn Gln Phe
 65                  70                  75                  80
Ser Leu Lys Leu Ser Ser Val Thr Ala Ala Asp Thr Ala Val Tyr Tyr
                85                  90                  95
Cys Ala Arg Leu Leu Asp Phe Asp Tyr Trp Gly Gln Gly Thr Leu Val
                100                 105                 110
Thr Val Ser Ser
        115
```

<210> SEQ ID NO 563
<211> LENGTH: 30
<212> TYPE: DNA
<213> ORGANISM: Artificial Sequence
<220> FEATURE:
<223> OTHER INFORMATION: Synthetic

<400> SEQUENCE: 563
ggtggctcca tcagcagtgg tggttactac                                           30

<210> SEQ ID NO 564
<211> LENGTH: 10
<212> TYPE: PRT
<213> ORGANISM: Artificial Sequence
<220> FEATURE:
<223> OTHER INFORMATION: Synthetic

<400> SEQUENCE: 564

```
Gly Gly Ser Ile Ser Ser Gly Gly Tyr Tyr
 1               5                  10
```

<210> SEQ ID NO 565
<211> LENGTH: 21
<212> TYPE: DNA
<213> ORGANISM: Artificial Sequence
<220> FEATURE:
<223> OTHER INFORMATION: Synthetic

<400> SEQUENCE: 565
atctattaca gtgggagcac c                                                    21

<210> SEQ ID NO 566
<211> LENGTH: 7
<212> TYPE: PRT
<213> ORGANISM: Artificial Sequence
<220> FEATURE:
<223> OTHER INFORMATION: Synthetic

<400> SEQUENCE: 566

```
Ile Tyr Tyr Ser Gly Ser Thr
 1               5
```

<210> SEQ ID NO 567
<211> LENGTH: 24
<212> TYPE: DNA
<213> ORGANISM: Artificial Sequence
<220> FEATURE:

<223> OTHER INFORMATION: Synthetic

<400> SEQUENCE: 567
gcgagactac tggattttga ctac                                        24

<210> SEQ ID NO 568
<211> LENGTH: 8
<212> TYPE: PRT
<213> ORGANISM: Artificial Sequence
<220> FEATURE:
<223> OTHER INFORMATION: Synthetic

<400> SEQUENCE: 568

Ala Arg Leu Leu Asp Phe Asp Tyr
1               5

<210> SEQ ID NO 569
<211> LENGTH: 321
<212> TYPE: DNA
<213> ORGANISM: Artificial Sequence
<220> FEATURE:
<223> OTHER INFORMATION: Synthetic

<400> SEQUENCE: 569
gccatccaga tgacccagtc tccatcctcc ctgtctgcat ctgtaggaga cagagtcact    60
atcacttgcc gggcaagtca gggcattaga aatgatttag ctggtatca gcagaaacca   120 gggaaagccc ctaagctcct gatctatgct gcatccagtt tacaaagtgg ggtcccatca   180
aggttcagcg gcagtggatc tggcagagat ttcactctca ccatcagcag cctgcagcct   240
gaagattttg cctcttatta ctgtctacaa gatcacaatt acccgctcac tttcggcgga   300
gggaccaagg tggagatcaa a                                           321

<210> SEQ ID NO 570
<211> LENGTH: 107
<212> TYPE: PRT
<213> ORGANISM: Artificial Sequence
<220> FEATURE:
<223> OTHER INFORMATION: Synthetic

<400> SEQUENCE: 570

Ala Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Arg Asn Asp
                20                  25                  30

Leu Gly Trp Tyr Gln Gln Lys Pro Gly Lys Ala Pro Lys Leu Leu Ile
            35                  40                  45

Tyr Ala Ala Ser Ser Leu Gln Ser Gly Val Pro Ser Arg Phe Ser Gly
        50                  55                  60

Ser Gly Ser Gly Arg Asp Phe Thr Leu Thr Ile Ser Ser Leu Gln Pro
65                  70                  75                  80

Glu Asp Phe Ala Ser Tyr Tyr Cys Leu Gln Asp His Asn Tyr Pro Leu
                85                  90                  95

Thr Phe Gly Gly Gly Thr Lys Val Glu Ile Lys
            100                 105

<210> SEQ ID NO 571
<211> LENGTH: 18
<212> TYPE: DNA
<213> ORGANISM: Artificial Sequence
<220> FEATURE:
<223> OTHER INFORMATION: Synthetic
<210> SEQ ID NO 572
<211> LENGTH: 6
<212> TYPE: PRT
<213> ORGANISM: Artificial Sequence
<220> FEATURE:
<223> OTHER INFORMATION: Synthetic

<400> SEQUENCE: 572

Gln Gly Ile Arg Asn Asp
1               5

<210> SEQ ID NO 573
<211> LENGTH: 9
<212> TYPE: DNA
<213> ORGANISM: Artificial Sequence
<220> FEATURE:
<223> OTHER INFORMATION: Synthetic

<400> SEQUENCE: 573 gctgcatcc                                                              9

<210> SEQ ID NO 574
<211> LENGTH: 3
<212> TYPE: PRT
<213> ORGANISM: Artificial Sequence
<220> FEATURE:
<223> OTHER INFORMATION: Synthetic

<400> SEQUENCE: 574

Ala Ala Ser
1

<210> SEQ ID NO 575
<211> LENGTH: 27
<212> TYPE: DNA
<213> ORGANISM: Artificial Sequence
<220> FEATURE:
<223> OTHER INFORMATION: Synthetic

<400> SEQUENCE: 575
ctacaagatc acaattaccc gctcact                                         27

<210> SEQ ID NO 576
<211> LENGTH: 9
<212> TYPE: PRT
<213> ORGANISM: Artificial Sequence
<220> FEATURE:
<223> OTHER INFORMATION: Synthetic

<400> SEQUENCE: 576

Leu Gln Asp His Asn Tyr Pro Leu Thr
1               5

<210> SEQ ID NO 577
<211> LENGTH: 348
<212> TYPE: DNA
<213> ORGANISM: Artificial Sequence
<220> FEATURE:
<223> OTHER INFORMATION: Synthetic

<400> SEQUENCE: 577
caggtgcagc tggtggagtc tgggggagac gtggtccagc ctggggaggtc cctgagactc    60

<400> SEQUENCE: 571
cagggcatta gaaatgat                                                   18

```
tcctgtgcag cgtctggatt caccttcagt agctatggca tgcactgggt ccgccaggct    120
ccaggcaagg ggctggaatg ggtggcaatt atatggaatg atggaagtaa taaatactat    180
acagactccg tgaagggccg attcaccatc tccagagaca attccaagaa cactctatat    240
ctgcaaatga atggcctgag agccgaggac acggctatat attactgtgc gcgagatcag    300
gaccagtttg actactgggg ccagggaacc ctggtcaccg tctcctca                 348
```

<210> SEQ ID NO 578
<211> LENGTH: 116
<212> TYPE: PRT
<213> ORGANISM: Artificial Sequence
<220> FEATURE:
<223> OTHER INFORMATION: Synthetic

<400> SEQUENCE: 578

```
Gln Val Gln Leu Val Glu Ser Gly Gly Asp Val Val Gln Pro Gly Arg
1               5                   10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ala Ile Ile Trp Asn Asp Gly Ser Asn Lys Tyr Tyr Thr Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Gly Leu Arg Ala Glu Asp Thr Ala Ile Tyr Tyr Cys
                85                  90                  95

Ala Arg Asp Gln Asp Gln Phe Asp Tyr Trp Gly Gln Gly Thr Leu Val
            100                 105                 110

Thr Val Ser Ser
        115
```

<210> SEQ ID NO 579
<211> LENGTH: 24
<212> TYPE: DNA
<213> ORGANISM: Artificial Sequence
<220> FEATURE:
<223> OTHER INFORMATION: Synthetic

<400> SEQUENCE: 579

```
ggattcacct tcagtagcta tggc                                            24
```

<210> SEQ ID NO 580
<211> LENGTH: 8
<212> TYPE: PRT
<213> ORGANISM: Artificial Sequence
<220> FEATURE:
<223> OTHER INFORMATION: Synthetic

<400> SEQUENCE: 580

```
Gly Phe Thr Phe Ser Ser Tyr Gly
1               5
```

<210> SEQ ID NO 581
<211> LENGTH: 24
<212> TYPE: DNA
<213> ORGANISM: Artificial Sequence
<220> FEATURE:
<223> OTHER INFORMATION: Synthetic

<400> SEQUENCE: 581

```
<210> SEQ ID NO 582
<211> LENGTH: 8
<212> TYPE: PRT
<213> ORGANISM: Artificial Sequence
<220> FEATURE:
<223> OTHER INFORMATION: Synthetic

<400> SEQUENCE: 582

Ile Trp Asn Asp Gly Ser Asn Lys
1               5

<210> SEQ ID NO 583
<211> LENGTH: 27
<212> TYPE: DNA
<213> ORGANISM: Artificial Sequence
<220> FEATURE:
<223> OTHER INFORMATION: Synthetic

<400> SEQUENCE: 583
gcgcgagatc aggaccagtt tgactac                                          27

<210> SEQ ID NO 584
<211> LENGTH: 9
<212> TYPE: PRT
<213> ORGANISM: Artificial Sequence
<220> FEATURE:
<223> OTHER INFORMATION: Synthetic

<400> SEQUENCE: 584

Ala Arg Asp Gln Asp Gln Phe Asp Tyr
1               5

<210> SEQ ID NO 585
<211> LENGTH: 324
<212> TYPE: DNA
<213> ORGANISM: Artificial Sequence
<220> FEATURE:
<223> OTHER INFORMATION: Synthetic

<400> SEQUENCE: 585
gaaatagtga tgacgcagtc tccagccacc ctgtctgtgt ctccagggga aagagccacc      60
ctctcctgca gggccagtca gagtattagc acaaacttag cctggtaccg gcagaaacct     120
ggccaggctc cccggctcct catctatgat gcatccacca gggccactgg tatcccagcc     180
aggttcagtg gcagtgggtc tgggacagac ttcactctca ccatcagcag cctgcagtct     240
gaagattttg cagtttatta ctgtcagcag tatagtaact ggcctccgta cactttggc     300
caggggacca gctggagat caaa                                             324

<210> SEQ ID NO 586
<211> LENGTH: 108
<212> TYPE: PRT
<213> ORGANISM: Artificial Sequence
<220> FEATURE:
<223> OTHER INFORMATION: Synthetic

<400> SEQUENCE: 586

Glu Ile Val Met Thr Gln Ser Pro Ala Thr Leu Ser Val Ser Pro Gly
1               5                   10                  15
Glu Arg Ala Thr Leu Ser Cys Arg Ala Ser Gln Ser Ile Ser Thr Asn
            20                  25                  30
```

```
Leu Ala Trp Tyr Arg Gln Lys Pro Gly Gln Ala Pro Arg Leu Leu Ile
         35                  40                  45

Tyr Asp Ala Ser Thr Arg Ala Thr Gly Ile Pro Ala Arg Phe Ser Gly
 50                  55                  60

Ser Gly Ser Gly Thr Asp Phe Thr Leu Thr Ile Ser Ser Leu Gln Ser
 65                  70                  75                  80

Glu Asp Phe Ala Val Tyr Tyr Cys Gln Gln Tyr Ser Asn Trp Pro Pro
                 85                  90                  95

Tyr Thr Phe Gly Gln Gly Thr Lys Leu Glu Ile Lys
            100                 105
```

<210> SEQ ID NO 587
<211> LENGTH: 18
<212> TYPE: DNA
<213> ORGANISM: Artificial Sequence
<220> FEATURE:
<223> OTHER INFORMATION: Synthetic

<400> SEQUENCE: 587
cagagtatta gcacaaac                                                       18

<210> SEQ ID NO 588
<211> LENGTH: 6
<212> TYPE: PRT
<213> ORGANISM: Artificial Sequence
<220> FEATURE:
<223> OTHER INFORMATION: Synthetic

<400> SEQUENCE: 588

```
Gln Ser Ile Ser Thr Asn
 1               5
```

<210> SEQ ID NO 589
<211> LENGTH: 9
<212> TYPE: DNA
<213> ORGANISM: Artificial Sequence
<220> FEATURE:
<223> OTHER INFORMATION: Synthetic

<400> SEQUENCE: 589 gatgcatcc                                                                  9

<210> SEQ ID NO 590
<211> LENGTH: 3
<212> TYPE: PRT
<213> ORGANISM: Artificial Sequence
<220> FEATURE:
<223> OTHER INFORMATION: Synthetic

<400> SEQUENCE: 590

```
Asp Ala Ser
 1
```

<210> SEQ ID NO 591
<211> LENGTH: 30
<212> TYPE: DNA
<213> ORGANISM: Artificial Sequence
<220> FEATURE:
<223> OTHER INFORMATION: Synthetic

<400> SEQUENCE: 591
cagcagtata gtaactggcc tccgtacact                                           30

<210> SEQ ID NO 592

```
<211> LENGTH: 10
<212> TYPE: PRT
<213> ORGANISM: Artificial Sequence
<220> FEATURE:
<223> OTHER INFORMATION: Synthetic

<400> SEQUENCE: 592

Gln Gln Tyr Ser Asn Trp Pro Pro Tyr Thr
1               5                   10

<210> SEQ ID NO 593
<211> LENGTH: 555
<212> TYPE: DNA
<213> ORGANISM: Homo sapiens

<400> SEQUENCE: 593
atgagccgca cagcctacac ggtgggagcc ctgcttctcc tcttggggac cctgctgccg      60
gctgctgaag ggaaaaagaa agggtcccaa ggtgccatcc ccccgccaga caaggcccag     120
cacaatgact cagagcagac tcagtcgccc cagcagcctg gctccaggaa ccggggcgg      180 ggccaagggc ggggcactgc catgcccggg gaggaggtgc tggagtccag ccaagaggcc     240
ctgcatgtga cggagcgcaa atacctgaag cgagactggt gcaaaaccca gccgcttaag     300
cagaccatcc acgaggaagg ctgcaacagt cgcaccatca tcaaccgctt ctgttacggc     360
cagtgcaact ctttctacat ccccaggcac atccggaagg aggaaggttc ctttcagtcc     420
tgctccttct gcaagcccaa gaaattcact accatgatgg tcacactcaa ctgccctgaa     480
ctacagccac ctaccaagaa gagagagtc acacgtgtga agcagtgtcg ttgcatatcc     540
atcgatttgg attaa                                                      555

<210> SEQ ID NO 594
<211> LENGTH: 184
<212> TYPE: PRT
<213> ORGANISM: Homo sapiens

<400> SEQUENCE: 594

Met Ser Arg Thr Ala Tyr Thr Val Gly Ala Leu Leu Leu Leu Leu Gly
1               5                   10                  15

Thr Leu Leu Pro Ala Ala Glu Gly Lys Lys Gly Ser Gln Gly Ala
            20                  25                  30

Ile Pro Pro Pro Asp Lys Ala Gln His Asn Asp Ser Glu Gln Thr Gln
        35                  40                  45

Ser Pro Gln Gln Pro Gly Ser Arg Asn Arg Gly Arg Gly Gln Gly Arg
    50                  55                  60

Gly Thr Ala Met Pro Gly Glu Glu Val Leu Glu Ser Ser Gln Glu Ala
65                  70                  75                  80

Leu His Val Thr Glu Arg Lys Tyr Leu Lys Arg Asp Trp Cys Lys Thr
                85                  90                  95

Gln Pro Leu Lys Gln Thr Ile His Glu Glu Gly Cys Asn Ser Arg Thr
            100                 105                 110

Ile Ile Asn Arg Phe Cys Tyr Gly Gln Cys Asn Ser Phe Tyr Ile Pro
        115                 120                 125

Arg His Ile Arg Lys Glu Glu Gly Ser Phe Gln Ser Cys Ser Phe Cys
    130                 135                 140

Lys Pro Lys Lys Phe Thr Thr Met Met Val Thr Leu Asn Cys Pro Glu
145                 150                 155                 160

Leu Gln Pro Pro Thr Lys Lys Lys Arg Val Thr Arg Val Lys Gln Cys
                165                 170                 175
```

```
Arg Cys Ile Ser Ile Asp Leu Asp
            180

<210> SEQ ID NO 595
<211> LENGTH: 184
<212> TYPE: PRT
<213> ORGANISM: Artificial Sequence
<220> FEATURE:
<223> OTHER INFORMATION: Synthetic

<400> SEQUENCE: 595

Met Ser Arg Thr Ala Tyr Thr Val Gly Ala Leu Leu Leu Leu Leu Gly
1               5                   10                  15

Thr Leu Leu Pro Ala Ala Glu Gly Lys Lys Gly Ser Gln Gly Ala
            20                  25                  30

Ile Pro Pro Asp Lys Ala Gln His Asn Asp Ser Glu Gln Thr Gln
        35                  40                  45

Ser Pro Gln Gln Pro Gly Ser Arg Asn Arg Gly Arg Gly Gln Gly Arg
    50                  55                  60

Gly Thr Ala Met Pro Gly Glu Glu Val Leu Glu Ser Ser Gln Glu Ala
65                  70                  75                  80

Leu His Val Thr Glu Arg Lys Tyr Leu Lys Arg Asp Trp Cys Lys Thr
                85                  90                  95

Gln Pro Leu Lys Gln Thr Ile His Glu Glu Gly Cys Asn Ser Arg Thr
            100                 105                 110

Ile Ile Asn Arg Phe Cys Tyr Gly Gln Cys Asn Ser Phe Tyr Ile Pro
        115                 120                 125

Arg His Ile Arg Lys Glu Glu Gly Ser Phe Gln Ser Cys Ser Phe Cys
    130                 135                 140

Lys Pro Lys Lys Phe Thr Thr Met Met Val Thr Leu Asn Cys Pro Glu
145                 150                 155                 160

Leu Gln Pro Pro Thr Lys Lys Lys Arg Val Thr Arg Val Lys Gln Cys
                165                 170                 175

Arg Cys Ile Ser Ile Asp Leu Asp
            180
```